United States Patent
Cooke et al.

(10) Patent No.: US 8,653,092 B2
(45) Date of Patent: Feb. 18, 2014

(54) TETRAHYDRO-PYRIDO-PYRIMIDINE DERIVATIVES

(75) Inventors: Nigel Graham Cooke, Oberwil (CH);
Paulo Fernandes Gomes Dos Santos, Basel (CH); Nadege Graveleau, Hesingue (FR); Christina Hebach, Muenchenstein (CH); Klemens Högenauer, Oberwil (CH); Gregory Hollingworth, Sevenoaks (GB); Alexander Baxter Smith, Niffer (FR); Nicolas Soldermann, Rosenau (FR); Frank Stowasser, Murg (DE); Ross Strang, Haut-Rhin (FR); Nicola Tufilli, Moehlin (CH); Anette Von Matt, Biel-Benken (CH); Romain Wolf, Schlierbach (FR); Frédéric Zecri, Brookline, MA (US)

(73) Assignee: Novartis AG, Basel (CH)

( * ) Notice: Subject to any disclaimer, the term of this patent is extended or adjusted under 35 U.S.C. 154(b) by 233 days.

(21) Appl. No.: 13/175,050

(22) Filed: Jul. 1, 2011

(65) Prior Publication Data
US 2012/0065183 A1    Mar. 15, 2012

Related U.S. Application Data

(60) Provisional application No. 61/361,589, filed on Jul. 6, 2010.

(51) Int. Cl.
| | | |
|---|---|---|
| *C07D 471/04* | (2006.01) | |
| *A61K 31/519* | (2006.01) | |
| *A61P 37/08* | (2006.01) | |
| *A61P 25/28* | (2006.01) | |
| *A61P 35/00* | (2006.01) | |
| *A61P 37/06* | (2006.01) | |

(52) U.S. Cl.
USPC .................... 514/264.11; 514/264.1; 544/279

(58) Field of Classification Search
USPC ........................ 544/279; 514/264.1, 264.11
See application file for complete search history.

(56) References Cited

U.S. PATENT DOCUMENTS 6,150,372 A * 11/2000 Palanki et al. ............ 514/264.1

FOREIGN PATENT DOCUMENTS

| WO | 94/24132 | 10/1994 |
|---|---|---|
| WO | 2004/058756 | 7/2004 |
| WO | 2005/121142 | 12/2005 |
| WO | 2006/062981 | 6/2006 |
| WO | 2006/119504 | 11/2006 |
| WO | WO 2008/130481 A1 | 10/2008 |
| WO | 2009/047255 | 4/2009 |
| WO | 2009/123967 | 10/2009 |

OTHER PUBLICATIONS

Marone et al.; "Targeting phosphoinositide 3-kinase—Moving towards therapy"; Biochimica et Biophysica Acta; 1784:159-185 (2008).

* cited by examiner

*Primary Examiner* — Susanna Moore
(74) *Attorney, Agent, or Firm* — John B. Alexander

(57) ABSTRACT

The invention relates to substituted tetrahydro-pyrido-pyrimidine derivatives of the formula (I),

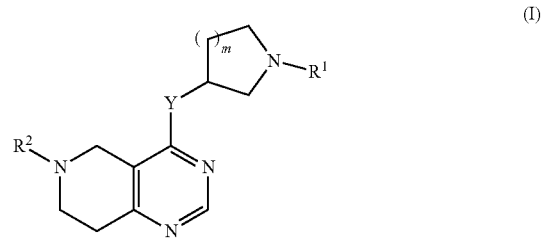

wherein Y, $R^1$, $R^2$ and m are as defined in the description. Such compounds are suitable for the treatment of a disorder or disease which is mediated by the activity of the PI3K enzymes.

21 Claims, 5 Drawing Sheets

TETRAHYDRO-PYRIDO-PYRIMIDINE DERIVATIVES

This application claims priority to U.S. Provisional Application Ser. No. 61/361,589 filed 6 Jul. 2010, the contents of which are incorporated herein by reference in their entirety.

FIELD OF THE INVENTION

The invention relates to the preparation and use of new tetrahydro-pyrido-pyrimidine derivatives as drug candidates in free form or in pharmaceutically acceptable salt form with valuable druglike properties, such as e.g. metabolic stability and suitable pharmacokinetics, form for the modulation, notably the inhibition of the activity or function of the phosphoinositide 3' OH kinase family (hereinafter PI3K).

BACKGROUND OF THE INVENTION

The invention relates to the treatment, either alone or in combination, with one or more other pharmacologically active compounds, of PI3K-related diseases including but not limited to autoimmune disorders, inflammatory diseases, allergic diseases, airway diseases, such as asthma and COPD, transplant rejection, cancers eg of hematopoietic origin or solid tumors. The invention also relates to the treatment, either alone or in combination, with one or more other pharmacologically active compounds, includes methods of treating conditions, diseases or disorders in which one or more of the functions of B cells such as antibody production, antigen presentation, cytokine production or lymphoid organogenesis are abnormal or are undesirable including rheumatoid arthritis, pemphigus vulgaris, idiopathic thrombocytopenia purpura, systemic lupus erythematosus, multiple sclerosis, myasthenia gravis, Sjögren's syndrome, autoimmune hemolytic anemia, ANCA-associated vasculitides, cryoglobulinemia, thrombotic thrombocytopenic purpura, chronic autoimmune urticaria, allergy (atopic dermatitis, contact dermatitis, allergic rhinitis), goodpasture's syndrome, AMR (antibody-mediated transplant rejection), B cell-mediated hyperacute, acute and chronic transplant rejection and cancers of haematopoietic origin including but not limited to multiple myeloma; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Waldenstroem disease.

SUMMARY OF THE INVENTION

In a first aspect, the invention relates to tetrahydro-pyridopyrimidine compounds of the formula (I) and/or pharmaceutically acceptable salts and/or solvates thereof,

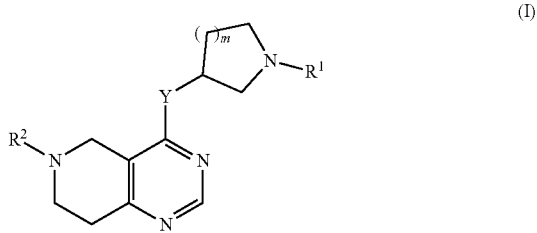

(I)

wherein
Y is selected from O or $NR^3$;
$R^1$ is selected from phenyl, pyridyl, pyrimidinyl, pyrazinyl, pyridazinyl, 1,2,3-triazinyl, 1,2,4-triazinyl, 1,3,5-triazinyl, or
—C(O)—$R^4$
  wherein
  $R^4$ is selected from $C_1$-$C_8$-alkyl, halo-$C_1$-$C_8$-alkyl, hydroxy-$C_1$-$C_8$-alkyl, $C_1$-$C_8$-alkoxy-$C_1$-$C_8$-alkyl, $C_1$-$C_8$-alkyl-sulfonyl-$C_1$-$C_8$-alkyl, heterocyclyl, heterocyclyl-oxy, heterocyclyl-$C_1$-$C_8$-alkyl, $C_3$-$C_{12}$-cycloalkyl, $C_3$-$C_{12}$-cycloalkyl-$C_1$-$C_8$-alkyl, heteroaryl, heteroaryl-oxy, heteroaryl-$C_1$-$C_8$-alkyl, hydroxy, $C_1$-$C_8$-alkoxy, amino, N—$C_1$-$C_8$-alkyl-amino or N,N-di-$C_1$-$C_8$-alkyl-amino,
  wherein '$C_1$-$C_8$-alkyl' in N—$C_1$-$C_8$-alkyl-amino and N,N-di-$C_1$-$C_8$-alkyl-amino may be unsubstituted or substituted by halogen, hydroxy or $C_1$-$C_4$-alkoxy;
  wherein '$C_3$-$C_{12}$-cycloalkyl' in $C_3$-$C_{12}$-cycloalkyl and $C_3$-$C_{12}$-cycloalkyl-$C_1$-$C_8$-alkyl may be unsubstituted or substituted by 1-5 substituents independently selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl;
  wherein 'heterocyclyl' is selected from oxiranyl, aziridinyl, oxetanyl, thiethanyl, azetidinyl, pyrrolidinyl, tetrahydrofuranyl, tetrahydrothiophenyl, 2,3-dihydrofuranyl, 2,5-dihydrofuranyl, 2,3-dihydrothiophenyl, 1-pyrrolinyl, 2-pyrrolinyl, 3-pyrrolinyl, tetrahydropyranyl, piperidinyl, tetrahydrothiopyranyl, morpholinyl, thiomorpholinyl, piperazinyl, azepanyl, thiepanyl or oxepanyl; each of which is unsubstituted or substituted by 1-5 substituents independently selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy -$C_1$-$C_8$-alkyl-carbonyl;
  wherein 'heterocyclyl' can be attached at a heteroatom or a carbon atom and where the N and/or S heteroatoms can also optionally be oxidized to various oxidation states;
  wherein 'heteroaryl' is selected from
  furanyl, thiophenyl, pyrrolyl, imidazolyl, pyrazolyl, thiazolyl, isothiazolyl, oxazolyl, isoxazolyl, 1,2,5-oxadiazolyl, 1,2,4-oxadiazolyl, 1,2,3-oxadiazolyl,1, 3,4-oxadiazolyl, 1,2,5-thiadiazolyl, 1,2,4-thiadiazolyl, 1,2,3-thiadiazolyl, 1,3,4-thiadiazolyl, 1,2,3-triazolyl, 1,2,4-triazolyl, 1,2,5-triazolyl, pyridyl, pyrimidinyl, pyrazinyl, pyridazinyl, 1,2,3-triazinyl, 1,2,4-triazinyl or 1,3,5-triazinyl; each of which is unsubstituted or substituted by 1-5 substituents independently selected from halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl; wherein 'heteroaryl' can be attached at a heteroatom or a carbon atom and where the N and/or S heteroatoms can also optionally be oxidized to various oxidation states;

$R^2$ is selected from phenyl, naphthyl, pyridyl, pyrimidinyl, pyrazinyl, pyridazinyl, quinolinyl or isoquinolinyl, each of which is unsubstituted or substituted by 1-5 substituents independently selected from halogen, cyano, nitro, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl;

$R^3$ is selected from H, $C_1$-$C_4$-alkyl or halo-$C_1$-$C_4$-alkyl; and m is selected from 0 or 1.

DETAILED DESCRIPTION OF THE INVENTION

Figure 1:
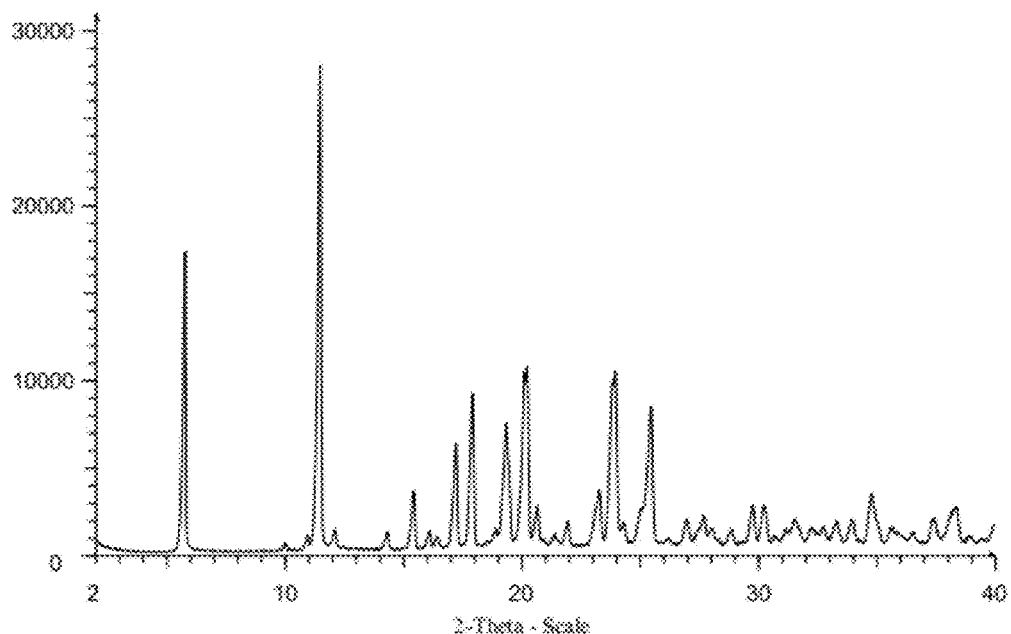
FIG. 1 discloses the X-ray Powder Diffraction Pattern of Example 1 citrate salt FIG. 2 discloses the X-ray Powder Diffraction Pattern of Example 1 fumarate salt FIG. 3 discloses the X-ray Powder Diffraction Pattern of Example 1 napadisylate salt FIG. 4 discloses the X-ray Powder Diffraction Pattern of Example 67 phosphate salt FIG. 5 discloses the: X-ray Powder Diffraction Pattern of Example 67 HCl salt FIG. 6 discloses the X-ray Powder Diffraction Pattern of Example 67 hippurate salt FIG. 7 discloses the X-ray Powder Diffraction Pattern of Example 1 anhydrous form FIG. 8 discloses the X-ray Powder Diffraction Pattern of Example 1 trihydrate FIG. 9 discloses the X-ray Powder Diffraction Pattern of Example 67 anhydrous form
Figure 2:
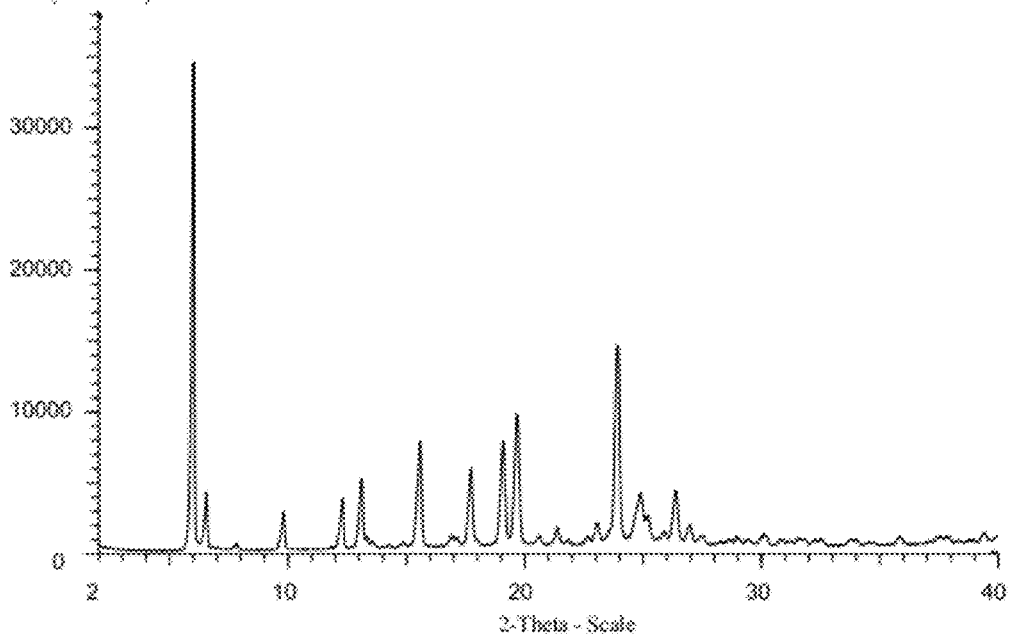
Figure 3:
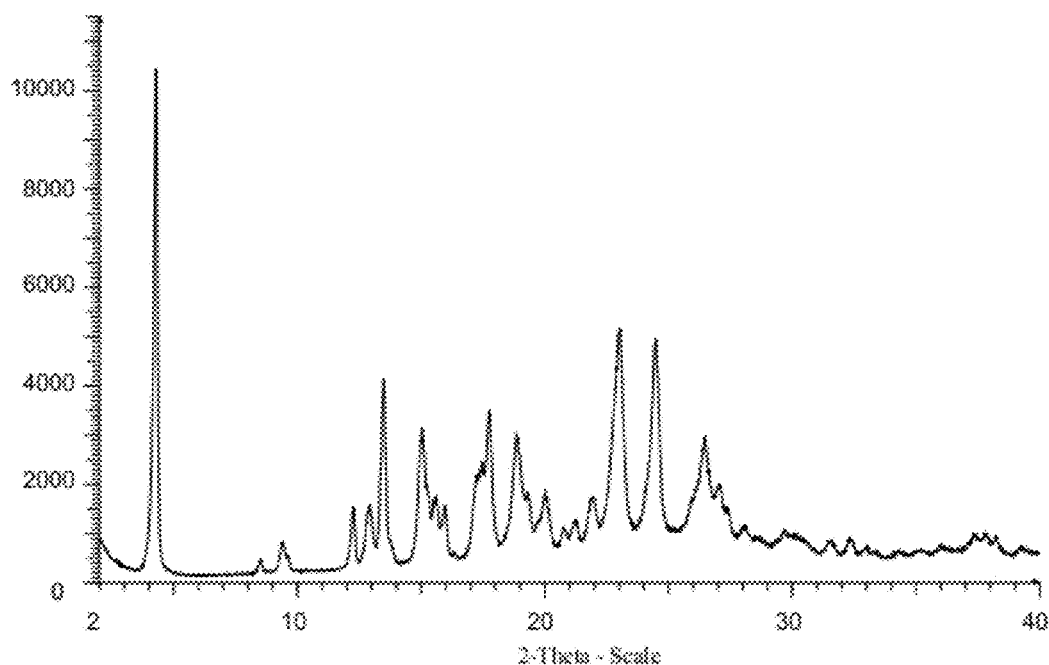
Figure 4:
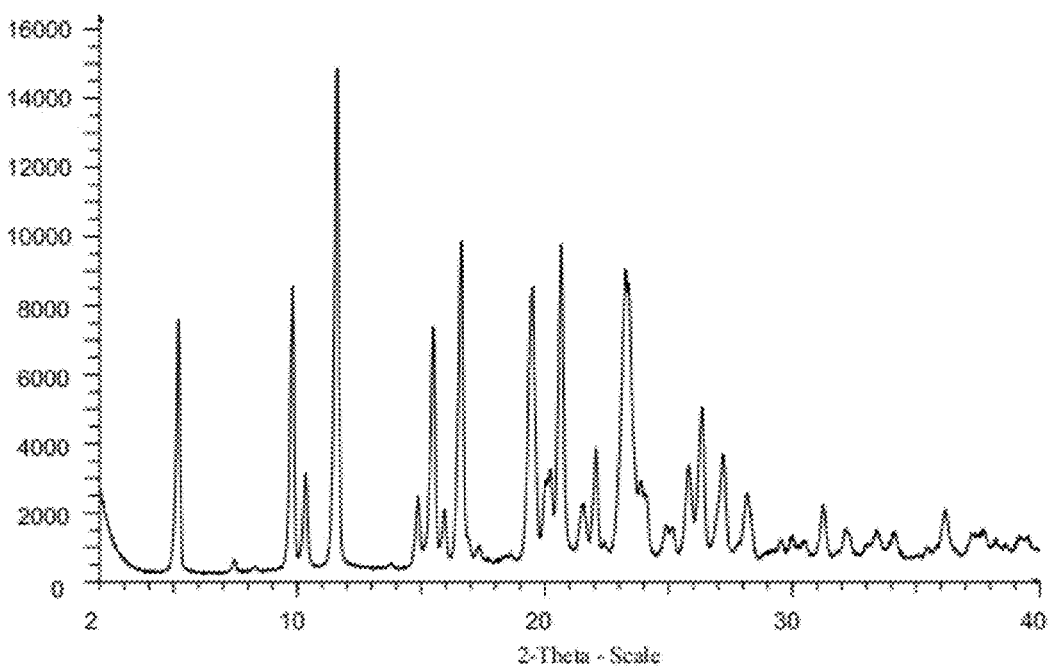
Figure 5:
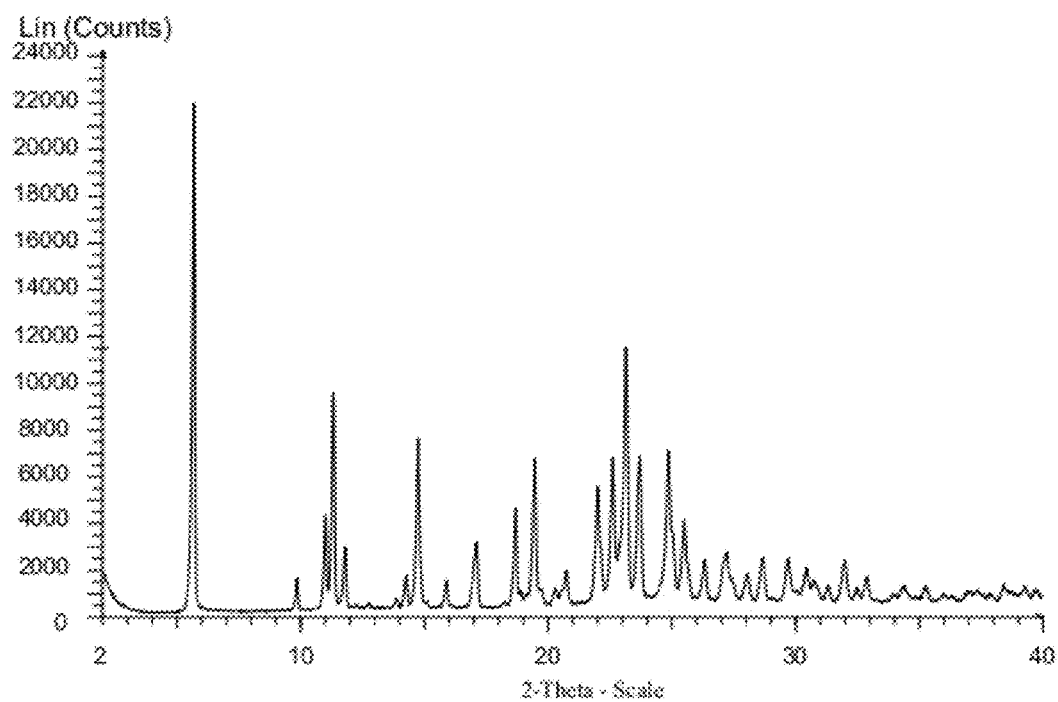
Figure 6:
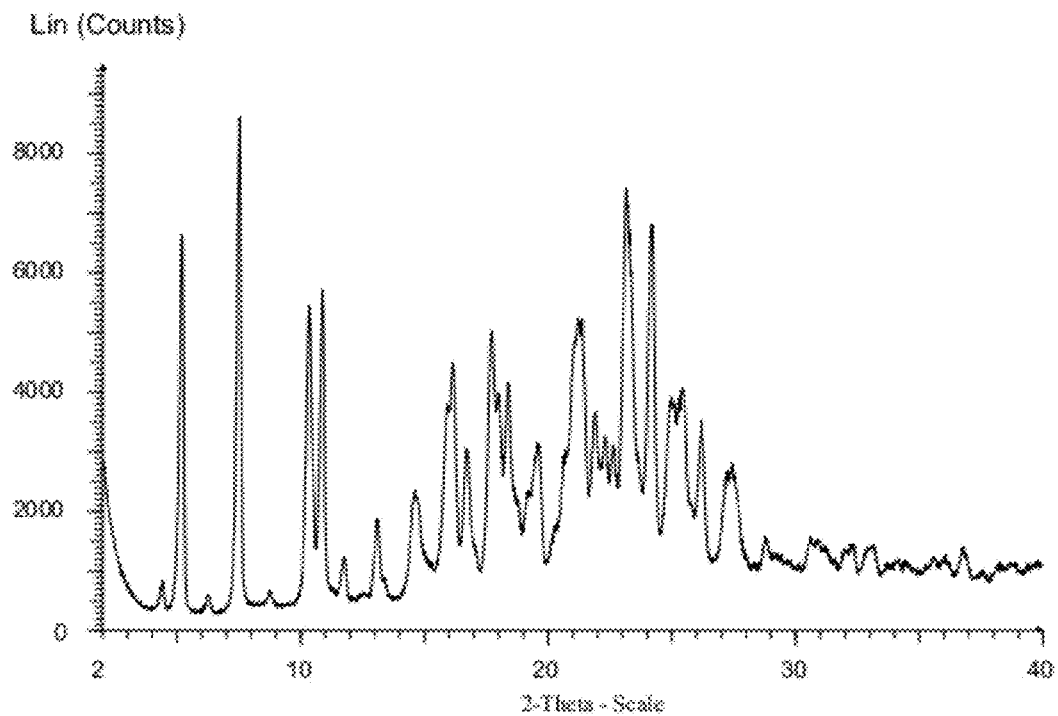
Figure 7:
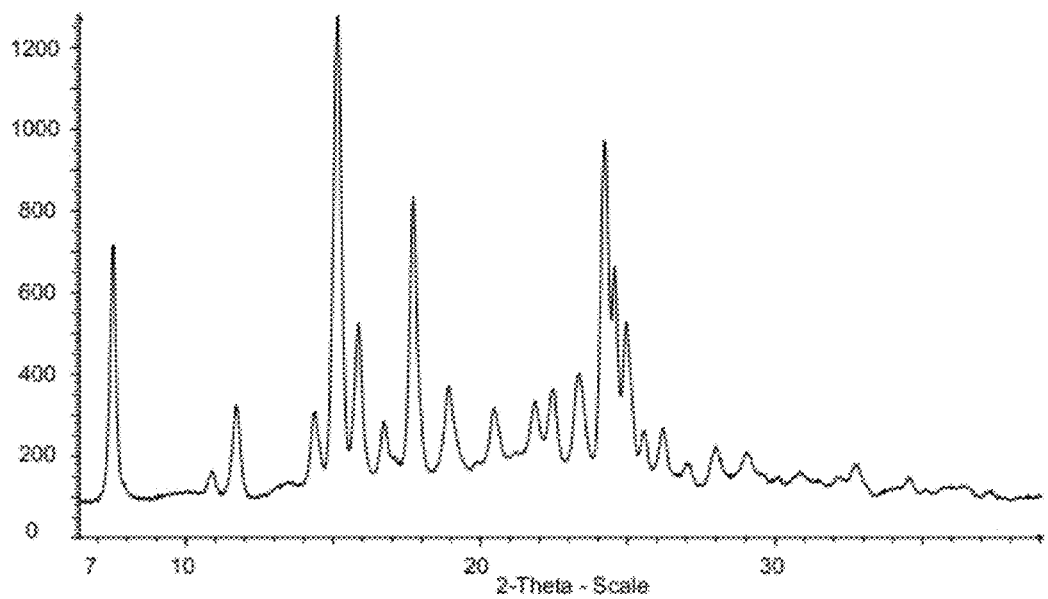
Figure 8:
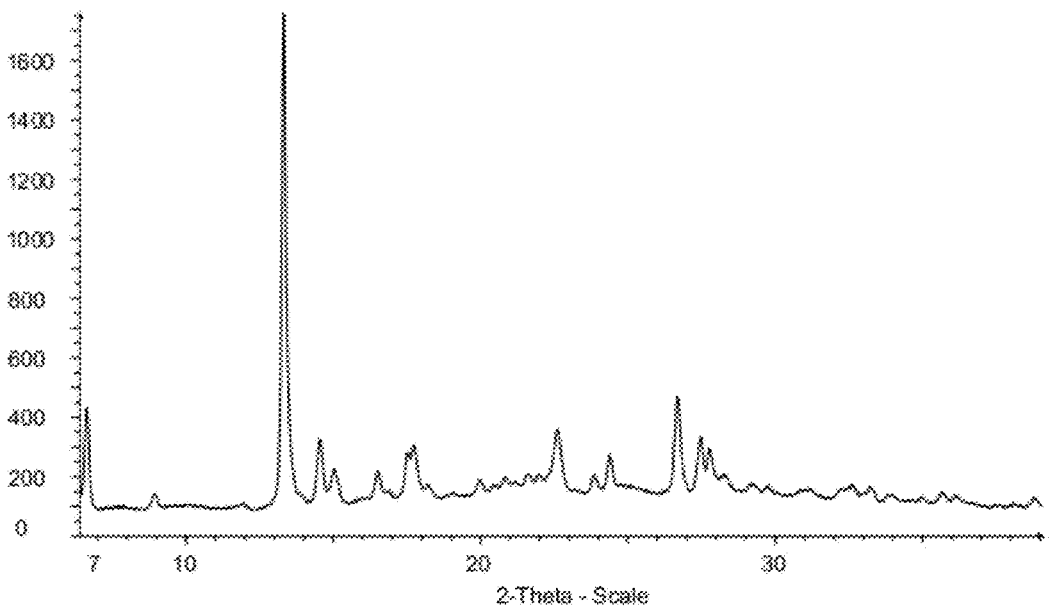
Figure 9:
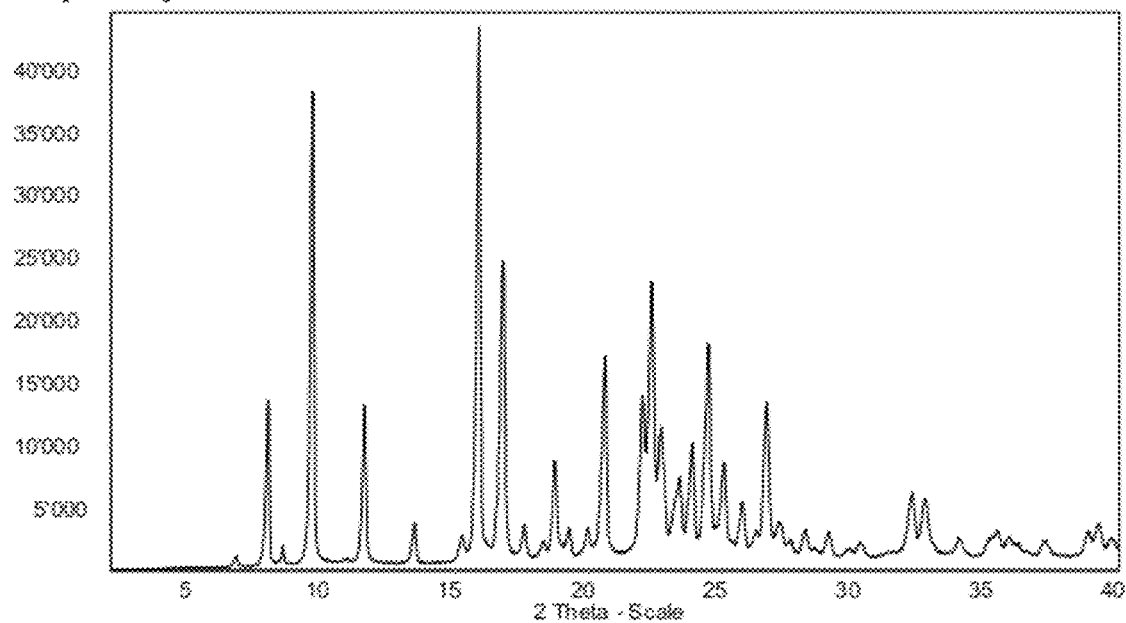

Any formula given herein is intended to represent hydrates, solvates, and polymorphs of such compounds, and mixtures thereof.

Unless otherwise specified, the term "compounds of the invention" refers to compounds of formula (I) and subformulae thereof, salts of the compounds, hydrates or solvates of the compounds, salts of the compounds as well as stereoisomers (including diastereoisomers and enantiomers), tautomers and isotopically labeled compounds (including deuterium substitutions).

As used herein, the term "a", "an", "the" and similar terms used in the context of the present invention, especially in the context of the claims, are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language, e.g. "such as", provided herein is intended merely to better illuminate the invention and does not pose a limitation on the scope of the invention otherwise claimed.

The invention may be more fully appreciated by reference to the following description, including the following glossary of terms and the concluding examples. As used herein, the terms "including", "containing" and "comprising" are used herein in their open, non-limiting sense. Where compounds of formula I are mentioned, this is meant to include also the tautomers and N-oxides of the compounds of formula I. Tautomers, such as tautomers between keto- and enol form, lactam- and lactim form, amid form and imidic acid form or enamine form and imine form, can be present for example in the R1 or R2 portion of compounds of formula I. The nitrogen atoms of the tetrahydro-pyrido-pyrimidine core of the compounds of formula I as well as nitrogen containing heterocyclyl and heteroaryl residues can form N-oxides.

Where the plural form is used for compounds, salts, and the like, this is taken to mean also a single compound, salt, or the like.

The general terms used hereinbefore and hereinafter preferably have within the context of this disclosure the following meanings, unless otherwise indicated:

As used herein, the term "alkyl" refers to a fully saturated branched, including single or multiple branching, or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Typically, alkyl groups have 1-7, more preferably 1-4 carbons.

As used herein, the term "halo-alkyl" refers to an alkyl as defined herein, which is substituted by one or more halo groups as defined herein. The halo-alkyl can be mono-halo-alkyl, di-halo-alkyl or poly-halo-alkyl including per-halo-alkyl. A mono-halo-alkyl can have one iodo, bromo, chloro or fluoro within the alkyl group. Di-halo-alky and poly-halo-alkyl groups can have two or more of the same halo atoms or a combination of different halo groups within the alkyl. Typically the poly-halo-alkyl contains up to 12, or 10, or 8, or 6, or 4, or 3, or 2 halo groups. Non-limiting examples of halo-alkyl include fluoro-methyl, di-fluoro-methyl, tri-fluoro-methyl, chloro-methyl, di-chloro-methyl, tri-chloro-methyl, penta-fluoro-ethyl, hepta-fluoro-propyl, di-fluoro-chloro-methyl, di-chloro-fluoro-methyl, di-fluoro-ethyl, di-fluoro-propyl, di-chloro-ethyl and dichloro-propyl. A per-halo-alkyl refers to an alkyl having all hydrogen atoms replaced with halo atoms.

As used herein, the term "heterocyclyl" or "heterocyclic" refers to a 3 to 7 membered monocyclic or 7 to 10 membered saturated or partially saturated ring or ring system, which contains at least one heteroatom selected from N, O and S, where the N and S can also optionally be oxidized to various oxidation states. 'Heterocyclyl' can be attached at a heteroatom or a carbon atom. 'heterocyclyl' can include fused or bridged rings as well as spirocyclic rings. Examples of heterocycles include oxiranyl, aziridinyl, oxetanyl, thiethanyl, azetidinvl, pyrrolidinyl, tetrahydrofuranyl, tetrahydrothiophenyl, 2,3-dihydrofuranyl, 2,5-dihydrofuranyl, 2,3-dihydrothiophenyl, 1-pyrrolinyl, 2-pyrrolinyl, 3-pyrrolinyl, tetrahydropyranyl, piperidinyl, tetrahydrothiopyranyl, morpholinyl thiomorpholinyl, piperazinyl, azepanyl, thiepanyl and oxepanyl.

As used herein, the term "heteroaryl" refers to a 4-, 5-, 6-, or 7-membered monocyclic, 7-, 8-, 9-, 10-, 11-, or 12-membered bicyclic or 10-, 11-, 12-, 13-, 14- or 15-membered tricyclic unsaturated ring or ring system—carrying the highest possible number of conjugated double bonds in the ring(s), which contains at least one heteroatom selected from N, O and S, wherein the N and S can also optionally be oxidized to various oxidation states. 'Heteroaryl' can be attached at a heteroatom or a carbon atom. 'Heteroaryl' can include fused or bridged rings as well as spirocyclic rings. Examples of heteroaryl include furanyl, thiophenyl, pyrrolyl, imidazolyl, pyrazolyl, thiazolyl, isothiazolyl, oxazolyl, isoxazolyl, 1,2,5-oxadiazolyl, 1,2,4-oxadiazolyl, 1,2,3-oxadiazolyl, 1,3,4-oxadiazolyl, 1,2,5-thiadiazolyl, 1,2,4-thiadiazolyl, 1,2,3-thiadiazolyl, 1,3,4-thiadiazolyl, 1,2,3-triazolyl, 1,2,4-triazolyl, 1,2,5-triazolyl, pyridyl, pyrimidinyl, pyrazinyl, pyridazinyl, 1,2,3-triazinyl, 1,2,4-triazinyl and 1,3,5-triazinyl.

As used herein, the term "cycloalkyl" refers to saturated or partially unsaturated monocyclic, bicyclic or tricyclic hydrocarbon groups of 3-12 carbon atoms. Unless otherwise provided, cycloalkyl refers to cyclic hydrocarbon groups having between 3 and 10 ring carbon atoms or between 3 and 7 ring carbon atoms. Exemplary bicyclic hydrocarbon groups include octahydroindyl, decahydronaphthyl. Exemplary tricyclic hydrocarbon bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octy. Exemplary tetracyclic hydrocarbon groups include adamantyl.

As used herein, the term "oxy" refers to an —O— linking group.

As used herein, the term "carboxy" or "carboxyl" is —COOH.

As used herein, all substituents are written in a way to show the order of functional groups (groups) they are composed of. The functional groups are defined herein above.

"Treatment" includes prophylactic (preventive) and therapeutic treatment as well as the delay of progression of a disease or disorder.

"Combination" refers to either a fixed combination in one dosage unit form, or a kit of parts for the combined administration where a compound of the formula (I) and a combination partner (e.g. an other drug as explained below, also referred to as "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof, e.g. a patient, and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) and a combination partner, are both administered to a patient simultaneously in the form of a single entity or dosage. The term "non-fixed combination" means that the active ingredients, e.g. a compound of formula (I) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

Various embodiments of the invention are described herein. It will be recognized that features specified in each embodiment may be combined with other specified features to provide further embodiments.

The invention further relates to pharmaceutically acceptable prodrugs of a compound of formula (I). Particularly, the present invention also relates to pro-drugs of a compound of formula I as defined herein that convert in vivo to the compound of formula I as such. Any reference to a compound of formula I is therefore to be understood as referring also to the corresponding pro-drugs of the compound of formula I, as appropriate and expedient.

The invention further relates to pharmaceutically acceptable metabolites of a compound of formula (I).

In one embodiment, the invention provides a compound of the formula (I) and/or a pharmaceutically acceptable salt and/or a solvate thereof, selected from a compound of the formula (Ia)

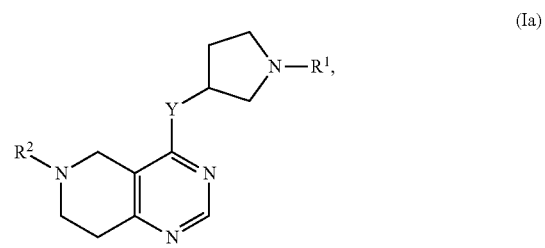

(Ia)

wherein $R^1$, $R^2$ and Y are as defined above.

In one embodiment, the invention provides a compound of the formula (I) and/or a pharmaceutically acceptable salt and/or a solvate thereof, selected from a compound of the formula (Ia')

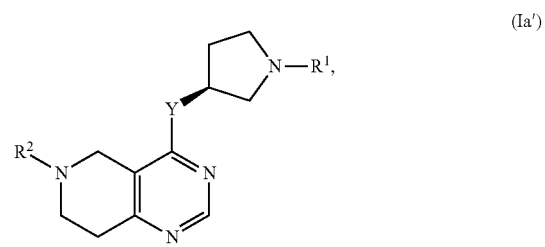

(Ia')

wherein $R^1$, $R^2$ and Y are as defined above.

In another embodiment, the invention provides a compound of the formula (I) and/or a pharmaceutically acceptable salt and/or a solvate thereof, selected from a compound of the formula (Ib)

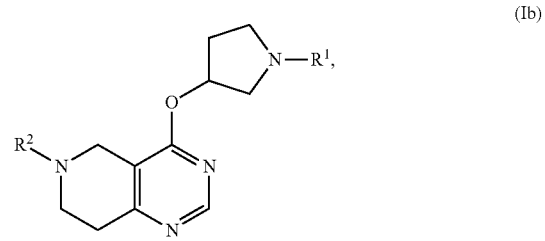

(Ib)

wherein $R^1$ and $R^2$ are as defined above.

In another embodiment, the invention provides a compound of the formula (I) and/or a pharmaceutically acceptable salt and/or a solvate thereof, selected from a compound of the formula (Ib')

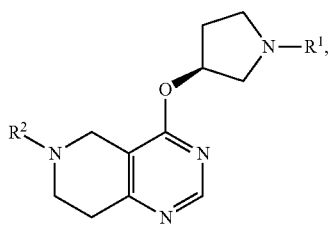

wherein R¹ and R² are as defined above.

In another embodiment, the invention provides a compound of the formula (I) and/or a pharmaceutically acceptable salt and/or a solvate thereof, selected from a compound of the formula (Ic)

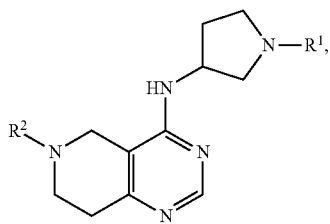

wherein R¹ and R² are as defined above.

In another embodiment, the invention provides a compound of the formula (I) and/or a pharmaceutically acceptable salt and/or a solvate thereof, selected from a compound of the formula (Ic')

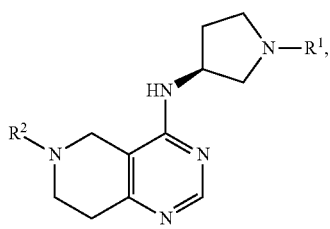

wherein R¹ and R² are as defined above.

In another embodiment, the invention provides a compound of the formula (I) and/or a pharmaceutically acceptable salt and/or a solvate thereof, selected from a compound of the formula (Id)

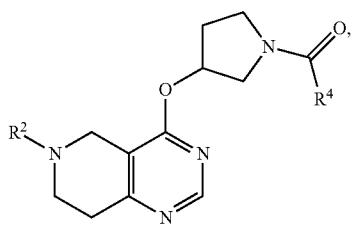

wherein R⁴ and R² are as defined above.

In another embodiment, the invention provides a compound of the formula (I) and/or a pharmaceutically acceptable salt and/or a solvate thereof, selected from a compound of the formula (Id')

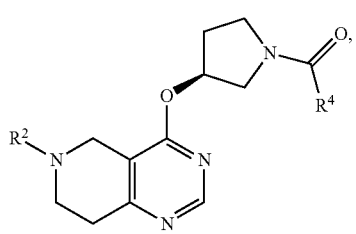

wherein R⁴ and R² are as defined above.

In another embodiment, the invention provides a compound of the formula (I) and/or a pharmaceutically acceptable salt and/or a solvate thereof, selected from a compound of the formula (Ie)

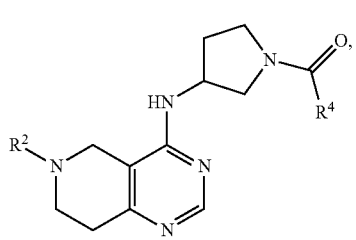

wherein R⁴ and R² are as defined above.

In another embodiment, the invention provides a compound of the formula (I) and/or a pharmaceutically acceptable salt and/or a solvate thereof, selected from a compound of the formula (Ie')

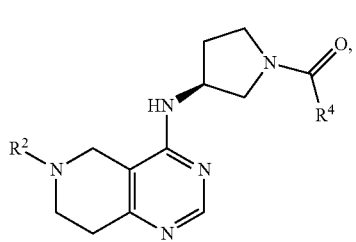

wherein R⁴ and R² are as defined above.

In another embodiment, the invention provides a compound of the formulae (I), (Ia), (Ia'), (Ib), (Ib') (Ic), (Ic'), (Id), (Id'), (Ie) or (Ie') and/or a pharmaceutically acceptable salt and/or a solvate thereof, wherein R² is selected from naphthyl, pyridyl or pyrimidinyl; each of which is unsubstituted or substituted by 1-3 substituents independently selected from halogen, cyano, nitro, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl.

In another embodiment, the invention provides a compound of the formulae (I), (Ia), (Ia'), (Ib), (Ib') (Ic), (Ic'), (Id), (Id'), (Ie) or (Ie') and/or a pharmaceutically acceptable salt and/or a solvate thereof, wherein $R^2$ is selected from 3-pyridyl or 5-pyrimidinyl; each of which is substituted by 1-2 substituents independently selected from halogen, cyano, nitro, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl, wherein one substituents is located in the para position relative to the point of connection of $R^2$ to the core of the compound.

In another embodiment, the invention provides a compound of the formulae (I), (Ia), (Ia'), (Ib), (Ib') (Ic), (Ic'), (Id), (Id'), (Ie) or (Ie') and/or a pharmaceutically acceptable salt and/or a solvate thereof, wherein $R^2$ is selected from 3-pyridyl or 5-pyrimidinyl; each of which is substituted by 1-2 substituents independently selected from halogen, cyano, $C_1$-$C_4$-alkyl, halo-$C_1$-$C_4$-alkyl, $C_1$-$C_4$-alkoxy or amino, wherein one substituents is located in the para position relative to the point of connection of $R^2$ to the core of the compound.

In another embodiment, the invention provides a compound of the formulae (I), (Ia), (Ia'), (Ib), (Ib') (Ic), (Ic'), (Id), (Id'), (Ie) or (Ie') and/or a pharmaceutically acceptable salt and/or a solvate thereof, wherein $R^2$ is selected from 3-pyridyl or 5-pyrimidinyl; each of which is substituted by 1-2 substituents independently selected from fluoro, chloro, cyano, methyl, trifluoromethyl, methoxy or amino, wherein one substituents is located in the para position relative to the point of connection of $R^2$ to the core of the compound.

In another embodiment, the invention provides a compound of the formulae (I), (Ia) or (Ia') and/or a pharmaceutically acceptable salt and/or a solvate thereof, wherein $R^3$ is H.

In another embodiment, the invention provides a compound of the formulae (I), (Ia), (Ia'), (Ib), (Ib'), (Ic) or (Ic') and/or a pharmaceutically acceptable salt and/or a solvate thereof, wherein $R^1$ is selected from phenyl, pyridyl, pyrimidinyl, pyrazinyl, pyridazinyl, 1,2,3-triazinyl, 1,2,4-triazinyl or 1,3,5-triazinyl.

In another embodiment, the invention provides a compound of the formulae (I), (Ia), (Ia'), (Ib), (Ib'), (Ic) or (Ic') and/or a pharmaceutically acceptable salt and/or a solvate thereof, wherein $R^1$ is selected from pyridyl or pyrimidinyl.

In another embodiment, the invention provides a compound of the formulae (I), (Ia), (Ia'), (Ib), (Ib'), (Ic) or (Ic') and/or a pharmaceutically acceptable salt and/or a solvate thereof, wherein $R^1$ is —C(O)—$R^4$, wherein $R^4$ is as defined above.

In another embodiment, the invention provides a compound of the formulae (I), (Ia), (Ia'), (Ib), (Ib'), (Ic) or (Ic') and/or a pharmaceutically acceptable salt and/or a solvate thereof, wherein $R^1$ is —C(O)—$R^4$, wherein $R^4$ is as defined above.

In another embodiment, the invention provides a compound of the formulae (I), (Ia), (Ia'), (Ib), (Ib'), (Ic) or (Ic') wherein $R^1$ is —C(O)—$R^4$; or a compound of the formulae (Id), (Id'), (Ie) or (Ie') and/or a pharmaceutically acceptable salt and/or a solvate thereof, wherein
  $R^4$ is selected from $C_1$-$C_8$-alkyl, $C_1$-$C_8$-alkoxy-$C_1$-$C_8$-alkyl, heterocyclyl, heterocyclyl-$C_1$-$C_8$-alkyl, $C_3$-$C_{12}$-cycloalkyl, heteroaryl, $C_1$-$C_8$-alkoxy or N,N-di-$C_1$-$C_8$-alkyl-amino, wherein '$C_1$-$C_8$-alkyl' in N,N-di-$C_1$-$C_8$-alkyl-amino may be unsubstituted or substituted by halogen, hydroxy or $C_1$-$C_4$-alkoxy;
  wherein '$C_3$-$C_{12}$-cycloalkyl' in $C_3$-$C_{12}$-cycloalkyl may be unsubstituted or substituted by 1-3 substituents independently selected from oxo, halogen, $C_1$-$C_8$-alkyl, hydroxyl, $C_1$-$C_8$-alkoxy, $C_1$-$C_8$-alkyl-carbonyl;
  wherein 'heterocyclyl' is selected from pyrrolidinyl, tetrahydropyranyl, piperidinyl, tetrahydrothiopyranyl, morpholinyl or piperazinyl; each of which is unsubstituted or substituted by 1-3 substituents independently selected from oxo, halogen, $C_1$-$C_8$-alkyl, hydroxyl, $C_1$-$C_8$-alkoxy, $C_1$-$C_8$-alkyl-carbonyl;
  wherein 'heterocyclyl' can be attached at a heteroatom or a carbon atom and where the N and/or S heteroatoms can also optionally be oxidized to various oxidation states;
  wherein 'heteroaryl' is selected from
  furanyl, imidazolyl, pyrazolyl, thiazolyl, oxazolyl, isoxazolyl, 1,3,4-oxadiazolyl, pyridyl, pyrazinyl; each of which is unsubstituted or substituted by 1-3 substituents independently selected from halogen, $C_1$-$C_8$-alkyl, hydroxyl, $C_1$-$C_8$-alkoxy, $C_1$-$C_8$-alkyl-carbonyl;
  wherein 'heteroaryl' can be attached at a heteroatom or a carbon atom and where the N and/or S heteroatoms can also optionally be oxidized to various oxidation states.

In another embodiment, the invention provides a compound of the formulae (I), (Ia), (Ia'), (Ib), (Ib'), (Ic) or (Ic') wherein $R^1$—C(O)—$R^4$; or a compound of the formulae (Id), (Id'), (Ie) or (Ie') and/or a pharmaceutically acceptable salt and/or a solvate thereof, wherein
  $R^4$ is selected from heterocyclyl, $C_4$-$C_8$-cycloalkyl or heteroaryl;
  wherein '$C_3$-$C_{12}$-cycloalkyl' may be unsubstituted or substituted by 1-3 substituents independently selected from fluoro, $C_1$-$C_4$-alkyl, hydroxyl, $C_1$-$C_4$-alkoxy;
  wherein 'heterocyclyl' is selected from pyrrolidinyl, tetrahydropyranyl, piperidinyl, tetrahydrothiopyranyl, morpholinyl or piperazinyl; each of which is unsubstituted or substituted by 1-3 substituents independently selected from oxo, halogen, $C_1$-$C_4$-alkyl, hydroxyl, $C_1$-$C_4$-alkyl-carbonyl;
  wherein 'heterocyclyl' can be attached at a heteroatom or a carbon atom and where the N and/or S heteroatoms can also optionally be oxidized to various oxidation states;
  wherein 'heteroaryl' is selected from
  furanyl, imidazolyl, pyrazolyl, thiazolyl, oxazolyl, isoxazolyl, 1,3,4-oxadiazolyl, pyridyl, pyrazinyl; each of which is unsubstituted or substituted by 1-3 substituents independently selected from $C_1$-$C_4$-alkyl, hydroxyl;
  wherein 'heteroaryl' can be attached at a heteroatom or a carbon atom and where the N and/or S heteroatoms can also optionally be oxidized to various oxidation states.

In another embodiment, the invention provides a compound of the formulae (I), (Ia), (Ia'), (Ib), (Ib'), (Ic) or (Ic') wherein $R^1$—C(O)—$R^4$; or a compound of the formulae (Id), (Id'), (Ie) or (Ie') and/or a pharmaceutically acceptable salt and/or a solvate thereof, wherein
  $R^4$ is selected from heterocyclyl;
  wherein 'heterocyclyl' is selected from pyrrolidinyl, tetrahydropyranyl, piperidinyl, tetrahydrothiopyranyl, morpholinyl or piperazinyl; each of which is unsubstituted or substituted by 1-3 substituents independently selected from oxo, halogen, $C_1$-$C_4$-alkyl, hydroxyl, $C_1$-$C_4$-alkyl-carbonyl;
  wherein 'heterocyclyl' can be attached at a heteroatom or a carbon atom and where the N and/or S heteroatoms can also optionally be oxidized to various oxidation states.

In another embodiment, the invention provides a compound of the formulae (I), (Ia), (Ia'), (Ib), (Ib'), (Ic) or (Ic') wherein $R^1$ is —C(O)—$R^4$; or a compound of the formulae (Id), (Id'), (Ie) or (Ie') and/or a pharmaceutically acceptable salt and/or a solvate thereof, wherein R⁴ is selected from $C_1$-$C_8$-alkyl, $C_1$-$C_8$-alkoxy-$C_1$-$C_8$-alkyl, $C_1$-$C_8$-alkoxy or N,N-di-$C_1$-$C_8$-alkyl-amino,
  wherein '$C_1$-$C_8$-alkyl' in N,N-di-$C_1$-$C_8$-alkyl-amino may be unsubstituted or substituted by halogen, hydroxy or $C_1$-$C_4$alkoxy.

In another embodiment, the invention provides a compound of the formulae (I), (Ia), (Ia'), (Ib), (Ib'), (Ic) or (Ic') wherein R¹ is —C(O)—R⁴; or a compound of the formulae (Id), (Id'), (Ie) or (Ie') and/or a pharmaceutically acceptable salt and/or a solvate thereof, wherein
  R⁴ is selected from $C_1$-$C_8$-alkyl.

In another embodiment, the invention provides a compound of the formulae (I), (Ia), (Ia'), (Ib), (Ib'), (Ic) or (Ic') wherein R¹ is —C(O)—R⁴; or a compound of the formulae (Id), (Id'), (Ie) or (Ie') and/or a pharmaceutically acceptable salt and/or a solvate thereof, wherein
  R² is selected from 3-pyridyl or 5-pyrimidinyl; each of which is substituted by 1-2 substituents independently selected from fluoro, chloro, cyano, methyl, trifluoromethyl, methoxy or amino, wherein one substituents is located in the para position relative to the point of connection of R² to the core of the compound and R⁴ is selected from heterocyclyl;
  wherein 'heterocyclyl' is selected from pyrrolidinyl, tetrahydropyranyl, piperidinyl, tetrahydrothiopyranyl, morpholinyl or piperazinyl; each of which is unsubstituted or substituted by 1-3 substituents independently selected from oxo, halogen, $C_1$-$C_4$-alkyl, hydroxyl, $C_1$-$C_4$-alkyl-carbonyl;
  wherein 'heterocyclyl' can be attached at a heteroatom or a carbon atom and where the N and/or S heteroatoms can also optionally be oxidized to various oxidation states.

In another embodiment, the invention provides a compound of the formulae (I), (Ia), (Ia'), (Ib), (Ib'), (Ic) or (Ic') wherein R¹ is —C(O)—R⁴; or a compound of the formulae (Id), (Id'), (Ie) or (Ie') and/or a pharmaceutically acceptable salt and/or a solvate thereof, wherein
  R² is selected from 3-pyridyl or 5-pyrimidinyl; each of which is substituted by 1-2 substituents independently selected from fluoro, chloro, cyano, methyl, trifluoromethyl, methoxy or amino, wherein one substituents is located in the para position relative to the point of connection of R² to the core of the compound and R⁴ is selected from $C_1$-$C_8$-alkyl, $C_1$-$C_8$-alkoxy-$C_1$-$C_8$-alkyl, $C_1$-$C_8$-alkoxy or N,N-di-$C_1$-$C_8$-alkyl-amino,
  wherein '$C_1$-$C_8$-alkyl' in N,N-di-$C_1$-$C_8$-alkyl-amino may be unsubstituted or substituted by halogen, hydroxy or $C_1$-$C_4$-alkoxy.

In another embodiment individual compounds according to the invention are those listed in the Examples section below.

In another embodiment, the invention provides a compound of the formula (I), selected from
{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone;
{3-[6-(6-Methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone;
{(S)-3-[6-(2,4-Dimethoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone;
{3-[6-(2,4-Dimethoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone;
2-Methoxy-5-{4-[(S)-1-(tetrahydro-pyran-4-carbonyl)-pyrrolidin-3-yloxy]-7,8-dihydro-5H-pyrido[4,3-d]pyrimidin-6-yl}-nicotinonitrile;
2-Methoxy-5-{4-[1-(tetrahydro-pyran-4-carbonyl)-pyrrolidin-3-yloxy]-7,8-dihydro-5H-pyrido[4,3-d]pyrimidin-6-yl}-nicotinonitrile;
1-{(S)-3-[6-(5,6-Dimethoxy-pyridin-3-yl)-5,6,7,8-tetrahydro-pyrido[4,3-d]pyrimidin-4-yloxy]-pyrrolidin-1-yl}-propan-1-one;
1-{3-[6-(5,6-Dimethoxy-pyridin-3-yl)-5,6,7,8-tetrahydro-pyrido[4,3-d]pyrimidin-4-yloxy]-pyrrolidin-1-yl}-propan-1-one;
{(S)-3-[6-(5,6-Dimethoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone;
{3-[6-(5,6-Dimethoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone;
2-Amino-5-{4-[(S)-1-(tetrahydro-pyran-4-carbonyl)-pyrrolidin-3-yloxy]-7,8-dihydro-5H-pyrido[4,3-d]pyrimidin-6-yl}-nicotinonitrile;
2-Amino-5-{4-[1-(tetrahydro-pyran-4-carbonyl)-pyrrolidin-3-yloxy]-7,8-dihydro-5H-pyrido[4,3-d]pyrimidin-6-yl}-nicotinonitrile;
(S)-(3-(6-(5-Fluoro-6-methoxypyridin-3-yl)-5,6,7,8-tetrahydropyrido[4,3-d]pyrimidin-4-yloxy)pyrrolidin-1-yl)(tetrahydro-2H-pyran-4-yl)methanone;
(3-(6-(5-Fluoro-6-methoxypyridin-3-yl)-5,6,7,8-tetrahydropyrido[4,3-d]pyrimidin-4-yloxy)pyrrolidin-1-yl)(tetrahydro-2H-pyran-4-yl)methanone;
(S)-2-Methoxy-5-(4-(1-(2-methoxyacetyl)pyrrolidin-3-yloxy)-7,8-dihydropyrido[4,3-d]pyrimidin-6(5H)-yl)nicotinonitrile;
2-Methoxy-5-(4-(1-(2-methoxyacetyl)pyrrolidin-3-yloxy)-7,8-dihydropyrido[4,3-d]pyrimidin-6(5H)-yl)nicotinonitrile;
(S)-5-(4-(1-(Cyclopentanecarbonyl)pyrrolidin-3-yloxy)-7,8-dihydropyrido[4,3-d]pyrimidin-6(5H)-yl)-2-methoxynicotinonitrile;
5-(4-(1-(Cyclopentanecarbonyl)pyrrolidin-3-yloxy)-7,8-dihydropyrido[4,3-d]pyrimidin-6(5H)-yl)-2-methoxynicotinonitrile;
(2,4-Dimethyl-oxazol-5-yl)-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
(2,4-Dimethyl-oxazol-5-yl)-{3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
Furan-3-yl-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
Furan-3-yl-{3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
Furan-3-yl-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
Furan-3-yl-{3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone;
{3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(2-methyl-oxazol-4-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(2-methyl-oxazol-4-yl)-methanone;

(3-Methoxy-cyclobutyl)-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone;

(3-Methoxy-cyclobutyl)-{3-[6-(6-methoxy-5-methyl-pyridin-3-yl)-5,6,7,8-tetrahydro-pyrido[4,3-d]pyrimidin-4-yloxy]-pyrrolidin-1-yl}-methanone;

({(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-oxazol-4-yl-methanone;

({3-[6-(6-Methoxy-5-methyl-pyridin-3-yl)-5,6,7,8-tetrahydro-pyrido[4,3-d]pyrimidin-4-yloxy]-pyrrolidin-1-yl}-oxazol-4-yl-methanone;

1-(4-{(S)-3-[6-(6-Methoxy-5-methyl-pyridin-3-yl)-5,6,7,8-tetrahydro-pyrido[4,3-d]pyrimidin-4-yloxy]-pyrrolidine-1-carbonyl}-piperidin-1-yl)-ethanone;

1-(4-{3-[6-(6-Methoxy-5-methyl-pyridin-3-yl)-5,6,7,8-tetrahydro-pyrido[4,3-d]pyrimidin-4-yloxy]-pyrrolidine-1-carbonyl}-piperidin-1-yl)-ethanone;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(4-methyl-oxazol-5-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(4-methyl-oxazol-5-yl)-methanone;

5-{(S)-3-[6-(6-Methoxy-5-methyl-pyridin-3-yl)-5,6,7,8-tetrahydro-pyrido[4,3-d]pyrimidin-4-yloxy]-pyrrolidine-1-carbonyl}-1H-pyridin-2-one;

5-{3-[6-(6-Methoxy-5-methyl-pyridin-3-yl)-5,6,7,8-tetrahydro-pyrido[4,3-d]pyrimidin-4-yloxy]-pyrrolidine-1-carbonyl}-1H-pyridin-2-one;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(1-methyl-1H-imidazol-4-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(1-methyl-1H-imidazol-4-yl)-methanone;

{(S)-3-[6-(5,6-Dimethoxy-pyridin-3-yl)-5,6,7,8-tetrahydro-pyrido[4,3-d]pyrimidin-4-yloxy]-pyrrolidin-1-yl}-oxazol-4-yl-methanone;

{3-[6-(5,6-Dimethoxy-pyridin-3-yl)-5,6,7,8-tetrahydro-pyrido[4,3-d]pyrimidin-4-yloxy]-pyrrolidin-1-yl}-oxazol-4-yl-methanone;

{(S)-3-[6-(5,6-Dimethoxy-pyridin-3-yl)-5,6,7,8-tetrahydro-pyrido[4,3-d]pyrimidin-4-yloxy]-pyrrolidin-1-yl}-oxazol-5-yl-methanone;

{3-[6-(5,6-Dimethoxy-pyridin-3-yl)-5,6,7,8-tetrahydro-pyrido[4,3-d]pyrimidin-4-yloxy]-pyrrolidin-1-yl}-oxazol-5-yl-methanone;

{(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2-methyl-oxazol-4-yl)-methanone;

{3-[6-(5,6-Dimethoxy-pyridin-3-yl)-5,6,7,8-tetrahydro-pyrido[4,3-d]pyrimidin-4-yloxy]-pyrrolidin-1-yl}-(2-methyl-oxazol-4-yl)-methanone;

{(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2,2-dimethyl-tetrahydro-pyran-4-yl)-methanone;

{3-[6-(5,6-Dimethoxy-pyridin-3-yl)-5,6,7,8-tetrahydro-pyrido[4,3-d]pyrimidin-4-yloxy]-pyrrolidin-1-yl}-(2,2-dimethyl-tetrahydro-pyran-4-yl)-methanone;

{(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2,4-dimethyl-oxazol-5-yl)-methanone;

{3-[6-(5,6-Dimethoxy-pyridin-3-yl)-5,6,7,8-tetrahydro-pyrido[4,3-d]pyrimidin-4-yloxy]-pyrrolidin-1-yl}-(2,4-dimethyl-oxazol-5-yl)-methanone;

(4,4-Difluoro-cyclohexyl)-{(S)-3-[6-(5,6-dimethoxy-pyridin-3-yl)-5,6,7,8-tetrahydro-pyrido[4,3-d]pyrimidin-4-yloxy]-pyrrolidin-1-yl}-methanone;

(4,4-Difluoro-cyclohexyl)-{3-[6-(5,6-dimethoxy-pyridin-3-yl)-5,6,7,8-tetrahydro-pyrido[4,3-d]pyrimidin-4-yloxy]-pyrrolidin-1-yl}-methanone;

2-Methoxy-5-{4-[(S)-1-(2-tetrahydro-pyran-4-yl-acetyl)-pyrrolidin-3-yloxy]-7,8-dihydro-5H-pyrido[4,3-d]pyrimidin-6-yl}-nicotinonitrile;

2-Methoxy-5-{4-[1-(2-tetrahydro-pyran-4-yl-acetyl)-pyrrolidin-3-yloxy]-7,8-dihydro-5H-pyrido[4,3-d]pyrimidin-6-yl}-nicotinonitrile;

5-{4-[(S)-1-(2,4-Dimethyl-oxazole-5-carbonyl)-pyrrolidin-3-yloxy]-7,8-dihydro-5H-pyrido[4,3-d]pyrimidin-6-yl}-2-methoxy-nicotinonitrile;

5-{4-[1-(2,4-Dimethyl-oxazole-5-carbonyl)-pyrrolidin-3-yloxy]-7,8-dihydro-5H-pyrido[4,3-d]pyrimidin-6-yl}-2-methoxy-nicotinonitrile;

5-{4-[(S)-1-(2,2-Dimethyl-tetrahydro-pyran-4-carbonyl)-pyrrolidin-3-yloxy]-7,8-dihydro-5H-pyrido[4,3-d]pyrimidin-6-yl}-2-methoxy-nicotinonitrile;

5-{4-[1-(2,2-Dimethyl-tetrahydro-pyran-4-carbonyl)-pyrrolidin-3-yloxy]-7,8-dihydro-5H-pyrido[4,3-d]pyrimidin-6-yl}-2-methoxy-nicotinonitrile;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-oxazol-4-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-oxazol-4-yl)-methanone;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-isoxazol-4-A-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-isoxazol-4-A-methanone;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-A-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-A-methanone;

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-A-methanone;

Isoxazol-3-yl-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;

Isoxazol-3-yl-{3-[6-(6-Methoxy-5-methyl-pyridin-3-A-5,6,7,8-tetrahydro-pyrido[4,3-d]pyrimidin-4-yloxy]-pyrrolidin-1-yl}-methanone;

Isoxazol-5-yl-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;

Isoxazol-5-yl-{3-[6-(6-Methoxy-5-methyl-pyridin-3-A-5,6,7,8-tetrahydro-pyrido[4,3-d]pyrimidin-4-yloxy]-pyrrolidin-1-yl}-methanone;

2-Methoxy-5-{4-[(S)-1-(thiazole-4-carbonyl)-pyrrolidin-3-yloxy]-7,8-dihydro-5H-pyrido[4,3-d]pyrimidin-6-yl}-nicotinonitrile;
2-Methoxy-5-{4-[1-(thiazole-4-carbonyl)-pyrrolidin-3-yloxy]-7,8-dihydro-5H-pyrido[4,3-d]pyrimidin-6-yl}-nicotinonitrile;
2-Methoxy-5-{4-[(S)-1-(1-methyl-1H-pyrazole-4-carbonyl)-pyrrolidin-3-yloxy]-7,8-dihydro-5H-pyrido[4,3-d]pyrimidin-6-yl}-nicotinonitrile;
2-Methoxy-5-{4-[1-(1-methyl-1H-pyrazole-4-carbonyl)-pyrrolidin-3-yloxy]-7,8-dihydro-5H-pyrido[4,3-d]pyrimidin-6-yl}-nicotinonitrile;
2-Methoxy-5-{4-[(S)-1-(1-methyl-1H-pyrazole-3-carbonyl)-pyrrolidin-3-yloxy]-7,8-dihydro-5H-pyrido[4,3-d]pyrimidin-6-yl}-nicotinonitrile;
2-Methoxy-5-{4-[1-(1-methyl-1H-pyrazole-3-carbonyl)-pyrrolidin-3-yloxy]-7,8-dihydro-5H-pyrido[4,3-d]pyrimidin-6-yl}-nicotinonitrile;
(2,2-Dimethyl-tetrahydro-pyran-4-yl)-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
(2,2-Dimethyl-tetrahydro-pyran-4-yl)-{3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
(1,1-Dioxo-hexahydro-1lambda*6*-thiopyran-4-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone;
(1,1-Dioxo-hexahydro-1lambda*6*-thiopyran-4-yl)-{3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone;
(S)-(2,4-Dimethyloxazol-5-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(2,4-Dimethyloxazol-5-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(thiazol-5-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(thiazol-5-yl)methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1-methyl-1H-pyrazol-5-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1-methyl-1H-pyrazol-5-yl)methanone;
4-((S)-3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)pyrrolidin-2-one;
4-(3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)pyrrolidin-2-one;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyridin-3-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyridin-3-yl)methanone;
(S)-(1H-Imidazol-4-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(1H-Imidazol-4-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
5-((S)-3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)pyrrolidin-2-one;
5-(3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)pyrrolidin-2-one;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyridin-4-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyridin-4-yl)methanone;
(S)-(1,3-Dimethyl-1H-pyrazol-4-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(1,3-Dimethyl-1H-pyrazol-4-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1H-pyrazol-4-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1H-pyrazol-4-yl)methanone;
(S)-(3-(6-(6-methoxy-5-(trifluoromethyl)pyridin-3-yl)-5,6,7,8-tetrahydropyrido[4,3-d]pyrimidin-4-yloxy)pyrrolidin-1-yl)(5-methyl-1,3,4-oxadiazol-2-yl)methanone;
(3-(6-(6-methoxy-5-(trifluoromethyl)pyridin-3-yl)-5,6,7,8-tetrahydropyrido[4,3-d]pyrimidin-4-yloxy)pyrrolidin-1-yl)(5-methyl-1,3,4-oxadiazol-2-yl)methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyrazin-2-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyrazin-2-yl)methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1-methyl-1H-imidazol-4-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1-methyl-1H-imidazol-4-yl)methanone;
{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(1-methyl-1H-pyrazol-4-yl)-methanone;
{3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(1-methyl-1H-pyrazol-4-yl)-methanone;
{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-thiazol-4-yl-methanone;
{3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-thiazol-4-yl-methanone;
{(S)-3-[6-(5-Chloro-6-methoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone;
{3-[6-(5-Chloro-6-methoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone;
(S)-(3-(6-(6-Amino-5-(trifluoromethyl)pyridin-3-yl)-5,6,7,8-tetrahydropyrido[4,3-d]pyrimidin-4-yloxy)pyrrolidin-1-yl)(tetrahydro-2H-pyran-4-yl)methanone;

(3-(6-(6-Amino-5-(trifluoromethyl)pyridin-3-yl)-5,6,7,8-tetrahydropyrido[4,3-d]pyrimidin-4-yloxy)pyrrolidin-1-yl)(tetrahydro-2H-pyran-4-yl)methanone;

(3-(6-(6-Methoxy-5-(trifluoromethyl)pyridin-3-yl)-5,6,7,8-tetrahydropyrido[4,3-d]pyrimidin-4-yloxy)azetidin-1-yl)(tetrahydro-2H-pyran-4-yl)methanone;

{(S)-3-[6-(2-Methoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone;

{3-[6-(2-Methoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone;

[(S)-3-(6-Quinolin-3-yl-5,6,7,8-tetrahydro-pyrido[4,3-d]pyrimidin-4-yloxy)-pyrrolidin-1-yl]-(tetrahydro-pyran-4-yl)-methanone;

[3-(6-Quinolin-3-yl-5,6,7,8-tetrahydro-pyrido[4,3-d]pyrimidin-4-yloxy)-pyrrolidin-1-yl]-(tetrahydro-pyran-4-yl)-methanone;

(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(tetrahydro-2H-pyran-4-yl)methanone;

(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(tetrahydro-2H-pyran-4-yl)methanone;

(S)-1-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)-3,3-dimethylbutan-1-one;

1-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)-3,3-dimethylbutan-1-one;

1-{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-propan-1-one;

1-{3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-propan-1-one;

2-Methoxy-5-[4-((S)-1-propionyl-pyrrolidin-3-yloxy)-7,8-dihydro-5H-pyrido[4,3-d]pyrimidin-6-yl]-nicotinonitrile;

2-Methoxy-5-[4-(1-propionyl-pyrrolidin-3-yloxy)-7,8-dihydro-5H-pyrido[4,3-d]pyrimidin-6-yl]-nicotinonitrile;

(S)-6-(6-Methoxy-5-(trifluoromethyl)pyridin-3-yl)-4-(1-(pyridin-2-yl)pyrrolidin-3-yloxy)-5,6,7,8-tetrahydropyrido[4,3-d]pyrimidine;

6-(6-Methoxy-5-(trifluoromethyl)pyridin-3-yl)-4-(1-(pyridin-2-yl)pyrrolidin-3-yloxy)-5,6,7,8-tetrahydropyrido[4,3-d]pyrimidine;

(S)-6-(6-Methoxy-5-(trifluoromethyl)pyridin-3-yl)-4-(1-(pyrimidin-2-yl)pyrrolidin-3-yloxy)-5,6,7,8-tetrahydropyrido[4,3-d]pyrimidine;

6-(6-Methoxy-5-(trifluoromethyl)pyridin-3-yl)-4-(1-(pyrimidin-2-yl)pyrrolidin-3-yloxy)-5,6,7,8-tetrahydropyrido[4,3-d]pyrimidine;

(S)-1-(3-(6-(6-Methoxy-5-(trifluoromethyl)pyridin-3-yl)-5,6,7,8-tetrahydropyrido[4,3-d]pyrimidin-4-ylamino)pyrrolidin-1-yl)propan-1-one;

1-(3-(6-(6-Methoxy-5-(trifluoromethyl)pyridin-3-yl)-5,6,7,8-tetrahydropyrido[4,3-d]pyrimidin-4-ylamino)pyrrolidin-1-yl)propan-1-one;

(S)-(3-(6-(6-Methoxy-5-(trifluoromethyl)pyridin-3-yl)-5,6,7,8-tetrahydropyrido[4,3-d]pyrimidin-4-ylamino)pyrrolidin-1-yl)(tetrahydro-2H-pyran-4-yl)methanone;

(3-(6-(6-Methoxy-5-(trifluoromethyl)pyridin-3-yl)-5,6,7,8-tetrahydropyrido[4,3-d]pyrimidin-4-ylamino)pyrrolidin-1-yl)(tetrahydro-2H-pyran-4-yl)methanone;

(S)-2-Methoxy-5-(4-(1-(tetrahydro-2H-pyran-4-carbonyl)pyrrolidin-3-ylamino)-7,8-dihydropyrido[4,3-d]pyrimidin-6(5H)-yl)nicotinonitrile;

2-Methoxy-5-(4-(1-(tetrahydro-2H-pyran-4-carbonyl)pyrrolidin-3-ylamino)-7,8-dihydropyrido[4,3-d]pyrimidin-6(5H)-yl)nicotinonitrile;

(S)-1-(4-(3-(6-(6-Methoxy-5-(trifluoromethyl)pyridin-3-yl)-5,6,7,8-tetrahydropyrido[4,3-d]pyrimidin-4-ylamino)pyrrolidine-1-carbonyl)piperidin-1-yl)ethanone;

1-(4-(3-(6-(6-Methoxy-5-(trifluoromethyl)pyridin-3-yl)-5,6,7,8-tetrahydropyrido[4,3-d]pyrimidin-4-ylamino)pyrrolidine-1-carbonyl)piperidin-1-yl)ethanone;

(2,2-Dimethyltetrahydro-2H-pyran-4-yl)((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

(2,2-Dimethyltetrahydro-2H-pyran-4-yl)(3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

(S)-(3-(6-(6-Methoxy-5-(trifluoromethyl)pyridin-3-yl)-5,6,7,8-tetrahydropyrido[4,3-d]pyrimidin-4-ylamino)pyrrolidin-1-yl)(oxazol-5-yl)methanone;

(3-(6-(6-Methoxy-5-(trifluoromethyl)pyridin-3-yl)-5,6,7,8-tetrahydropyrido[4,3-d]pyrimidin-4-ylamino)pyrrolidin-1-yl)(oxazol-5-yl)methanone;

((S)-3-(6-(6-Methoxy-5-(trifluoromethyl)pyridin-3-yl)-5,6,7,8-tetrahydropyrido[4,3-d]pyrimidin-4-ylamino)pyrrolidin-1-yl)((1s,4R)-4-methoxycyclohexyl)methanone;

(3-(6-(6-Methoxy-5-(trifluoromethyl)pyridin-3-yl)-5,6,7,8-tetrahydropyrido[4,3-d]pyrimidin-4-ylamino)pyrrolidin-1-yl)((1s,4R)-4-methoxycyclohexyl)methanone;

((S)-3-(6-(6-Methoxy-5-(trifluoromethyl)pyridin-3-yl)-5,6,7,8-tetrahydropyrido[4,3-d]pyrimidin-4-ylamino)pyrrolidin-1-yl)((1r,4S)-4-methoxycyclohexyl)methanone;

(3-(6-(6-Methoxy-5-(trifluoromethyl)pyridin-3-yl)-5,6,7,8-tetrahydropyrido[4,3-d]pyrimidin-4-ylamino)pyrrolidin-1-yl)((1r,4S)-4-methoxycyclohexyl)methanone;

((1s,4R)-4-Hydroxycyclohexyl)((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

((1s,4R)-4-Hydroxycyclohexyl)(3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

((1r,4S)-4-Hydroxycyclohexyl)((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

((1r,4S)-4-Hydroxycyclohexyl)(3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

(S)-(3-(6-(6-Methoxy-5-methylpyridin-3-yl)-5,6,7,8-tetrahydropyrido[4,3-d]pyrimidin-4-ylamino)pyrrolidin-1-yl)(1-methyl-1H-imidazol-4-yl)methanone;

(3-(6-(6-Methoxy-5-methylpyridin-3-yl)-5,6,7,8-tetrahydropyrido[4,3-d]pyrimidin-4-ylamino)pyrrolidin-1-yl)(1-methyl-1H-imidazol-4-yl)methanone;

(S)-(3-(6-(6-Methoxy-5-methylpyridin-3-yl)-5,6,7,8-tetrahydropyrido[4,3-d]pyrimidin-4-ylamino)pyrrolidin-1-yl)(oxazol-5-yl)methanone;

(3-(6-(6-Methoxy-5-methylpyridin-3-yl)-5,6,7,8-tetrahydropyrido[4,3-d]pyrimidin-4-ylamino)pyrrolidin-1-yl)(oxazol-5-yl)methanone;

(S)-(3-(6-(6-Methoxy-5-methylpyridin-3-yl)-5,6,7,8-tetrahydropyrido[4,3-d]pyrimidin-4-ylamino)pyrrolidin-1-yl)(oxazol-4-yl)methanone;

(3-(6-(6-Methoxy-5-methylpyridin-3-yl)-5,6,7,8-tetrahydropyrido[4,3-d]pyrimidin-4-ylamino)pyrrolidin-1-yl)(oxazol-4-yl)methanone;

(2,2-Dimethyltetrahydro-2H-pyran-4-yl)((S)-3-(6-(6-methoxy-5-methylpyridin-3-yl)-5,6,7,8-tetrahydropyrido[4,3-d]pyrimidin-4-ylamino)pyrrolidin-1-yl)methanone;

(2,2-Dimethyltetrahydro-2H-pyran-4-yl)(3-(6-(6-methoxy-5-methylpyridin-3-yl)-5,6,7,8-tetrahydropyrido[4,3-d]pyrimidin-4-ylamino)pyrrolidin-1-yl)methanone;

(S)-1-(3-(6-(6-Methoxy-5-methylpyridin-3-yl)-5,6,7,8-tetrahydropyrido[4,3-d]pyrimidin-4-ylamino)pyrrolidin-1-yl)propan-1-one;

1-(3-(6-(6-Methoxy-5-methylpyridin-3-yl)-5,6,7,8-tetrahydropyrido[4,3-d]pyrimidin-4-ylamino)pyrrolidin-1-yl)propan-1-one;

(S)-(3-(6-(5-Chloro-6-methoxypyridin-3-yl)-5,6,7,8-tetrahydropyrido[4,3-d]pyrimidin-4-ylamino)pyrrolidin-1-yl)(tetrahydro-2H-pyran-4-yl)methanone;

(3-(6-(5-Chloro-6-methoxypyridin-3-yl)-5,6,7,8-tetrahydropyrido[4,3-d]pyrimidin-4-ylamino)pyrrolidin-1-yl)(tetrahydro-2H-pyran-4-yl)methanone;

(S)-(3-(6-(6-Methoxy-5-methylpyridin-3-yl)-5,6,7,8-tetrahydropyrido[4,3-d]pyrimidin-4-ylamino)pyrrolidin-1-yl)(tetrahydro-2H-pyran-4-yl)methanone;

(3-(6-(6-Methoxy-5-methylpyridin-3-yl)-5,6,7,8-tetrahydropyrido[4,3-d]pyrimidin-4-ylamino)pyrrolidin-1-yl)(tetrahydro-2H-pyran-4-yl)methanone;

(Tetrahydro-pyran-4-yl)-{(S)-3-{6-(5-(trifluoromethyl)pyridin-3-yl)-5,6,7,8-tetrahydropyrido[4,3-d]pyrimidin-4-ylamino)pyrrolidin-1-yl}-methanone;

(Tetrahydro-pyran-4-yl)-{3-{6-(5-(trifluoromethyl)pyridin-3-yl)-5,6,7,8-tetrahydropyrido[4,3-d]pyrimidin-4-ylamino)pyrrolidin-1-yl}methanone;

(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(4-methylpiperazin-1-yl)methanone;

(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(4-methylpiperazin-1-yl)methanone;

(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(morpholino)methanone;

(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(morpholino)methanone;

(S)-(4-Hydroxypiperidin-1-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;

4-Hydroxypiperidin-1-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;

(S)—N-(2-Hydroxyethyl)-3-(6-(6-methoxy-5-(trifluoromethyl)pyridin-3-yl)-5,6,7,8-tetrahydropyrido[4,3-d]pyrimidin-4-yloxy)-N-methylpyrrolidine-1-carboxamide;

N-(2-Hydroxyethyl)-3-(6-(6-methoxy-5-(trifluoromethyl)pyridin-3-yl)-5,6,7,8-tetrahydropyrido[4,3-d]pyrimidin-4-yloxy)-N-methylpyrrolidine-1-carboxamide;

(S)-1-(4-(3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)piperazin-1-yl)ethanone;

1-(4-(3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)piperazin-1-yl)ethanone;

(S)-2-Methoxy-5-(4-(1-(morpholine-4-carbonyl)pyrrolidin-3-yloxy)-7,8-dihydropyrido[4,3-d]pyrimidin-6(5H)-yl)nicotinonitrile;

2-Methoxy-5-(4-(1-(morpholine-4-carbonyl)pyrrolidin-3-yloxy)-7,8-dihydropyrido[4,3-d]pyrimidin-6(5H)-yl)nicotinonitrile;

(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(oxazol-4-yl)methanone;

(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(oxazol-4-yl)methanone;

1-(4-{(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-piperidin-1-yl)-ethanone;

1-(4-{3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-piperidin-1-yl)-ethanone;

{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone;

{3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone;

{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-oxazol-5-yl-methanone;

{3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-oxazol-5-yl-methanone;

{(S)-3-[6-(6-Methoxy-pyridin-3-yl)-5,6,7,8-tetrahydropyrido[4,3-d]pyrimidin-4-yloxy)pyrrolidin-1-yl]-(tetrahydro-pyran-4-yl)-methanone; or {3-[6-(6-Methoxy-pyridin-3-yl)-5,6,7,8-tetrahydropyrido[4,3-d]pyrimidin-4-yloxy)pyrrolidin-1-yl]-(tetrahydro-pyran-4-yl)-methanone.

Compounds of the formula (I) may have different isomeric forms. As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)— and (S)— isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfomate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns 1 to 12 of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

For isolation or purification purposes it is also possible to use pharmaceutically unacceptable salts, for example picrates or perchlorates. For therapeutic use, only pharmaceutically acceptable salts or free compounds are employed.

In view of the close relationship between the novel compounds of the formula (I) in free form and those in the form of their salts, including those salts that can be used as intermediates, for example in the purification or identification of the novel compounds, any reference to the compounds or a compound of the formula (I) hereinbefore and hereinafter is to be understood as referring to the compound in free form and/or also to one or more salts thereof, as appropriate and expedient, as well as to one or more solvates, e.g. hydrates.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F, $^{31}$P, $^{32}$P, $^{35}$S, $^{36}$Cl, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of the formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of the formula (I) that contain groups capable of acting as donors and/or acceptors for hydrogen bonds may be capable of forming co-crystals with suitable co-crystal formers. These co-crystals may be prepared from compounds of the formula (I) by known co-crystal forming procedures. Such procedures include grinding, heating, co-subliming, co-melting, or contacting in solution compounds of the formula (I) with the co-crystal former under crystallization conditions and isolating co-crystals thereby formed. Suitable co-crystal formers include those described in WO 2004/078163. Hence the invention further provides co-crystals comprising a compound of the formula (I).

Any asymmetric atom (e.g., carbon or the like) of the compound(s) of the present invention can be present in racemic or enantiomerically enriched, for example the (R)—, (S)— or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)— or (S)— configuration. Substituents at atoms with unsaturated bonds may, if possible, be present in cis-(Z)— or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent. Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, which contain one or more protective groups and are converted to an active form by metabolism or solvolysis. Both the active drug form and any released metabolic products should have acceptably low toxicity.

Carrier prodrugs are drug compounds that contain a transport moiety, e.g. that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the omega-(amino, mono- or di-lower alkylamino, carboxy, lower alkoxycarbonyl)-lower alkyl esters, the alpha-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

The invention relates in a second aspect to the manufacture of a compound of formula I. The compounds of formula I or salts thereof are prepared in accordance with processes known per se, though not previously described for the manufacture of the compounds of the formula I.

General Reaction Processes:

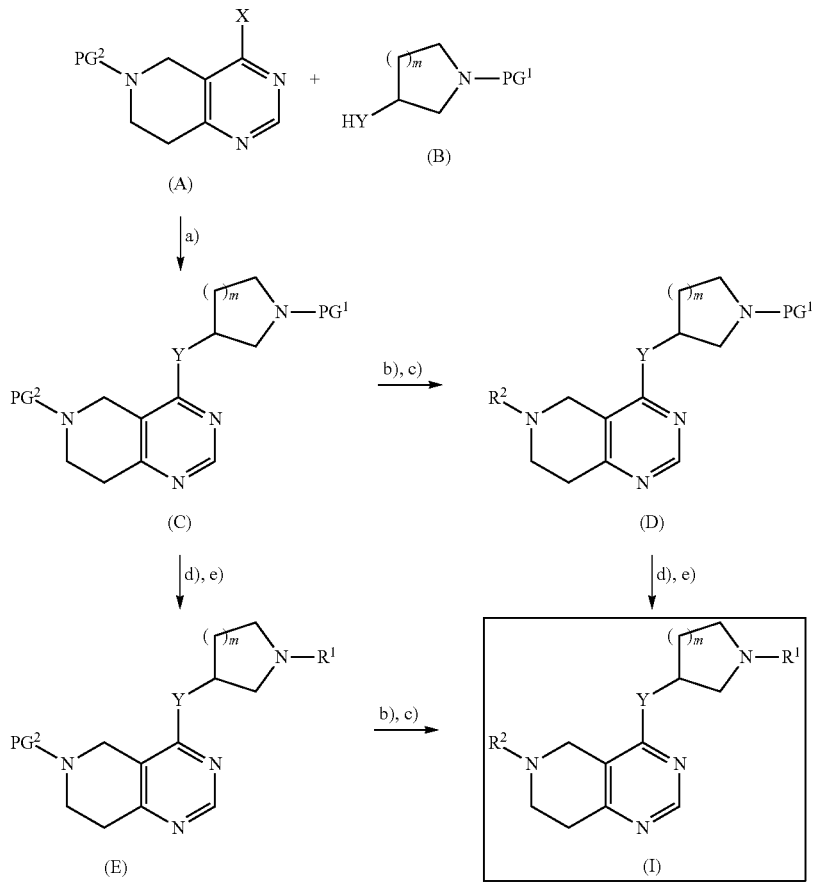

Scheme A

In one embodiment, the invention relates to a process for manufacturing a compound of formula I (Method A) comprising steps a, d, e, b, and c.

The compound of formula I is obtained via the step b of deprotecting PG² from the compound of formula (E), wherein PG² represents a suitable protectiong group, preferable a benzyl group, and the other substituents are as defined above,

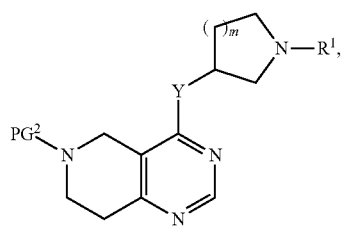

(E)

followed by reaction step c with
R²—Hal,
Wherein R² is defined above and Hal represents halogen, particularly iodo or bromo; under customary Buchwald-Hartwig conditions using a ligand such as X-Phos, di-tert-butyl(2'-methylbiphenyl-2-yl)phosphine or 2-di-t-bu-tylphosphino-2'-(N,N-dimethylamino)biphenyl with a palladium catalyst such as Pd$_2$(dba)$_3$ or Pd$_2$(dba)$_3$·CHCl$_3$ or Pd(OAc)$_2$, preferably Pd$_2$(dba)$_3$ with X-Phos, in the presence of a base such as preferably Cs$_2$CO$_3$ or tert-BuONa, in an organic solvent such as an ether, preferably dioxane or THF. The reaction is preferably stirred at a temperature of approximately 80-120° C., preferably 120° C. The reaction is preferably carried out under an inert gas such as nitrogen or argon.

The compound of formula (E) is prepared comprising the step d of deprotecting PG¹ from the compound of formula (C), wherein PG¹ represents a suitable protecting group, for example BOC, and the other substituents are as defined above,

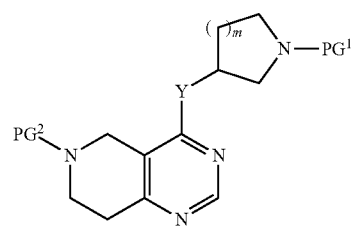

(C)

followed by coupling reaction step e with
R¹-Act, step e1: Where $R^1$ is —C(O)—$R^4$, wherein $R^4$ is defined above, and Act represents an activating group or a hydroxy group: The coupling reaction is an amide, urea or carbamic ester formation. There are many known ways of preparing amides urea or carbamic ester. The coupling reaction step can be carried out with Act representing an activating group, preferably in a one step procedure or with Act representing a hydroxy group either involving a one or two step procedure. For examples of amide bond formations, see Mantalbetti, C.A.G.N and Falque, V., Amide bond formation and peptide coupling, Tetrahedron, 2005, 61(46), pp 10827-10852 and references cited therein. For examples of urea synthesis, see Sartori, G.; Maggi, R. Acyclic and cyclic ureas, Science of Synthesis (2005), 18, 665-758; Gallou, Isabelle. Unsymmetrical ureas Synthetic methodologies and application in drug design, Organic Preparations and Procedures International (2007), 39(4), 355-383. For examples of carbamate synthesis see Adams, Philip; Baron, Frank A. Esters of carbamic acid, Chemical Reviews (1965), 65(5), 567-602. The examples provided herein are thus not intended to be exhaustive, but merely illustrative;

step e2: Where $R^1$ is selected from phenyl, pyridyl, pyrimidinyl, pyrazinyl, pyridazinyl, 1,2,3-triazinyl, 1,2,4-triazinyl or 1,3,5-triazinyl and Act represents halogen, particularly iodo or bromo: The coupling reaction is carried out in the presence of an amine base such as N,N-diisopropylethylamine. The reaction is carried out in the presence of an organic solvent or, preferably without a solvent under microwave heating e.g. at 160° C. for 20 min. Alternatively, the reaction can be carried out under customary Buchwald-Hartwig conditions using a ligand such as X-Phos or 2-di-t-butylphosphino-2'-(N,N-dimethylamino)biphenyl with a palladium catalyst such as $Pd_2(dba)_3$ or $Pd_2(dba)_3 \cdot CHCl_3$ or $Pd(OAc)_2$, preferably $Pd_2(dba)_3$ with X-Phos, in the presence of a base such as preferably $Cs_2CO_3$ or tert-BuONa, in an organic solvent such as an ether, preferably dioxane or THF. The reaction is preferably stirred at a temperature of approximately 80-120° C., preferably 120° C. The reaction is preferably carried out under an inert gas such as nitrogen or argon.

The compound of formula (C) is prepared comprising the step a of coupling a compound of formula (A), wherein $PG^2$ represents a suitable protectiong group, for example a benzyl group and X represents halogen, particularly chloro, or hydroxy; with a compound of formula (B) wherein $PG^1$ represents a suitable protecting group, for example BOC, and the other substituents are as defined above,

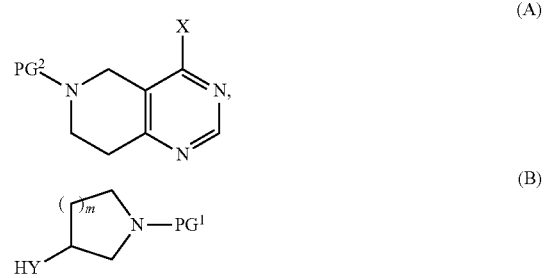

step a1: Where YH is OH and X represents halogen: The reaction takes place in the presence of a suitable base such as sodium hydroxide (NaH) or potassium t-butoxide (tBuOK) and polar organic solvent such as THF, 2-methyltetrahydrofuran or Dioxane under inert gas conditions at room temperature.

step a2: Where YH is $NR^3H$ and X represents halogen: The reaction takes place in the presence of a suitable base such as for example potassium carbonate or a suitable amine base such as triethylamine or N,N-diisopropylethylamine at elevated temperature (e.g. 120° C.) for 20-48 h. Typical conditions comprise the use of 1.0 equivalent of a compound of formula (A), 1.0 equivalent of a compound of formula (B) and 1.5 equivalents of the base at 120° C. for 48 h.

step a3: Where YH is $NR^3H$ and X represents hydroxy: A base promoted phosphonium coupling reaction is employed, whereby a compound of the formula (A) in a suitable solvent such as acetonitrile is reacted with a phosphonium salt such as benzotriazol-1-yloxytris(dimethylamino) phosphonium hexafluorophosphate (BOP) in the presence of a base such as 1,8-diaza-7-bicyclo[5.4.0]undecene (DBU) followed by addition of a compound of the formula (B). The reaction mixture is preferably stirred at a temperature of 20° C. to 90° C. for 18-72 h. The reaction may preferably be carried out under an inert gas, e.g. nitrogen or argon. Typical conditions comprise of 1 equivalent of a compound of the formula (A), 1.0-1.5 equivalents of BOP, 2.0-4.0 equivalents of DBU and 2.0-3.0 equivalents of a compound of the formula (B) in acetonitrile at 65° C. for 72 hours under argon.

In another embodiment, the invention relates to a process for manufacturing a compound of formula I, comprising steps a, d and e as defined above, starting from a compound of formula (A) wherein $PG^2$ represents $R^2$ (Method A-a).

Scheme B

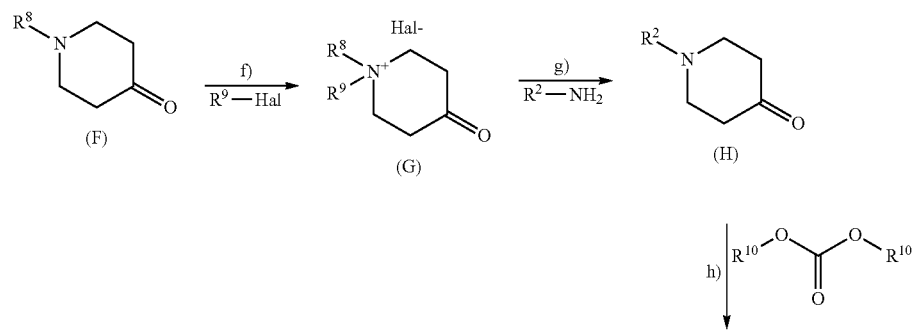

-continued

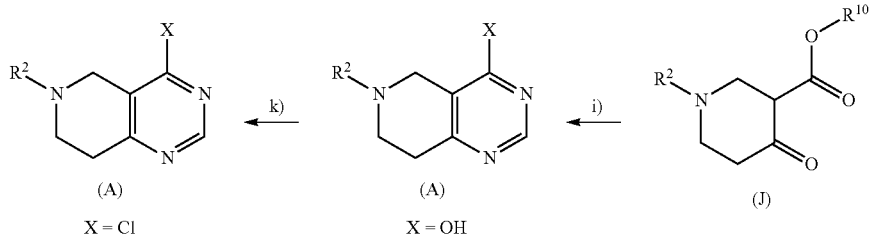

(A) X=Cl    (A) X=OH    (J)

The process for manufacturing a compound of formula (A) wherein $PG^2$ represents $R^2$ comprises the steps f, g, h, i and optionally k.

step f) Quaternarization of compound of formula (F), $R^8$=alkyl e.g. benzyl with compound of general formula $R^9$—Hal, wherein $R^9$ represents alkyl, particularly methyl and Hal represents halogen, particularly iodo or bromo, under customary condition using in particular acetone as organic solvent leads to the formation of compound of general formula (G).

step g) The compound of formula (H) is prepared by reaction of $R^2$—$NH_2$ with compound of general formula (G). The reaction is performed by using a base such a in particular $K_2CO_3$ in an organic solvent such as in particular a 2/1 mixture of ethanol and water and heating the reaction mixture at 80-100° C., in particular 80° C.

step h) The compound of formula (J) is prepared by reaction of a compound of formula (H) with base such as in particular NaH and compound of general formula $(R^{10}O)_2CO_3$ wherein $R^{10}$ represents alkyl, particularly methyl. The reaction mixture is stirred under high temperature (90° C.).

step i) The compound of formula (A), X=OH is prepared by pyrimidine ring formation, reacting the compound of formula (J) with formamidine acetate in the presence of a base such as sodium methoxide and in an organic solvent such as methanol at elevated temperature such as 90° C. for 2-18 h.

step k) The compound of formula (A), X=Cl is prepared by reaction of a compound of formula (A), X=OH with phosphoryl chloride in the presence of a base such as triethylamine in an organic solvent such as toluene at elevated temperature such as 100° C. for 12-18 h.

In another embodiment, the invention relates to a process for manufacturing a compound of formula I (Method B) comprising steps a, b, c, d, and e.

The compound of formula I is obtained via the step d of deprotecting $PG^1$ from the compound of formula, (D), wherein $PG^1$ represents a suitable protectiong group, preferable a BOC group, and the other substituents are as defined above,

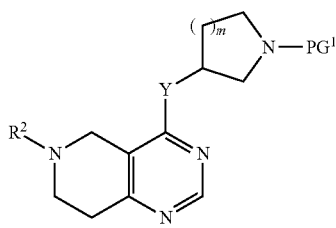

(D)

followed by reaction step e with $R^1$-Act, step e1: Where $R^1$ is —C(O)—$R^4$, wherein $R^4$ is defined above, and Act represents an activating group or a hydroxy group: The coupling reaction is an amide, urea or carbamic ester formation. There are many known ways of preparing amides urea or carbamic ester. The coupling reaction step can be carried out with Act representing an activating group, preferably in a one step procedure or with Act representing a hydroxy group either involving a one or two step procedure. For examples of amide bond formations, see Mantalbetti, C.A.G.N and Falque, V., Amide bond formation and peptide coupling, Tetrahedron, 2005, 61(46), pp 10827-10852 and references cited therein. For examples of urea synthesis, see Sartori, G.; Maggi, R. Acyclic and cyclic ureas, Science of Synthesis (2005), 18, 665-758; Gallou, Isabelle. Unsymmetrical ureas Synthetic methodologies and application in drug design, Organic Preparations and Procedures International (2007), 39(4), 355-383. For examples of carbamate synthesis see Adams, Philip; Baron, Frank A. Esters of carbamic acid, Chemical Reviews (1965), 65(5), 567-602. The examples provided herein are thus not intended to be exhaustive, but merely illustrative;

step e2: Where $R^1$ is selected from phenyl, pyridyl, pyrimidinyl, pyrazinyl, pyridazinyl, 1,2,3-triazinyl, 1,2,4-triazinyl or 1,3,5-triazinyl and Act represents halogen, particularly iodo or bromo: The coupling reaction is carried out in the presence of an amine base such as N,N-diisopropylethylamine. The reaction is carried out in the presence of an organic solvent or, preferably without a solvent under microwave heating e.g. at 160° C. for 20 min. Alternatively, the reaction can be carried out under customary Buchwald-Hartwig conditions using such a ligand such as X-Phos or 2-di-t-butylphosphino-2'-(N,N-dimethylamino)biphenyl with a palladium catalyst such as $Pd_2(dba)_3$ or $Pd_2(dba)_3.CHCl_3$ or $Pd(OAc)_2$, preferably $Pd_2(dba)_3$ with X-Phos, in the presence of a base such as preferably $Cs_2CO_3$ or tert-BuONa, in an organic solvent such as an ether, preferably dioxane or THF. The reaction is preferably stirred at a temperature of approximately 80-120° C., preferably 120° C. The reaction is preferably carried out under an inert gas such as nitrogen or argon.

The compound of formula (D) is prepared comprising the step b of deprotecting $PG^2$ from the compound of formula (C), wherein $PG^2$ represents a suitable protecting group, for example a benzyl group, and the other substituents are as defined above,

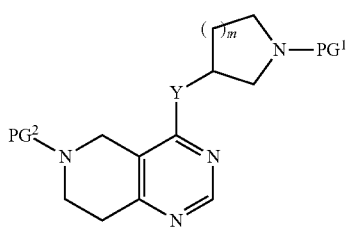

(C)

followed by reaction step c with
R²-Hal,
Wherein R² is defined above and Hal represents halogen, particularly iodo or bromo; under customary Buchwald-Hartwig conditions using such a ligand such as X-Phos or 2-di-t-butylphosphino-2'-(N,N-dimethylamino)biphenyl with a palladium catalyst such as Pd₂(dba)₃ or Pd₂(dba)₃.CHCl₃ or Pd(OAc)₂, preferably Pd₂(dba)₃ with X-Phos, in the presence of a base such as preferably Cs₂CO₃ or tert-BuONa, in an organic solvent such as an ether, preferably dioxane or THF. The reaction is preferably stirred at a temperature of approximately 80-120° C., preferably 120° C. The reaction is preferably carried out under an inert gas such as nitrogen or argon.

The compound of formula (C) is prepared as described above for method A.

In another embodiment, the invention relates to a process for manufacturing a compound of formula I, comprising steps a, b and c as defined above, starting from a compound of formula (B) wherein PG¹ represents R¹ (Method B-a).

The term "activating group" as used herein relates to a group that can activate a carboxylic acid, carbonic acid or carbamic acid derivative, for coupling with an amine moiety to form an amide, urea or carbamic ester moiety, respectively. Such groups are chlorides, or groups resulting from the reaction of the acid derivative with an activating agent. Suitable activating agents are known to the skilled person, examples of such activating reagents are carbodiimide derivatives, pentafluorophenyl ester derivatives, triazole derivatives, imidazole derivatives.

"Protecting Group":

In the methods describe above, functional groups which are present in the starting materials and are not intended to take part in the reaction, are present in protected form if necessary, and protecting groups that are present are cleaved, whereby said starting compounds may also exist in the form of salts provided that a salt-forming group is present and a reaction in salt form is possible. In additional process steps, carried out as desired, functional groups of the starting compounds which should not take part in the reaction may be present in unprotected form or may be protected for example by one or more protecting groups. The protecting groups are then wholly or partly removed according to one of the known methods. Protecting groups, and the manner in which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be removed readily, i.e. without the occurrence of undesired secondary reactions, for example by solvolysis, reduction, photolysis or alternatively under physiological conditions.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art. Intermediates and final products can be worked up and/or purified according to standard methods, e.g. using chromatographic methods, distribution methods, (re-) crystallization, and the like.

The following applies in general to all processes mentioned herein before and hereinafter. All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described herein above.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning. The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Members of the phosphoinositide-3 kinase (PI3K) family are involved in cell growth, differentiation, survival, cytoskeletal remodeling and the trafficking of intracellular organelles in many different types of cells (Okkenhaug and Wymann, Nature Rev. Immunol. 3:317 (2003).

To date, eight mammalian PI3Ks have been identified, divided into three main classes (I, II and III) on the basis of their genetic sequence, structure, adapter molecules, expression, mode of activation, and preferred substrate.

PI3Ks is a lipid kinase belonging to the class I PI3K family (PI3K α, β, γ and δ) that generates second messenger signals downstream of tyrosine kinase-linked receptors. PI3Kδ is a heterodimer composed of an adaptor protein and a p110δ catalytic subunit which converts phosphatidylinositol-4,5-bis-phosphate (PtdInsP2) to phosphatidylinositol-3,4,5-tri-phosphate (PtdInsP3). Effector proteins interact with PtdInsP3 and trigger specific signaling pathways involved in cell activation, differentiation, migration, and cell survival.

Expression of the p110δ and p110γ catalytic subunits is preferential to leukocytes. Expression is also observed in smooth muscle cells, myocytes and endothelial cells. In contrast, p110α and p110β are expressed by all cell types (Marone et al. Biochimica et Biophysica Acta 1784:159 (2008)).

PI3Kδ is associated with B cell development and function (Okkenhaug et al. Science 297:1031 (2002)).

B cells play also a critical role in the pathogenesis of a number of autoimmune and allergic diseases as well as in the process of transplant rejection (Martin and Chan, Annu. Rev. Immunol. 24:467 (2006)).

Chemotaxis is involved in many autoimmune or inflammatory diseases, in angiogenesis, invasion/metastasis, neurodegeneration or wound healing (Gerard et al. Nat. Immunol. 2:108 (2001)). Temporarily distinct events in leukocyte migration in response to chemokines are fully dependent on PI3Kδ and PI3Kγ (Liu et al. Blood 110:1191 (2007)).

PI3Kα and PI3Kβ play an essential role in maintaining homeostasis and pharmacological inhibition of these molecular targets has been associated with cancer therapy (Maira et al. Expert Opin. Ther. Targets 12:223 (2008)).

PI3Kα is involved in insulin signaling and cellular growth pathways (Foukas et al. Nature 441:366 (2006)). PI3Kδ isoform-selective inhibition is expected to avoid potential side effects such as hyperglycemia, and metabolic or growth dis-regulation.

The invention relates in a third aspect to the use of compounds of the present invention as pharmaceuticals. Particularly, the compounds of formula I have valuable pharmacological properties, as described hereinbefore and hereinafter. The invention thus provides:

a compound of the formula (I) as defined herein, as pharmaceutical/for use as pharmaceutical;

a compound of the formula (I) as defined herein, as medicament/for use as medicament;

a compound of the formula (I) as defined herein, for use in therapy;

a compound of the formula (I) as defined herein, for the prevention and/or treatment of conditions, diseases or disorders which are mediated by the activity of the PI3K enzymes, preferably by the activity of the PI3Kδ isoform;

the use of a compound of formula (I) as defined herein, for the manufacture of a medicament for the prevention and/or treatment of conditions, diseases or disorders which are mediated by the activity of the PI3K enzymes, preferably by the activity of the PI3Kδ isoform;

the use of a compound of formula (I) as defined herein, for the prevention and/or treatment of conditions, diseases or disorders which are mediated by the activity of the PI3K enzymes, preferably by the activity of the PI3Kδ isoform;

the use of a compound of formula I as defined herein for the inhibition of the PI3K, enzymes, preferably of the PI3Kδ isoform;

the use of a compound of formula (I) as defined herein, for the treatment of a disorder or disease selected from autoimmune disorders, inflammatory diseases, allergic diseases, airway diseases, such as asthma and COPD, transplant rejection, cancers eg of hematopoietic origin or solid tumors.

the use of a compound of formula (I) as defined herein, for the treatment of a disorder or disease selected from antibody production, antigen presentation, cytokine production or lymphoid organogenesis are abnormal or are undesirable including rheumatoid arthritis, pemphigus vulgaris, idiopathic thrombocytopenia purpura, systemic lupus erythematosus, multiple sclerosis, myasthenia gravis, Sjögren's syndrome, autoimmune hemolytic anemia, ANCA-associated vasculitides, cryoglobulinemia, thrombotic thrombocytopenic purpura, chronic autoimmune urticaria, allergy (atopic dermatitis, contact dermatitis, allergic rhinitis), goodpasture's syndrome, AMR (antibody-mediated transplant rejection), B cell-mediated hyperacute, acute and chronic transplant rejection and cancers of haematopoietic origin including but not limited to multiple myeloma; acute myelogenous leukemia; chronic myelogenous leukemia; lymphocytic leukemia; myeloid leukemia; non-Hodgkin lymphoma; lymphomas; polycythemia vera; essential thrombocythemia; myelofi-brosis with myeloid metaplasia; and Walden stroem disease.

the use of a compound of formula (I) as defined herein, for the treatment of a disorder or disease selected from rheumatoid arthritis (RA), pemphigus vulgaris (PV), idiopathic thrombocytopenia purpura (ITP), thrombotic thrombocytopenic purpura (TTP), autoimmune hemolytic anemia (AIHA), acquired hemophilia type A (AHA), systemic lupus erythematosus (SLE), multiple sclerosis (MS), myasthenia gravis (MG), Sjögren's syndrome (SS), ANCA-associated vasculitides, cryoglobulinemia, chronic autoimmune urticaria (CAU), allergy (atopic dermatitis, contact dermatitis, allergic rhinitis), goodpasture's syndrome, transplant rejection and cancers of haematopoietic origin.

a method of modulating the activity of the PI3K enzymes, preferably the PI3Kδ isoform, in a subject, comprising the step of administering to a subject a therapeutically effective amount of a compound of formula I as defined herein;

a method for the treatment of a disorder or disease mediated by the PI3K enzymes, preferably by the PI3Kδ isoform. comprising the step of administering to a subject a therapeutically effective amount of a compound of formula (I) as defined herein;

a method for inhibition of the PI3K enzymes, preferably the PI3Kδ isoform, in a cell, comprising contacting said cell with an effective amount of a compound of formula I as defined herein.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

The term "administration" or "administering" of the subject compound means providing a compound of the invention and prodrugs thereof to a subject in need of treatment. Administration "in combination with" one or more further therapeutic agents includes simultaneous (concurrent) and consecutive administration in any order, and in any route of administration.

The invention relates to the use of new tetrahydro-pyridopyrimidine derivates for the prevention and/or treatment of conditions, diseases or disorders which are mediated by the activity of the PI3K enzymes.

Suitably, the invention relates to the treatment, either alone or in combination, with one or more other pharmacologically active compounds, of PI3K-related diseases including but not limited to autoimmune disorders, inflammatory diseases, allergic diseases, airway diseases, such as asthma and COPD, transplant rejection, cancers eg of hematopoietic origin or solid tumors.

The invention also relates to the treatment, either alone or in combination, with one or more other pharmacologically active compounds, includes methods of treating conditions, diseases or disorders in which one or more of the functions of B cells such as antibody production, antigen presentation, cytokine production or lymphoid organogenesis are abnormal or are undesirable including rheumatoid arthritis, pemphigus vulgaris, idiopathic thrombocytopenia purpura, systemic lupus erythematosus, multiple sclerosis, myasthenia gravis, Sjögren's syndrome, autoimmune hemolytic anemia, ANCA-associated vasculitides, cryoglobulinemia, thrombotic thrombocytopenic purpura, chronic autoimmune urticaria, allergy (atopic dermatitis, contact dermatitis, allergic rhinitis), goodpasture's syndrome, AMR (antibody-mediated transplant rejection), B cell-mediated hyperacute, acute and chronic transplant rejection and cancers of haematopoietic origin including but not limited to multiple myeloma; acute myelogenous leukemia; chronic myelogenous leukemia; lymphocytic leukemia; myeloid leukemia; non-Hodgkin lymphoma; lymphomas; polycythemia vera; essential thrombocythemia; myelofibrosis with myeloid metaplasia; and Walden stroem disease.

The invention includes methods of treating conditions, diseases or disorders in which one or more of the functions of neutrophils, such as superoxide release, stimulated exocytosis, or chemoatractic migration are abnormal or are undesirable including rheumatoid arthritis, sepsis, pulmonary or respiratory disorders such as asthma, inflammatory dermatoses such as psoriasis and others.

The invention includes methods of treating conditions, diseases or disorders in which one or more of the functions of basophil and mast cells such as chemoatractic migration or allergen-IgE-mediated degranulation are abnormal or are undesirable including allergic diseases (atopic dermatitis, contact dermatitis, allergic rhinitis) as well as other disorders such as COPD, asthma or emphysema.

The invention includes methods of treating conditions, diseases or disorders in which one or more of the functions of T cells such as cytokine production or cell-mediated cytotoxicity abnormal or are undesirable including rheumatoid arthritis, multiple sclerosis, acute or chronic rejection of cell tissue or organ grafts or cancers of haematopoietic origin.

Further, the invention includes methods of treating neurodegenerative diseases, cardiovascular diseases and platelet aggregation.

Further, the invention includes methods of treating skin diseases such as porphyria cutanea tarda, polymorphous light eruption, dermatomyositis, solar urticaria, oral lichen planus, panniculitis, scleroderma, urticarial vasculitis.

Further, the invention includes methods of treating chronic inflammatory diseases such as sarcoidosis, granuloma annulare.

In other embodiments, the condition or disorder (e.g. PI3K-mediated) is selected from the group consisting of: polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia greata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

In another embodiment, the compounds of the present invention are useful in the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankolsing spondylitis, Reiter syndrome, reactive arthritis, psoriatic arthritis, and enterophathics arthritis, hypersensitivity (including both airways hypersensitivity and dermal hypersensitivity) and allergies. Specific auto-immune diseases for which antibodies of the invention may be employed include autoimmune haematological disorders (including e.g. hemolytic anaemia, aplastic anaemia, pure red cell anaemia and idiopa-thic thrombocytopenia), acquired hemophilia A, cold agglutinin disease, cryoglobulinemia, thrombotic thrombocytopenic purpura, Sjögren's syndrome, systemic lupus erythematosus, inflammatory muscle disorders, polychondritis, sclerodoma, anti-neutrophil cytoplasmic antibody-associated vasculitis, IgM mediated neuropathy, opsoclonus myoclonus syndrome, Wegener granulomatosis, dermatomyositis, chronic active hepatitis, myasthenia gravis, psoriasis, Steven-Johnson syndrome, pemphigus vulgaris, pemphigus foliacius, idio-pathic sprue, autoimmune inflammatory bowel disease (including e.g. ulcerative colitis, Crohn's disease and Irritable Bowel Syndrome), endocrine ophthalmopathy, Graves' disease, sarcoidosis, multiple sclerosis, neuromyelitis optica, primary biliary cirrhosis, juvenile diabetes (diabetes mellitus type I), uveitis (anterior, intermediate and posterior as well as panuveitis), keratoconjunctivitis sicca and vernal keratoconjunctivitis, interstitial lung fibrosis, psoriatic arthritis and glomerulonephritis (with and without nephrotic syndrome, e.g. including idiopathic nephro-tic syndrome or minimal change nephropathy), tumors, inflammatory disease of skin and cornea, myositis, loosening of bone implants, metabolic disorders, such as atherosclerosis, diabetes, and dislipidemia.

In another embodiment, the compounds of the present invention are useful in the treatment of conditions or disorders selected from the group consisting of, primary cutaneous B-cell lymphoma, immunobullous disease, pemphigus vulgaris, pemphigus foliaceus, paraneoplastic pemphigus, bullous pemphigoid, mucous membrane pemphigoid, epidermolysis bullosa acquisita, chronic graft versus host disease, dermatomyositis, systemic lupus erythematosus, vasculitis, small vessel vasculitis, hypocomplementemic urticarial vasculitis, antineutrophil cytoplasmic antibody-vasculitis, cryoglobulinemia, Schnitzler syndrome, Waldenstrom's macroglobulinemia, angioedema, vitiligo, systemic lupus erythematosus, idiopathic thrombocytopenic purpura, multiple sclerosis, cold agglutinin disease, autoimmune hemolytic anemia, antineutrophil cytoplasmic antibody-associated vasculitis, graft versus host disease, cryoglobulinemia and thrombotic thrombocytopenic.

In a further embodiment, the invention relates to a process or a method for the treatment of one of the disorders or diseases mentioned hereinabove, especially a disease which responds to the inhibition of the PI3K enzymes. The compounds of formula I, or a pharmaceutically acceptable salt thereof, can be administered as such or in the form of pharmaceutical compositions, prophylactically or therapeutically, preferably in an amount effective against the said diseases, to a warm-blooded animal, for example a human, requiring such treatment, the compounds especially being used in the form of pharmaceutical compositions.

In a further embodiment, the invention relates to the use of a compound of formula I, or a pharmaceutically acceptable salt thereof, as such or in the form of a pharmaceutical composition with at least one pharmaceutically acceptable carrier, for the therapeutic and also prophylactic management of one or more of the diseases mentioned hereinabove, mediated by the PI3K enzymes.

In a further embodiment, the invention relates to the use of a compound of formula I, or a pharmaceutically acceptable salt thereof, especially a compound of formula I which is said to be preferred, or a pharmaceutically acceptable salt thereof, for the preparation of a pharmaceutical composition for the therapeutic and also prophylactic management of one or more of the diseases mentioned hereinabove, especially a disorder or disease selected from autoimmune disorders, inflammatory diseases, allergic diseases, airway diseases, such as asthma and COPD, transplant rejection, cancers eg of hematopoietic origin or solid tumors.

The invention relates in a fourth aspect to pharmaceutical compositions comprising a compound of the present invention. The invention thus provides

- a pharmaceutical composition comprising (i.e. containing or consisting of) a compound as defined herein and one or more carriers/excipients;
- a pharmaceutical composition comprising a therapeutically effective amount of a compound of formula I as defined herein, and one or more pharmaceutically acceptable carriers/excipients.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art. Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder, either alone, as a mixture, for example a dry blend with lactose, or a mixed component particle, for example with phospholipids, from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers, e.g., vials, blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

Suitable excipients/carriers may be any solid, liquid, semisolid or, in the case of an aerosol composition, gaseous excipient that is generally available to one of skill in the art. Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like.

Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of the formula (I) in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The dosage of the active ingredient depends upon the disease to be treated and upon the species, its age, weight, and individual condition, the individual pharmacokinetic data, and the mode of administration. The amount of the compound in a formulation can vary within the full range employed by those skilled in the art. Typically, the formulation will contain, on a weight percent (wt %) basis, from about 0.01-99.99 wt % of a compound of formula (I) based on the total formulation, with the balance being one or more suitable pharmaceutical excipients.

Pharmaceutical compositions comprising a compound of formula (I) as defined herein in association with at least one pharmaceutical acceptable carrier (such as excipient a and/or diluent) may be manufactured in conventional manner, e.g. by means of conventional mixing, granulating, coating, dissolving or lyophilising processes.

In a further embodiment, the invention relates to a pharmaceutical composition for administration to a warm-blooded animal, especially humans or commercially useful mammals suffering from a disease which responds to an inhibition of the PI3K enzymes, comprising an effective quantity of a compound of formula I for the inhibition of the PI3K enzymes, or a pharmaceutically acceptable salt thereof, together with at least one pharmaceutically acceptable carrier.

In a further embodiment, the invention relates to a pharmaceutical composition for the prophylactic or especially therapeutic management of a disorder or disease selected from autoimmune disorders, inflammatory diseases, allergic diseases, airway diseases, such as asthma and COPD, transplant rejection, cancers eg of hematopoietic origin or solid tumors; of a warm-blooded animal, especially a human or a commercially useful mammal requiring such treatment.

The invention relates in a fifth aspect to combinations comprising a compound of formula I and one or more additional active ingredients. The invention thus provides
 a combination in particular a pharmaceutical combination, comprising a therapeutically effective amount of a compound of formula I and one or more therapeutically active agents, e.g. an immunosuppressant, immunomodulatory, anti-inflammatory or chemotherapeutic agent, e.g. as indicated below;
 a combined pharmaceutical composition, adapted for simultaneous or sequential administration, comprising a therapeutically effective amount of a compound of formula (I) as defined herein; therapeutically effective amount(s) of one or more combination partners e.g. an immunosuppressant, immunomodulatory, anti-inflammatory or chemotherapeutic agent, e.g. as indicated below; one or more pharmaceutically acceptable excepients;
 a combined pharmaceutical composition as defined herein (i) as pharmaceutical, (ii) for use in the treatment of a disease mediated by the PI3K enzymes, (iii) in a method of treatment of a disease mediated by the PI3K enzymes.

By "combination", there is meant either a fixed combination in one dosage unit form, or a kit of parts for the combined administration where a compound of the formula (I) and a combination partner may be administered independently at the same time or separately within time intervals that especially allow that the combination partners show a cooperative, e.g. synergistic effect.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by the dysregulation of PI3K delta, or (ii) associated with the dysregulation of PI3K delta, or (iii) characterized by the dysregulation of the PI3K delta; or (2) reducing or inhibiting the activity of the PI3K delta. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting PI3K delta.

The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of alto- or xenograft acute or chronic rejection or inflammatory or autoimmune disorders, or a chemotherapeutic agent, e.g a malignant cell anti-proliferative agent. For example, the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CC1779, ABT578, AP23573, TAFA-93, biolimus-7 or biolimus-9; an ascomycin having immuno-suppressive properties, e.g. ABT-281, ASM981, etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide α-cyano-(3,4-dihydroxy)]N-benzylcinnamamide (Tyrphostin AG 490), prodigiosin 25-C (PNU156804), [4-(4'-hydroxyphenyl)-amino-6,7-dimethoxyquinazoline] (WHI—P131), [4-(3'-bromo-4'-hydroxylphenyl)-amino-6,7-dimethoxyquinazoline] (WHI—P154), [4-(3',5'-dibromo-4'-hydroxylphenyl)-amino-6,7-dimethoxyquinazoline] WHI—P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or antihistamines; or antitussives, or a bronchodilatory agent; or an angiotensin receptor blockers; or an anti-infectious agent.

Where the compounds of formula I are administered in conjunction with other immunosuppressive/immunomodulatory, anti-inflammatory, chemotherapeutic or anti-infectious therapy, dosages of the co-administered immunosuppressant, immunomodulatory, anti-inflammatory, chemotherapeutic or anti-infectious compound will of course vary depending on the type of co-drug employed, e.g. whether it is a steroid or a calcineurin inhibitor, on the specific drug employed, on the condition being treated and so forth.

A compound of the formula (I) may also be used to advantage in combination with each other or in combination with other therapeutic agents, especially other antiproliferative agents. Such antiproliferative agents include, but are not limited to, aromatase inhibitors; antiestrogens; topoisomerase I inhibitors; topoisomerase II inhibitors; microtubule active agents; alkylating agents; histone deacetylase inhibitors; compounds, which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (TEMODAL®); and leucovorin.

The term "aromatase inhibitor", as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g., under the trademark AROMASIN. Formestane can be administered, e.g., in the form as it is marketed, e.g., under the trademark LENTARON. Fadrozole can be administered, e.g., in the form as it is marketed, e.g., under the trademark AFEMA. Anastrozole can be administered, e.g., in the form as it is marketed, e.g., under the trademark ARIMIDEX. Letrozole can be administered, e.g., in the form as it is marketed, e.g., under the trademark FEMARA or FEMAR. Aminoglutethimide can be administered, e.g., in the form as it is marketed, e.g., under the trademark ORIMETEN. A combination of the invention comprising a chemotherapeutic agent which is an aromatase inhibitor is particularly useful for the treatment of hormone receptor positive tumors, e.g., breast tumors.

The term "anti-estrogen", as used herein, relates to a compound which antagonizes the effect of estrogens at the estrogen receptor level. The term includes, but is not limited to, tamoxifen, fulvestrant, raloxifene and raloxifene hydrochloride. Tamoxifen can be administered, e.g., in the form as it is marketed, e.g., under the trademark NOLVADEX. Raloxifene hydrochloride can be administered, e.g., in the form as it is marketed, e.g., under the trademark EVISTA. Fulvestrant can be formulated as disclosed in U.S. Pat. No. 4,659,516 or it can be administered, e.g., in the form as it is marketed, e.g., under the trademark FASLODEX. A combination of the invention comprising a chemotherapeutic agent which is an antiestrogen is particularly useful for the treatment of estrogen receptor positive tumors, e.g., breast tumors.

The term "anti-androgen", as used herein, relates to any substance which is capable of inhibiting the biological effects of androgenic hormones and includes, but is not limited to, bicalutamide (CASODEX), which can be formulated, e.g., as disclosed in U.S. Pat. No. 4,636,505.

The term "gonadorelin agonist", as used herein, includes, but is not limited to, abarelix, goserelin and goserelin acetate. Goserelin is disclosed in U.S. Pat. No. 4,100,274 and can be administered, e.g., in the form as it is marketed, e.g., under the trademark ZOLADEX. Abarelix can be formulated, e.g., as disclosed in U.S. Pat. No. 5,843,901. The term "topoisomerase I inhibitor", as used herein, includes, but is not limited to, topotecan, gimatecan, irinotecan, camptothecian and its analogues, 9-nitrocamptothecin and the macromolecular camptothecin conjugate PNU-166148 (compound A1 in WO 99/17804). Irinotecan can be administered, e.g., in the form as it is marketed, e.g., under the trademark CAMPTOSAR. Topotecan can be administered, e.g., in the form as it is marketed, e.g., under the trademark HYCAMTIN.

The term "topoisomerase II inhibitor", as used herein, includes, but is not limited to, the anthracyclines, such as doxorubicin, including liposomal formulation, e.g., CAELYX; daunorubicin; epirubicin; idarubicin; nemorubicin; the anthraquinones mitoxantrone and losoxantrone; and the podophillotoxines etoposide and teniposide. Etoposide can be administered, e.g., in the form as it is marketed, e.g., under the trademark ETOPOPHOS. Teniposide can be administered, e.g., in the form as it is marketed, e.g., under the trademark VM 26-BRISTOL. Doxorubicin can be administered, e.g., in the form as it is marketed, e.g., under the trademark ADRIBLASTIN or ADRIAMYCIN. Epirubicin can be administered, e.g., in the form as it is marketed, e.g., under the trademark FARMORUBICIN. Idarubicin can be administered, e.g., in the form as it is marketed, e.g., under the trademark ZAVEDOS. Mitoxantrone can be administered, e.g., in the form as it is marketed, e.g., under the trademark NOVANTRON.

The term "microtubule active agent" relates to microtubule stabilizing, microtubule destabilizing agents and microtublin polymerization inhibitors including, but not limited to, taxanes, e.g., paclitaxel and docetaxel; vinca alkaloids, e.g., vinblastine, especially vinblastine sulfate; vincristine, especially vincristine sulfate and vinorelbine; discodermolides; cochicine; and epothilones and derivatives thereof, e.g., epothilone B or D or derivatives thereof. Paclitaxel may be administered, e.g., in the form as it is marketed, e.g., TAXOL. Docetaxel can be administered, e.g., in the form as it is marketed, e.g., under the trademark TAXOTERE. Vinblastine sulfate can be administered, e.g., in the form as it is marketed, e.g., under the trademark VINBLASTIN R.P. Vincristine sulfate can be administered, e.g., in the form as it is marketed, e.g., under the trademark FARMISTIN. Discodermolide can be obtained, e.g., as disclosed in U.S. Pat. No. 5,010,099. Also included are epothilone derivatives which are disclosed in WO 98/10121, U.S. Pat. No. 6,194,181, WO 98/25929, WO 98/08849, WO 99/43653, WO 98/22461 and WO 00/31247. Especially preferred are epothilone A and/or B.

The term "alkylating agent", as used herein, includes, but is not limited to, cyclophosphamide, ifosfamide, melphalan or nitrosourea (BCNU or Gliadel).

Cyclophosphamide can be administered, e.g., in the form as it is marketed, e.g., under the trademark CYCLOSTIN. Ifosfamide can be administered, e.g., in the form as it is marketed, e.g., under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes suberoylanilide hydroxamic acid (SAHA).

The term "antineoplastic antimetabolite" includes, but is not limited to, 5-fluorouracil or 5-FU; capecitabine; gemcitabine; DNA demethylating agents, such as 5-azacytidine and decitabine; methotrexate and edatrexate; and folic acid antagonists, such as pemetrexed. Capecitabine can be administered, e.g., in the form as it is marketed, e.g., under the trademark XELODA. Gemcitabine can be administered, e.g., in the form as it is marketed, e.g., under the trademark GEMZAR. Also included is the monoclonal antibody trastuzumab which can be administered, e.g., in the form as it is marketed, e.g., under the trademark HERCEPTIN.

The term "platin compound", as used herein, includes, but is not limited to, carboplatin, cis-platin, cisplatinum and oxaliplatin. Carboplatin can be administered, e.g., in the form as it is marketed, e.g., under the trademark CARBOPLAT. Oxaliplatin can be administered, e.g., in the form as it is marketed, e.g., under the trademark ELOXATIN.

The term "compounds targeting/decreasing a protein or lipid kinase activity; or a protein or lipid phosphatase activity; or further anti-angiogenic compounds", as used herein, includes, but is not limited to, protein tyrosine kinase and/or serine and/or threonine inhibitors or lipid kinase inhibitors, e.g.,
  a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g., a N-phenyl-2-pyrimidine-amine derivative, e.g., imatinib, SU101, SU6668 and GFB-111;
  b) compounds targeting, decreasing or inhibiting the activity of the fibroblast growth factor-receptors (FGFR);
  c) compounds targeting, decreasing or inhibiting the activity of the insulin-like growth factor receptors (IGF-IR), such as compounds which target, decrease or inhibit the activity of IGF-IR, especially compounds which inhibit the IGF-IR receptor, such as those compounds disclosed in WO 02/092599;
  d) compounds targeting, decreasing or inhibiting the activity of the Trk receptor tyrosine kinase family;
  e) compounds targeting, decreasing or inhibiting the activity of the AxI receptor tyrosine kinase family;
  f) compounds targeting, decreasing or inhibiting the activity of the c-Met receptor;
  g) compounds targeting, decreasing or inhibiting the activity of the Kit/SCFR receptor tyrosine kinase;
  h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g., imatinib;
  i) compounds targeting, decreasing or inhibiting the activity of members of the c-Abl family and their gene-fusion products, e.g., BCR-Abl kinase, such as compounds which target decrease or inhibit the activity of c-Abl family members and their gene fusion products, e.g., a N-phenyl-2-pyrimidine-amine derivative, e.g., imatinib, PD180970, AG957, NSC 680410 or PD173955 from ParkeDavis;
  j) compounds targeting, decreasing or inhibiting the activity of members of the protein kinase C(PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g., midostaurin; examples of further compounds include, e.g., UCN-01; safingol; BAY 43-9006; Bryostatin 1; Perifosine; Ilmofosine; RO 318220 and RO 320432; GO 6976; Isis 3521; LY333531/LY379196; isochinoline compounds, such as those disclosed in WO 00/09495; FTIs; PD184352; or QAN697 (a P13K inhibitor);
  k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556, AG957 and adaphostin (4-{[(2,5-dihydroxyphenyl)methyl]amino}-benzoic acid adamantyl ester, NSC 680410, adaphostin; and
  l) compounds targeting, decreasing or inhibiting the activity of the epidermal growth factor family of receptor tyrosine kinases (EGFR, ErbB2, ErbB3, ErbB4 as homo- or hetero-dimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF related ligands, and are in particular those compounds, proteins or monoclonal antibodies generically and specifically disclosed in WO 97/02266, e.g., the compound of Example 39, or in EP 0 564 409; WO 99/03854; EP 0520722; EP 0 566 226; EP 0 787 722; EP 0 837 063; U.S. Pat. No. 5,747,498; WO 98/10767; WO 97/30034; WO 97/49688; WO 97/38983 and, especially, WO 96/30347, e.g., compound known as CP 358774; WO 96/33980, e.g., compound ZD 1839; and WO 95/03283, e.g., compound ZM105180, e.g., trastuzumab (HERCEPTIN), cetuximab, Iressa, Tarceva, OSI-774, CI-1033, EKB-569, GW-2016, E1.1, E2.4, E2.5, E6.2, E6.4, E2.11, E6.3 or E7.6.3; and 7H-pyrrolo-[2,3-d] pyrimidine derivatives which are disclosed in WO 03/013541.

Further anti-angiogenic compounds include compounds having another mechanism for their activity, e.g., unrelated to protein or lipid kinase inhibition, e.g., thalidomide (THALOMID) and TNP-470.

Compounds which target, decrease or inhibit the activity of a protein or lipid phosphatase are, e.g., inhibitors of phosphatase 1, phosphatase 2A, PTEN or CDC25, e.g., okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor, as used herein, includes, but is not limited to, e.g., Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g., 5-methyl-2-(2'-chloro-6'-fluoroanilino)phenyl acetic acid or lumiracoxib. The term "bisphosphonates", as used herein, includes, but is not limited to, etridonic, clodronic, tiludronic, pamidronic, alendronic, ibandronic, risedronic and zoledronic acid. "Etridonic acid" can be administered, e.g., in the form as it is marketed, e.g., under the trademark DIDRONEL. "Clodronic acid" can be administered, e.g., in the form as it is marketed, e.g., under the trademark BONEFOS. "Tiludronic acid" can be administered, e.g., in the form as it is marketed, e.g., under the trademark SKELID. "Pamidronic acid" can be administered, e.g., in the form as it is marketed, e.g., under the trademark AREDIA™ "Alendronic acid" can be administered, e.g., in the form as it is marketed, e.g., under the trademark FOSAMAX. "Ibandronic acid" can be administered, e.g., in the form as it is marketed, e.g., under the trademark BONDRANAT. "Risedronic acid" can be administered, e.g., in the form as it is marketed, e.g., under the trademark ACTONEL. "Zoledronic acid" can be administered, e.g., in the form as it is marketed, e.g., under the trademark ZOMETA. The term "mTOR inhibitors" relates to compounds which inhibit the mammalian target of rapamycin (mTOR) and which possess antiproliferative activity, such as sirolimus (Rapamune®), everolimus (Certican™), CCI-779 and ABT578.

The term "heparanase inhibitor", as used herein, refers to compounds which target, decrease or inhibit heparin sulphate degradation. The term includes, but is not limited to, PI-88. The term "biological response modifier", as used herein, refers to a lymphokine or interferons, e.g., interferon γ.

The term "inhibitor of Ras oncogenic isoforms", e.g., H-Ras, K-Ras or N-Ras, as used herein, refers to compounds which target, decrease or inhibit the oncogenic activity of Ras, e.g., a "farnesyl transferase inhibitor", e.g., L-744832, DK8G557 or R115777 (Zarnestra). The term "telomerase inhibitor", as used herein, refers to compounds which target, decrease or inhibit the activity of telomerase. Compounds which target, decrease or inhibit the activity of telomerase are especially compounds which inhibit the telomerase receptor, e.g., telomestatin.

The term "methionine aminopeptidase inhibitor", as used herein, refers to compounds which target, decrease or inhibit the activity of methionine aminopeptidase. Compounds which target, decrease or inhibit the activity of methionine aminopeptidase are, e.g., bengamide or a derivative thereof.

The term "proteasome inhibitor", as used herein, refers to compounds which target, decrease or inhibit the activity of the proteasome. Compounds which target, decrease or inhibit the activity of the proteasome include, e.g., PS-341 and MLN 341.

The term "matrix metalloproteinase inhibitor" or "MMP inhibitor", as used herein, includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies", as used herein, includes, but is not limited to, FMS-like tyrosine kinase inhibitors, e.g., compounds targeting, decreasing or inhibiting the activity of FMS-like tyrosine kinase receptors (Flt-3R); interferon, 1-b-D-arabinofuransyl-cytosine (ara-c) and bisulfan; and ALK inhibitors, e.g., compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g., PKC412, midostaurin, a staurosporine derivative, SU11248 and MLN518.

The term "HSP90 inhibitors", as used herein, includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90, e.g., 17-allylamino, 17-demethoxygeldanamycin (17AAG), a geldanamycin derivative, other geldanamycin related compounds, radicicol and HDAC inhibitors.

The term "antiproliferative antibodies", as used herein, includes, but is not limited to, trastuzumab (Herceptin™), Trastuzumab-DM1, erlotinib (Tarceva™), bevacizumab (Avastin™), rituximab (Rituxan®), PRO64553 (anti-CD40) and 2C4 antibody. By antibodies is meant, e.g., intact monoclonal antibodies, polyclonal antibodies, multispecific antibodies formed from at least two intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g., Patents International, e.g., IMS World Publications.

The above-mentioned compounds, which can be used in combination with a compound of the formula (I), can be prepared and administered as described in the art, such as in the documents cited above.

A compound of the formula (I) may also be used to advantage in combination with known therapeutic processes, e.g., the administration of hormones or especially radiation.

A compound of formula (I) may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound of the formula (I) and a combination partner may be administered independently at the same time or separately within time intervals that especially allow that the combination partners show a cooperative, e.g., synergistic, effect or any combination thereof. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a combination partner, are both administered to a patient simultaneously in the form of a single entity or dosage. The term "non-fixed combination" means that the active ingredients, e.g. a compound of formula (I) and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

Experimental Details:

Insofar as the production of the starting materials is not particularly described, the compounds are known or may be prepared analogously to methods known in the art or as described hereafter.

The following examples are illustrative of the invention without any limitation.

| Abbreviations: | |
|---|---|
| AcOH | acetic acid |
| aq | aqueous |
| Ar | aryl |
| BOC | tert-butyl-carbonate |
| BOP | benzotriazol-1-yloxytris(dimethylamino)phosphonium hexafluorophosphate |
| br.s. | broad singlet |
| $CDCl_3$ | chloroform-d |
| CDI | 1,1'-carbonyldiimidazole |
| $CH_2Cl_2$ | dichloromethane |
| $CH_3CN$ | acetonitrile |
| $Cs_2CO_3$ | cesium carbonate |
| d | doublet |
| dd | doublet of doublets |
| DIPEA | N-ethyldiisopropylamine |
| DME | 1,4-dimethoxyethane |
| DMF | N,N-dimethylformamide |
| DBU | 1,8-diaza-7-bicyclo[5.4.0]undecene |
| DMSO | dimethylsulfoxide |
| dt | doublet of triplets |
| EDC | 1-ethyl-3-(3-dimethylaminopropyl)carbodiimide hydrochloride |
| eq. | equivalent |
| EtOAc | ethyl acetate |
| FCC | flash column chromatography |
| h | hour |
| HBTU | (2-(1H-benzotriazole-1-yl)-1,1,3,3-tetramethyluronium hexafluorophosphate |
| HCl | hydrochloric acid |
| HOBT | benztriazol-1-ol |
| HPLC | high pressure liquid chromatography |
| HT | high throughput |
| $H_2O$ | water |
| Hyflo | Hyflo Super Cel Medium |
| Isolute ® SCX-2 | polymer supported sulfonic acid macroporous polystyrene |
| K | kelvin |
| $K_2CO_3$ | potassium carbonate |
| LC | liquid chromatography |
| M | molar |
| MeCN | acetonitrile |
| MeOD | methanol-d4 |
| MeOH | methanol |
| 2-Me-THF | 2-methyltetrahydrofuran |
| MgSO4 | magnesium sulfate |
| MHz | mega herz |
| MS | mass spectroscopy |
| m | multiplet |
| mBar | millibar |
| mL | millilitre |
| mm | millimeter |
| mM | millimolar |
| min. | minute |
| mw | microwave |

-continued

| Abbreviations: | |
|---|---|
| NaOH | sodium hydroxide |
| $Na_2SO_4$ | sodium sulfate |
| $NaHCO_3$ | sodium hydrogen carbonate |
| NaO$^t$Bu | sodium tert-butoxide |
| $NEt_3$ | triethylamine |
| $NH_3$ | ammonia |
| $NH_4OH$ | concentrated solution of ammonia in water possessing a specific gravity of 0.88 |
| NMP | N-methylpyrrolidinone |
| NMR | nuclear magnetic resonance |
| OBD | optimum bed density |
| $Pd(OAc)_2$ | palladium acetate |
| $Pd(OH)_2/C$ | palladium hydroxide on carbon |
| $Pd_2(dba)_3$ | tris(dibenzylideneacetone)dipalladium |
| $Pd_2(dba)_3\cdot CHCl_3$ | tris(dibenzylideneacetone)dipalladium chloroform complex |
| PL-$HCO_3$ MP | polymer supported hydrogen carbonate macroporous polystyrene |
| PL-$SO_3$H MP | polymer supported sulfonic acid macroporous polystyrene |
| rt | room temperature |
| Rt | retention time |
| s | singulet |
| SCX-2 | polymer supported sulfonic acid macroporous polystyrene |
| t | triplet |
| TBME | tert-butylmethyl ether |
| tBuOK | potassium tert-butoxide |
| tert-BuONa | sodium tert-butoxide |
| TFA | trifluoroacetic acid |
| THF | tetrahydrofuran |
| UPLC | ultra performance liquid chromatography |
| X-Phos | dicyclohexyl(2',4',6'-triisopropylbiphenyl-2-yl)phosphine |

Microwave equipment used is a Biotage Initiator®
All compounds are named using AutoNom.

LCMS Methods Used:

LC method 1 (Rt$^{(1)}$): The retention times (Rt) were obtained on a Agilent HPLC system with an Ascentis®Express column C18 30×2.1 mm, 2.7 μm (Supelco) applying a gradient ($H_2O$+0.05% formic acid+3.75 mM Ammonium acetate)/($CH_3CN$+0.04% formic acid) 90/10 to 5/95 over 3.7 min and 1.2 mL/min as solvent flow and then 5/95 over 0.7 min with 1.4 mL/min as solvent flow and 40° C. for the oven temperature. Detection method UV 220-400 nm-MS.

LC method 2 (Rt$^{(2)}$): The retention times (Rt) were obtained on a Agilent HPLC system with an Ascentis®Express column C18 30×2.1 mm, 2.7 μm (Supelco) applying a gradient ($H_2O$+0.05% formic acid+3.75 mM Ammonium acetate)/($CH_3CN$+0.04% formic acid) 95/5 to 5/95 over 3.7 min and 1.2 mL/min as solvent flow and then 5/95 over 0.7 min with 1.4 mL/min as solvent flow and 40° C. for the oven temperature. Detection method UV 220-400 nm-MS.

LC method 3 (Rt$^{(3)}$): The retention times (Rt) were obtained on a Agilent HPLC system with an Ascentis®Express column C18 30×2.1 mm, 2.7 μm (Supelco) applying a gradient ($H_2O$+0.05% formic acid+3.75 mM Ammonium acetate)/($CH_3CN$+0.04% formic acid) 99/1 over 0.5 min and 1.2 mL/min as solvent flow then 99/1 to 5/95 over 1.7 min and 1.2 mL/min as solvent flow and then 5/95 over 0.7 min with 1.4 mL/min as solvent flow and 40° C. for the oven temperature. Detection method UV 220-400 nm-MS.

LC method 4 (Rt$^{(4)}$): The retention times (Rt) were obtained on a Agilent HPLC system with an Ascentis®Express column C18 30×2.1 mm, 2.7 μm (Supelco) applying a gradient (H₂O+0.05% formic acid+3.75 mM Ammonium acetate)/(CH₃CN+0.04% formic acid) 90/10 to 5/95 over 1.7 min and 1.2 mL/min as solvent flow and then 5/95 over 0.7 min with 1.4 mL/min as solvent flow and 40° C. for the oven temperature. Detection method UV 220-400 nm-MS.

LC method 5 (Rt$^{(5)}$): The retention times (Rt) were obtained on a Agilent HPLC system with an Ascentis®Express column C18 30×2.1 mm, 2.7 μm (Supelco) applying a gradient (H₂O+0.05% TFA)/(CH₃CN+0.04% TFA) 95/5 to 5/95 over 3.7 min and 1.2 mL/min as solvent flow and then 5/95 over 0.7 min with 1.4 mL/min as solvent flow and 40° C. for the oven temperature. Detection method UV 220-400 nm-MS.

LC method 6 (Rt$^{(6)}$): The retention times (Rt) were obtained on a Agilent HPLC system with an Ascentis®Express column C18 30×2.1 mm, 2.7 μm (Supelco) applying a gradient (H₂O+TFA)/(CH₃CN+0.04% TFA) 99/1 over 0.5 min and 1.2 mL/min as solvent flow then 99/1 to 5/95 over 1.7 min and 1.2 mL/min as solvent flow and then 5/95 over 0.7 min with 1.4 mL/min as solvent flow and 40° C. for the oven temperature. Detection method UV 220-400 nm-MS.

LC method 7 (Rt$^{(7)}$): The retention times (Rt) were obtained on a Waters Agilent HPLC system with an Ascentis®Express column C18 30×2.1 mm, 2.7 μm (Supelco) applying a gradient (H₂O+0.05% TFA)/(CH₃CN+0.04% TFA) 90/10 to 5/95 over 1.7 min and 1.2 mL/min as solvent flow and then 5/95 over 0.7 min with 1.4 mL/min as solvent flow and 40° C. for the oven temperature. Detection method UV 220-400 nm-MS.

LC method 8 (Rt$^{(8)}$): The retention times (Rt) were obtained on a Waters HPLC alliance-HT system with an XTerra column MS C18, 50×4.6 mm, 5 μm, reverse phase, applying a gradient (H₂O+0.1% TFA)/(CH₃CN+0.1% TFA) 95/5 to 0/100 over 8.0 min and 2.0 mL/min as solvent flow and 45° C. for the oven temperature. Detection method UV 220-400 nm-MS.

Purification Method:
Preparative Reverse Phase Gilson HPLC
- Method A: Column SunFire prep C18 OBD 5 μm, 30×100 mm from WATERS, with H₂O+0.1% TFA and Acetonitrile+0.1% TFA as mobile phase. Detection method UV 220-400 nm
- Method B: Column Atlantis prep T3 OBD 5 μm, 30×150 mm from WATERS, with H₂O+0.1% TFA and Acetonitrile+0.1% TFA as mobile phase. Detection method UV 220-400 nm
- Method C: Column XTerra RP18 OBD 5 μm, 19×50 mm from WATERS, with H₂O+0.1% TFA and Acetonitrile+0.1% TFA as mobile phase. Detection method UV 220-400 nm X-ray Powder Diffraction
Instrumentation:
Method X1

| Instrument | Bruker AXS, D8 Advance |
| --- | --- |
| Irradiation | CuKα (30 kV, 40 mA) |
| Detector | PSD (Vantec) detector |
| Scan range | 2°-40° (2 theta value) |

Method X2

| Instrument | Bruker D8 GADDS Discover |
| --- | --- |
| Irradiation | CuKα (40 kV, 40 mA) |
| Detector | HI-STAR Area detector |
| Scan range | 6°-40° (2 theta value) |

Preparation of Intermediate Compounds

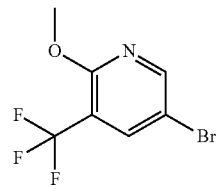

INTERMEDIATE 1

5-Bromo-2-methoxy-3-trifluoromethyl-pyridine

To 2-methoxy-3-(trifluoromethyl)pyridine (20.0 g, 113.0 mmol) and 1,3-dibromo-5,5-dimethylimidazolidine-2,4-dione (43.6 g, 152.0 mmol) was added TFA (80 mL) and the resulting mixture stirred at rt for 18 h under argon. The TFA was removed in vacuo (50 mbar, 45° C.) and the residue suspended in tert-butyl methyl ether (200 mL). The resulting colourless solid was removed by filtration and washed with tert-butyl methyl ether (50 mL). The filtrate was concentrated in vacuo and suspended in EtOAc (50 mL) The insoluble colourless solid was removed by filtration and washed with EtOAc (50 mL). The filtrate was concentrated in vacuo, diluted with heptane/tert-butyl methyl ether (5/1, 20 mL) and the insoluble colourless solid was removed by filtration. The filtrate was purified by column chromatography on silica gel with heptane/EtOAc, 100/0 to 90/10. The crude product was filtered through a plug of NaHCO₃ (20 g) and the filtrate evaporated in vacuo to give a golden oil (27.9 g). The oil was dissolved in heptanes (20 mL) and purified by filtered through a plug of silica gel (80 g), eluting with heptane to give 5-bromo-2-methoxy-3-(trifluoromethyl)pyridine as a colourless oil (22.5 g, 74% yield). ¹H-NMR (400 MHz, DMSO-d₆, 298 K): δ ppm 4.03 (s, 3H) 7.95 (d, 1H) 8.4 (d, 1H).

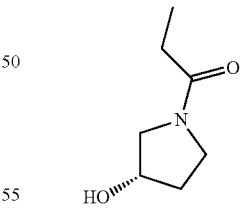

INTERMEDIATE 2

1-((S)-3-Hydroxy-pyrrolidin-1-yl)-propan-1-one (S)-Pyrrolidin-3-ol (10.0 g, 81.0 mmol), triethylamine (23.6 mL, 170.0 mmol) and CH₂Cl₂ (150 mL) were combined in a pear-shaped flask to give a beige suspension. The mixture was cooled to −10° C. and propionyl chloride (7.06 mL, 81.0 mmol) was added dropwise over 15 min, maintaining the temperature between −10 to 0° C. The resulting beige suspension was stirred for 2 h at 0° C. MeOH (9.8 mL) was added and the mixture allowed to warm to room temperature then stirred for 1 h to give a brown solution. The mixture was evaporated in vacuo to give a beige residue which was stirred in diethylether (200 mL) and filtered. The filtrate was evaporated in vacuo to give 1-((S)-3-hydroxy-pyrrolidin-1-yl)-propan-1-one as a yellow oil (11.23 g, 95% yield). $^1$H-NMR (400 MHz, DMSO-$d_6$, 298 K): δ ppm 0.92-1.02 m, 3H) 1.67-1.97 (m, 2H) 2.13-2.28 (m, 2H) 3.18-3.52 (m, 4H) 4.17-4.32 (m, 1H) 4.85-4.97 (m, 1H). LCMS: [M+H]+=144.0

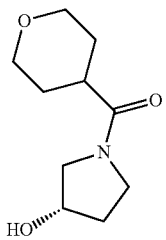

INTERMEDIATE 3

((S)-3-Hydroxy-pyrrolidin-1-yl)-(tetrahydro-pyran-4-yl)-methanone

The (S)-pyrrolidin-3-ol hydrochloride (3.69 g, 29.9 mmol) and triethylamine (6.65 g, 9.16 mL, 65.7 mmol) were put in $CH_2Cl_2$ (15 mL). The suspension was cooled at ~3° C. To this mixture, a solution of tetrahydro-pyran-4-carbonyl chloride (4.67 g, 29.9 mmol) in $CH_2Cl_2$ (15 mL) was added slowly. Then the resulting reaction mixture was stirred for 1.5 h at 3-10° C. The reaction mixture was then concentrated to give a powder. To this powder, addition of EtOAc (100 mL). The solid was filtered and washed with EtOAc. The recovered filtrate was then concentrated to give ((S)-3-hydroxy-pyrrolidin-1-yl)-(tetrahydro-pyran-4-yl)-methanone as beige powder. (6.77 g, 98% yield). $^1$H-NMR (400 MHz, Methanol-$d_4$, 298 K): δ ppm 1.59-2.15 (m, 6H) 2.69-2.86 (m, 1H) 3.43-3.75 (m, 6H) 3.94-4.00 (m, 2H) 4.37-4.48 (m, 1H). LCMS: [M+H]+=199.9, Rt$^{(6)}$=0.86 min

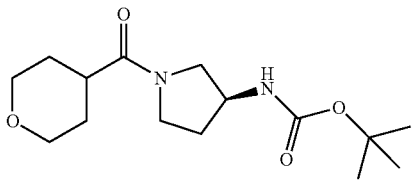 [SMILES: CC(C)(C)OC(=O)N[C@H]1CCN(C(=O)C2CCOCC2)C1]

INTERMEDIATE 4

[(S)-1-(Tetrahydro-pyran-4-carbonyl)-pyrrolidin-3-yl]-carbamic acid tert-butyl ester To a vigorously stirring solution of tetrahydro-2H-pyran-4-carbonyl chloride (0.455 g, 3.06 mmol) in $CH_2Cl_2$ (10 mL) was added simultaneously portionwise sat. $NaHCO_3$(aq) (10 mL) and a solution of the (S)-pyrrolidin-3-yl]-carbamic acid tert-butyl ester (570 mg, 3.06 mmol) at rt. The resulting biphasic mixture was stirred vigorously at rt for 3 h. The organic layer was separated by filtration through a phase separation tube, concentrated in vacuo and purified by flash chromatography on silica gel with $CH_2Cl_2$/MeOH to give [(S)-1-(tetrahydro-pyran-4-carbonyl)-pyrrolidin-3-yl]-carbamic acid tert-butyl ester as a colourless gum (0.623 g, 68% yield) LCMS: [M+H]+=299.6, Rt$^{(7)}$=0.73 min.

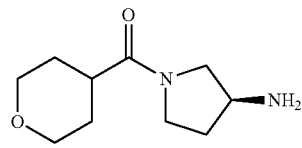 [SMILES: N[C@H]1CCN(C(=O)C2CCOCC2)C1]

INTERMEDIATE 5

(S)-3-Amino-pyrrolidin-1-yl-(tetrahydro-pyran-4-yl)-methanone

To (S)-1-(tetrahydro-pyran-4-carbonyl)-pyrrolidin-3-yl]-carbamic acid tert-butyl ester (intermediate 4) (0.623 g, 2.09 mmol) in $CH_2Cl_2$ (2.0 mL) was added TFA (2.0 mL) and the resulting mixture stood at rt for 8 h. Evaporated in vacuo and eluted through an Isolute® SCX-2 cartridge, eluting with methanol, then with 2M ammonia in methanol. Basic fractions were concentrated in vacuo to give [(S)-3-amino-pyrrolidin-1-yl-(tetrahydro-pyran-4-yl)-methanone as a colourless solid (0.34 g, 82% yield) LCMS: [M+H]+=199.0, Rt$^{(3)}$=0.1 min.

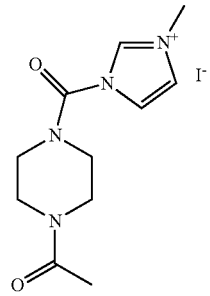 [SMILES: CC(=O)N1CCN(C(=O)n2cc[n+](C)c2)CC1 ; [I-]]

INTERMEDIATE 6

3-(4-Acetyl-piperazine-1-carbonyl)-1-methyl-3H-imidazol-3-ium iodide 1-(piperazin-1-yl)ethanone (143 mg, 1.12 mmol) and CDI (199 mg, 1.23 mmol) were refluxed in THF (10 mL) under argon overnight. Cooled to room temperature, diluted with $CH_2Cl_2$ (20 mL) and water (5 mL) and the organic layer filtered through a phase separation tube and concentrated in vacuo. Dissolved in acetonitrile (5 mL) in a glass vial and methyl iodide (0.279 mL, 4.46 mmol) was added. The vial was capped and stood at room temperature for 24 h. The solvent was evaporated in vacuo and the residue triturated with heptane/EtOAc, 10/1 (10 mL) to give 3-(4-acetyl-piperazine-1-carbonyl)-1-methyl-3H-imidazol-3-ium iodide as a colourless gum (400 mg) which was used without further purification.

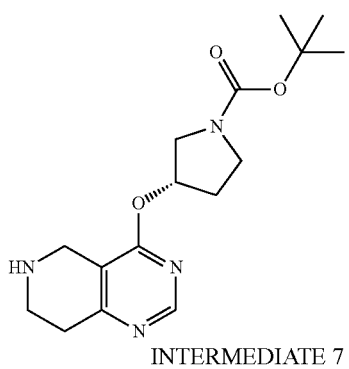

INTERMEDIATE 7

(S)-3-(5,6,7,8-Tetrahydro-pyrido[4,3-d]pyrimidin-4-yloxy)-pyrrolidine-1-carboxylic acid tert-butyl ester Pd(OH)$_2$/C (1.2 g, 1.71 mmol) was flushed with argon, (S)-3-(6-Benzyl-5,6,7,8-tetrahydro-pyrido[4,3-d]pyrimidin-4-yloxy)-pyrrolidine-1-carboxylic acid tert-butyl ester (10.95 g, 26.7 mmol) dissolved in methanol (25 mL) was added followed by the addition of ammonium formate (1.68 g, 26.7 mmol). The reaction mixture was refluxed for 1 h, cooled down to room temperature, filtered through a celite pad and concentrated under vacuum. Purification by flash chromatography on silica gel (CH$_2$Cl$_2$ then TBME then TBME/MeOH 100/0 to 90/10 then TBME/MeOH/NH$_4$OH 85/15/5) gave (S)-3-(5,6,7,8-tetrahydro-pyrido[4,3-d]pyrimidin-4-yloxy)-pyrrolidine-1-carboxylic acid tert-butyl ester (7.39 g, 87% yield) as a yellow sticky oil. $^1$H NMR (400 MHz, methanol-d$_4$, 298K) δ ppm 1.46-1.46 (m, 9 H) 2.10-2.30 (m, 2 H) 2.78-2.83 (m, 2 H) 3.11-3.14 (m, 2 H) 3.41-3.60 (m, 3 H) 3.65-3.72 (m, 1 H) 3.78 (s, 2 H) 5.68 (m, 1 H) 8.52 (s, 1 H). LCMS: [M+H]$^+$=321.2, Rt$^{(2)}$=0.87 min Alternative Synthesis for Intermediate 7:

Pd(OH)$_2$/C (1.54 g, 2.2 mmol) was flushed with nitrogen, (S)-3-(6-benzyl-5,6,7,8-tetrahydro-pyrido[4,3-d]pyrimidin-4-yloxy)-pyrrolidine-1-carboxylic acid tert-butyl ester (8.5 g, 20.67 mmol) dissolved in methanol (50 mL) was added followed by the addition of triethylammonium formate (7.9 g, 53.7 mmol). The reaction mixture was refluxed for 1 h, cooled down to room temperature, filtered through a celite pad and the filtrate was partitioned between 2-Me-THF (50 mL) and water (20 mL). The upper organic phase was collected and the bottom aqueous phase was re-extracted with 2-Me-THF (10 mL). All the organic layers were combined and concentrated under vacuum to provide (S)-3-(5,6,7,8-tetrahydro-pyrido[4,3-d]pyrimidin-4-yloxy)-pyrrolidine-1-carboxylic acid tert-butyl ester (6.2 g, 94% yield) as a yellow gum.

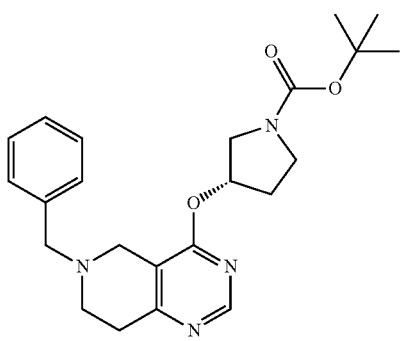 [SMILES: CC(C)(C)OC(=O)N1CC[C@H](Oc2ncnc3c2CN(Cc2ccccc2)CC3)C1]

(S)-3-(6-Benzyl-5,6,7,8-tetrahydro-pyrido[4,3-d]pyrimidin-4-yloxy)-pyrrolidine-1-carboxylic acid tert-butyl ester To a solution of (S)-3-hydroxypyrrolidine-1-carboxylic acid tert-butyl ester (0.94 g, 5.01 mmol) in THF (20 mL) was added under argon NaH (0.23 g, 5.78 mmol). The mixture was stirred at rt for 25 min., then 6-benzyl-4-chloro-5,6,7,8-tetrahydro-pyrido[4,3-d]pyrimidine (1 g, 3.85 mmol) was added and stirring continued at rt for 4 h. The mixture was quenched with H$_2$O, extracted with CH$_2$Cl$_2$. The organic layer was filtered and evaporated to dryness. Purification by flash chromatography on silica gel (heptanes/ethyl acetate, 1/1) gave the (S)-3-(6-benzyl-5,6,7,8-tetrahydro-pyrido[4,3-d]pyrimidin-4-yloxy)-pyrrolidine-1-carboxylic acid tert-butyl ester (1.35 g, 85% yield) as a yellow gum. $^1$H NMR (400 MHz, DMSO-d6, 298K) δ ppm 1.39 (s, 9 H) 2.00-2.20 (m, 2 H) 2.35-2.81 (m, 4 H) 3.36-3.63 (m, 6 H) 3.70 (br.s, 2 H) 5.50-5.59 (m, 1 H) 7.25-7.37 (m, 5 H) 8.56 (s, 1 H). LCMS: [M+H]+=411.6, Rt$^{(7)}$=1.00 min Alternative Synthesis for (S)-3-(6-Benzyl-5,6,7,8-tetrahydro-pyrido[4,3-d]pyrimidin-4-yloxyl)-pyrrolidine-1-carboxylic acid tert-butyl ester To a solution of (S)-3-hydroxypyrrolidine-1-carboxylic acid tert-butyl ester (6.21 g, 33.16 mmol) and 6-benzyl-4-chloro-5,6,7,8-tetrahydro-pyrido[4,3-d]pyrimidine (9 g, 34.65 mmol) in 2-Me-THF (100 mL) was added under nitrogen tBuOK (8.17 g, 72.95 mmol). The mixture was stirred at rt for 25 min. The mixture was quenched with H$_2$O. The organic layer was washed with brine. The resulting organic solution was concentrated in vacuo to provide (S)-3-(6-benzyl-5,6,7,8-tetrahydro-pyrido[4,3-d]pyrimidin-4-yloxy)-pyrrolidine-1-carboxylic acid tert-butyl ester (12.6 g, 89% yield) as a yellow gum.

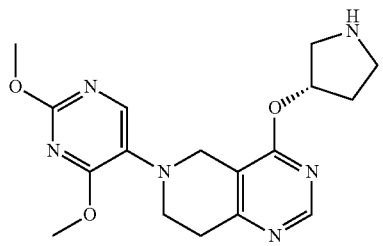 [SMILES: COc1ncc(N2CCc3ncnc(O[C@H]4CCNC4)c3C2)c(OC)n1]

INTERMEDIATE 8

6-(2,4-Dimethoxy-pyrimidin-5-yl)-4-((S)-pyrrolidin-3-yloxy)-5,6,7,8-tetrahydro-pyrido[4,3-d]pyrimidine 5-Bromo-2,4-dimethoxy-pyrimidine (89 mg, 0.41 mmol), X-Phos (46 mg, 0.09 mmol) bis(dibenzylideneacetone)palladium(0) (29 mg, 0.03 mmol), cesium carbonate (203 mg, 0.62 mmol) were combined and flushed 10 min with Argon. To this mixture was added (S)-3-(5,6,7,8-tetrahydro-pyrido[4,3-d]pyrimidin-4-yloxy)-pyrrolidine-1-carboxylic acid tert-butyl ester (intermediate 7) (100 mg, 0.31 mmol) in dioxane (4 mL), the vial was capped and the reaction mixture was stirred at 120° C. for 4.5 h. The mixture was allowed to cool to rt and filtered through a celite pad. The filtrate was diluted with EtOAc (20 mL) and washed with sat. NaHCO$_3$(aq) (10 mL), brine (10 mL), dried (Na$_2$SO$_4$) and concentrated in vacuo.

Dissolved in dioxane (4 mL) and added to a glass vial containing 5-bromo-2,4-dimethoxy-pyrimidine (89 mg, 0.41 mmol), X-Phos (46 mg, 0.09 mmol) tris(dibenzylideneacetone)dipalladium(0) (29 mg, 0.03 mmol), cesium carbonate (203 mg, 0.62 mmol). The vial was capped and the reaction mixture was stirred at 120° C. for 4.5 h. The mixture was allowed to cool to rt and filtered through a celite pad. The filtrate was diluted with EtOAc (20 mL) and washed with sat. NaHCO$_3$(aq) (10 mL) then brine (10 mL), dried (Na$_2$SO$_4$) and concentrated in vacuo to give (S)-3-(6-(2,4-dimethoxy-pyrimidin-5-yl)-5,6,7,8-tetrahydropyrido[4,3-d]pyrimidin-4-yloxy)pyrrolidine-1-carboxylic acid tert-butyl ester which was used without further purification. (S)-3-(6-(2,4-dimethoxy-pyrimidin-5-yl)-5,6,7,8-tetrahydropyrido[4,3-d]pyrimidin-4-yloxy)pyrrolidine-1-carboxylic acid tert-butyl ester was dissolved in CH$_2$Cl$_2$ (2.0 mL) and TFA added (1 mL). The resulting mixture was stirred for 30 min. at room temperature. The reaction mixture was concentrated in vacuo. Purification by preparative reverse phase Gilson HPLC and subsequent neutralization of the combined fractions by PL-HCO3 cartridge & lyophilisation gave 6-(2,4-dimethoxy-pyrimidin-5-yl)-4-((S)-pyrrolidin-3-yloxy)-5,6,7,8-tetrahydro-pyrido[4,3-d]pyrimidine as a yellow powder (11 mg, 10% yield over 2 steps). LCMS: [M+H]+=359.1, Rt$^{(2)}$=0.79 min

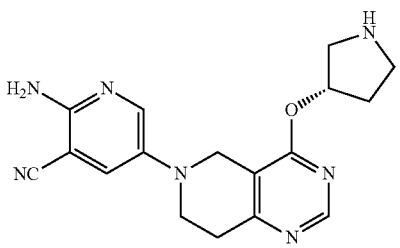 [SMILES: N#Cc1cc(N2CCc3ncnc(O[C@H]4CCNC4)c3C2)cnc1N]

INTERMEDIATE 9

2-Amino-5-[4-((S)-pyrrolidin-3-yloxy)-7,8-dihydro-5H-pyrido[4,3-d]pyrimidin-6-yl]nicotinonitrile (S)-3-(5,6,7,8-Tetrahydro-pyrido[4,3-d]pyrimidin-4-yloxy)-pyrrolidine-1-carboxylic acid tert-butyl ester (intermediate 7) (84 mg, 0.263 mmol), imidodicarbonic acid, 2-[5-bromo-3-(cyano)-2-pyridinyl]-, 1,3-bis(1,1-dimethylethyl) ester (115 mg, 0.289 mmol), X-Phos (376 mg, 0.079 mmol), tris(dibenzylideneacetone)dipalladium(0) (24 mg, 0.026 mmol), cesium carbonate (171 mg, 0.526 mmol) were combined in a glass vial and flushed 10 min with Argon. To this mixture was added dioxane (4.0 mL), the vial was capped and the reaction mixture stirred at 120° C. for 1.5 h. The reaction was allowed to cool to rt and filtered through a celite pad, The filtrate was diluted with EtOAc (20 mL) and washed with sat. NaHCO$_3$(aq) (10 mL) and brine (10 mL), dried (Na$_2$SO$_4$) and concentrated in vacuo to give (S)-tert-butyl 3-(6-(6-(bis(tert-butoxycarbonyl)amino)-5-(cyano)pyridin-3-yl)-5,6,7,8-tetrahydropyrido[4,3-d]pyrimidin-4-yloxy)pyrrolidine-1-carboxylate which was used without further purification. (S)-tert-butyl 3-(6-(6-(bis(tert-butoxycarbonyl)amino)-5-(cyano)pyridin-3-yl)-5,6,7,8-tetrahydropyrido[4,3-d]pyrimidin-4-yloxy)pyrrolidine-1-carboxylate was dissolved in CH$_2$Cl$_2$ (2.0 mL) and TFA added (1 mL). The resulting mixture was stirred for 30 min at room temperature. The reaction mixture was concentrated in vacuo. Purification by preparative reverse phase Gilson HPLC and subsequent neutralization of the combined fractions by PL-HCO3 cartridge & lyophilisation gave 2-amino-5-[4-((S)-pyrrolidin-3-yloxy)-7,8-dihydro-5H-pyrido[4,3-d]pyrimidin-6-yl]nicotinonitrile as a yellow powder (17 mg, 19% yield over 2 steps). LCMS: [M+H]+=338.3, Rt$^{(3)}$=1.16 min.

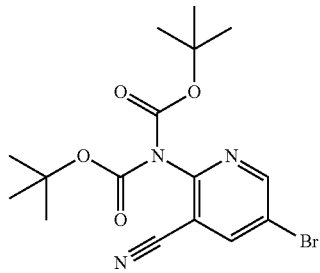 [SMILES: CC(C)(C)OC(=O)N(C(=O)OC(C)(C)C)c1ncc(Br)cc1C#N]

Imidodicarbonic acid, 2-[5-bromo-3-(cyano)-2-pyridinyl]-, 1,3-bis(1,1-dimethylethyl)ester To 2-amino-5-bromonicotinonitrile (0.785 g, 3.96 mmol), triethylamine (0.553 mL, 3.96 mmol) and 4-dimethylaminoyridine (20 mg, 0.164 mmol) in CH$_2$Cl$_2$ (25 mL) was added di-tert-butyl-dicarbonate (2.16 g, 9.91 mmol) and the resulting mixture stirred at room temperature for 18 h. Evaporated to dryness in vacuo and triturated in heptane (25 mL) for 72 h. The resulting precipitate was filtered and washed with heptane (10 mL) to give imidodicarbonic acid, 2-[5-bromo-3-(cyano)-2-pyridinyl]-, 1,3-bis(1,1-dimethylethyl)ester as a beige solid (1.1 g, 70% yield). $^1$H NMR (400 Mhz, CDCl$_3$, 298K) 1.51 (s, 18H) 8.16 (d, 1 H) 8.77 (d, 1 H). LCMS: [M+H]+=398/400.1, Rt$^{(4)}$=1.43 min.

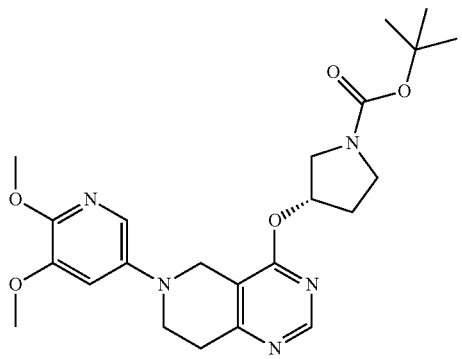 [SMILES: COc1cc(N2CCc3ncnc(O[C@H]4CCN(C(=O)OC(C)(C)C)C4)c3C2)cnc1OC]

INTERMEDIATE 10

(S)-3-[6-(5,6-Dimethoxy-pyridin-3-yl)-5,6,7,8-tetrahydro-pyrido[4,3-d]pyrimidin-4-yloxy]-pyrrolidine-1-carboxylic acid tert-butyl ester To a glass vial was added (S)-3-(5,6,7,8-tetrahydro-pyrido[4,3-d]pyrimidin-4-yloxy)-pyrrolidine-1-carboxylic acid tert-butyl ester (intermediate 7) (1.00 g, 3.12 mmol), 5-bromo-2,3-dimethoxypyridine (0.82 g, 3.75 mmol), sodium tert-butoxide (0.46 g, 4.68 mmol), tris(dibenzylideneacetone)dipalladium(0) (0.11 g, 0.13 mmol), 2-di-t-butylphosphino-2'-(N,N-dimethylamino)biphenyl (0.06 g, 0.18 mmol) and anhydrous toluene (10 mL). The vial was flushed with a stream of argon for 15 sec and capped. The mixture was heated with stirring for 18 h at 80° C. Allowed to cool and filtered through a celite pad. The filtrate was diluted with EtOAc (50 mL) and washed with brine (20 mL). The organic layer was separated, dried (Na$_2$SO$_4$) and concentrated in vacuo. Purified by flash column chromatography on silica gel with EtOAc/MeOH, 98/2 to 92/18 to give (S)-3-[6-(5,6-dimethoxy-pyridin-3-yl)-5,6,7,8-tetrahydro-pyrido[4,3-d]pyrimidin-4-yloxy]-pyrrolidine-1-carboxylic acid tert-butyl ester as a pale yellow foam (1.05 g, 74% yield). LCMS: [M+H]+=458.1, Rt$^{(4)}$=1.02 min.

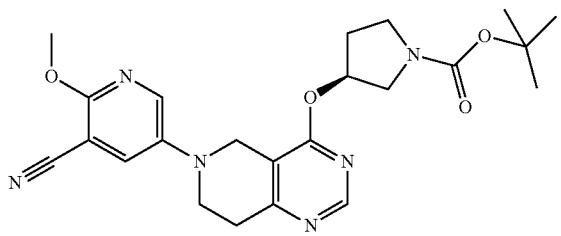 [SMILES: COc1ncc(N2CCc3ncnc(O[C@H]4CCN(C(=O)OC(C)(C)C)C4)c3C2)cc1C#N]

INTERMEDIATE 11

(S)-3-[6-(5-Cyano-6-methoxy-pyridin-3-yl)-5,6,7,8-tetrahydro-pyrido[4,3-d]pyrimidin-4-yloxy]-pyrrolidine-1-carboxylic acid tert-butyl ester To a glass vial was added (S)-3-(5,6,7,8-tetrahydro-pyrido[4,3-d]pyrimidin-4-yloxy)-pyrrolidine-1-carboxylic acid tert-butyl ester (intermediate 7) (630 mg, 1.97 mmol), 5-bromo-2-methoxynicotinonitrile (419 mg, 1.97 mmol), cesium carbonate (1281.0 mg, 3.93 mmol), tris(dibenzylideneacetone)dipalladium(0) (180 mg, 0.20 mmol), X-Phos (319 mg, 0.67 mmol) and anhydrous dioxane (10.0 mL). The vial was flushed with a stream of argon for 15 sec and capped. The mixture was heated with stirring for 1 h at 110° C. and then stirred at room temperature for 18 h. Diluted with CH$_2$Cl$_2$ (100 mL) and water (30 mL) and filtered through a celite pad. The organic phase was separated by filtering through a phase separation tube and concentrated in vacuo. Purified by flash chromatography on silica gel with heptanes/EtOAc, 80/20 to 0/100 to give (S)-3-[6-(5-cyano-6-methoxy-pyridin-3-yl)-5,6,7,8-tetrahydro-pyrido[4,3-d]pyrimidin-4-yloxy]-pyrrolidine-1-carboxylic acid tert-butyl ester as a brown gum (350 mg, 39% yield) LCMS: [M+H]+=453.6, Rt$^{(7)}$=1.29 min.

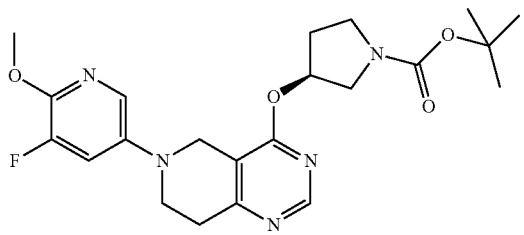 [SMILES: COc1ncc(N2CCc3ncnc(O[C@H]4CCN(C(=O)OC(C)(C)C)C4)c3C2)cc1F]

INTERMEDIATE 12

(S)-3-[6-(5-Fluoro-6-methoxy-pyridin-3-yl)-5,6,7,8-tetrahydro-pyrido[4,3-d]pyrimidin-4-yloxy]-pyrrolidine-1-carboxylic acid tert-butyl ester To a glass vial was added (S)-3-(5,6,7,8-tetrahydro-pyrido[4,3-d]pyrimidin-4-yloxy)-pyrrolidine-1-carboxylic acid tert-butyl ester (intermediate 7) (150 mg, 0.47 mmol), 5-bromo-3-fluoro-2-methoxypyridine (96 mg, 0.47 mmol), cesium carbonate (305 mg, 0.94 mmol), tris(dibenzylideneacetone)dipalladium(0) (43 mg, 0.05 mmol), X-Phos (76 mg, 0.16 mmol) and anhydrous dioxane (2.0 mL). The vial was flushed with a stream of argon for 15 sec and capped. The mixture was heated with stirring for 1.5 h at 110° C. and then stirred at room temperature for 18 h. Diluted with CH$_2$Cl$_2$ (25 mL), filtered through a celite pad and concentrated in vacuo. Purified by reverse phase Gilson HPLC (Method A) to give (S)-3-[6-(5-fluoro-6-methoxy-pyridin-3-yl)-5,6,7,8-tetrahydro-pyrido[4,3-d]pyrimidin-4-yloxy]-pyrrolidine-1-carboxylic acid tert-butyl ester trifluoroacetate as a brown gum (45 mg, 17% yield) LCMS: [M+H]+=446.4, Rt$^{(4)}$=1.41 min.

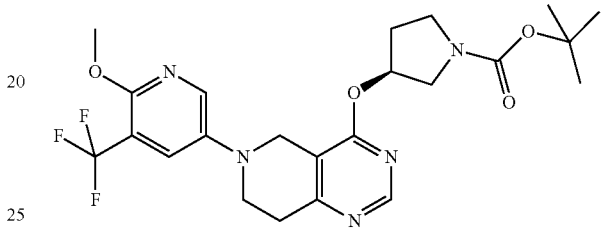

INTERMEDIATE 13

(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carboxylic acid tert-butyl ester To a glass vial was added (S)-3-(5,6,7,8-tetrahydro-pyrido[4,3-d]pyrimidin-4-yloxy)-pyrrolidine-1-carboxylic acid tert-butyl ester (intermediate 7) (150 mg, 0.47 mmol) 5-bromo-2-methoxy-3-(trifluoromethyl)pyridine (intermediate 1) (120 mg, 0.47 mmol), cesium carbonate (305 mg, 0.94 mmol), tris(dibenzylideneacetone)dipalladium(0) (43 mg, 0.05 mmol), X-Phos (76 mg, 0.16 mmol) and anhydrous dioxane (2.0 mL). The vial was flushed with a stream of argon for 15 sec and capped. The mixture was heated with stirring for 1 h at 110° C. and then stirred at room temperature for 18 h. Diluted with CH$_2$Cl$_2$ (10 mL) and water (2 mL), filtered through a celite pad. The organic phase was separated by filtering through a phase separation tube and concentrated in vacuo. Purified by reverse phase Gilson HPLC (Method A) to give (S)-tert-butyl 3-(6-(6-methoxy-5-(trifluoromethyl)pyridin-3-yl)-5,6,7,8-tetrahydropyrido[4,3-d]pyrimidin-4-yloxy)pyrrolidine-1-carboxylate trifluoroacetate(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carboxylic acid tert-butyl ester trifluoroacetate as a brown gum (90 mg, 32% yield) LCMS: [M+H]+=496.5, Rt$^{(7)}$=1.43 min.

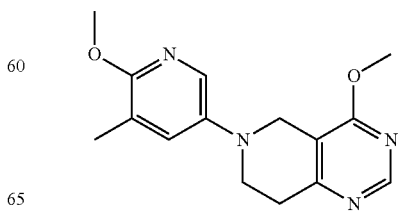

INTERMEDIATE 14

4-Methoxy-6-(6-methoxy-5-methyl-pyridin-3-yl)-5,6,7,8-tetrahydro-pyrido[4,3-d]pyrimidine To a glass vial was added 4-methoxy-5,6,7,8-tetrahydro-pyrido[4,3-d]pyrimidine (WO 2008/130481, p 47) (0.570 g, 3.45 mmol), 5-bromo-2-methoxy-3-methylpyridine (0.697 g, 3.45 mmol), cesium carbonate (2.25 g, 6.90 mmol), tris(dibenzylideneacetone)dipalladium(0) (0.316 g, 0.345 mmol), X-Phos (0.493 g, 1.04 mmol) and anhydrous dioxane (5 mL). The vial was flushed with a stream of argon for 15 sec and capped. The mixture was heated with stirring for 1 h 45 min at 110° C. then allowed to cool to room temperature and stirred at RT for 3 days. The reaction mixture was filtered through a celite pad and concentrated in vacuo. Purified by flash chromatography on silica gel with heptane/EtOAc, 100/0 to 0/100 then EtOAc/MeOH, 90/10 to give 4-methoxy-6-(6-methoxy-5-methyl-pyridin-3-yl)-5,6,7,8-tetrahydro-pyrido[4,3-d]pyrimidine as a brown gum (0.36 g, 36% yield) LCMS: [M+H]+=287.0, Rt$^{(7)}$=0.80 min.

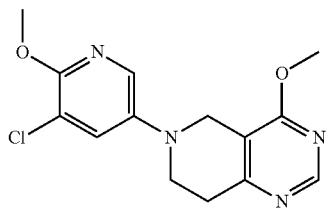 [SMILES: COc1ncc(N2CCc3ncnc(OC)c3C2)cc1Cl]

INTERMEDIATE 15

6-(5-Chloro-6-methoxy-pyridin-3-yl)-4-methoxy-5,6,7,8-tetrahydro-pyrido[4,3-d]pyrimidine To a glass vial was added 4-methoxy-5,6,7,8-tetrahydro-pyrido[4,3-d]pyrimidine (WO 2008/130481, p 47) (0.273 g, 1.65 mmol), 5-bromo-3-chloro-2-methoxypyridine (0.368 g, 1.65 mmol), sodium tert-butoxide (318 mg, 3.31 mmol), diacetoxypalladium (0.037 g, 0.17 mmol), X-Phos (0.079 g, 0.17 mmol) and anhydrous toluene/tert-butanol, 5/1 (6 mL). The vial was flushed with a stream of argon for 15 sec and capped. The mixture was heated with stirring for 2 h at 110° C. then allowed to cool to room temperature and stirred at rt for 5 days. Diluted with CH$_2$Cl$_2$ (10 mL) and water (2 mL), filtered through a celite pad. The organic phase was separated by filtering through a phase separation tube and concentrated in vacuo. Purified by flash chromatography on silica gel with heptane/EtOAc 100/0 to 0/100 to give 6-(5-chloro-6-methoxy-pyridin-3-yl)-4-methoxy-5,6,7,8-tetrahydro-pyrido[4,3-d]pyrimidine as a yellow solid (95 mg, 19% yield) LCMS: [M+H]+=307.0/308.9, Rt$^{(3)}$=1.62 min.

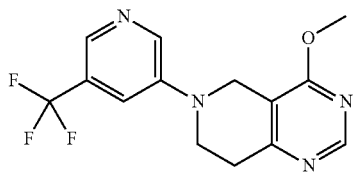 [SMILES: COc1ncnc2c1CN(c1cncc(C(F)(F)F)c1)CC2]

INTERMEDIATE 16

4-Methoxy-6-(5-trifluoromethyl-pyridin-3-yl)-5,6,7,8-tetrahydro-pyrido[4,3-d]pyrimidine To a glass vial was added 4-methoxy-5,6,7,8-tetrahydro-pyrido[4,3-d]pyrimidine (0.273 g, 1.65 mmol), 3-bromo-5-(trifluoromethyl)pyridine (0.373 g, 1.65 mmol), cesium carbonate (1.08 g, 3.31 mmol), tris(dibenzylideneacetone)dipalladium(0) (0.076 g, 0.083 mmol), X-Phos (0.079 g, 0.165 mmol) and anhydrous dioxane (5 mL). The vial was flushed with a stream of argon for 15 sec and capped. The mixture was heated with stirring for 1.5 h at 110° C. Filtered through a celite pad, concentrated in vacuo and purified by flash chromatography on silica gel with heptanes/EtOAc, 100/0 to 0/100 to give 4-methoxy-6-(5-trifluoromethyl-pyridin-3-yl)-5,6,7,8-tetrahydro-pyrido[4,3-d]pyrimidine as an orange gum (195 mg, 34% yield) $^1$H NMR (DMSO-d6, 298K) 2.95 (t, 2H) 3.77 (t, 2H) 4.02 (s, 3H) 4.37 (s, 2H) 7.67-7.71 (m, 1H) 8.30-8.34 (m, 1H) 8.63 (s, 1H) 8.67-8.71 (1H, m) LCMS: [M+H]+=311.2, Rt$^{(4)}$=0.94 min.

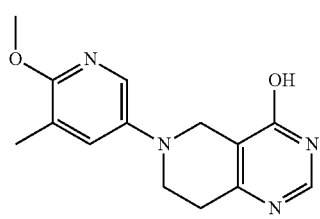 [SMILES: COc1ncc(N2CCc3ncnc(O)c3C2)cc1C]

INTERMEDIATE 17

6-(6-Methoxy-5-methyl-pyridin-3-yl)-5,6,7,8-tetrahydro-pyrido[4,3-d]pyrimidin-4-ol To 4-methoxy-6-(6-methoxy-5-methyl-pyridin-3-yl)-5,6,7,8-tetrahydro-pyrido[4,3-d]pyrimidine (intermediate 14)(360 mg, 1.26 mmol) in MeOH (2.0 mL) in a glass vial was added 2M NaOH(aq) (2.0 mL). The vial was capped and heated at 90° C. for 24 h. Acidified with glacial AcOH to pH 6, evaporated in vacuo and the residue extracted with CH$_2$Cl$_2$ (2×30 mL). With each extraction, the CH$_2$Cl$_2$ layer was decanted from the solid residue. The CH$_2$Cl$_2$ layers were combined and eluted through an Isolute SCX-2 cartridge, eluting with methanol, then with 2M ammonia in methanol. Basic fractions were concentrated in vacuo to give 6-(6-methoxy-5-trifluoromethyl-pyridin-3-yl)-5,6,7,8-tetrahydropyrido[4,3-d]pyrimidin-4-ol as a brown gum (260 mg, 76% yield) LCMS: [M+H]+=273.1, Rt$^{(3)}$=1.33 min.

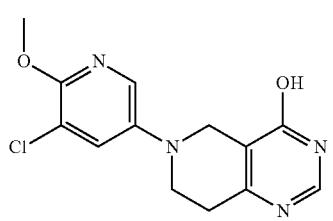 [SMILES: COc1ncc(N2CCc3ncnc(O)c3C2)cc1Cl]

INTERMEDIATE 18

6-(5-Chloro-6-methoxy-pyridin-3-yl)-5,6,7,8-tetrahydro-pyrido[4,3-d]pyrimidin-4-ol To 6-(5-chloro-6-methoxy-pyridin-3-yl)-4-methoxy-5,6,7,8-tetrahydro-pyrido[4,3-d]pyrimidine (intermediate 15)(95 mg, 0.31 mmol) in MeOH (5.0 mL) in a glass vial was added 2M NaOH(aq) (3.0 mL). The vial was capped and heated at 90° C. for 24 h. Acidified with glacial AcOH to pH 6, evaporated in vacuo and the residue extracted with CH$_2$Cl$_2$ (1×50 mL with stirring). With each extraction, the CH$_2$Cl$_2$ layer was decanted from the solid residue. The CH$_2$Cl$_2$ layers were combined. The solid residue was then washed with water (10 mL) and filtered. This filtered solid was combined with the CH$_2$Cl$_2$ layers and evaporated in vacuo to give 6-(5-chloro-6-methoxy-pyridin-3-yl)-5,6,7,8-tetrahydro-pyrido[4,3-d]pyrimidin-4-ol as a yellow solid (90 mg, 107% yield) LCMS: [M+H]+=293.0/294.8, Rt$^{(3)}$=1.38 min.

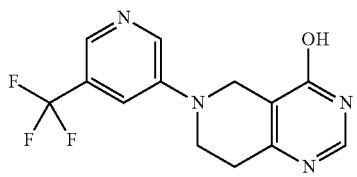 [SMILES: Oc1ncnc2c1CN(c1cncc(C(F)(F)F)c1)CC2]

INTERMEDIATE 19

6-(5-Trifluoromethyl-pyridin-3-yl)-5,6,7,8-tetrahydro-pyrido[4,3-d]pyrimidin-4-ol To 4-methoxy-6-(5-trifluoromethyl-pyridin-3-yl)-5,6,7,8-tetrahydro-pyrido[4,3-d]pyrimidine (intermediate 16) (190 mg, 0.612 mmol) in MeOH (2.0 mL) in a glass vial was added 2M NaOH(aq) (2.0 mL). The vial was capped and heated at 90° C. for 24 h. Acidified with glacial AcOH to pH 6, evaporated in vacuo and the residue extracted with CH$_2$Cl$_2$ (2×30 mL with sonication). With each extraction, the CH$_2$Cl$_2$ layer was decanted from the solid residue. The CH$_2$Cl$_2$ layers were combined and eluted through an Isolute® SCX-2 cartridge, eluting with methanol, then with 2M ammonia in methanol. Basic fractions were concentrated in vacuo to give 6-(5-(trifluoromethyl-pyridin-3-yl)-5,6,7,8-tetrahydro-pyrido[4,3-d]pyrimidin-4-ol as a yellow solid (167 mg) LCMS: [M+H]+=297.2, Rt$^{(4)}$=0.69 min.

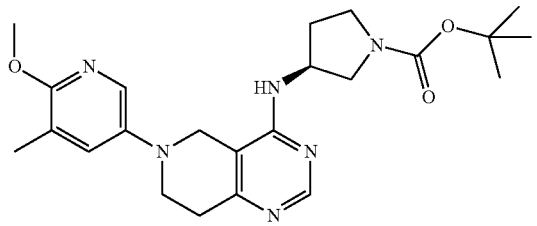 [SMILES: COc1ncc(N2CCc3ncnc(N[C@H]4CCN(C(=O)OC(C)(C)C)C4)c3C2)cc1C]

INTERMEDIATE 20

(S)-3-[6-(6-Methoxy-5-methyl-pyridin-3-yl)-5,6,7,8-tetrahydro-pyrido[4,3-d]pyrimidin-4-ylamino)-pyrrolidine-1-carboxylic acid tert-butyl ester To 6-(6-methoxy-5-trifluoromethyl-pyridin-3-yl)-5,6,7,8-tetrahydro-pyrido[4,3-d]pyrimidin-4-ol (intermediate 17) (178 mg, 0.654 mmol) in acetonitrile (2.0 mL) was added BOP (376 mg, 0.854 mmol) and DBU (0.197 mL, 1.31 mmol). The resulting solution was stood at rt for 2 min then added (S)-tert-butyl 3-aminopyrrolidine-1-carboxylate (365 mg, 1.96 mmol) in acetonitrile (2.0 mL) and heated the mixture at 75° C. for 72 h. The reaction mixture was evaporated in vacuo and purified by reverse phase Gilson HPLC (Method A) to give (S)-3-[6-(6-methoxy-5-methyl-pyridin-3-yl)-5,6,7,8-tetrahydro-pyrido[4,3-d]pyrimidin-4-ylamino)-pyrrolidine-1-carboxylic acid tert-butyl ester trifluoroacetate (60 mg, 17% yield) as a brown gum. LCMS: [M+H]+=441.2, Rt$^{(3)}$=1.50 min

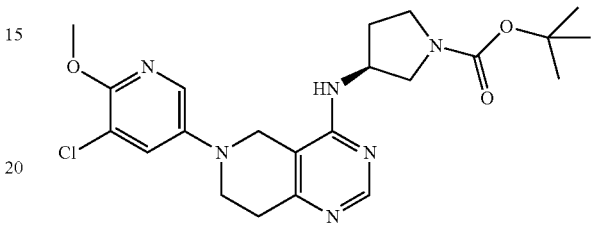

INTERMEDIATE 21

(S)-3-[6-(5-Chloro-6-methoxy-pyridin-3-yl)-5,6,7,8-tetrahydro-pyrido[4,3-d]pyrimidin-4-ylamino]-pyrrolidine-1-carboxylic acid tert-butyl ester To 6-(5-chloro-6-methoxypyridin-3-yl)-5,6,7,8-tetrahydro-pyrido[4,3-d]pyrimidin-4-ol (intermediate 18) (90 mg, 0.31 mmol) in acetonitrile (3.0 mL) was added BOP (177 mg, 0.40 mmol) and DBU (0.15 mL, 0.99 mmol). The resulting solution was stood at rt for 2 min then added (S)-tert-butyl 3-aminopyrrolidine-1-carboxylate (0.17, 0.93 mmol) and heated the mixture at 70° C. for 96 h. The reaction mixture was evaporated in vacuo and purified by reverse phase Gilson HPLC (Method A) to give (S)-3-[6-(5-chloro-6-methoxy-pyridin-3-yl)-5,6,7,8-tetrahydro-pyrido[4,3-d]pyrimidin-4-ylamino]-pyrrolidine-1-carboxylic acid tert-butyl ester trifluoroacetate (50 mg, 35% yield) as a brown gum. LCMS: [M+H]+=461.1/463.0, Rt$^{(4)}$=0.93 min.

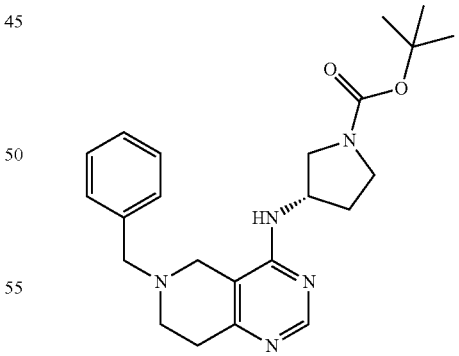

INTERMEDIATE 22

(S)-3-(6-Benzyl-5,6,7,8-tetrahydro-pyrido[4,3-d]pyrimidin-4-ylamino)-pyrrolidine-1-carboxylic acid tert-butyl ester 6-Benzyl-4-chloro-5,6,7,8-tetrahydro-pyrido[4,3-d]pyrimidine (5.0 g, 19.06 mmol), (S)-tert-butyl 3-aminopyrrolidine-1-carboxylate (4.11 g, 20.96 g) and triethylamine (3.98 mL, 28.6 mmol) were heated in a sealed vial at 120° C. for 42 h. The mixture was allowed to cool, diluted with tert-butyl methyl ether (100 mL) and the resulting suspension stirred for 10 min. The mixture was diluted with water (50 mL) and the organic layer separated. The organic layer was washed with brine (20 mL), dried (Na$_2$SO$_4$) and evaporated in vacuo to give a brown gum. The residue was purified by column chromatography on silica gel with EtOAc/MeOH, 98/2 to 82/18 to give (S)-3-(6-benzyl-5,6,7,8-tetrahydro-pyrido[4,3-d]pyrimidin-4-ylamino)-pyrrolidine-1-carboxylic acid tert-butyl ester as a pale yellow foam (7.36 g, 93% yield). $^1$H-NMR (400 MHz, CDCl$_3$, 298 K): δ ppm 1.48 (s, 9H) 2.10-2.31 (m, 2H) 2.80-2.96 (m, 4H) 3.15-3.87 (m, 8H) 4.44-4.77 (m, 1H) 5.62-5.73 (m, 1H) 7.29-7.45 (m, 5H) 8.50 (s, 1H). LCMS: [M+H]+=410.0, Rt$^{(6)}$=1.39 min.

Alternative Synthesis for Intermediate 22:

(S)-tert-Butyl-3-aminopyrrolidine-1-carboxylate (50 g, 192.5 mmol) was added to 6-benzyl-4-chloro-5,6,7,8-tetrahydro-pyrido[4,3-d]pyrimidine (39.440 g, 211.8 mmol) in NMP (200 mL) solution followed by the addition of K$_2$CO$_3$ (39.9 g, 288.8 mmol). The mixture was heated to 120° C. for 20 h. The mixture was allowed to cool, partitioned between water (300 mL) and ethylacetate (500 mL). the bottom aqueous phase was discarded and the upper organic phase was washed with brine (150 mL) and concentrated in vacuo to provide crude (S)-3-(6-benzyl-5,6,7,8-tetrahydro-pyrido[4,3-d]pyrimidin-4-ylamino)-pyrrolidine-1-carboxylic acid tert-butyl ester as a pale yellow foam (76.44 g, 97% yield).

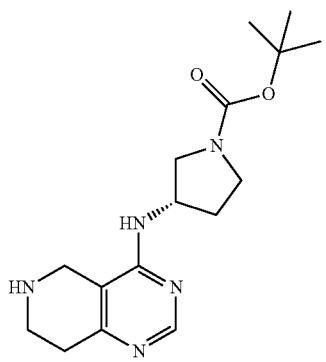 [SMILES: CC(C)(C)OC(=O)N1CC[C@H](Nc2ncnc3c2CNCC3)C1]

INTERMEDIATE 23

(S)-3-(5,6,7,8-Tetrahydro-pyrido[4,3-d]pyrimidin-4-ylamino)-pyrrolidine-1-carboxylic acid tert-butyl ester To a solution of (S)-3-(6-benzyl-5,6,7,8-tetrahydro-pyrido[4,3-d]pyrimidin-4-ylamino)-pyrrolidine-1-carboxylic acid tert-butyl ester (intermediate 22) (30.1 g, 73.5 mmol) in MeOH (100 mL) was added 20% palladium hydroxide on carbon (3.3 g) then ammonium formate (4.63 g, 73.5 mmol) and the mixture heated at reflux for 1 h. Added ammonium formate (0.38 g, 6.02 mmol) and continued heating at reflux for 30 min. The reaction mixture was allowed to cool and filtered through a celite pad, washing with MeOH (50 mL) then CH$_2$Cl$_2$ (50 mL). The filtrate was evaporated in vacuo to give a brown oil. Dissolved in CH$_2$Cl$_2$ (100 mL), added solid NaHCO$_3$ (10 g) and filtered through a celite pad. The filtrate was evaporated in vacuo to give a brown oil. Dissolved in EtOAc (50 mL) and a solid precipitated which was filtered to give (S)-3-(5,6,7,8-tetrahydro-pyrido[4,3-d]pyrimidin-4-ylamino)-pyrrolidine-1-carboxylic acid tert-butyl ester as a beige solid (15.55 g, 66% yield). $^1$H-NMR (400 MHz, DMSO-d$_6$, 298 K): δ ppm 1.40 (s, 9H) 1.81-1.98 (m, 1H) 2.05-2.17 (m, 1H) 2.92 (t, 2H) 3.10-3.46 (m, 5H) 3.49-3.63 (m, 3H) 4.47-4.63 (m, 1H) 6.46 (d, 1H, N—H) 8.25 (s, 1H). LCMS: [M+H]+=320.0, Rt$^{(6)}$=1.29 min.

Alternative Synthesis for Intermediate 23:

Pd(OH)$_2$/C (6.60 g, 5.3 mmol) was flushed with nitrogen, (S)-3-(6-benzyl-5,6,7,8-tetrahydro-pyrido[4,3-d]pyrimidin-4-ylamino)-pyrrolidine-1-carboxylic acid tert-butyl ester (intermediate 22) dissolved in methanol (164 mL) was added followed by the addition of triethylammonium formate (28.4 g, 188.0 mmol). The reaction mixture was refluxed for 1 h, cooled down to room temperature, filtered through a celite pad and the filtrate was concentrated under vacuum. the residue was recrystallized with methyl tert-butyl ether (200 mL) and heptanes (50 mL) to provide (S)-3-(5,6,7,8-tetrahydro-pyrido[4,3-d]pyrimidin-4-ylamino)-pyrrolidine-1-carboxylic acid tert-butyl ester as a beige solid (25.7 g, 85% yield).

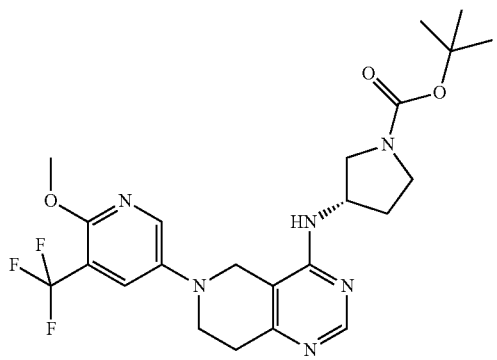 [SMILES: COc1ncc(N2CCc3ncnc(N[C@H]4CCN(C(=O)OC(C)(C)C)C4)c3C2)cc1C(F)(F)F]

INTERMEDIATE 24

(S)-3-[6-(6-Methoxy-5-trifluoromethyl-pyridin-3-yl)-5,6,7,8-tetrahydro-pyrido[4,3-d]pyrimidin-4-ylamino]-pyrrolidine-1-carboxylic acid tert-butyl ester To a glass vial was added (S)-3-(5,6,7,8-tetrahydro-pyrido[4,3-d]pyrimidin-4-ylamino)-pyrrolidine-1-carboxylic acid tert-butyl ester (intermediate 23) (3.5 g, 10.96 mmol), 5-bromo-2-methoxy-3-(trifluoromethyl)pyridine (intermediate 1) (3.09 g, 12.05 mmol), sodium tert-butoxide (1.58 g, 16.44 mmol), tris(dibenzylideneacetone)dipalladium(0) (0.502 g, 0.548 mmol), 2-di-t-butylphosphino-2'-(N,N-dimethylamino)biphenyl (0.225 g, 0.657 mmol) and anhydrous tert-butanol (6 mL). The vial was flushed with a stream of argon for 15 sec and capped. The mixture was heated with stirring for 5 h at 100° C. Allowed to cool and partitioned between EtOAc (100 mL) and water (20 mL) and filtered the biphasic mixture through a celite pad. The organic layer was separated, dried (MgSO$_4$) and concentrated in vacuo. Purified by flash column chromatography through Biotage® amino silica gel eluting with heptane/EtOAc, 100/0 to 0/100 then EtOAc/MeOH (90/10) to give (S)-3-[6-(6-methoxy-5-trifluoromethyl-pyridin-3-yl)-5,6,7,8-tetrahydro-pyrido[4,3-d]pyrimidin-4-ylamino]-pyrrolidine-1-carboxylic acid tert-butyl ester as a yellow foam (4.00 g, 74% yield). LCMS: [M+H]+=495.2, Rt$^{(3)}$=1.59 min.

Alternative Synthesis for Intermediate 24:

To a glass flask was added (S)-3-(5,6,7,8-tetrahydro-pyrido[4,3-d]pyrimidin-4-ylamino)-pyrrolidine-1-carboxylic acid tert-butyl ester (intermediate 23) (6.331 g, 15.86 mmol), 5-bromo-2-methoxy-3-(trifluoromethyl)pyridine (intermediate 1) (4.465 g, 17.442 mmol), sodium tert-butoxide (2.29 g, 23.78 mmol), tris(dibenzylideneacetone)dipalladium(0)

(0.726 g, 0.793 mmol), di-tert-butyl(2'-methylbiphenyl-2-yl)phosphine (0.297 g, 0.951 mmol) and anhydrous tert-butanol (30 mL). The flask was flushed with a stream of nitrogen for 15 sec and capped. The mixture was heated with stirring for 4 h under reflux. The mixture was allowed to cool to rt and partitioned between EtOAc (100 mL) and water (20 mL). The biphasic mixture was filtered the through a celite pad. The organic layer was separated and concentrated in vacuo to give crude (S)-3-[6-(6-methoxy-5-trifluoromethyl-pyridin-3-yl)-5,6,7,8-tetrahydro-pyrido[4,3-d]pyrimidin-4-ylamino]-pyrrolidine-1-carboxylic acid tert-butyl ester as a yellow foam (7.46 g, 95% yield).

INTERMEDIATE 25

(S)-3-[6-(5-Cyano-6-methoxy-pyridin-3-yl)-5,6,7,8-tetrahydro-pyrido[4,3-d]pyrimidin-4-ylamino]-pyrrolidine-1-carboxylic acid tert-butyl ester To a glass vial was added (S)-3-(5,6,7,8-tetrahydro-pyrido[4,3-d]pyrimidin-4-ylamino)-pyrrolidine-1-carboxylic acid tert-butyl ester (intermediate 23) (566 mg, 1.77 mmol), 5-bromo-2-methoxynicotinonitrile (453 mg, 2.13 mmol), cesium carbonate (1155 mg, 3.54 mmol), tris(dibenzylideneacetone)dipalladium(0) (162 mg, 0.18 mmol), X-Phos (287 mg, 0.60 mmol) and anhydrous tert-butanol (5 mL). The vial was flushed with a stream of argon for 15 sec and capped. The mixture was heated with stirring for 18 h at 110° C. Allowed to cool and partitioned between $CH_2Cl_2$ (20 mL) and water (10 mL) and filtered the biphasic mixture through a celite pad. The organic layer was separated by filtering through a phase separation tube and concentrated in vacuo. Purified by flash column chromatography on silica gel with heptane/EtOAc, 100/0 to 0/100 then EtOAc/MeOH (90/10) to give (S)-3-[6-(5-cyano-6-methoxy-pyridin-3-yl)-5,6,7,8-tetrahydro-pyrido[4,3-d]pyrimidin-4-ylamino]-pyrrolidine-1-carboxylic acid tert-butyl ester as a brown gum (234 mg, 29% yield). LCMS: [M+H]+=452.1, $Rt^{(4)}$=0.90 min.

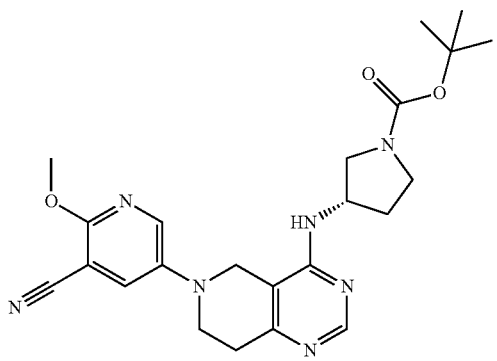 [SMILES: COc1ncc(N2CCc3ncnc(N[C@H]4CCN(C(=O)OC(C)(C)C)C4)c3C2)cc1C#N]

PREPARATION OF EXAMPLES

Scheme 1

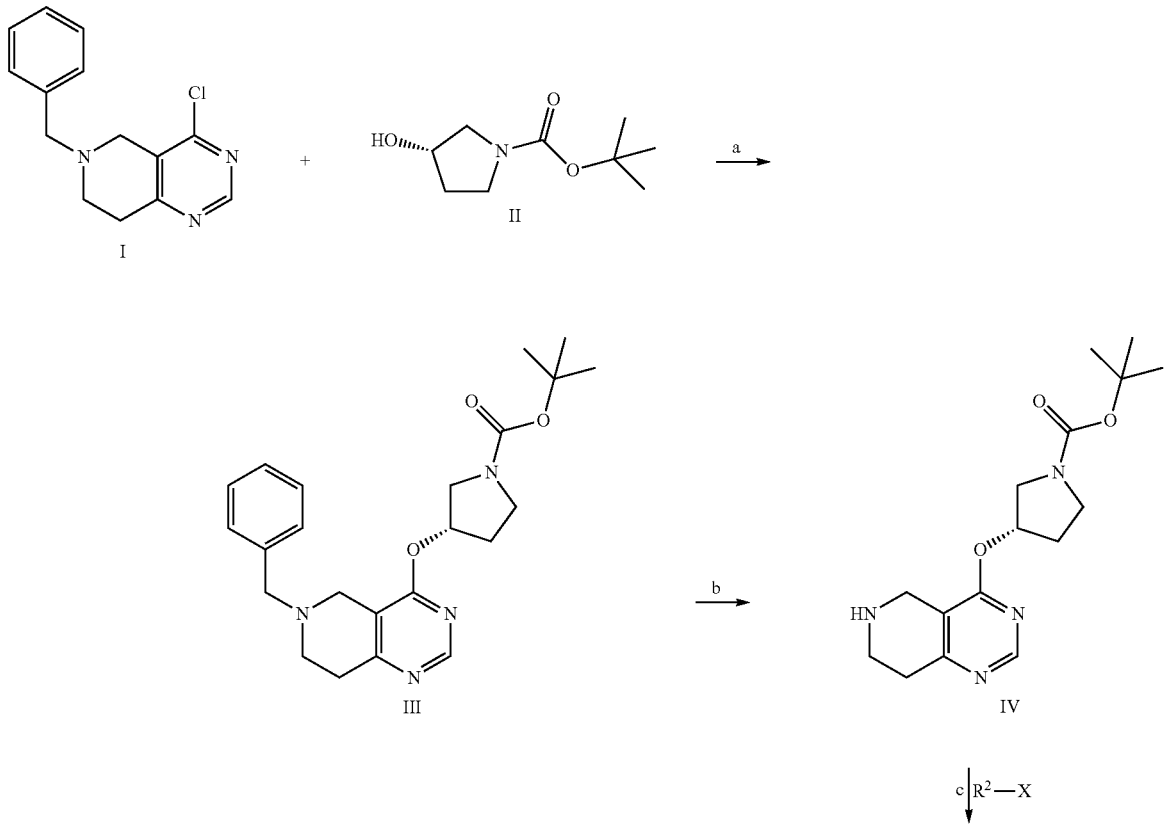

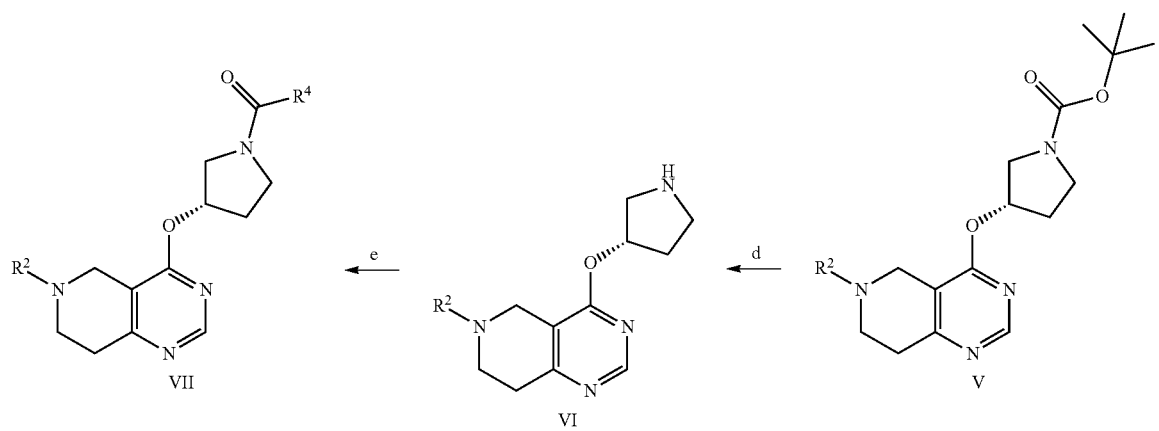

a) (S)-3-(6-Benzyl-5,6,7,8-tetrahydro-pyrido[4,3-d]pyrimidin-4-yloxy)-pyrrolidine-1-carboxylic acid tert-butyl ester III is firstly prepared by reacting 6-benzyl-4-chloro-5,6,7,8-tetrahydro-pyrido[4,3-d]pyrimidine with (S)-3-hydroxy-pyrrolidine-1-carboxylic acid tert-butyl ester in the presence of a suitable base such as sodium hydride (NaH) and polar organic solvent such as THF or dioxane under inert gas conditions at room temperature. b) N-debenzylation is performed under customary transfer hydrogenation conditions, using among the possible palladium catalysts, preferably palladium hydroxide on carbon Pd(OH)$_2$/C and among the possible formate salt preferably ammonium formate and organic solvent such as preferably methanol. The reaction is preferably carried out under refluxing conditions. c) Buchwald-Hartwig cross coupling between (S)-3-(5,6,7,8-tetrahydro-pyrido[4,3-d]pyrimidin-4-yloxy)-pyrrolidine-1-carboxylic acid tert-butyl ester IV and aryl bromide of the general formula R$^2$—X where X=Bromo or Iodo is performed under customary Buchwald-Hartwig conditions using such a ligand such as X-Phos or 2-di-t-butylphosphino-2'-(N,N-dimethylamino) biphenyl with a palladium catalyst such as Pd$_2$(dba)$_3$ or Pd$_2$(dba)$_3$.CHCl$_3$ or Pd(OAc)$_2$, preferably Pd$_2$(dba)$_3$ with X-Phos, base such as preferably Cs$_2$CO$_3$ or preferably tert-BuONa, and organic solvent such as preferably dioxane or preferably THF. The reaction is preferably stirred at a temperature of approximately 80-120° C., preferably 120° C. The reaction may preferably carry out under an inert gas such as nitrogen or argon. d) N—BOC deprotection is performed under customary BOC deprotection conditions using among the possible acid preferably trifluoro-acetic acid or HCl and suitable organic solvent such as CH$_2$Cl$_2$ or diethyl ether. The reaction is preferably performed at room temperature. e) Reaction of compounds of general formula VI with an acid chloride of formula R$^4$C(O)Cl or carboxylic acid of formula R$^4$C(O)OH. Those skilled in the art will appreciate that there are many known ways of preparing amides. For example, see Mantalbetti, C.A.G.N and Falque, V., Amide bond formation and peptide coupling, Tetrahedron, 2005, 61(46), pp 10827-10852 and references cited therein. The examples provided herein are thus not intended to be exhaustive, but merely illustrative.

The following general methods i-v have been used.

i. To a vigorously stirring solution of the acid chloride (1.3 eq.) in CH$_2$Cl$_2$ was added simultaneously portionwise excess sat. NaHCO$_3$(aq) and a solution of the amine of general formula VI (1.0 eq.) in CH$_2$Cl$_2$ at rt. The resulting biphasic mixture was stirred vigorously at rt for 2 h. The organic layer was separated, dried (MgSO$_4$), concentrated in vacuo and purified by either reverse phase chromatography, normal phase chromatography or crystallisation.

ii. To the amine of general formula VI (1.0 eq.) in CH$_2$Cl$_2$ was added the acid chloride (1.1 eq.) and triethylamine (3.0 eq.) at rt. The reaction mixture was stirred at room temperature for 1 h. The reaction mixture was concentrated under vacuum and subsequently partitioned between water and a suitable organic solvent and purified either reverse phase chromatography, normal phase chromatography or crystallisation.

iii. To the carboxylic acid (1.0 eq.) and HBTU (1.2 eq.) in DMF was added triethylamine (4.0 eq.). The mixture was stirred for 20 min and then the amine of general formula VI (1.0 eq.) in DMF was added. The mixture was allowed to stir overnight at room temperature and subsequently partitioned between water and a suitable organic solvent. The organic phase was separated, dried (MgSO$_4$), concentrated in vacuo and purified by either reverse phase chromatography, normal phase chromatography or crystallisation.

iv. To the carboxylic acid (1.0 eq.) and the amine general formula VI (1.0 eq.) in DMF was added DCC (1.2 eq.) in DMF. The reaction mixture was stirred at rt for 18 h and concentrated in vacuo and purified by either reverse phase chromatography, normal phase chromatography or crystallisation.

v. To the carboxylic acid (1.1 eq.) and the amine general formula VI (1.0 eq.) in CH$_2$Cl$_2$ was added benztriazol-1-ol (1.1 eq.) and EDC (1.6 eq.). The reaction mixture was stirred at rt for 18 h and subsequently partitioned between water and a suitable organic solvent. The organic phase was separated, dried (MgSO$_4$), concentrated in vacuo and purified by either reverse phase chromatography, normal phase chromatography or crystallization.

Scheme 2

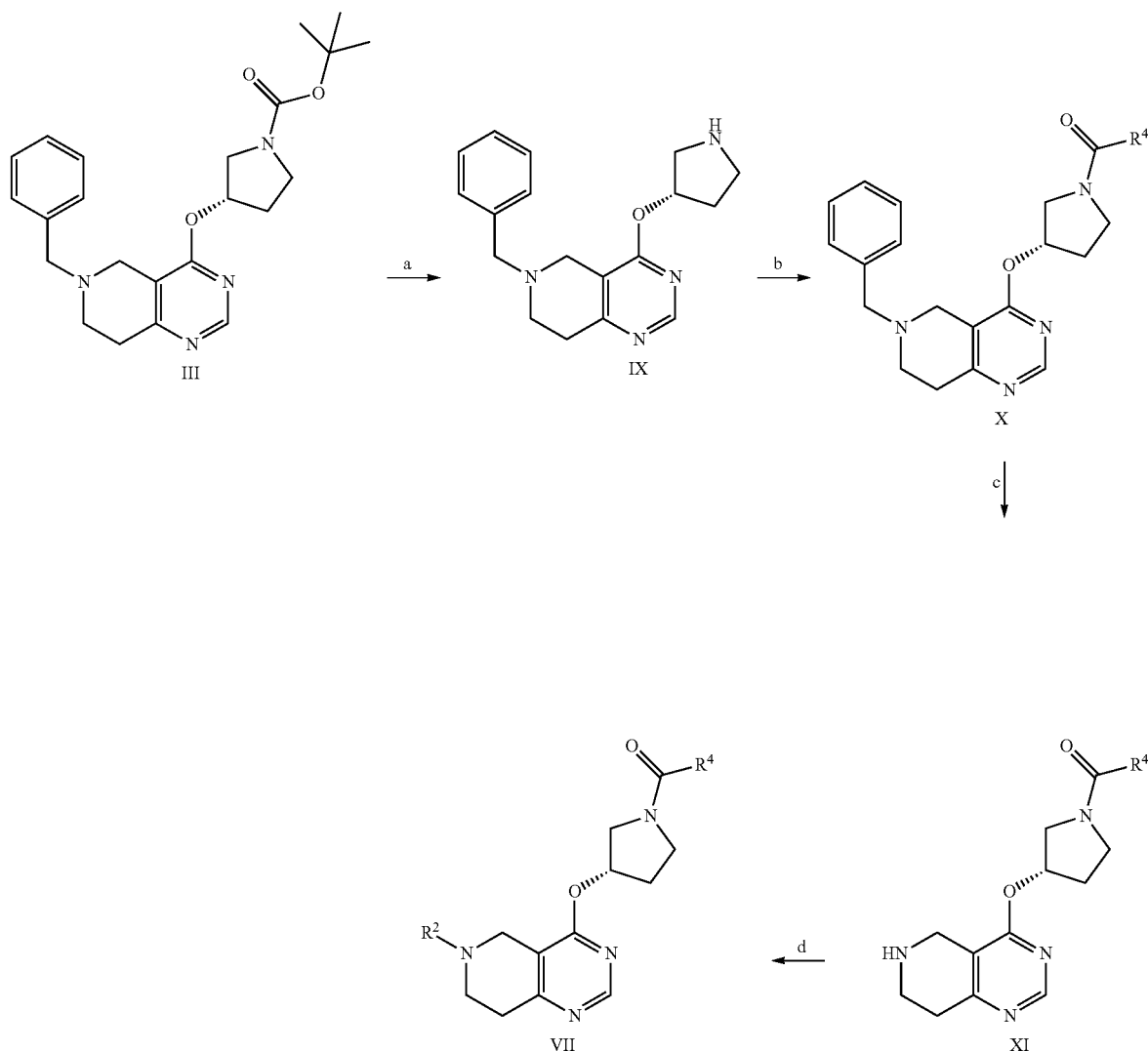

a) N—BOC deprotection is performed under customary BOC deprotection conditions using among the possible acid preferably trifluoro-actetic acid and organic solvent preferably $CH_2Cl_2$. The reaction is preferably performed at room temperature. b) Reaction of compound of general formula IX with an acid chloride of formula $R^4C(O)Cl$ or carboxylic acid of formula $R^4C(O)OH$ using general methods i-v as described in Scheme 1, step e. Those skilled in the art will appreciate that there are many known ways of preparing amides. For example, see Mantalbetti, C.A.G.N and Falque, V., Amide bond formation and peptide coupling, Tetrahedron, 2005, 61(46), pp 10827-10852 and references cited therein. The examples provided herein are thus not intended to be exhaustive, but merely illustrative.

c) Removal of the benzyl protecting group is performed using standard methodology as described in "Protecting groups in Organic Synthesis" by T. W. Greene and P. Wutz, $3^{rd}$ edition, 1999, John Wiley and Sons. Typical conditions comprise of 1.0 eq. of compound of general formula X (8.0 eq. of ammonium formate and 20% (w/w) palladium hydroxide $Pd(OH)_2/C$ (catalyst) heated under reflux in methanol. d) Buchwald-Hartwig cross coupling between compound of general formula XI and compounds of general formula $R^2$—X where X=Bromo or Iodo is performed under customary Buchwald-Hartwig conditions using such a ligand such as X-Phos or 2-di-t-butylphosphino-2'-(N,N-dimethylamino) biphenyl with a palladium catalyst such as $Pd_2(dba)_3$ or $Pd_2(dba)_3.CHCl_3$ or $Pd(OAc)_2$, preferably $Pd_2(dba)_3$ with X-Phos, base such as preferably $Cs_2CO_3$ or preferably tert-BuONa, and organic solvent such as preferably dioxane or preferably THF. The reaction is preferably stirred at a temperature of approximately 80-150° C., preferably 120° C. The reaction may preferably be carried out under an inert gas such as nitrogen or argon.

Scheme 3
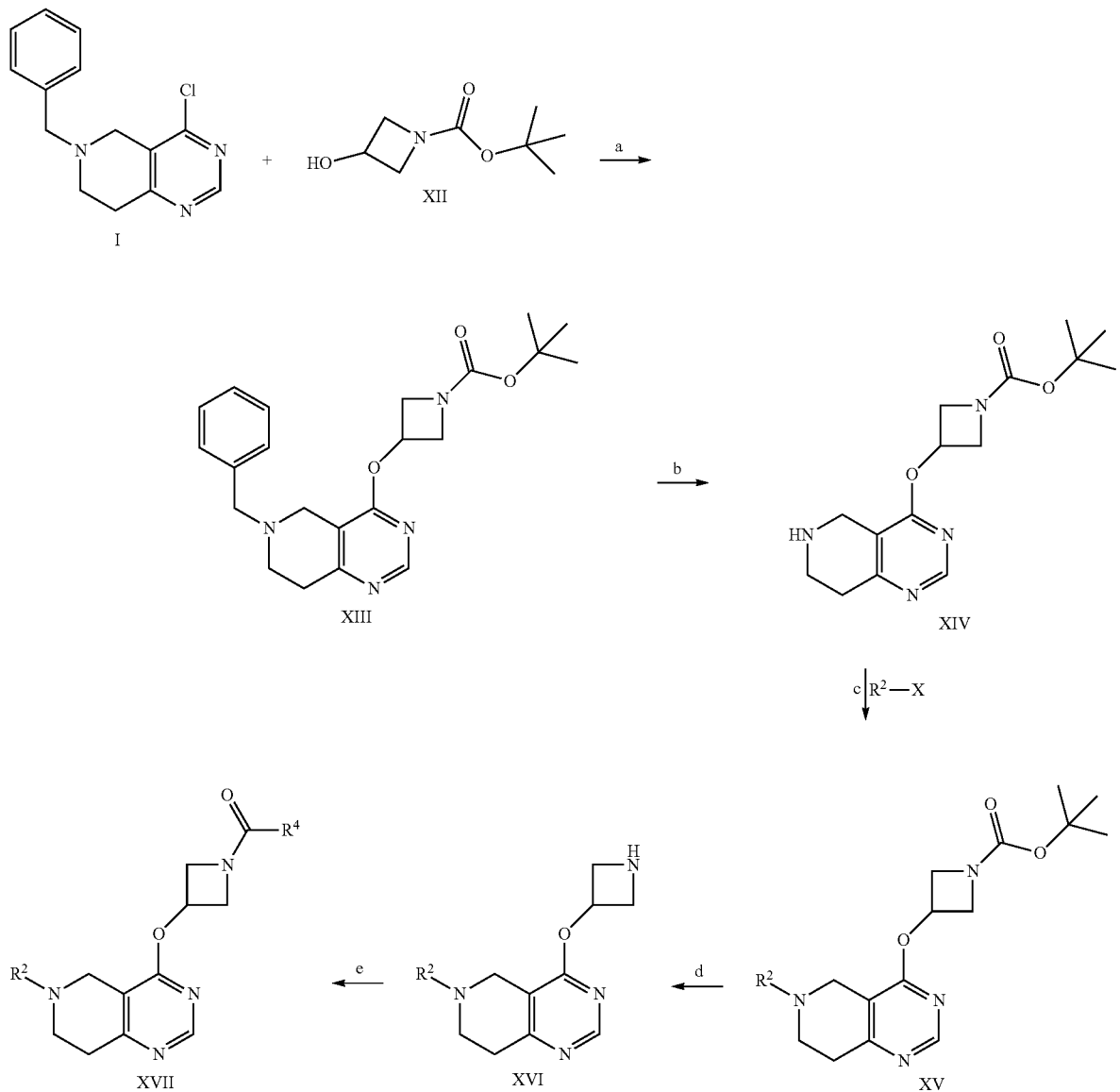
Compounds of general formula XVII can be prepared in a similar manner as described for steps a-e in Scheme 1, starting from 6-benzyl-4-chloro-5,6,7,8-tetrahydro-pyrido[4,3-d]pyrimidine (I) and tert-butyl 3-hydroxyazetidine-1-carboxylate (XII).
Scheme 4
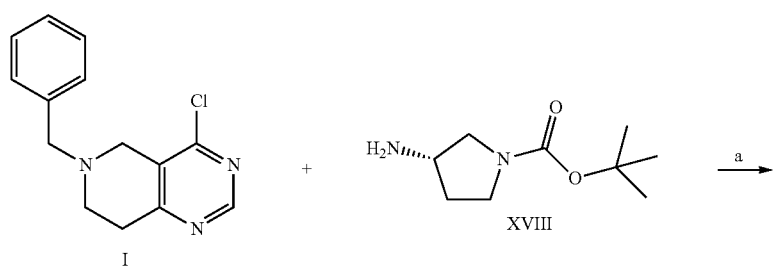

-continued

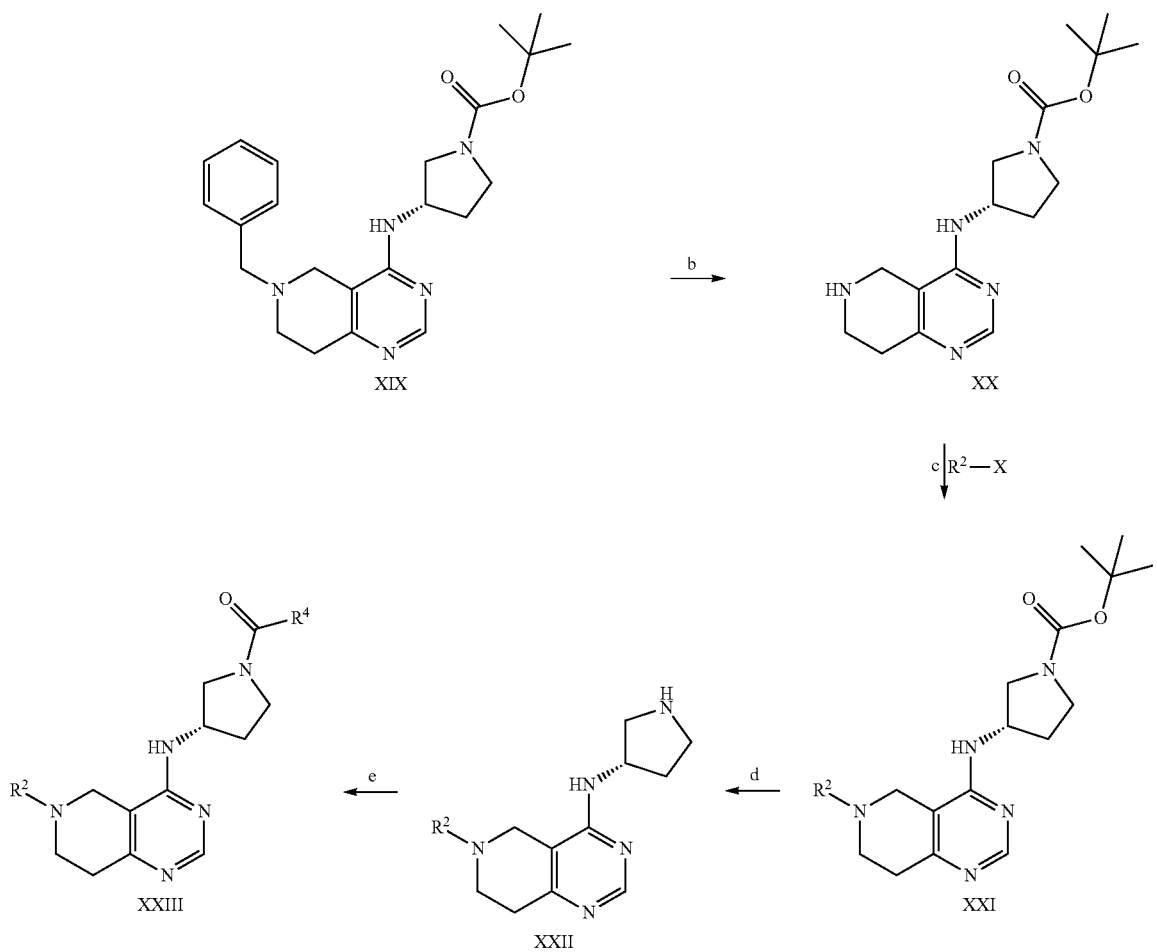

a) (S)-3-(6-Benzyl-5,6,7,8-tetrahydro-pyrido[4,3-d]pyrimidin-4-yloxy)-pyrrolidine-1-carboxylic acid tert-butyl ester XIX is firstly prepared by reacting 6-benzyl-4-chloro-5,6,7,8-tetrahydro-pyrido[4,3-d]pyrimidine with (S)-3-Amino-pyrrolidine-1-carboxylic acid tert-butyl ester in the presence of a suitable base such as triethylamine or N,N-diisopropyl-ethylamine at elevated temperature (e.g. 120° C.) for 24-48 h. Typical conditions comprise of 1.0 eq. of 6-benzyl-4-chloro-5,6,7,8-tetrahydro-pyrido[4,3-d]pyrimidine, 1.0 eq. of (S)-3-amino-pyrrolidine-1-carboxylic acid tert-butyl ester and 1.5 eq. of triethylamine at 120° C. for 48 h. b) Removal of the benzyl protecting group is performed using standard methodology as described in "Protecting groups in Organic Synthesis" by T. W. Greene and P. Wutz, 3$^{rd}$ edition, 1999, John Wiley and Sons. Typical conditions comprise of 1.0 eq.t of (S)-3-(6-benzyl-5,6,7,8-tetrahydro-pyrido[4,3-d]pyrimidin-4-yloxy)-pyrrolidine-1-carboxylic acid tert-butyl ester XIX, 1.1-8.0 eq. of ammonium formate and 20% (w/w) palladium hydroxide Pd(OH)$_2$/C (catalyst) heated under reflux in methanol. c) (S)-3-(5,6,7,8-Tetrahydro-pyrido[4,3-d]pyrimidin-4-yloxy)-pyrrolidine-1-carboxylic acid tert-butyl ester XX is reacted with halide R$^2$—X (where R$^2$ is defined above and X is halo and preferably bromo or iodo), in the presence of a suitable base such as sodium tert-butoxide or cesium carbonate and a suitable catalyst system such as Pd$_2$(dba)$_3$ with 2-di-t-butylphosphino-2'-(N,N-dimethylamino)biphenyl or Pd$_2$(dba)$_3$ with X-Phos in a suitable solvent such as anhydrous tert-butanol or anhydrous dioxane, heated at elevated temperature (e.g. 100° C.). The reaction may preferably be carried out under an inert gas such as nitrogen or argon. Typical conditions comprise of 1 eq. of (S)-3-(5,6,7,8-tetrahydro-pyrido[4,3-d]pyrimidin-4-yloxy)-pyrrolidine-1-carboxylic acid tert-butyl ester XX, 1-1.5 eq. of R2-X, 1.5-2.0 eq. of sodium tert-butoxide, 5-10 mol % Pd$_2$(dba)$_3$ and 5-10 mol % 2-di-t-butylphosphino-2'-(N,N-dimethylamino)biphenyl in anhydrous tert-butanol at 100° C. for 5-24 hours under an atmosphere of argon. d) N-Boc deprotection is performed under customary Boc deprotection conditions with a suitable acid such as trifluoroactetic acid in a suitable solvent such as CH$_2$Cl$_2$ at room temperature. Typical conditions comprise of 1 eq. of compound of general formula XII in excess trifluoroacetic acid in CH$_2$Cl$_2$ at room temperature for 1-3 h. e) Reaction of compounds of general formula XXII with an acid chloride of formula R$^4$C(O)Cl or carboxylic acid of formula R$^4$C(O)OH using general methods i-v as described in Scheme 1, step e. Those skilled in the art will appreciate that there are many known ways of preparing amides. For example, see Mantalbetti, C.A.G.N and Falque, V., Amide bond formation and peptide coupling, Tetrahedron, 2005, 61(46), pp 10827-10852 and references cited therein. The examples provided herein are thus not intended to be exhaustive, but merely illustrative.

Scheme 5

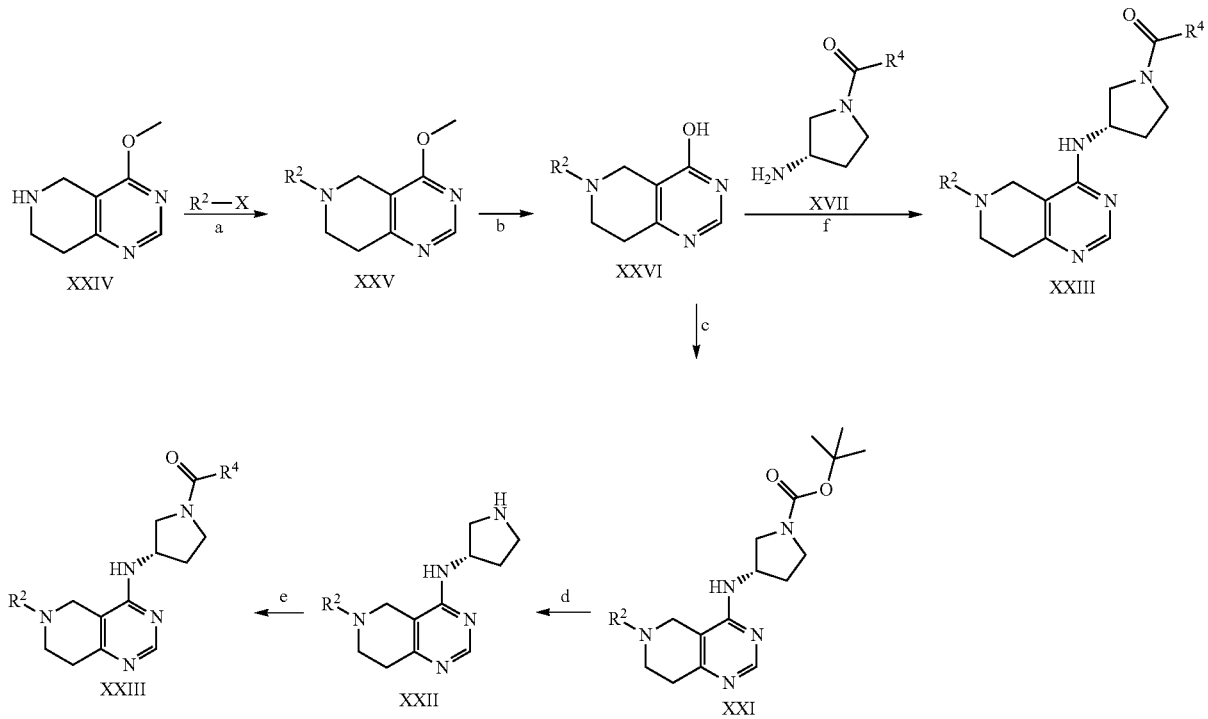

a) 4-Methoxy-5,6,7,8-tetrahydro-pyrido[4,3-d]pyrimidine (WO 2008/130481, p 47) is reacted with halide $R^2$—X (where $R^2$ is defined above and X is halo and preferably bromo or iodo), in the presence of a suitable base such as cesium carbonate or sodium tert-butoxide and a suitable catalyst system such as $Pd_2(dba)_3$ with X-Phos or $Pd(OAc)_2$ with X-Phos in a suitable solvent such as dioxane or THF, heated at elevated temperature (e.g. 110° C.). The reaction may preferably be carried out under an inert gas such as nitrogen or argon. Typical conditions comprise of 1 eq. of 4-methoxy-5,6,7,8-tetrahydro-pyrido[4,3-d]pyrimidine, 1-1.5 eq. of R2-X, 1.5-2.0 eq. of cesium carbonate, 5-10 mol % $Pd_2(dba)_3$ and 5-10 mol % X-Phos in dioxane at 110° C. for 5-24 hours under an atmosphere of argon. b) Compounds of general formula XXV is reacted with aqueous sodium hydroxide in a suitable solvent such as methanol or dioxane at elevated temperature (e.g. 100° C.) for 18-24 h. Typical conditions comprise of 1 eq. of compounds of general formula XXV in excess 2N sodium hydroxide(aq) in methanol at 100° C. for 18 h. c) Compounds of general formula XXI can be prepared using a base promoted phosphonium coupling reaction whereby compounds of general formula)(XVI in a suitable solvent such as acetonitrile is reacted with a phosphonium salt such as benzotriazol-1-yloxytris(dimethylamino)phosphonium hexafluorophosphate (BOP) in the presence of a base such as 1,8-diaza-7-bicyclo[5.4.0]undecene (DBU) followed by addition of (S)-tert-butyl 3-aminopyrrolidine-1-carboxylate. The reaction mixture is preferably stirred at a temperature of 20° C. to 90° C. for 18-72 h. The reaction may preferably be carried out under an inert gas, e.g. nitrogen or argon. Typical conditions comprise of 1 equivalent of compounds of general formula)(XVI, 1.0-1.5 eq. of BOP, 2.0-4.0 eq. of DBU and 2.0-3.0 eq. of (S)-tert-butyl 3-aminopyrrolidine-1-carboxylate in acetonitrile at 65° C. for 72 hours under argon. Steps d) and e) can be carried out in a similar manner described for steps d) and e) in Scheme 1. Step f) can be carried out using a base promoted phosphonium coupling reaction in a similar manner as step c) in Scheme 5. Typical conditions comprise of 1 eq. of compounds of general formula)(XVI, 1.0-1.5 eq. of BOP, 2.0-4.0 eq. of DBU and 2.0-3.0 eq. of amine of general formula XVII in acetonitrile at 90° C. for 24 hours under argon.

Scheme 6

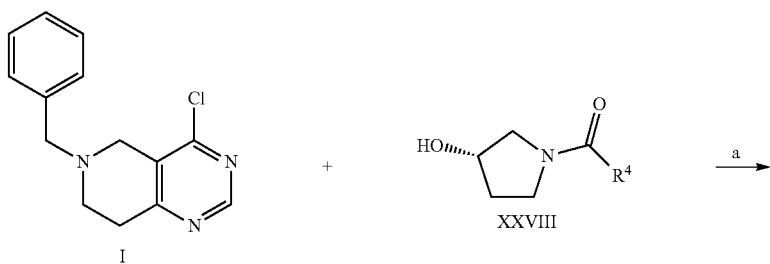

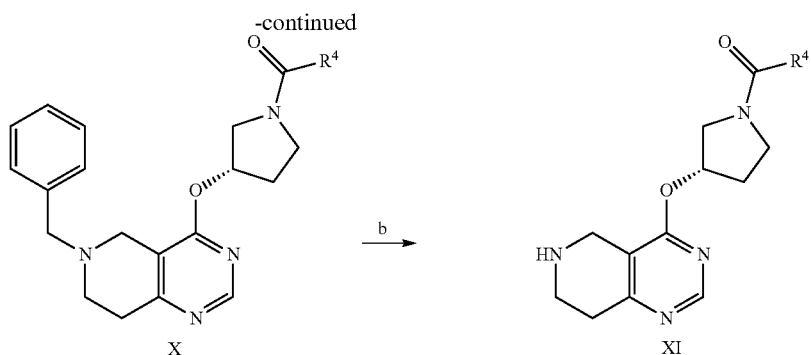

a) Alcohol of general formula XXVIII is reacted with the 6-benzyl-4-chloro-5,6,7,8-tetrahydro-pyrido[4,3-d]pyrimidine under customary conditions by deprotonation of the secondary alcohol using sodium hydride (NaH) and organic solvent THF under inert gaz conditions at room temperature.
b) N-debenzylation is performed under customary transfer hydrogenation conditions, using among the possible palladium catalysts, preferably palladium hydroxide Pd(OH)$_2$ and among the possible formate salt preferably ammonium formate and organic solvent such as preferably methanol. The reaction is preferably carried out under refluxing conditions.
c) Buchwald-Hartwig cross coupling between compound of general formula XI and compounds of general formula $R^2$—X is performed under customary Buchwald-Hartwig conditions using such a ligand such as X-Phos or 2-di-t-butylphosphino-2'-(N,N-dimethylamino)biphenyl with a palladium catalyst such as Pd$_2$(dba)$_3$ or Pd$_2$(dba)$_3$.CHCl$_3$ or Pd(OAc)$_2$, preferably Pd$_2$(dba)$_3$ with X-Phos, base such as preferably Cs$_2$CO$_3$ or preferably tert-BuONa, and organic solvent such as preferably dioxane or preferably THF. The reaction is preferably stirred at a temperature of approximately 80-150° C., preferably 120° C. The reaction may preferably carried out under an inert gas such as nitrogen or argon.

Scheme 7

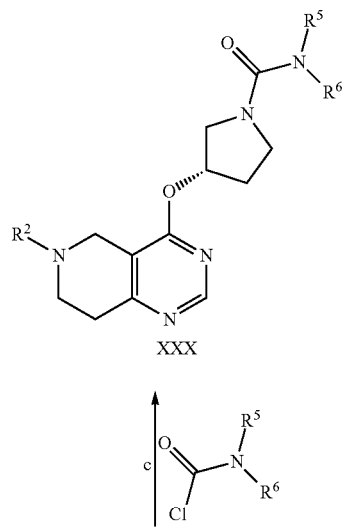

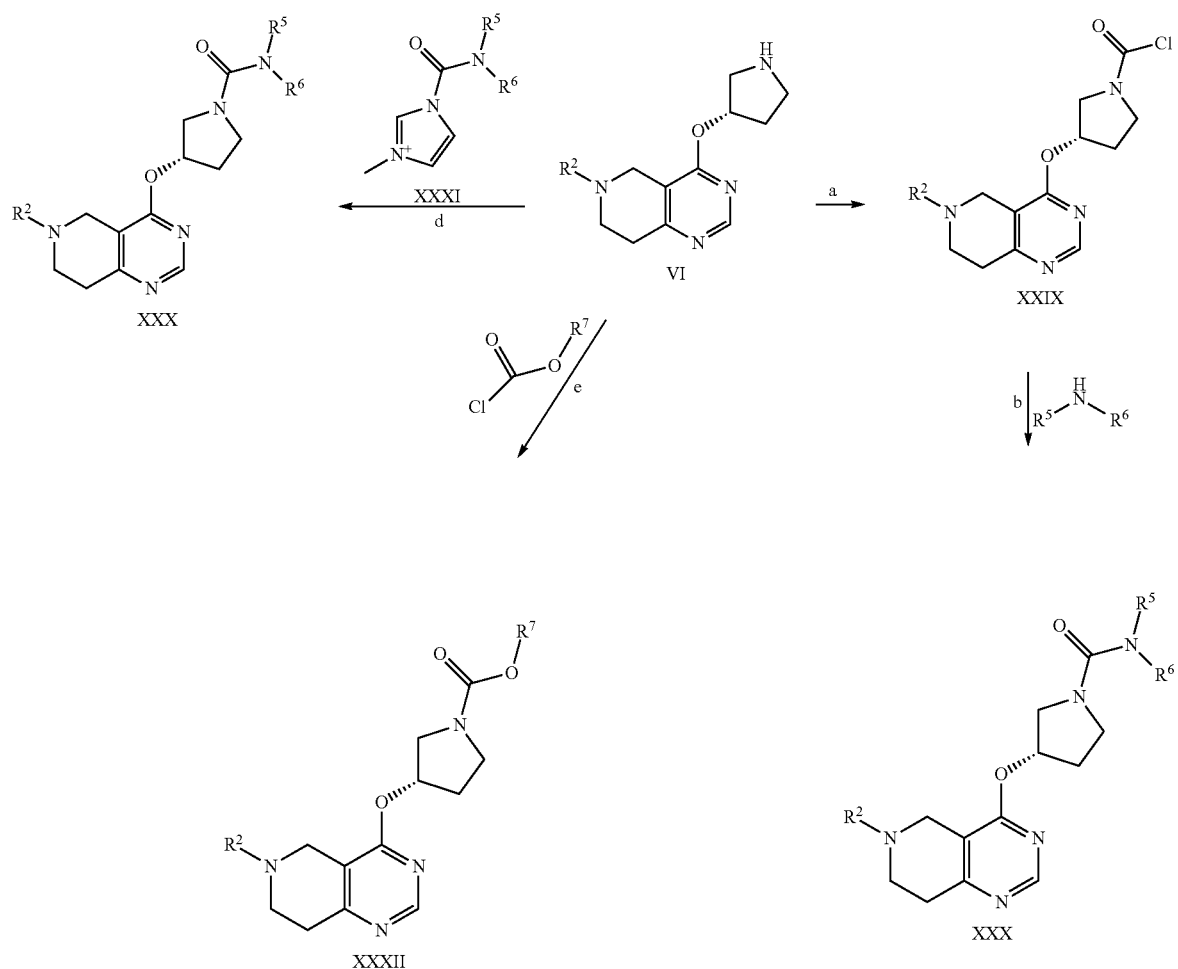

a) Compounds of general formula VI is reacted with phosgene in a suitable solvent such as CH$_2$Cl$_2$ in the presence of a suitable base such as triethylamine or N,N-diisopropylethylamine at a temperature of 0° C. to 25° C. for 1-2 hours. The reaction may preferably be carried out under an inert gas such as nitrogen or argon. Typical conditions comprise 1.0 eq. of compound of general formula VI, 1.0-5.0 eq. of phosgene, 3.0-4.0 eq. of triethylamine in CH$_2$Cl$_2$ under argon for 1 hour. b) Compound of general formula XXIX is reacted with amine R5R6NH in the presence of a suitable base such as triethylamine or N,N-diisopropylethylamine in a suitable solvent such as CH$_2$Cl$_2$ or N,N-dimethylformamide at a temperature of 10° C. to 30° C. for 1-18 h. The reaction may preferably be carried out under an inert gas such as nitrogen or argon. Typical conditions comprise 1.0 eq. of compound of general formula XXIX, 1.0-1.2 eq. of R$^5$R$^6$NH, 3.0-4.0 eq. of triethylamine in CH$_2$Cl$_2$ under argon for 2 hours. c) Compounds of general formula VI is reacted with carbamoyl chloride R$^5$R$^6$NCOCl in the presence of a suitable base such as triethylamine or N,N-diisopropylethylamine in a suitable solvent such as CH$_2$Cl$_2$ or N,N-dimethylformamide at a temperature of 0° C. to 25° C. for 1-18 hours. The reaction may preferably be carried out under an inert gas such as nitrogen or argon. Typical conditions comprise 1.0 eq. of compound of general formula VI, 1.0-1.2 eq. of R$^5$R$^6$NCOCl, 3.0-4.0 eq. of triethylamine in CH$_2$Cl$_2$ under argon for 18 hours. d) Compounds of general formula VI is reacted with compounds of general formula XXXI in the presence of a suitable base such as triethylamine or N,N-diisopropylethylamine in a suitable solvent such as CH$_2$Cl$_2$ or N,N-dimethylformamide at a temperature of 0° C. to 25° C. for 1-18 hours. The reaction may preferably be carried out under an inert gas such as nitrogen or argon. Typical conditions comprise 1.0 eq. of compound of general formula VI, 1.0-1.2 eq. of compound of general formula XXXI, 1.0-2.0 eq. of triethylamine in CH$_2$Cl$_2$ under argon for 18 hours. e) Compounds of general formula VI is reacted with compounds of formula R$^7$OCOCl in the presence of a suitable base such as triethylamine or N,N-diisopropylethylamine in a suitable solvent such as CH$_2$Cl$_2$ or N,N-dimethylformamide at a temperature of 0° C. to 25° C. for 1-18 hours. The reaction may preferably be carried out under an inert gas such as nitrogen or argon. Typical conditions comprise 1.0 eq. of compound of general formula VI, 1.0-1.2 eq. of compounds of general formula R$^7$OCOCI, 3.0-4.0 eq. of triethylamine in CH$_2$Cl$_2$ under argon for 18 hours.

Scheme 8

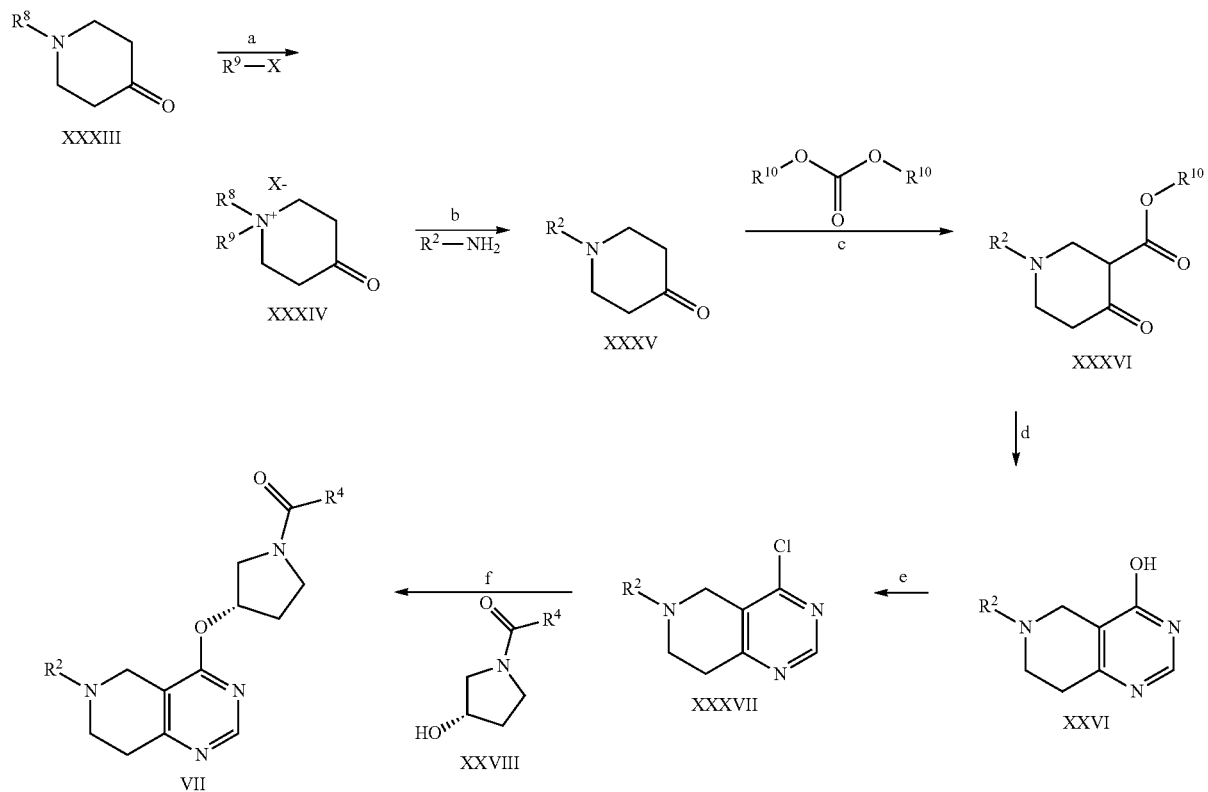

a) Quaternarization of the tertiary amine of general formula XXXIII (where $R^8$=alkyl e.g. benzyl) with compound of general formula $R^9$—X (where $R^9$=alkyl e.g. methyl and X=Bromo or Iodo) under customary conditions using in particular acetone as organic solvent. b) Alkylation of amine of general formula $R^2$—$NH_2$ with quaternary amine XXXIV was performed by using base such a in particular $K_2CO_3$ and organic solvent such as in particular a 2/1 mixture of ethanol and water and heating the reaction mixture at 80-100° C., in particular 80° C. c) Compound of general formula XXXV was reacted with base such as in particular NaH and compound of general formula $(R^{10}O)_2CO$ (where $R^{10}$=alkyl e.g. carbonic acid dimethyl ester). The reaction mixture is stirred under high temperature (90° C.). d) Pyrimidine ring formation was obtained by reacting the compound of general formula XXXVI with formamidine acetate with a base such as sodium methoxide and organic solvent such as methanol at elevated temperature such as 90° C. for 2-18 h. e) Compound of general formula XXVI was reacted with phosphoryl chloride in presence of base such as triethylamine in organic solvent such as toluene at elevated temperature such as 100° C. for 12-18 h. f) Alcohol of general formula XXVIII is reacted with Compound of general formula XXXVII under customary conditions by deprotonation of the secondary alcohol using sodium hydride (NaH) and organic solvent THF under inert gas conditions at room temperature.

Where it is stated that compounds were prepared in the manner described for an earlier example, the skilled person will appreciate that reaction times, number of equivalents of reagents and reaction temperatures may be modified for each specific reaction, and that it may nevertheless be necessary or desirable to employ different work-up or purification conditions.

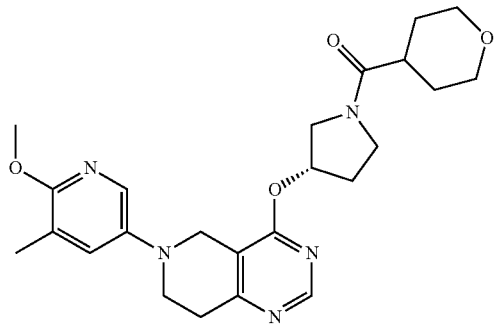 [SMILES: COc1ncc(N2CCc3ncnc(O[C@H]4CCN(C(=O)C5CCOCC5)C4)c3C2)cc1C]

Example 1

{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone Synthesis of Example 1—Method 1a (According to Scheme 8)

Sodium hydride (60% in dispersion oil, 17.88 mg, 0.447 mmol) was added under argon to a solution of intermediate 3 (75 mg, 0.378 mmol) in 2 mL of dry THF. The suspension was stirred under an atmosphere of argon at ambient temperature for 15 min. 4-Chloro-6-(6-methoxy-5-methyl-pyridin-3-yl)-5,6,7,8-tetrahydro-pyrido[4,3-d]pyrimidine (100 mg, 0.344 mmol) was added and stirred at rt for an additional 3 hours.

The reaction mixture was quenched with H₂O, extracted with CH₂Cl₂. The organic layer was washed with brine, dried over Na₂SO₄, filtered and evaporated to dryness. Purification by flash-chromatography on silica gel (CH₂Cl₂/MeOH 95/5) gave {(S)-3-[6-(6-methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone as a light yellow gum (115 mg, 74% yield). ¹H-NMR (400 MHz, methanol-d4, 298K) δ ppm 1.59-1.87 (m, 4H) 2.20 (s, 3H) 2.27-2.43 (m, 2H) 2.74-2.91 (m, 1H) 2.97-3.03 (m, 2H) 3.42-4.14 (m, 15H) 5.75-5.86 (m, 1H) 7.39-7.43 (m, 1H) 7.63-7.68 (m, 1H) 8.57-8.61 (m, 1H). LCMS: [M+H]⁺=454.2, Rt⁽³⁾=1.46 min.

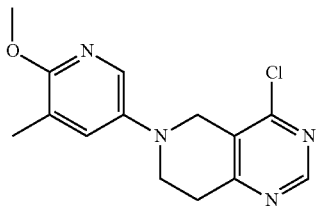 [SMILES: COc1ncc(N2CCc3ncnc(Cl)c3C2)cc1C]

4-Chloro-6-(6-methoxy-5-methyl-pyridin-3-yl)-5,6,7,8-tetrahydro-pyrido[4,3-d]pyrimidine A mixture of 6-(6-methoxy-5-methyl-pyridin-3-yl)-5,6,7,8-tetrahydro-pyrido[4,3-d]pyrimidin-4-ol (650 mg, 2.387 mmol), phosphoroxy chloride (0.334 mL, 3.58 mmol), triethylamine (0.665 mL, 4.77 mmol) and toluene (12 mL) was heated at 100° C. for 16 h. The mixture was neutralized with the addition of solid sodium bicarbonate, filtered and the solution was concentrated in vacuum. The remaining black residue was taken up in CH₂Cl₂ and water, the layers were separated and the organic phase washed with brine, dried over sodium sulfate, filtered and concentrated to give a dark brown solid. The solid was triturated in ethylacetate, filtered and dried under high vacuum to yield 4-chloro-6-(6-methoxy-5-methyl-pyridin-3-yl)-5,6,7,8-tetrahydro-pyrido[4,3-d]pyrimidine (630 mg, 91% yield) as a tan solid. ¹H-NMR (400 MHz, DMSO-d6, 298K) δ ppm 2.15 (s, 3H) 3.03 (t, 2H) 3.53 (t, 2H) 3.82 (s, 3H) 4.26 (s, 2H) 7.49 (dd, 1H) 7.74 (d, 1H) 8.85 (s, 1H). LCMS: [M+H]⁺=291.1, Rt⁽⁴⁾=0.97 min.

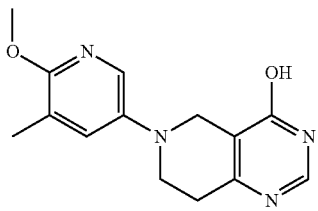 [SMILES: COc1ncc(N2CCc3ncnc(O)c3C2)cc1C]

6-(6-Methoxy-5-methyl-pyridin-3-yl)-5,6,7,8-tetrahydro-pyrido[4,3-d]pyrimidin-4-ol A mixture of 6'-methoxy-5'-methyl-4-oxo-3,4,5,6-tetrahydro-2H-[1,3']bipyridinyl-3-carboxylic acid methyl ester (900 mg, 3.23 mmol), formamidine acetate (521 mg, 4.85 mmol), sodium methoxide (5.4 Molar) in methanol (2.395 mL, 12.94 mmol) and methanol (4 mL) was heated to 90° C. for 3 h. The mixture was allowed to cool down to rt, diluted in CH₂Cl₂, neutralized with acetic acid (0.741 mL, 12.94 mmol) and quenched with H₂O. The layers were separated and aqueous was washed twice with CH₂Cl₂, organics were combined, washed with brine, dried over sodium sulfate, filtered and evaporated to give a yellow solid. The solid was triturated in ethylacetate to yield 6-(6-methoxy-5-methyl-pyridin-3-yl)-5,6,7,8-tetrahydro-pyrido[4,3-d]pyrimidin-4-ol (669 mg, yield 76%) as a white powder. ¹H-NMR (400 MHz, DMSO-d6, 298K) δ ppm 2.14 (s, 3H) 2.72 (t, 2H) 3.39 (t, 2H) 3.81 (s, 3H) 3.90 (s, 2H) 7.42 (d, 1H) 7.67 (d, 1H) 8.07 (s, 1H) 12.46 (br.s., 1H). LCMS: [M+H]⁺=273.1, Rt⁽³⁾=1.30 min.

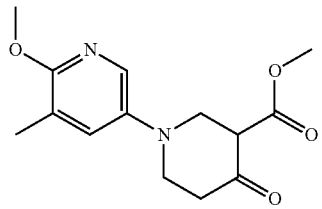 [SMILES: COC(=O)C1CN(c2cnc(OC)c(C)c2)CCC1=O]

6'-Methoxy-5'-methyl-4-oxo-3,4,5,6-tetrahydro-2H-[1,3']bipyridinyl-3-carboxylic acid methyl ester To a stirred suspension of sodium hydride (60%, 153 mg, 6.36 mmol) in dimethyl carbonate (3.82 mL, 45.4 mmol) at room temperature was slowly added 6'-methoxy-5'-methyl-2,3,5,6-tetrahydro-[1,3']bipyridinyl-4-one (1 g, 4.54 mmol). The reaction mixture was heated to reflux (90° C.) for 1 h and then cooled to room temperature. The mixture was partitioned between CH₂Cl₂ and water and a solution of 1N HCl was added cautiously. The aqueous layer was separated and washed with an addition portion of CH₂Cl₂. The combined organic extracts were washed with brine, dried over sodium sulfate, filtered and evaporated to give the crude product, which was purified by flash-chromatography on silica gel (heptane/ethylacetate 3/1) to afford 6'-methoxy-5'-methyl-4-oxo-3,4,5,6-tetrahydro-2H-[1,3']bipyridinyl-3-carboxylic acid methyl ester (975 mg, yield 77%) as a white solid. ¹H-NMR (400 MHz, DMSO, 298K) (mixture of keto and enol tautomers observed) δ ppm 2.12 (s, 6H) 2.36-2.69 (m, 4H) 3.26-3.96 (m, 20H) 7.34-7.77 (m, 4H) 11.84 (s, 1H). LCMS: [M+H]⁺=279.1, Rt⁽³⁾=1.51 min (tautomer 1) and 1.70 min (tautomer 2).

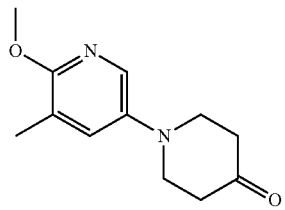 [SMILES: COc1ncc(N2CCC(=O)CC2)cc1C]

6'-Methoxy-5'-methyl-2,3,5,6-tetrahydro-[1,3']bipyridinyl-4-one

A slurry of iodide salt 1-benzyl-1-methyl-4-oxo-piperidinium (Ref: Tortolani, R.; Org. Lett., Vol. 1, No 8, 1999) (3.61 g, 10.86 mmol) in water (10 mL) was added slowly to a refluxing solution of 2-methoxy-5-amino-3-picolin (1 g, 7.24 mmol) and potassium carbonate (0.140 g, 1.013 mmol) in ethanol (20 mL). The reaction mixture was heated to reflux for an additional 3 h. The reaction mixture was cooled to rt and partitioned between CH₂Cl₂ and water. The organic layer was separated and washed with an addition portion of CH$_2$Cl$_2$. The combined organic layers were washed with brine, dried over sodium sulfate, filtered and concentrated to give the crude product which was purified by flash-chromatography on silica gel (heptane/ethylacetate 1/1) to afford 6'-methoxy-5'-methyl-2,3,5,6-tetrahydro-[1,3]bipyridinyl-4-one (1.15 g, yield 72%) as a light yellow gum. $^1$H-NMR (400 MHz, DMSO, 298K) δ ppm 2.12 (s, 3H) 2.42 (t, 4H) 3.46 (t, 4H) 3.80 (s, 3H) 7.40 (d, 1H) 7.71 (d, 1H). LCMS: [M+H]$^+$=221.1, Rt$^{(3)}$=1.41 min.

Synthesis of Example 1—Method 1b (According to Scheme 1)

Step 3

To a mixture 6-(6-methoxy-5-methyl-pyridin-3-yl)-4-((S)-pyrrolidin-3-yloxy)-5,6,7,8-tetrahydro-pyrido[4,3-d]pyrimidine (639 mg, 1.87 mmol) in CH$_2$Cl$_2$ (5 mL) was added the acid chloride tetrahydro-2H-pyran-4-carbonyl chloride (306 mg, 2.06 mmol) and triethylamine (0.522 mL, 3.74 mmol) at rt. The reaction mixture was stirred at rt for 10 min. The reaction mixture was concentrated under vacuum. Purification by preparative reverse phase Gilson HPLC and subsequent neutralization of the combined fractions by extraction with CH$_2$Cl$_2$/1N NaOH, separation of the organic phase through a phase separation tube and evaporated gave {(S)-3-[6-(6-methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone (432 mg, 51% yield) as a white powder. $^1$H-NMR (400 MHz, DMSO-d6, 298K) δ ppm 1.50-1.65 (m, 4H) 2.10-2.32 (m, 5H) 2.62-2.78 (m, 1H) 2.85-2.95 (m, 2H) 3.30-3.95 (m, 13H) 4.0-4.20 (m, 2H) 5.61-5.72 (m, 1H) 7.42 (br, 1H) 7.68 (m, 1H) 8.60-8.61 (m, 1H). LCMS: [M+H]$^+$=454.2, Rt$^{(1)}$=1.42 min.

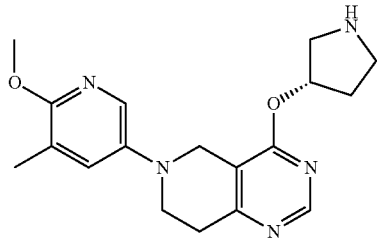 [SMILES: COc1ncc(N2CCc3ncnc(O[C@H]4CCNC4)c3C2)cc1C]

6-(6-Methoxy-5-methyl-pyridin-3-yl)-4-((S)-pyrrolidin-3-yloxy)-5,6,7,8-tetrahydro-pyrido[4,3-d]pyrimidine Step 2

(S)-3-[6-(6-Methoxy-5-methyl-pyridin-3-yl)-5,6,7,8-tetrahydro-pyrido[4,3-d]pyrimidin-4-yloxy]-pyrrolidine-1-carboxylic acid tert-butyl ester (2.05 g, 4.63 mmol) was dissolved in TFA/CH$_2$Cl$_2$ (1/2) and stirred at rt for 1 h. The reaction mixture was concentrated under vacuum, the residue was diluted with CH$_2$Cl$_2$, the organic layer washed with NaOH 1N then brine, dried over Na$_2$SO$_4$, filtered and evaporated to give 6-(6-methoxy-5-methyl-pyridin-3-yl)-4-((S)-pyrrolidin-3-yloxy)-5,6,7,8-tetrahydro-pyrido[4,3-d]pyrimidine. $^1$H NMR (400 MHz, CDCl$_3$, 298K) δ ppm 2.20-2.30 (m, 2 H), 2.22 (s, 3 H), 3.00-3.06 (t, 2 H), 3.09-3.18 (m, 1 H), 3.22-3.37 (m, 3 H), 3.45-3.50 (t, 2 H), 3.95 (s 3 H), 4.10 (s, 2 H), 4.20-4.65 (br.s 1 H), 5.63-5.69 (m, 1 H), 7.21-7.252 (m, 1 H), 7.70-7.74 (m, 1 H), 8.60 (s, 1 H). LCMS: [M+H]$^+$=341.9, Rt$^{(7)}$=0.61 min.

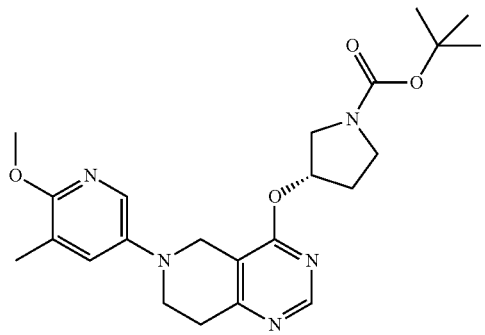 [SMILES: COc1ncc(N2CCc3ncnc(O[C@H]4CCN(C(=O)OC(C)(C)C)C4)c3C2)cc1C]

(S)-3-[6-(6-Methoxy-5-methyl-pyridin-3-yl)-5,6,7,8-tetrahydro-pyrido[4,3-d]pyrimidin-4-yloxy]-pyrrolidine-1-carboxylic acid tert-butyl ester Step 1

X-Phos (0.96 g, 2.01 mmol, 0.3 eq.), Pd$_2$(dba)$_3$ (0.615 g, 0.672 mmol, 0.1 eq.), Cs$_2$CO$_3$ (4.38 g, 13.44 mmol, 2 eq.) were combined and flushed 10 min with Argon. To this mixture, a solution of (S)-3-(5,6,7,8-tetrahydro-pyrido[4,3-d]pyrimidin-4-yloxy)-pyrrolidine-1-carboxylic acid tert-butyl ester (intermediate 7) (2.15 g, 6.72 mmol) in dioxane (6 mL) and 5-bromo-2-methoxy-3-methylpyridine (1.76 g, 8.73 mmol) were added at rt and the reaction mixture was stirred at 120° C. for 2 h. The reaction was cooled down to rt, the reaction mixture filtered over Hyflo, AcOEt was added and the organic layer was washed with brine, dried over Na$_2$SO$_4$, filtered and concentrated under vacuum. The residue was dissolved in dioxane (6 mL) and added to a glass vial containing 5-bromo-2-methoxy-3-methylpyridine (1.76 g, 8.73 mmol), X-Phos (0.96 g, 2.01 mmol), Pd$_2$(dba)$_3$ (0.615 g, 0.672 mmol), Cs$_2$CO$_3$ (4.38 g, 13.44 mmol). The vial was capped and the reaction mixture was stirred at 120° C. for 2 h. The reaction was cooled down to rt, the reaction mixture filtered over Hyflo, AcOEt was added and the organic layer was washed with brine, dried over Na$_2$SO$_4$, filtered and concentrated under vacuum. Purification by flash chromatography on silica gel (CH$_2$Cl$_2$ then TBME then TBME/MeOH 99/1 to 90/10) gave (S)-3-[6-(6-methoxy-5-methyl-pyridin-3-yl)-5,6,7,8-tetrahydro-pyrido[4,3-d]pyrimidin-4-yloxy]-pyrrolidine-1-carboxylic acid tert-butyl ester as a yellow foam (2.05 g, 69% yield). $^1$H NMR (400 MHz, DMSO-d6, 298K) δ ppm 1.35-1.44 (br.s., 9H) 2.07-2.23 (m, 2 H), 2.14 (s, 3 H), 2.87-2.93 (m, 2 H), 3.39-3.68 (m, 6 H), 3.81 (s, 3 H), 4.03-4.08 (m, 2 H), 5.56-5.63 (m, 1 H), 7.41-7.46 (m, 1 H), 7.67-7.73 (m, 1 H), 8.60 (s, 1 H). LCMS: [M+H]$^+$=342.2, Rt$^{(2)}$=0.94 min.

Crystallization of Example 1 by Heating and Cooling in Acetonitrile 1 part of Example 1 (eg. 100 mg) was mixed with 5 parts of acetonitrile (0.5 mL for each 100 mg of compound) with stirring. A solution was obtained by heating up to 40-60° C. The mixture was then allowed to slowly cooled down to RT. After further cooling overnight (5° C.), precipitation was observed. In case no precipitation is not observed, the volume of ethanol can be reduce using a nitrogen stream and repeating the overnight cooling step. The mixture was centrifuged to remove the ethanol. The solid was dried under vacuum at 25° C. and 70 mbar. A crystalline anhydrous form of Example 1 with a MP of 131° C. was obtained. This crystalline form was also observed under other methods and/or solvents, such as heating and cooling in ethanol, acetone, ethyl acetate, isopropanol, by slurry in heptane, or by antisolvent addition in THF or 3-methyl-1-butanol using heptane as antisolvent. These results show the reproducibility and scalability of the crystalline form as well as suggests that the same form can be prepared under different experimental conditions than the ones described above.

List of most significant peaks from X-ray Powder Diffraction Pattern of Example 1 anhydrous form (Method X2):

| 2-Theta in deg | Intensity in % |
| --- | --- |
| 7.5 | 56 |
| 10.9 | 12.5 |
| 11.7 | 25.1 |
| 14.3 | 23.8 |
| 15.1 | 100 |
| 15.8 | 40.9 |
| 16.7 | 22.1 |
| 17.7 | 65.1 |
| 18.9 | 28.9 |
| 20.5 | 24.7 |
| 21.8 | 26 |
| 22.5 | 28.3 |
| 23.3 | 31.3 |
| 24.2 | 76.1 |
| 24.6 | 51.8 |
| 25.0 | 41.3 |
| 25.6 | 20.4 |
| 26.2 | 20.8 |
| 27.0 | 14.2 |
| 28.0 | 17.5 |
| 29.1 | 16.1 |
| 32.8 | 14 |
| 34.6 | 11.4 |

Crystallization of Trihydrate Form of Example 1 by Slurry in Water

Slurry of Example 1 in water e.g., 1 part of Example 1 in 10 parts of water, at RT produced a trihydrate form of Example 1. The crystals were separated by centrifugation and dried at room environment.

List of most significant peaks from X-ray Powder Diffraction Pattern of Example 1 trihydrate form (Method X2):

| 2-Theta in deg | Intensity in % |
| --- | --- |
| 6.6 | 24.3 |
| 8.9 | 7.9 |
| 13.3 | 100 |
| 14.5 | 18.3 |
| 15.0 | 12.6 |
| 16.5 | 12.4 |
| 17.5 | 15.7 |
| 17.7 | 17.2 |
| 18.2 | 9.8 |
| 20.0 | 10.7 |
| 21.6 | 11.7 |
| 22.6 | 20.3 |
| 23.8 | 11.4 |
| 24.4 | 15.2 |
| 26.7 | 26.5 |
| 27.5 | 18.7 |
| 27.8 | 16.6 |
| 29.2 | 9.8 |
| 33.3 | 9 |
| 33.9 | 7.6 |
| 35.7 | 8.2 |
| 38.8 | 7 |

Preparation of Citrate Salt of Example 1

0.5 g of Example 1 (assay 91.8%) were dissolved in 5 mL of methylethylketone and 0.25 mL of water and heated at 60° C. 213 mg of citric acid were added at 50° C. and the mixture was allowed to cool down to RT within 30 min. Crystallization occurs at 45° C. The mixture was stirred for 16 h at RT. The crystals were collected by filtration. The filter cake was washed 3 times with 1 mL of methylethylketone and afterwards dried for 16 h at 50° C. and ca. 10 mbar vacuum. Elementary analysis of the citrate salt showed a 1:1 (monohydrate) form. List of most significant peaks from X-ray Powder Diffraction Pattern of Example 1 citrate salt (Method X1):

| 2-Theta in deg | Intensity in % |
| --- | --- |
| 5.7 | 62 |
| 11.5 | 100 |
| 12.1 | 4 |
| 14.3 | 4 |
| 15.4 | 12 |
| 17.2 | 21 |
| 17.9 | 31 |
| 19.3 | 25 |
| 20.2 | 37 |
| 20.7 | 8 |
| 21.9 | 5 |
| 23.3 | 11 |
| 23.9 | 36 |
| 25.5 | 28 |
| 27.0 | 5 |
| 27.7 | 6 |
| 29.8 | 8 |
| 30.3 | 7 |

Preparation of Fumarate Salt of Example 1

0.5 g Example 1 (assay 91.8%) were dissolved in 15 mL of acetonitrile and 0.2 mL of water and heated at 76° C. 129 mg of fumaric acid were added at 60° C. The solution was allowed to cool down to RT within 30 min. The salt precipitated and the suspension was stirred for 16 h at RT. The crystals were collected by filtration. The filter cake was washed 3 times with 1 mL of acetonitrile and afterwards dried for 16 h at 50° C. and ca. 10 mbar vacuum. Elementary analysis of the fumarate salt showed a 1:1 (monohydrate) form. List of most significant peaks from X-ray Powder Diffraction Pattern of Example 1 fumarate salt (Method X1):

| 2-Theta in deg | Intensity in % |
| --- | --- |
| 6.0 | 100 |
| 6.5 | 12 |
| 9.8 | 8 |
| 12.3 | 10 |
| 13.1 | 14 |
| 15.6 | 22 |
| 17.7 | 16 |
| 19.1 | 21 |
| 19.7 | 27 |
| 23.9 | 40 |
| 24.7 | 6 |
| 24.9 | 10 |
| 25.2 | 5 |
| 26.4 | 11 |
| 27.0 | 4 |

Preparation of Napadisylate Salt of Example 1

0.5 g Example 1 (assay 91.8%) were dissolved in 5 mL of ethanol absolute and 0.25 mL of water at 60° C. 250 mg of naphthalendisulfonic acid were added at 50° C. and the mixture was allowed to cool down to RT within 30 min. Crystallization occurs at 40° C. The mixture was stirred for 16 h at RT. The crystals were collected by filtration. The filter cake was washed 3 times with 1 mL of ethanol and afterwards dried for 16 h at 50° C. and ca. 10 mbar vacuum. Elementary analysis of the napadisylate salt showed a 2:1 (monohydrate) form. List of most significant peaks from X-ray Powder Diffraction Pattern of Example 1 napadisylate salt (Method X1):

| 2-Theta in deg | Intensity in % |
|---|---|
| 4.3 | 100 |
| 8.5 | 3 |
| 9.4 | 6 |
| 12.2 | 12 |
| 12.9 | 12 |
| 13.5 | 37 |
| 15.0 | 26 |
| 15.6 | 12 |
| 16.0 | 11 |
| 17.7 | 28 |
| 18.9 | 23 |
| 19.3 | 11 |
| 20.0 | 11 |
| 20.8 | 3 |
| 21.2 | 5 |
| 22.0 | 9 |
| 23.0 | 41 |
| 24.5 | 39 |
| 26.5 | 20 |

Examples 2-9 were prepared using procedures analogous to those used in Example 1 (method 1b) using appropriate starting materials.

Example 2

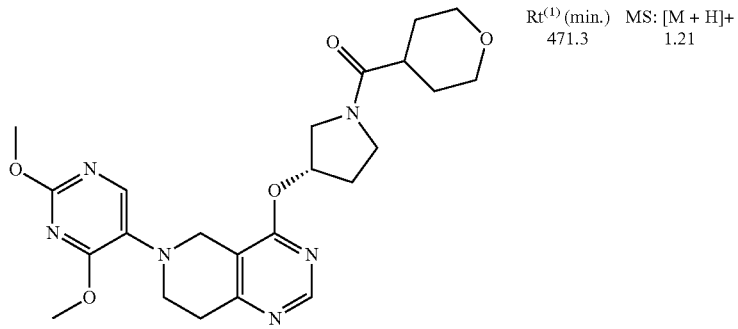

Rt(1) (min.) 1.21
MS: [M + H]+ 471.3

Name: {(S)-3-[6-(2,4-Dimethoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone
Purification method: Reverse phase method C
Prepared using process step 3 of method 1b from intermediate 8 and tetrahydro-pyran-4-carbonyl chloride
$^1$H NMR (400 MHz, methanol-d4, 298K) δ ppm 1.50-1.86 (m, 4H) 2.20-2.45 (m, 2H) 2.70-2.87 (m, 1H) 2.96-2.99 (m, 2H) 3.35-4.14 (m, 18H) 5.69-5.85 (m, 1H) 7.96 (m, 1H) 8.58 (m, 1H)

Example 3

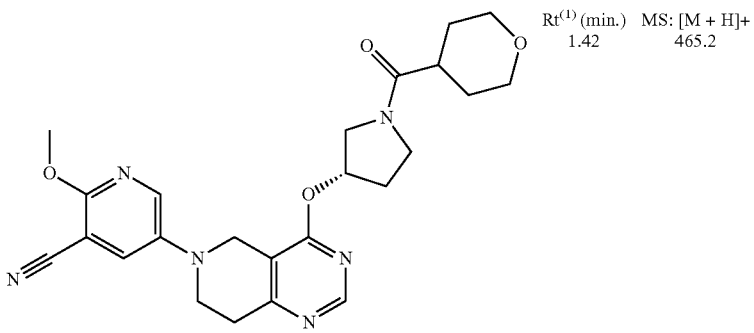

Rt(1) (min.) 1.42
MS: [M + H]+ 465.2

Name: 2-Methoxy-5-{4-[(S)-1-(tetrahydro-pyran-4-carbonyl)-pyrrolidin-3-yloxy]-7,8-dihydro-5H-pyrido[4,3-d]pyrimidin-6-yl}-nicotinonitrile
Purification method: Reverse phase method A
Prepared using process steps 2-3 of method 1b from intermediate 11 and tetrahydro-pyran-4-carbonyl chloride
$^1$H NMR (400 MHz, DMSO-d6, 298K) δ ppm 1.50-1.64 (m, 4H) 2.10-2.31 (m, 2H) 2.62-2.77 (m, 1H) 2.87-2.95 (m, 2H) 3.29-3.96 (m, 13H) 4.08-4.21 (m, 2H) 5.58-5.73 (m, 1H) 8.06-8.09 (m, 1H) 8.23-8.27 (m, 1H) 8.60-8.64 (m, 1H)

Example 4    Rt⁽¹⁾ (min.)  MS: [M + H]+
             1.27          414.2

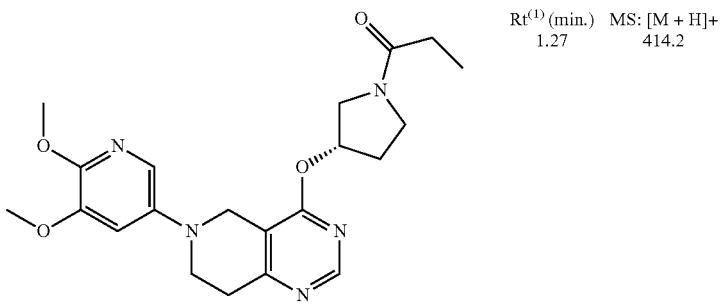

Name: 1-{(S)-3-[6-(5,6-Dimethoxy-pyridin-3-yl)-5,6,7,8-tetrahydro-pyrido[4,3-d]pyrimidin-4-yloxy]-pyrrolidin-1-yl}-propan-1-one
Purification method: Reverse phase method A
Prepared using process steps 2-3 of method 1b from intermediate 10 and propionyl chloride
$^1$H NMR (400 MHz, CDCl$_3$-d, 298K) δ ppm 1.10-1.20 (m, 3H) 2.19-2.49 (m, 4H) 3.02-3.08 (m, 2H) 3.45-3.52 (m, 2H) 3.56-3.68 (m, 2H) 3.72-3.90 (m, 2H) 3.91 (s, 3H) 3.99 (s, 3H) 4.07-4.12 (m, 2H) 5.75-5.78 (m, 1H) 6.89-7.01 (m, 1H) 7.44-7.46 (m, 1H) 8.60-8.62 (m, 1H)

Example 5    Rt⁽¹⁾ (min.)  MS: [M + H]+
             1.25          470.2

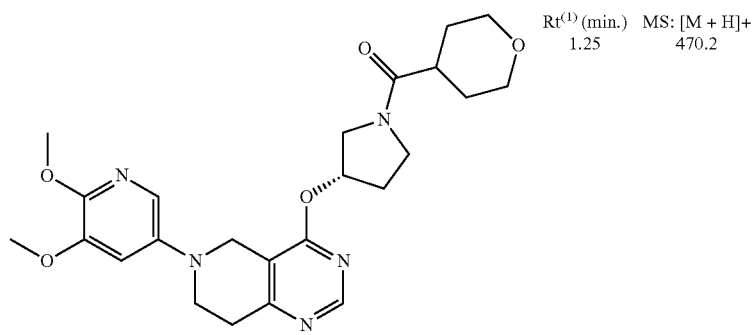

Name: {(S)-3-[6-(5,6-Dimethoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone
Purification method: Reverse phase method A
Prepared using process steps 2-3 of method 1b from intermediate 10 and tetrahydro-pyran-4-carbonyl chloride
$^1$H NMR (400 MHz, CDCl$_3$-d, 298K) δ ppm 1.56-1.68 (m, 2H) 1.88-2.00 (m, 2H) 2.20-2.38 (m, 2H) 2.53-2.70 (m, 1H) 3.05-3.10 (m, 2H) 3.39-3.54 (m, 4H) 3.59-3.82 (m, 4H) 3.91 (s, 3H) 3.99 (s, 3H) 4.01-4.10 (m, 4H) 5.62-5.78 (m, 1H) 6.89-6.90 (m, 1H) 7.40-7.43 (m, 1H) 8.60-8.65 (m, 1H)

Example 6    Rt⁽¹⁾ (min.)  MS: [M + H]+
             1.10          450.2

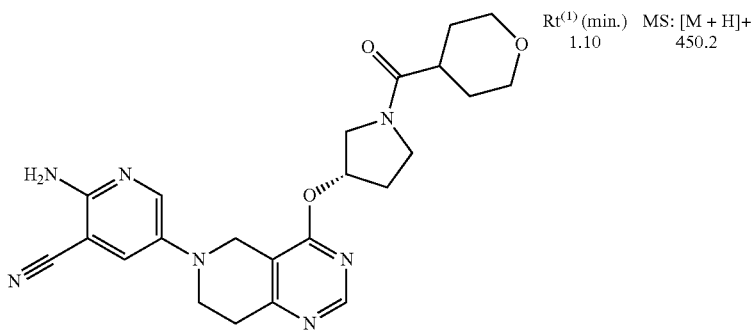

Name: 2-Amino-5-{4-[(S)-1-(tetrahydro-pyran-4-carbonyl)-pyrrolidin-3-yloxy]-7,8-dihydro-5H-pyrido[4,3-d]pyrimidin-6-yl}-nicotinonitrile
Prepared using process step 3 of method 1b from intermediate 9 and tetrahydro-pyran-4-carbonyl chloride
Purification method:
1 - Normal phase chromatography CH$_2$Cl$_2$/MeOH as solvent
2 - Reverse phase method A
$^1$H NMR (400 MHz, CDCl$_3$-d, 298K) δ ppm 1.45-1.75 (m, 2H) 1.86-2.02 (m, 2H) 2.20-2.40 (m, 2H) 2.50-2.75 (m, 1H) 3.02-3.09 (m, 2H) 3.38-4.20 (m, 12H) 4.96 (s, 1H) 5.70-5.78 (m, 1H) 7.39 (m, 1H) 8.13-8.14 (m, 1H) 8.62-8.64 (m, 1H)

Example 7  Rt⁽¹⁾ (min.) MS: [M + H]+
            1.41          458.1

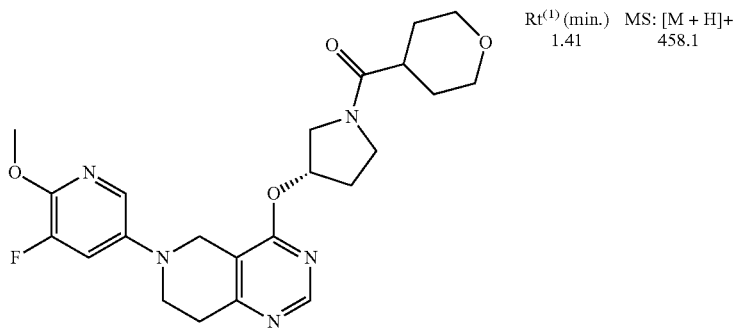

Name: {(S)-3-[6-(5-Fluoro-6-methoxy-pyridin-3-yl)-5,6,7,8-tetrahydro-pyrido[4,3-d]pyrimidin-4-yloxyl-pyrrolidin-1-yl}-(tetrahydro-pyran-4-yl)-methanone
Purification method: Biotage 11 g KP-NH cartridge eluting with Heptane/EtOAc 100/0 to 0/100
Prepared using process steps 2-3 of method 1b from intermediate 12 and tetrahydro-pyran-4-carbonyl chloride
$^1$H NMR (400 MHz, CDCl$_3$, 298K) δ ppm 1.56-1.74 (m, 2H) 1.87-2.02 (m, 2H) 2.19-2.42 (m, 2H) 2.51-2.74 (m, 1H) 3.01-3.09 (m, 2H) 3.39-4.20 (m, 15H) 5.70-5.79 (m, 1H) 7.13-7.20 (m, 1H) 7.63-7.69 (m, 1H) 8.59-8.66 (m, 1H)

Example 8  Rt⁽¹⁾ (min.) MS: [M + H]+
            1.35          425.1

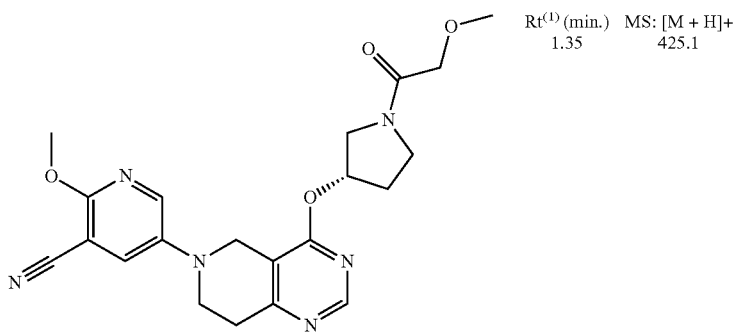

Name: 2-Methoxy-5-{4-[(S)-1-(2-methoxy-acetyl)-pyrrolidin-3-yloxy]-7,8-dihydro-5H-pyrido[4,3-d]pyrimidin-6-yl}-nicotinonitrile
Purification method: Reverse phase method A
Prepared using process steps 2-3 of method 1b from intermediate 11 and methoxy acetyl chloride
$^1$H NMR (400 MHz, DMSO-d6, 298K) δ ppm 2.11-2.32 (m, 2H) 2.88-2.95 (m, 2H) 3.26-3.32 (m, 3H) 3.46-3.84 (m, 6H) 3.91-3.95 (m, 3H) 3.98-4.08 (m, 2H) 4.13-4.19 (m, 2H) 5.59-5.71 (m, 1H) 8.07-8.10 (m, 1H) 8.25-8.28 (m, 1H) 8.61-8.62 (m, 1H)

Example 9  Rt⁽⁸⁾ (min.) MS: [M + H]+
            3.79          449.1

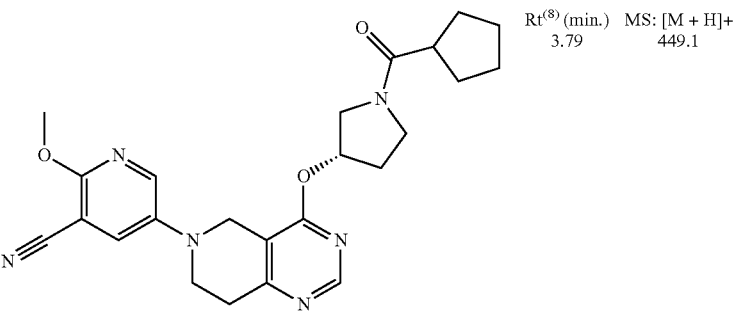

Name: 5-[4-((S)-1-Cyclopentanecarbonyl-pyrrolidin-3-yloxy)-7,8-dihydro-5H-pyrido[4,3-d]pyrimidin-6-yl]-2-methoxy-nicotinonitrile
Purification method: Reverse phase method A
Prepared using process steps 2-3 of method 1b from intermediate 11 and cyclopentanecarbonyl chloride

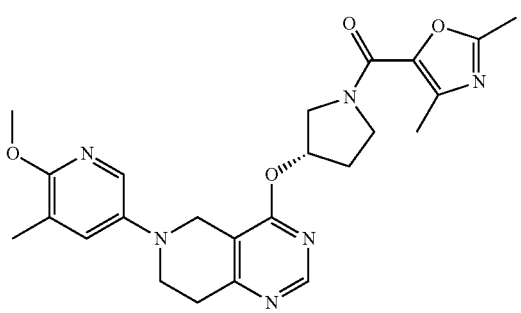 [SMILES: COc1ncc(N2CCc3ncnc(O[C@H]4CCN(C(=O)c5oc(C)nc5C)C4)c3C2)cc1C]

Example 10

(2,4-Dimethyl-oxazol-5-yl)-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone Step 1

A mixture of 2,4-dimethyl-oxazole-5-carboxylic acid (36.4 mg, 0.258 mmol), HTBU (98 mg, 0.258 mmol), DIPEA (86 µl, 0.49 mmol) in DMF (5 mL) was stirred at rt for 20 min. then a solution of 6-(6-methoxy-5-methyl-pyridin-3-yl)-4-((S)-pyrrolidin-3-yloxy)-5,6,7,8-tetrahydro-pyrido[4,3-d]pyrimidine (prepared in example 1, method 1b, step 2) (80 mg, 0.23 mmol) and DIPEA (86 µl, 0.49 mmol) in DMF (0.4 mL) was added. The reaction mixture was stirred 30 min at rt. The reaction mixture was directly purified by preparative reverse phase Gilson HPLC and subsequent neutralization of the combined fractions over PL-HCO₃ MP gave (2,4-dimethyl-oxazol-5-yl)-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone (91 mg, 84% yield) as a white lyophilized powder. $^1$H-NMR (400 MHz, methanol-d4, 298K) δ ppm 2.17 (s, 3H) 2.27-2.52 (m, 8H) 2.95-3.03 (m, 2H) 3.44-3.55 (m, 2H) 3.70-4.26 (m, 9H) 5.76-5.92 (m, 1H) 7.40 (br. s., 1H) 7.64 (br. s., 1H) 8.55-8.62 (m, 1H), LCMS: [M+H]+=465.2, Rt$^{(1)}$=1.51 min.

Examples 11-49 and 51-53 were prepared using procedures analogous to those used in Example 10, step 1 using appropriate starting materials.

Example 11

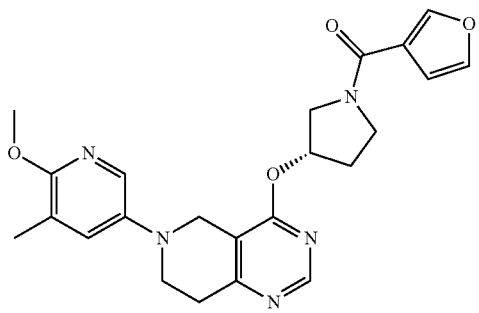 [SMILES: COc1ncc(N2CCc3ncnc(O[C@H]4CCN(C(=O)c5ccoc5)C4)c3C2)cc1C]

Rt$^{(1)}$ (min.) 1.57   MS: [M + H]+ 436.2

Name: Furan-3-yl-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using furan-3-carboxylic acid
$^1$H NMR (400 MHz, methanol-d4, 298K) δ ppm 2.17 (s, 3H) 2.30-2.45 (m, 2H) 2.93-3.05 (m, 2H) 3.45-3.54 (m, 2H) 3.72-4.21 (m, 9H) 5.79-5.86 (m, 1H) 6.78-6.82 (m, 1H) 7.37-7.44 (m, 1H) 7.56-7.61 (m, 1H) 7.61-7.69 (m, 1H) 8.01-8.12 (m, 1H) 8.54-8.62 (m, 1H)

Example 12

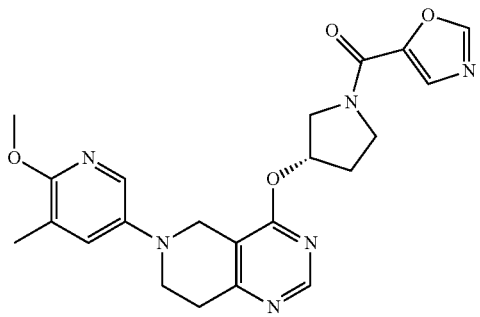 [SMILES: COc1ncc(N2CCc3ncnc(O[C@H]4CCN(C(=O)c5cnco5)C4)c3C2)cc1C]

Rt$^{(1)}$ (min.) 1.36   MS: [M + H]+ 437.2

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-oxazol-5-yl-methanone
Purification method: Reverse phase method A
Prepared using oxazole-5-carboxylic acid
$^1$H NMR (400 MHz, methanol-d4, 298K) δ ppm 2.17 (s, 3H) 2.30-2.39 (m, 1H) 2.41-2.50 (m, 1H) 2.95-3.03 (m, 2H) 3.45-3.52 (m, 2H) 3.76-4.32 (m, 9H) 5.79-5.94 (m, 1H) 7.40 (br. s., 1H) 7.62-7.66 (m, 1H) 7.75-7.82 (m, 1H) 8.34-8.40 (m, 1H) 8.56-8.61 (m, 1H)

Example 13

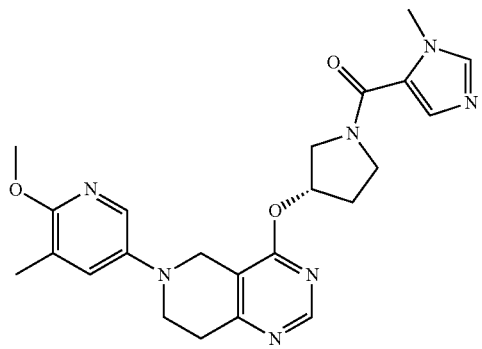 [SMILES: COc1ncc(N2CCc3ncnc(O[C@H]4CCN(C(=O)c5cncn5C)C4)c3C2)cc1C]

Rt(1) (min.) 1.13  MS: [M + H]+ 450.2

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone
Purification method: Reverse phase method A
Prepared using 3-methyl-3H-imidazole-4-carboxylic acid
$^1$H NMR (400 MHz, methanol-d4, 298K) δ ppm 2.17 (s, 3H) 2.30-2.45 (m, 2H) 2.93-3.05 (m, 2H) 3.43-3.55 (m, 2H) 3.74-4.24 (m, 12H) 5.82 (br. s., 1H) 7.35-7.56 (m, 2H) 7.66 (m, 1H) 7.76 (br. s., 1H) 8.55-8.60 (m, 1H)

Example 14

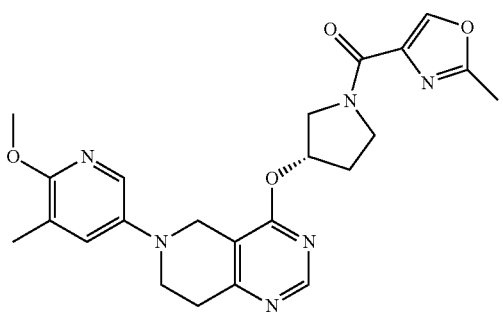 [SMILES: COc1ncc(N2CCc3ncnc(O[C@H]4CCN(C(=O)c5coc(C)n5)C4)c3C2)cc1C]

Rt(1) (min.) 1.49  MS: [M + H]+ 451.2

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(2-methyl-oxazol-4-yl)-methanone
Purification method: Reverse phase method A
Prepared using 2-methyl-oxazole-4-carboxylic acid
$^1$H NMR (400 MHz, methanol-d4, 298K) δ ppm 2.17 (s, 3H) 2.27-2.43 (m, 2H) 2.43-2.50 (m, 3H) 2.95-3.02 (m, 2H) 3.45-3.53 (m, 2H) 3.72-4.33 (m, 9H) 5.78-5.89 (m, 1H) 7.37-7.43 (m, 1H) 7.61-7.67 (m, 1H) 8.25-8.31 (m, 1H) 8.57-8.60 (m, 1H)

Example 15

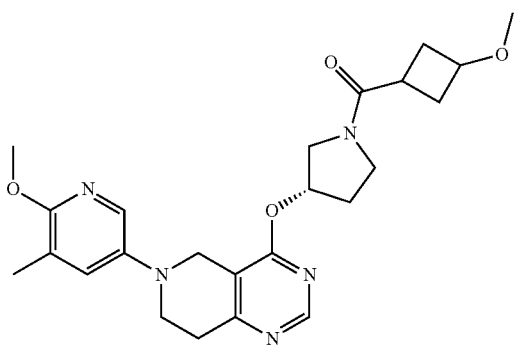 [SMILES: COc1ncc(N2CCc3ncnc(O[C@H]4CCN(C(=O)C5CC(OC)C5)C4)c3C2)cc1C]

Rt(1) (min.) 1.53  MS: [M + H]+ 454.2

Name: (3-Methoxy-cyclobutyl)-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using 3-methoxy-cyclobutanecarboxylic acid
$^1$H NMR (400 MHz, methanol-d4, 298K) δ ppm 1.99-2.55 (m, 9H) 2.78-2.95 (m, 1H), 2.95-3.02 (m, 2H) 3.20-3.23 (m, 3H) 3.47-3.52 (m, 2H) 3.52-4.10 (m, 10H) 5.73-5.81 (m, 1H) 7.38-7.42 (m, 1) 7.63-7.67 (m, 1H) 8.57 (s, 1H)

Example 16 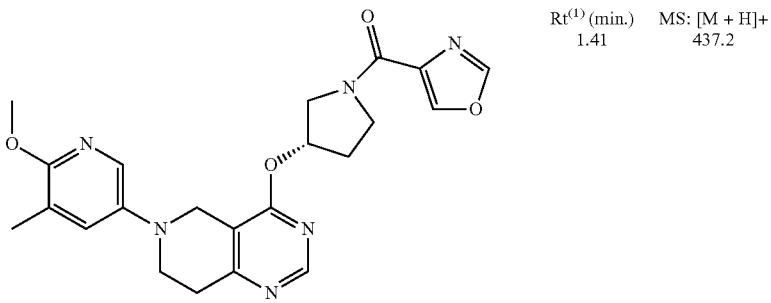 Rt⁽¹⁾ (min.) 1.41  MS: [M + H]+ 437.2

Name: ({(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-oxazol-4-yl)-methanone
Purification method: Reverse phase method A
Prepared using oxazole-4-carboxylic acid
¹H NMR (400 MHz, methanol-d4, 298K) δ ppm 2.17 (s, 3H) 2.29-2.37 (m, 1H) 2.37-2.44 (m, 1H) 2.94-3.03 (m, 2H) 3.45-3.53 (m, 2H) 3.75-4.38 (m, 9H) 5.79-5.89 (m, 1H) 7.38-7.42 (m, 1H) 7.62-7.66 (m, 1H) 8.19-8.26 (m, 1H) 8.44-8.48 (m, 1H) 8.56-8.61 (m, 1H)

Example 17 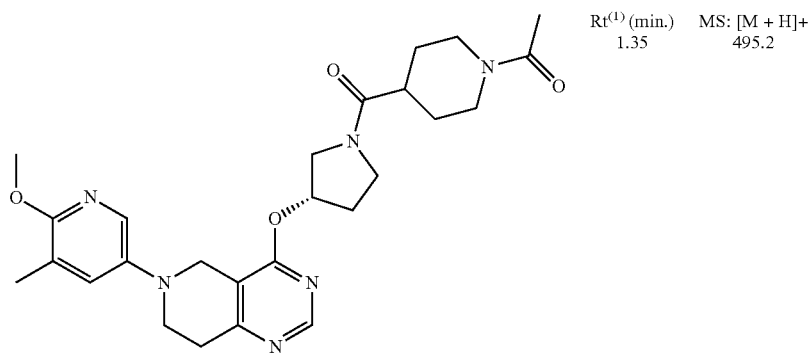 Rt⁽¹⁾ (min.) 1.35  MS: [M + H]+ 495.2

Name: 1-(4-{(S)-3-[6-(6-Methoxy-5-methyl-pyridin-3-yl)-5,6,7,8-tetrahydro-pyrido[4,3-d]pyrimidin-4-yloxy]-pyrrolidine-1-carbonyl}-piperidin-1-yl)-ethanone
Purification method: Reverse phase method A
Prepared using 1-acetyl-piperidine-4-carboxylic acid
¹H NMR (400 MHz, methanol-d4, 298K) δ ppm 1.49-1.89 (m, 4H) 2.06-2.13 (m, 3H) 2.18 (s, 3H) 2.23-2.43 (m, 2H) 2.61-2.93 (m, 2H) 2.95-3.04 (m, 2H) 3.15-3.25 (m, 1H) 3.42-3.53 (m, 2H) 3.55-4.12 (m, 10H) 4.46-4.59 (m, 1H) 5.74-5.86 (m, 1H) 7.38-7.45 (m, 1H) 7.62-7.67 (m, 1H) 8.56-8.61 (m, 1H)

Example 18 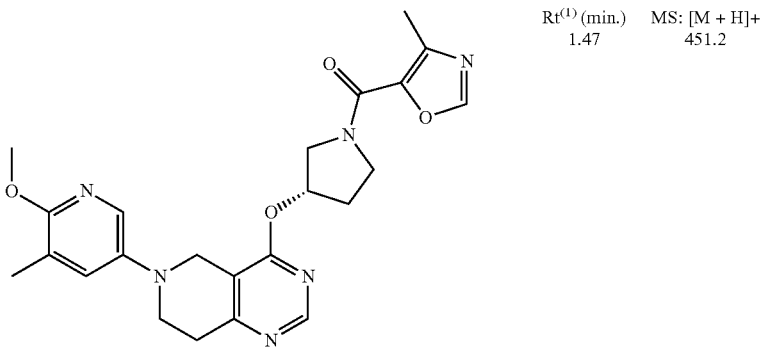 Rt⁽¹⁾ (min.) 1.47  MS: [M + H]+ 451.2

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(4-methyl-oxazol-5-yl)-methanone
Purification method: Reverse phase method A
Prepared using 4-methyl-oxazole-5-carboxylic acid
¹H NMR (400 MHz, methanol-d4, 298K) δ ppm 2.17 (s, 3H) 2.29-2.47 (m, 5H) 2.95-3.3.03 (m, 2H) 3.45-3.52 (m, 2H) 3.73-4.30 (m, 9H) 5.79-5.90 (m, 1H) 7.41 (m, 1H) 7.65 (br.s., 1H) 8.19-8.24 (m, 1H) 8.55-8.61 (m, 1H)

| Example 19 | 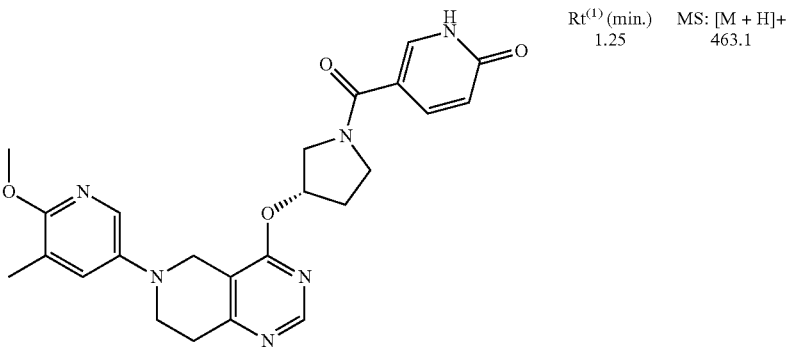 | Rt(1) (min.) 1.25 | MS: [M + H]+ 463.1 |

Name: 5-{(S)-3-[6-(6-Methoxy-5-methyl-pyridin-3-yl)-5,6,7,8-tetrahydro-pyrido[4,3-d]pyrimidin-4-yloxy]-pyrrolidine-1-carbonyl}-1H-pyridin-2-one
Purification method: Reverse phase method A
Prepared using 6-oxo-1,6-dihydro-pyridine-3-carboxylic acid
1H NMR (400 MHz, methanol-d4, 298K) δ ppm 2.19 (s, 3H) 2.30-2.40 (m, 2H) 2.95-3.05 (m, 2H) 3.45-3.55 (m, 2H) 3.74-4.22 (m, 9H) 5.73-5.85 (m, 1H) 6.50-6.56 (m, 1H) 7.39-7.45 (m, 1H) 7.60-7.70 (m, 1H) 7.78-7.90 (m, 2H) 8.50-8.60 (m, 1H)

| Example 20 | 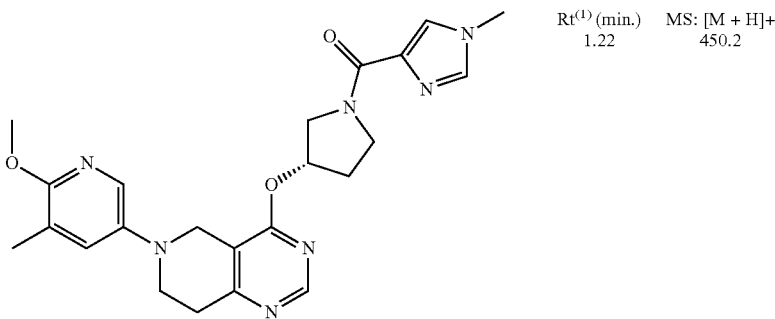 | Rt(1) (min.) 1.22 | MS: [M + H]+ 450.2 |

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(1-methyl-1H-imidazol-4-yl)-methanone
Purification method: Reverse phase method A
Prepared using 1-methyl-1H-imidazole-4-carboxylic acid
1H NMR (400 MHz, methanol-d4, 298K) δ ppm 2.17 (s, 3H) 2.28-2.41 (m, 2H) 2.94-3.02 (m, 2H) 3.45-3.52 (m, 2H) 3.73-4.35 (m, 12H) 5.80-5.85 (m, 1H) 7.38-7.43 (m, 1H) 7.60-7.69 (m, 3H) 8.55-8.61 (m, 1H)

| Example 21 | 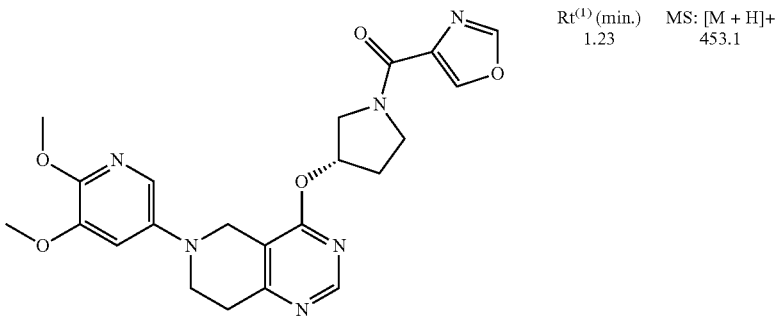 | Rt(1) (min.) 1.23 | MS: [M + H]+ 453.1 |

Name: {(S)-3-[6-(5,6-Dimethoxy-pyridin-3-yl)-5,6,7,8-tetrahydro-pyrido[4,3-d]pyrimidin-4-yloxy]-pyrrolidin-1-yl}-oxazol-4-yl-methanone
Purification method: Normal phase chromatography with EtOAc/MeOH as solvent
Prepared using intermediate 10 and method 1b of process step 2 of example 1 followed by process step 1 of example 10 using oxazole-4-carboxylic acid
1H NMR (400 MHz, DMSO-d6, 298K) δ ppm 2.10-2.37 (m, 2H) 2.81-2.99 (m, 2H) 3.46-4.27 (m, 14H) 5.58-5.77 (m, 1H) 7.08-7.20 (m, 1H) 7.30-7.42 (m, 1H) 8.43-8.54 (m, 1H) 8.55-8.69 (m, 2H)

| Example 22 | 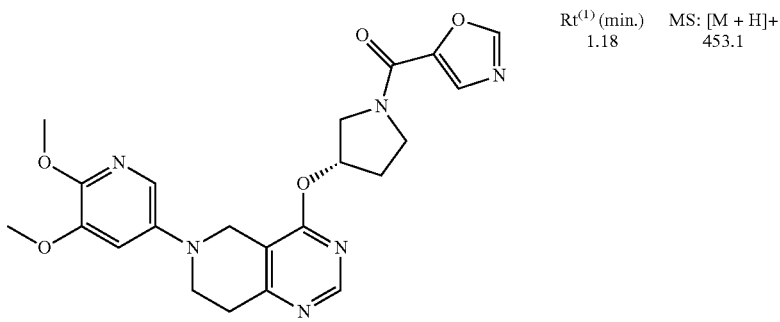 | Rt(1) (min.) 1.18 | MS: [M + H]+ 453.1 |

Name: {(S)-3-[6-(5,6-Dimethoxy-pyridin-3-yl)-5,6,7,8-tetrahydro-pyrido[4,3-d]pyrimidin-4-yloxy]-pyrrolidin-1-yl}-oxazol-5-yl-methanone
Purification method: Reverse phase method A
Prepared using intermediate 10 and process step 2, method 1b of example 1 followed by process step 1 of example 10 using oxazole-5-carboxylic acid
1H NMR (400 MHz, DMSO-d6, 373K) δ ppm 2.22-2.42 (m, 2H) 2.80-3.00 (m, 2H) 3.50-4.30 (m, 14H) 5.63-5.83 (m, 1H) 7.06-7.09 (m, 1H) 7.38-7.40 (m, 1H) 7.69 (s, 1H) 8.40 (s, 1H) 8.57 (s, 1H)

| Example 23 | 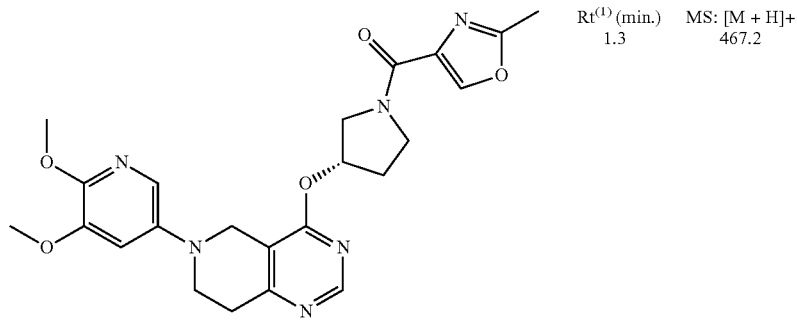 | Rt(1) (min.) 1.3 | MS: [M + H]+ 467.2 |

Name: {(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2-methyl-oxazol-4-yl)-methanone
Purification method: Reverse phase method A
Prepared using intermediate 10 and process step 2, method 1b of example 1 followed by process step 1 of example 10 using 2-methyl-oxazole-4-carboxylic acid
1H NMR (400 MHz, DMSO-d6, 298K) δ ppm 2.11-2.36 (m, 2H) 2.40-2.44 (m, 3H) 2.81-2.97 (m, 2H) 3.40-4.28 (m, 14H) 5.62-5.78 (m, 1H) 7.11-7.21 (m, 1H) 7.29-7.41 (m, 1H) 8.42-8.52 (m, 1H) 8.59-8.67 (m, 1H)

| Example 24 | 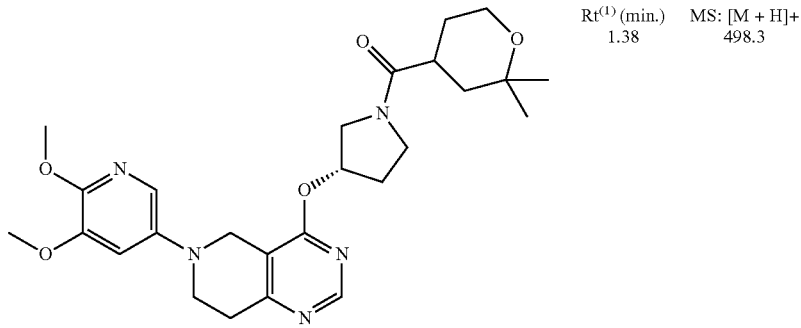 | Rt(1) (min.) 1.38 | MS: [M + H]+ 498.3 |

Name: {(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2,2-dimethyl-tetrahydro-pyran-4-yl)-methanone
Purification method: Reverse phase method A
Prepared using intermediate 10 and process step 2, method 1b of example 1 followed by process step 1 of example 10 using 2,2-dimethyl-tetrahydro-pyran-4-carboxylic acid
1H NMR (400 MHz, DMSO-d6, 298K) δ ppm 0.97-1.24 (m, 6H) 1.28-1.58 (m, 4H) 2.08-2.34 (m, 2H) 2.72-2.97 (m, 3H) 3.43-4.12 (m, 16H) 5.55-5.76 (m, 1H) 7.14-7.20 (m, 1H) 7.31-7.37 (m, 1H) 8.59-8.64 (m, 1H)

| | | Rt⁽¹⁾ (min.) | MS: [M + H]+ |
|---|---|---|---|
| Example 25 | 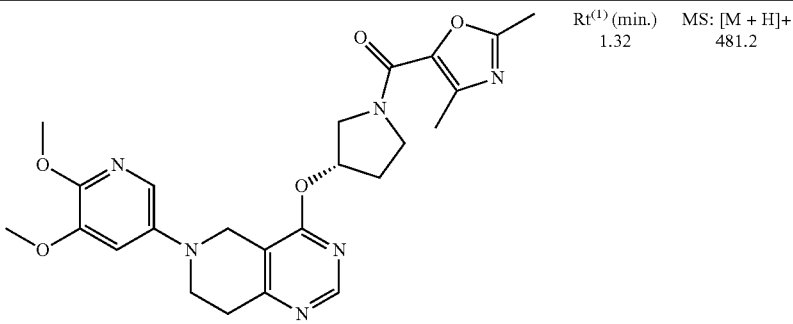 | 1.32 | 481.2 |

Name: {(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2,4-dimethyl-oxazol-5-yl)-methanone
Purification method: Reverse phase method A
Prepared using intermediate 10 and process step 2, method 1b of example 1 followed by process step 1 of example 10 using 2,2-dimethyl-tetrahydro-pyran-4-carboxylic acid
$^1$H NMR (400 MHz, DMSO-d6, 298K) δ ppm 2.11-2.48 (m, 8H) 2.83-2.98 (m, 2H) 3.43-4.18 (m, 14H) 5.56-5.89 (m, 1H) 7.12-7.20 (m, 1H) 7.32-7.40 (m, 1H) 8.57-8.67 (m, 1H)

| | | Rt⁽¹⁾ (min.) | MS: [M + H]+ |
|---|---|---|---|
| Example 26 | 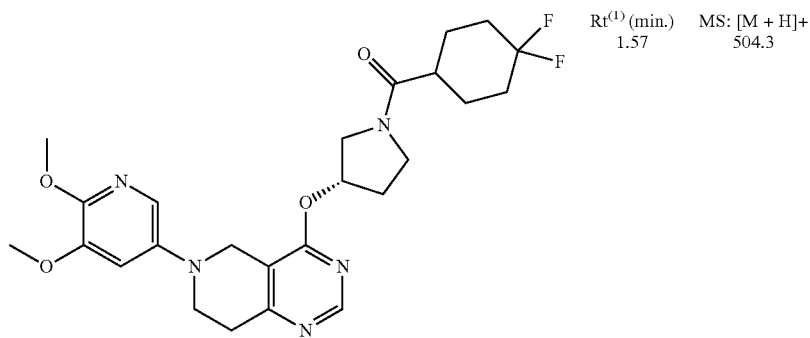 | 1.57 | 504.3 |

Name: (4,4-Difluoro-cyclohexyl)-{(S)-3-[6-(5,6-dimethoxy-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using intermediate 10 and process step 2, method 1b of example 1 followed by process step 1 of example 10 using 4,4-difluoro-cyclohexanecarboxylic acid
$^1$H NMR (400 MHz, DMSO-d6, 298K) δ ppm 1.49-2.35 (m, 10H) 2.61-2.67 (m, 1H) 2.84-2.99 (m, 2H) 3.42-3.83 (m, 12H) 4.00-4.19 (m, 2H) 5.57-5.78 (m, 1H) 7.11-7.25 (m, 1H) 7.29-7.43 (m, 1H) 8.52-8.68 (m, 1H)

| | | Rt⁽¹⁾ (min.) | MS: [M + H]+ |
|---|---|---|---|
| Example 27 | 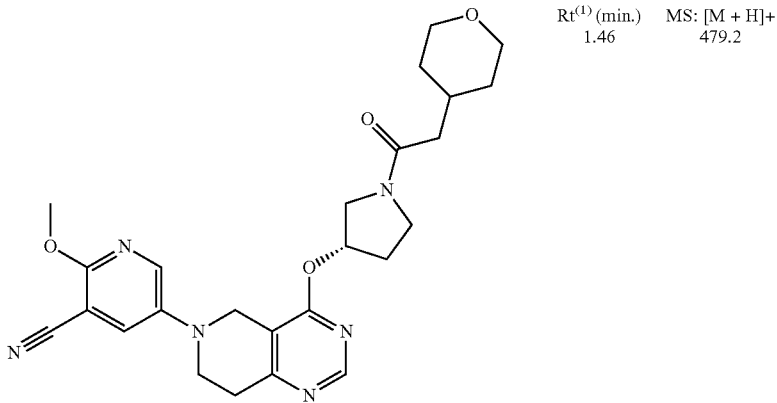 | 1.46 | 479.2 |

Name: 2-Methoxy-5-{4-[(S)-1-(2-tetrahydro-pyran-4-yl-acetyl)-pyrrolidin-3-yloxy]-7,8-dihydro-5H-pyrido[4,3-d]pyrimidin-6-yl}-nicotinonitrile
Purification method: Reverse phase method A
Prepared using intermediate 11 and process step 2, method 1b of example 1 followed by process step 1 of example 10 using (tetrahydro-pyran-4-yl)-acetic acid
$^1$H NMR (400 MHz, DMSO-d6, 298K) δ ppm 1.11-1.28 (m, 2H) 1.49-1.64 (m, 2H) 1.87-1.99 (m, 1H) 2.07-2.29 (m, 4H) 2.86-2.95 (m, 2H) 3.19-3.30 (m, 2H) 3.42-3.88 (m, 8H) 3.90-3.96 (m, 3H) 4.09-4.19 (m, 2H) 5.57-5.70 (m, 1H) 8.07-8.11 (m, 1H) 8.22-8.28 (m, 1H) 8.58-8.65 (m, 1H)

Example 28 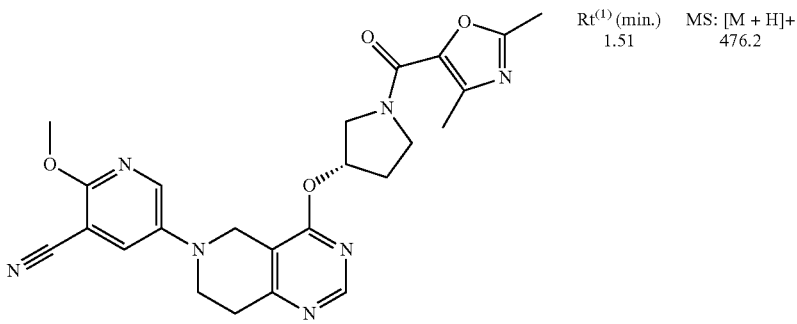 Rt⁽¹⁾ (min.) 1.51    MS: [M + H]+ 476.2

Name: 5-{4-[(S)-1-(2,4-Dimethyl-oxazole-5-carbonyl)-pyrrolidin-3-yloxy]-7,8-dihydro-5H-pyrido[4,3-d]pyrimidin-6-yl}-2-methoxy-nicotinonitrile
Purification method: Reverse phase method A
Prepared using intermediate 11 and process step 2, method 1b of example 1 followed by process step 1 of example 10 using 2,4-dimethyl-oxazole-5-carboxylic acid
¹H NMR (400 MHz, DMSO-d6, 298K) δ ppm 2.16-2.46 (m, 5H) 2.30 (s, 3H) 2.85-2.96 (m, 2H) 3.50-4.20 (m, 8H) 3.92 (s, 3H) 5.64-5.80 (m, 1H) 8.04-8.12 (m, 1H) 8.22-8.30 (m, 1H) 8.62 (s, 1H)

Example 29 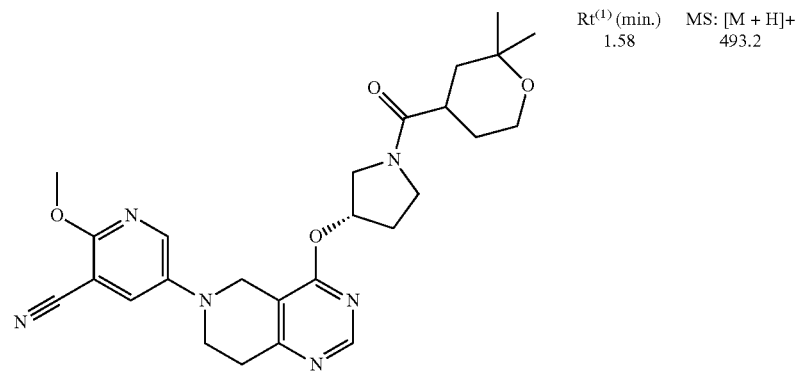 Rt⁽¹⁾ (min.) 1.58    MS: [M + H]+ 493.2

Name: 5-{4-[(S)-1-(2,2-Dimethyl-tetrahydro-pyran-4-carbonyl)-pyrrolidin-3-yloxy]-7,8-dihydro-5H-pyrido[4,3-d]pyrimidin-6-yl}-2-methoxy-nicotinonitrile
Purification method: Reverse phase method A
Prepared using intermediate 11 and process step 2, method 1b of example 1 followed by process step 1 of example 10 using 2,2-dimethyl-tetrahydro-pyran-4-carboxylic acid
¹H NMR (400 MHz, DMSO-d6, 298K) δ ppm 1.00-1.24 (m, 6H) 1.28-1.73 (m, 4H) 2.10-2.34 (m, 2H) 2.62-2.97 (m, 3H) 3.43-3.84 (m, 8H) 3.94 (s, 3H) 4.09-4.20 (m, 2H) 5.58-5.75 (m, 1H) 8.05-8.11 (m, 1H) 8.20-8.29 (m, 1H) 8.59-8.65 (m, 1H)

Example 30 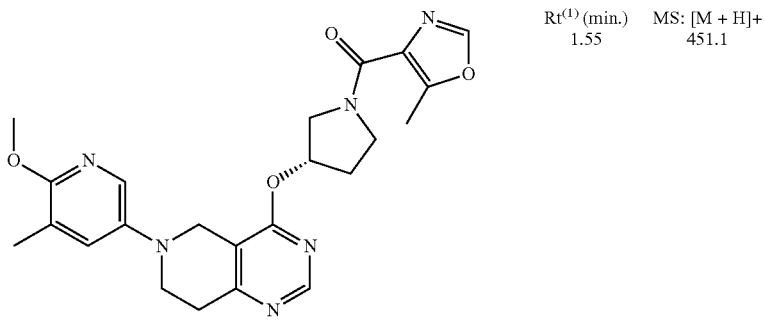 Rt⁽¹⁾ (min.) 1.55    MS: [M + H]+ 451.1

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-oxazol-4-yl)-methanone
Purification method: Reverse phase method A
Prepared using 5-methyl-oxazole-4-carboxylic acid
¹H NMR (400 MHz, DMSO-d6, 298K) δ ppm 2.10-2.32 (m, 2H) 2.13 (s, 3H) 2.52.2.54 (m, 3H) 2.85-2.93 (m, 2H) 3.42-3.50 (m, 2H) 3.61-4.22 (m, 6H) 3.81 (s, 3H) 5.64-5.72 (m, 1H) 7.41-7.45 (m, 1H) 7.67-7.71 (m, 1H) 8.27-8.33 (m, 1H) 8.59-8.64 (m, 1H)

Example 31 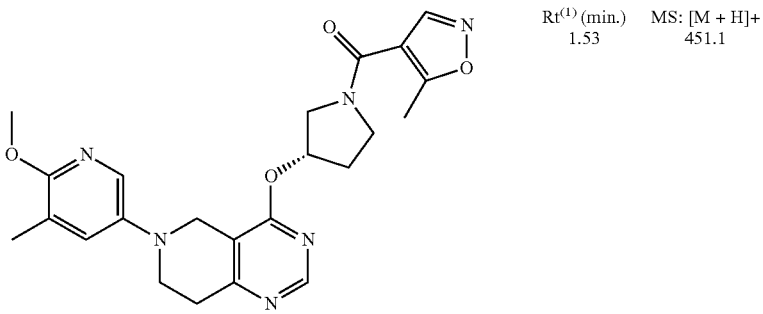 Rt(1) (min.) 1.53  MS: [M + H]+ 451.1

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-isoxazol-4-yl)-methanone
Purification method: Reverse phase method A
Prepared using 5-methyl-isoxazole-4-carboxylic acid
1H NMR (400 MHz, DMSO-d6, 298K) δ ppm 2.10-2.31 (m, 2H) 2.14 (s, 3H) 2.54-2.59 (m, 3H) 2.83-2.97 (m, 2H) 3.41-3.53 (m, 2H) 3.59-4.15 (m, 6H) 3.81 (s, 3H) 5.65-5.73 (m, 1H) 7.40-7.48 (m, 1H) 7.67-7.74 (m, 1H) 8.56-8.66 (m, 1H) 8.83-8.95 (m, 1H)

Example 32 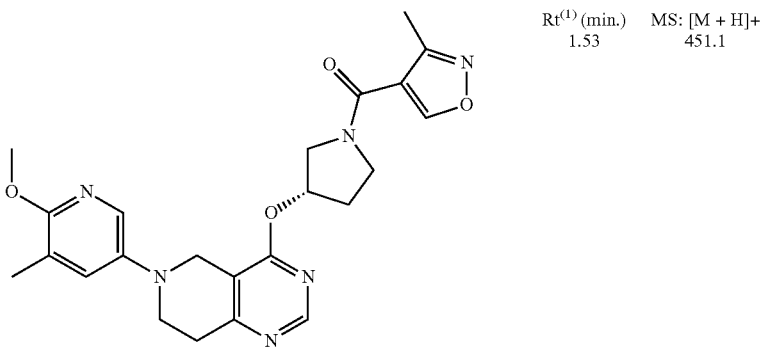 Rt(1) (min.) 1.53  MS: [M + H]+ 451.1

Name: {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-yl)-methanone
Purification method: Reverse phase method A
Prepared using 3-methyl-isoxazole-4-carboxylic acid
1H NMR (400 MHz, DMSO-d6, 298K) δ ppm 2.08-2.37 (m, 8H) 2.82-2.95 (m, 2H) 3.40-3.53 (m, 2H) 3.55-4.16 (m, 9H) 5.65-5.75 (m, 1H) 7.41-7.48 (m, 1H) 7.68-7.73 (m, 1H) 8.57-8.65 (m, 1H) 9.28-9.40 (m, 1H)

Example 33 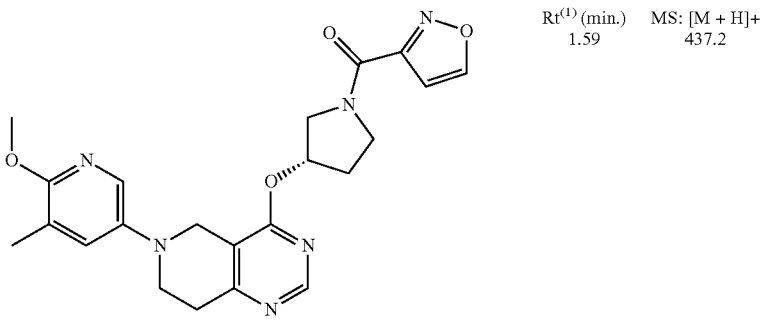 Rt(1) (min.) 1.59  MS: [M + H]+ 437.2

Name: Isoxazol-3-yl-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using isoxazole-3-carboxylic acid
1H NMR (400 MHz, DMSO-d6, 298K) δ ppm 2.13 (m, 3H) 2.21-2.31 (m, 2H) 2.86-2.94 (m, 2H) 3.43-3.50 (m, 2H) 3.66-4.15 (m, 9H) 5.67-5.73 (m, 1H) 6.84-6.91 (m, 1H) 7.42-7.46 (m, 1H) 7.67-7.74 (m, 1H) 8.57-8.64 (m, 1H) 9.05-9.13 (m, 1H)

Example 34 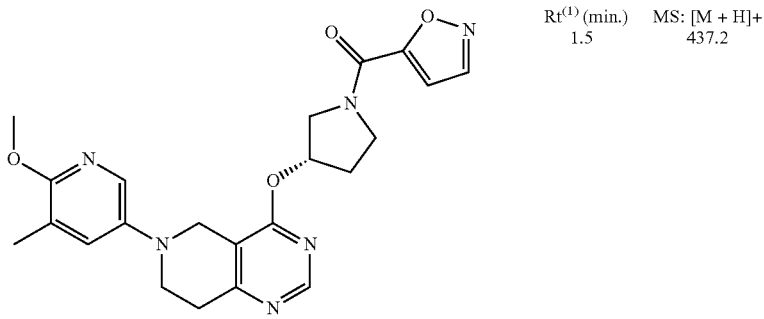 Rt(1) (min.) 1.5  MS: [M + H]+ 437.2

Name: Isoxazol-5-yl-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using isoxazole-5-carboxylic acid
1H NMR (400 MHz, DMSO-d6, 298K) δ ppm 2.08-2.16 (m, 3H) 2.19-2.36 (m, 2H) 2.85-2.95 (m, 2H) 3.42-3.49 (m, 2H) 3.66-4.23 (m, 9H) 5.66-5.78 (m, 1H) 7.06-7.13 (m, 1H) 7.41-7.46 (m, 1H) 7.68-7.74 (m, 1H) 8.59-8.64 (m, 1H) 8.73-8.79 (m, 1H)

Example 35 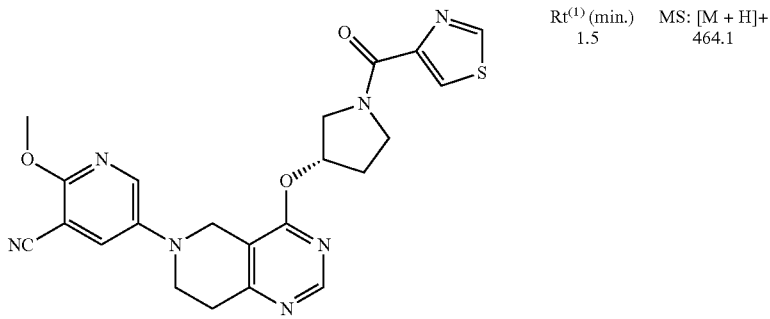 Rt(1) (min.) 1.5  MS: [M + H]+ 464.1

Name: 2-Methoxy-5-{4-[(S)-1-(thiazole-4-carbonyl)-pyrrolidin-3-yloxy]-7,8-dihydro-5H-pyrido[4,3-d]pyrimidin-6-yl}-nicotinonitrile
Purification method: Reverse phase method A
Prepared using intermediate 11 and process step 2, method 1b of example 1 followed by process step 1 of example 10 using thiazole-4-carboxylic acid
1H NMR (400 MHz, CDCl3-d, 298K) δ ppm 2.30-2.37 (m, 2H) 3.07-3.12 (m, 2H) 3.46-3.53 (m, 2H) 3.81-4.43 (m, 9H) 5.80-5.85 (m, 1H) 7.55-7.59 (m, 1H) 8.09-8.13 (m, 1H) 8.18-8.23 (m, 1H) 8.63-8.69 (m, 1H) 8.75-8.85 (m, 1H)

Example 36 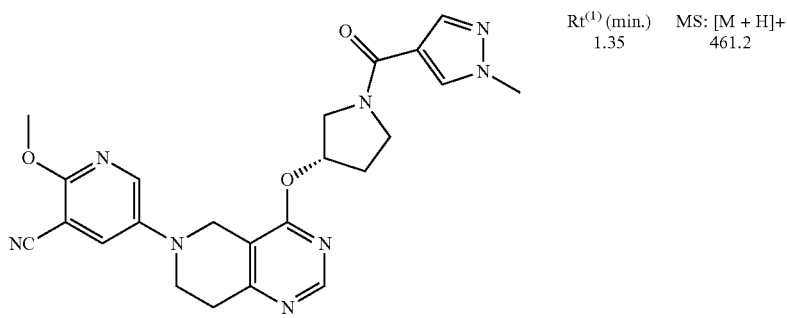 Rt(1) (min.) 1.35  MS: [M + H]+ 461.2

Name: 2-Methoxy-5-{4-[(S)-1-(1-methyl-1H-pyrazole-4-carbonyl)-pyrrolidin-3-yloxy]-7,8-dihydro-5H-pyrido[4,3-d]pyrimidin-6-yl}-nicotinonitrile
Purification method: Reverse phase method A
Prepared using intermediate 11 and process step 2, method 1b of example 1 followed by process step 1 of example 10 using 1-methyl-1H-imidazole-4-carboxylic acid
1H NMR (400 MHz, CDCl3-d, 298K) δ ppm 2.24-2.47 (m, 2H) 3.03-3.17 (m, 2H) 3.45-3.58 (m, 2H) 3.87-4.20 (m, 12H) 5.75-5.85 (m, 1H) 7.54-7.60 (m, 1H) 7.73-7.90 (m, 2H) 8.09-8.14 (m, 1H) 8.61-8.68 (m, 1H)

Example 37 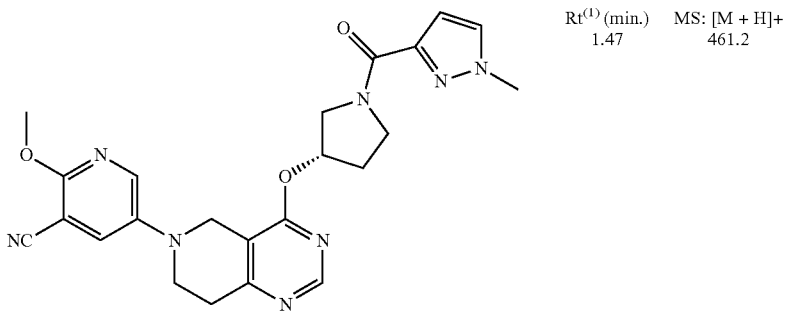 Rt⁽¹⁾ (min.) 1.47  MS: [M + H]+ 461.2

Name: 2-Methoxy-5-{4-[(S)-1-(1-methyl-1H-pyrazole-3-carbonyl)-pyrrolidin-3-yloxy]-7,8-dihydro-5H-pyrido[4,3-d]pyrimidin-6-yl}-nicotinonitrile
Purification method: Reverse phase method A
Prepared using intermediate 11 and process step 2, method 1b of example 1 followed by process step 1 of example 10 using 1-methyl-1H-pyrazole-3-carboxylic acid
$^1$H NMR (400 MHz, CDCl$_3$-d, 298K) δ ppm 2.24-2.41 (m, 2H) 3.07-3.14 (m, 2H) 3.44-3.58 (m, 2H) 3.74-4.44 (m, 12H) 5.77-5.86 (m, 1H) 6.78-6.84 (m, 1H) 7.33-7.39 (m, 1H) 7.54-7.59 (m, 1H) 8.08-8.14 (m, 1H) 8.63-8.70 (m, 1H)

Example 38 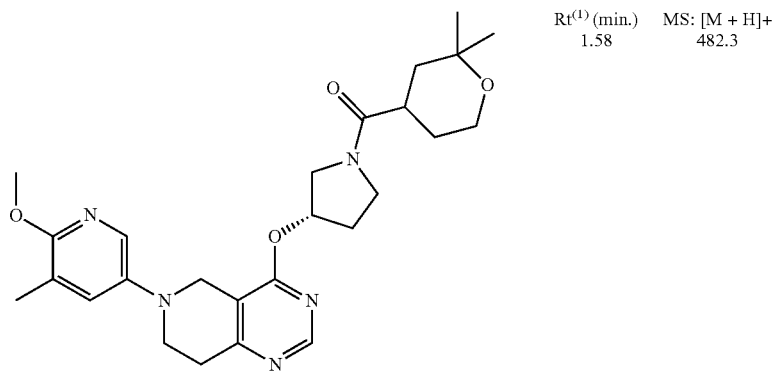 Rt⁽¹⁾ (min.) 1.58  MS: [M + H]+ 482.3

Name: (2,2-Dimethyl-tetrahydro-pyran-4yl)-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using 2,2-dimethyl-tetrahydro-pyran-4-carboxylic acid
$^1$H NMR (400 MHz, DMSO-d6, 298K) δ ppm 1.02-1.21 (m, 6H) 1.27-1.71 (m, 4H) 2.08-2.32 (m, 5H) 2.67-2.94 (m, 3H) 3.41-4.08 (m, 13H) 5.60-5.73 (m, 1H) 7.41-7.46 (m, 1H) 7.65-7.72 (m, 1H) 8.58-8.65 (m, 1H)

Example 39 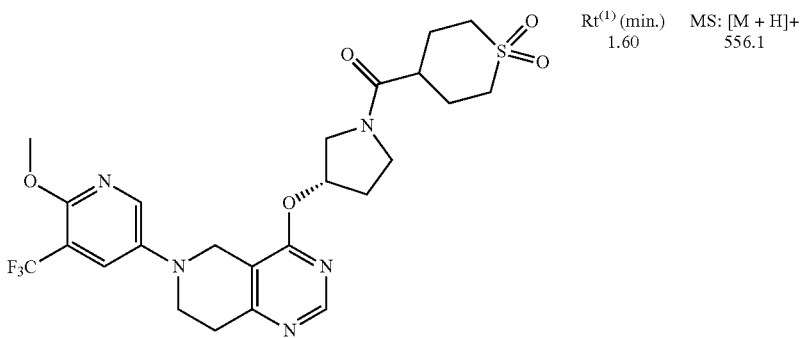 Rt⁽¹⁾ (min.) 1.60  MS: [M + H]+ 556.1

Name: (1,1-Dioxo-hexahydro-1lambda*6*-thiopyran-4-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using intermediate 13 and process step 2, method 1b of example 1 followed by process step 1 of example 10 using 1,1-dioxo-hexahydro-1lambda*6*-thiopyran-4-carboxylic acid
$^1$H NMR (400 MHz, DMSO-d6, 298K) δ ppm 1.90-2.37 (m, 6H) 2.72-3.27 (m, 7H) 3.43-3.81 (m, 6H) 3.89-3.97 (m, 3H) 4.13-4.20 (m, 2H) 5.61-5.75 (m, 1H) 7.80-7.86 (m, 1H) 8.15-8.22 (m, 1H) 8.60-8.65 (m, 1H)

Example 40

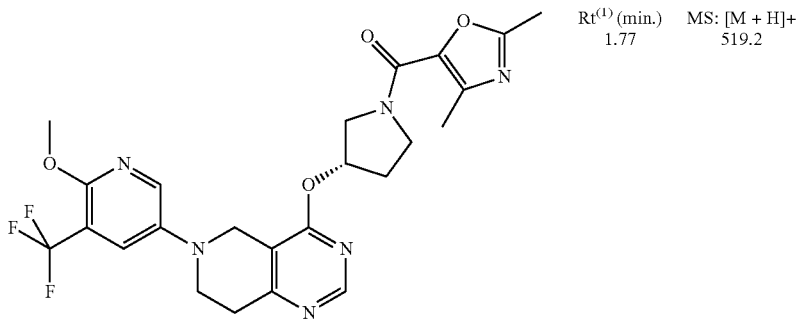

Rt⁽¹⁾ (min.) 1.77　MS: [M + H]+ 519.2

Name: (2,4-Dimethyl-oxazol-5-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using intermediate 13 and process step 2, method 1b of example 1 followed by process step 1 of example 10 using 2,4-dimethyl-oxazole-5-carboxylic acid
¹H NMR (400 MHz, DMSO-d6, 298K) δ ppm 2.13-2.45 (m, 8H) 2.89-2.96 (m, 2H) 3.54-4.21 (m, 11H) 5.64-5.79 (m, 1H) 7.81-7.85 (m, 1H) 8.218-8.22 (m., 1H) 8.61-8.65 (m, 1H)

Example 41

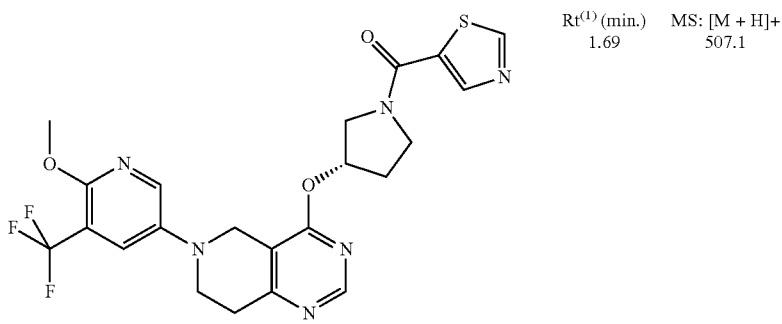

Rt⁽¹⁾ (min.) 1.69　MS: [M + H]+ 507.1

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-thiazol-5-yl-methanone
Purification method: Reverse phase method A
Prepared using intermediate 13 and process step 2, method 1b of example 1 followed by process step 1 of example 10 using thiazole-5-carboxylic acid
¹H NMR (400 MHz, DMSO-d6, 298K) δ ppm 2.15-2.42 (m, 2H) 2.88-2.97 (m, 2H) 3.53-3.61 (m, 2H) 3.67-4.11 (m, 7H) 4.15-4.24 (m, 2H) 5.67-5.79 (m, 1H) 7.81-7.88 (m, 1H) 8.18-8.23 (m, 1H) 8.35-8.45 (m, 1H) 8.60-8.66 (m, 1H) 9.22-9.29 (m, 1H)

Example 42

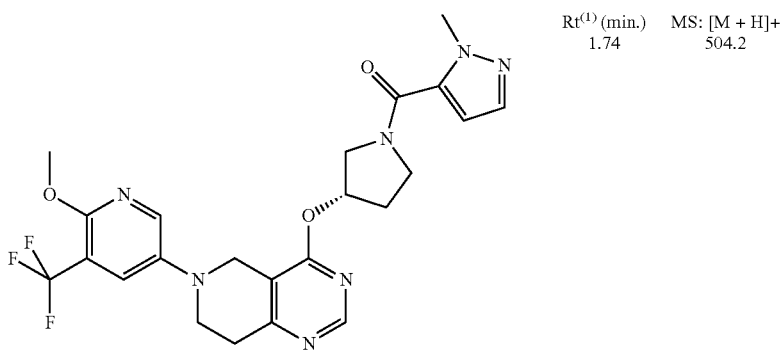

Rt⁽¹⁾ (min.) 1.74　MS: [M + H]+ 504.2

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(2-methyl-2H-pyrazol-3-yl)-methanone
Purification method: Reverse phase method A
Prepared using intermediate 13 and process step 2, method 1b of example 1 followed by process step 1 of example 10 using 2-methyl-2H-pyrazole-3-carboxylic acid
¹H NMR (400 MHz, DMSO-d6, 298K) δ ppm 2.15-2.35 (m, 2H) 2.88-2.97 (m, 2H) 3.51-4.13 (m, 12H) 4.13-4.25 (m, 2H) 5.63-5.74 (m, 1H) 6.63-6.74 (m, 1H) 7.43-7.52 (m, 1H) 7.81-7.89 (m, 1H) 8.17-8.25 (m, 1H) 8.57-8.67 (m, 1H)

Example 43 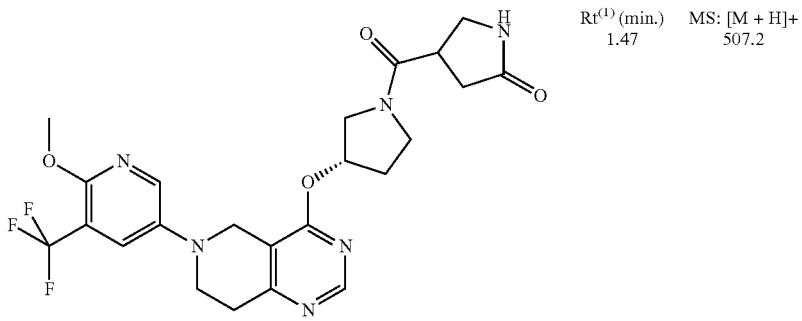 Rt⁽¹⁾ (min.) 1.47  MS: [M + H]+ 507.2

Name: 4-{(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-pyrrolidin-2-one
Purification method: Reverse phase method A
Prepared using intermediate 13 and process step 2, method 1b of example 1 followed by process step 1 of example 10 using 5-oxo-pyrrolidine-3-carboxylic acid
$^1$H NMR (400 MHz, DMSO-d6, 298K) δ ppm 2.10-2.43 (m, 4H) 2.89-2.96 (m, 2H) 3.35-3.79 (m, 9H) 3.90-3.94 (m, 3H) 4.15-4.20 (m, 2H) 5.60-5.73 (m, 1H) 7.53-7.62 (m, 1H) 7.81-7.87 (m, 1H) 8.17-8.22 (m, 1H) 8.60-8.64 (m, 1H)

Example 44 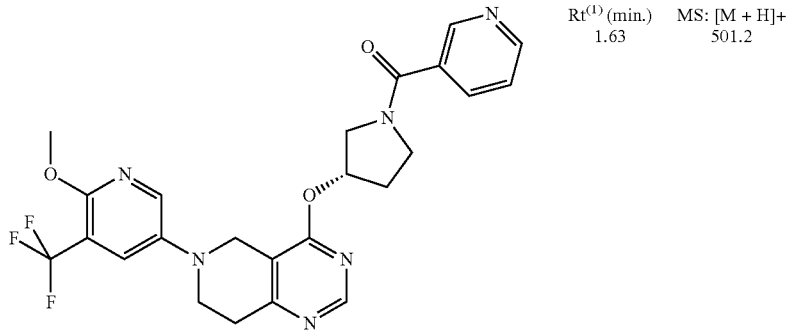 Rt⁽¹⁾ (min.) 1.63  MS: [M + H]+ 501.2

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-pyridin-3-yl-methanone
Purification method: Reverse phase method A
Prepared using intermediate 13 and process step 2, method 1b of example 1 followed by process step 1 of example 10 using nicotinic acid
$^1$H NMR (400 MHz, DMSO-d6, 298K) δ ppm 2.11-2.37 (m, 2H) 2.87-2.99 (m, 2H) 3.51-4.13 (m, 9H) 4.13-4.29 (m, 2H) 5.60-5.75 (m, 1H) 7.43-7.53 (m, 1H) 7.81-8.04 (m, 2H) 8.17-8.28 (m, 1H) 8.53-8.82 (m, 3H)

Example 45 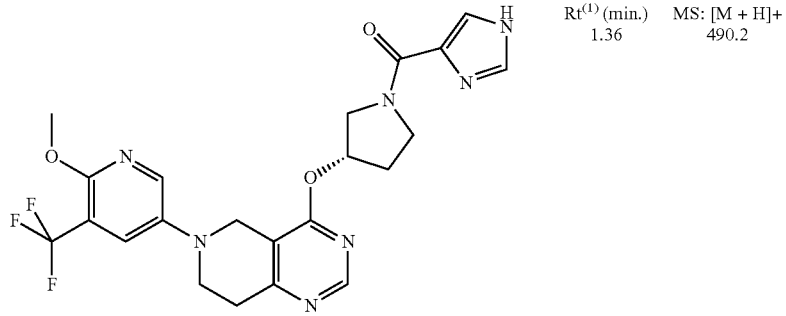 Rt⁽¹⁾ (min.) 1.36  MS: [M + H]+ 490.2

Name: (1H-Imidazol-4-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using intermediate 13 and process step 2, method 1b of example 1 followed by process step 1 of example 10 using 1H-imidazole-4-carboxylic acid
$^1$H NMR (400 MHz, DMSO-d6, 298K) δ ppm 2.12-2.35 (m, 2H) 2.87-2.95 (m, 2H) 3.60-4.31 (m, 11H) 5.63-5.76 (m, 1H) 7.57-7.65 (m, 1H) 7.70-7.78 (m, 1H) 7.80-7.85 (m, 1H) 8.16-8.21 (m, 1H) 8.61-8.65 (m, 1H)

Example 46 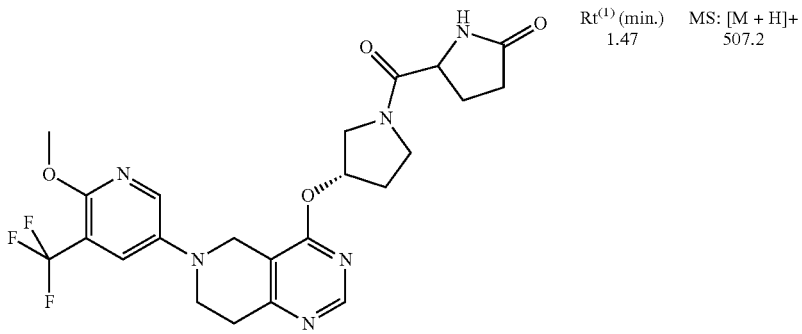 Rt⁽¹⁾ (min.) 1.47  MS: [M + H]+ 507.2

Name: 5-{(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-pyrrolidin-2-one
Purification method: Reverse phase method A
Prepared using intermediate 13 and process step 2, method 1b of example 1 followed by process step 1 of example 10 using 5-oxo-pyrrolidine-2-carboxylic acid
$^1$H NMR (400 MHz, DMSO-d6, 298K) δ ppm 1.78-2.40 (m, 6H) 2.89-2.97 (m, 2H) 3.43-3.86 (m, 6H) 3.90-3.94 (m, 3H) 4.15-4.20 (m, 2H) 4.30-4.45 (m, 1H) 5.60-5.75 (m, 1H) 7.70-7.89 (m, 2H) 8.16-8.22 (m, 1H) 8.61-8.63 (m, 1H)

Example 47 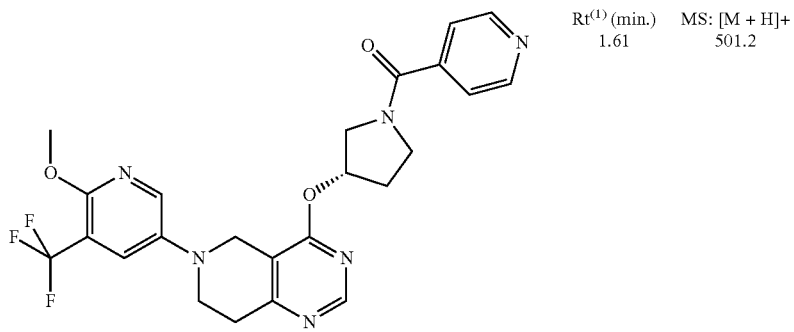 Rt⁽¹⁾ (min.) 1.61  MS: [M + H]+ 501.2

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-pyridin-4-yl-methanone
Purification method: Reverse phase method A
Prepared using intermediate 13 and process step 2, method 1b of example 1 followed by process step 1 of example 10 using isonicotinic acid
$^1$H NMR (400 MHz, DMSO-d6, 298K) δ ppm 2.12-2.36 (m, 2H) 2.86-2.99 (m, 2H) 3.46-3.81 (m, 5H) 3.84-4.13 (m, 4H) 4.14-4.28 (m, 2H) 5.59-5.74 (m, 1H) 7.44-7.56 (m, 2H) 7.82-7.91 (m, 1H) 8.18-8.27 (m, 1H) 8.52-8.72 (m, 3H)

Example 48 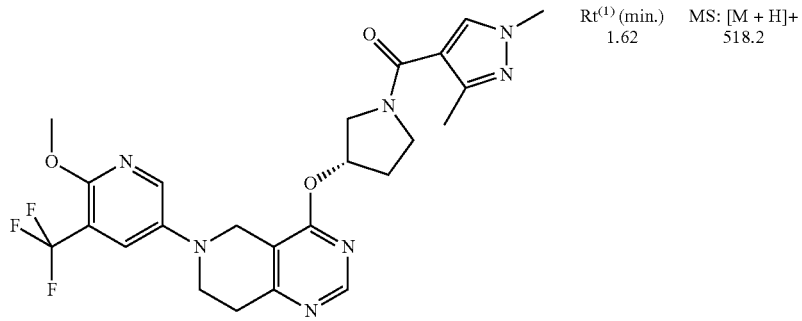 Rt⁽¹⁾ (min.) 1.62  MS: [M + H]+ 518.2

Name: (1,3-Dimethyl-1H-pyrazol-4-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone
Purification method: Reverse phase method A
Prepared using intermediate 13 and process step 2, method 1b of example 1 followed by process step 1 of example 10 using 1,3,-dimethyl-1H-pyrazole-4-carboxylic acid
$^1$H NMR (400 MHz, DMSO-d6, 298K) δ ppm 2.13-2.35 (m, 5H) 2.89-2.97 (m, 2H) 3.53-4.06 (m, 12H) 4.14-4.22 (m, 2H) 5.64-5.72 (m, 1H) 7.80-7.88 (m, 1H) 7.99-8.11 (m, 1H) 8.16-8.22 (m, 1H) 8.58-8.66 (m, 1H)

Example 49 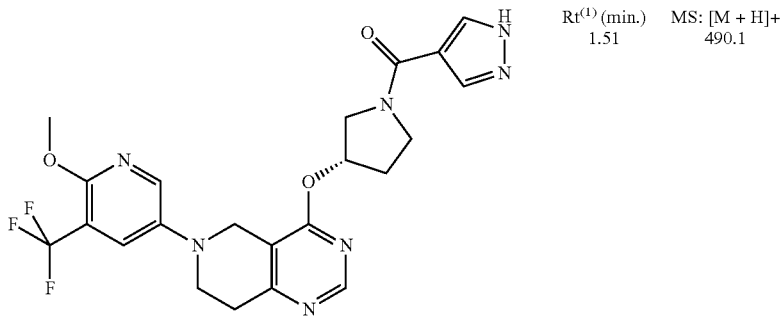 Rt⁽¹⁾ (min.) 1.51   MS: [M + H]+ 490.1

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(1H-pyrazol-4-yl)-methanone
Purification method: Reverse phase method A
Prepared using intermediate 13 and process step 2, method 1b of example 1 followed by process step 1 of example 10 using 1H-pyrazole-4-carboxylic acid
¹H NMR (400 MHz, DMSO-d6, 298K) δ ppm 2.12-2.39 (m, 2H) 2.87-2.97 (m, 2H) 3.43-4.11 (m, 9H) 4.12-4.22 (m, 2H) 5.63-5.79 (m, 1H) 7.78-7.94 (m, 2H) 8.10-8.25 (m, 3H) 8.59-8.68 (m, 1H)

Example 51 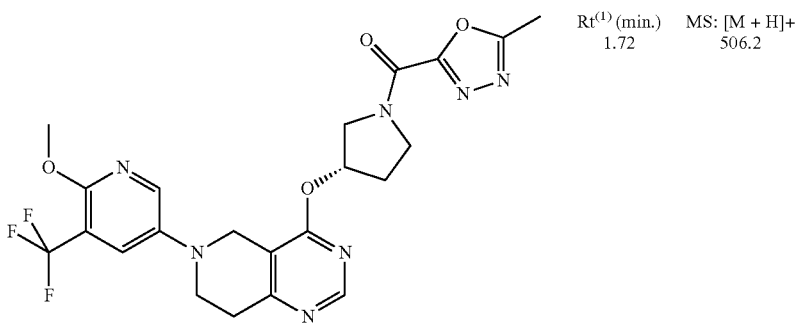 Rt⁽¹⁾ (min.) 1.72   MS: [M + H]+ 506.2

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(5-methyl-[1,3,4]oxadiazol-2-yl)-methanone
Purification method: Reverse phase method A
Prepared using intermediate 13 and process step 2, method 1b of example 1 followed by process step 1 of example 10 using 5-methyl-[1,3,4]oxadiazole-2-carboxylic acid Example 52 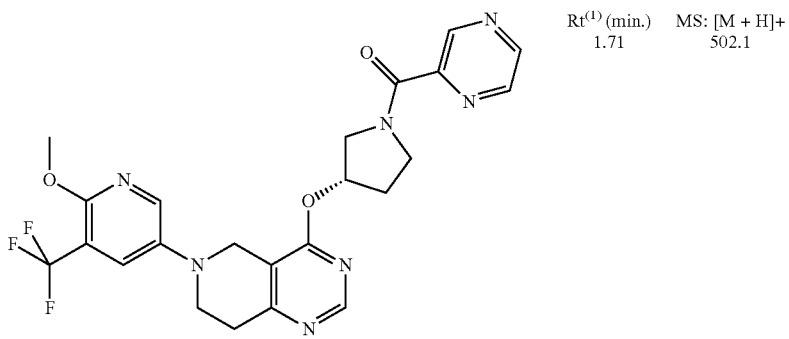 Rt⁽¹⁾ (min.) 1.71   MS: [M + H]+ 502.1

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-pyrazin-2-yl-methanone
Purification method: Reverse phase method A
Prepared using intermediate 13 and process step 2, method 1b of example 1 followed by process step 1 of example 10 using pyrazine-2-carboxylic acid
¹H NMR (400 MHz, DMSO-d6, 298K) δ ppm 2.15-2.36 (m, 2H) 2.87-2.97 (m, 2H) 3.52-3.64 (m, 2H) 3.66-4.11 (m, 7H) 4.12-4.24 (m, 2H) 5.67-5.75 (m, 1H) 7.81-7.87 (m, 1H) 8.17-8.25 (m, 1H) 8.56-8.80 (m, 3H) 8.97-9.02 (m, 1H)

| Example 53 | | Rt(1) (min.) | MS: [M + H]+ |
|---|---|---|---|
| | 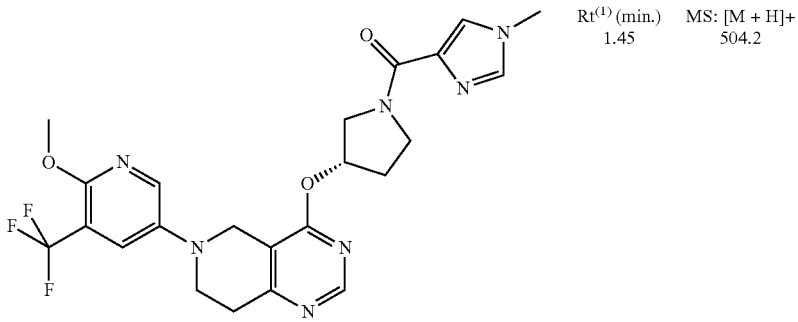 | 1.45 | 504.2 |

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(1-methyl-1H-imidazol-4-yl)-methanone
Purification method: Reverse phase method A
Prepared using intermediate 13 and process step 2, method 1b of example 1 followed by process step 1 of example 10 using 1-methyl-1H-imidazole-4-carboxylic acid
$^1$H NMR (400 MHz, DMSO-d6, 298K) δ ppm 2.07-2.36 (m, 2H) 2.82-3.05 (m, 2H) 3.20-4.43 (m, 14H) 5.60-5.74 (m, 1H) 7.59-7.72 (m, 2H) 7.78-7.87 (m, 1H) 8.14-8.21 (m, 1H) 8.59-8.66 (m, 1H)

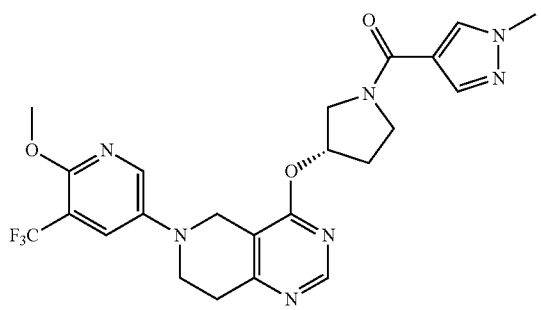 [SMILES: COc1ncc(N2CCc3ncnc(O[C@H]4CCN(C(=O)c5cnn(C)c5)C4)c3C2)cc1C(F)(F)F]

Example 54

{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(1-methyl-1H-pyrazol-4-yl)-methanone To a mixture of 6-(6-methoxy-5-trifluoromethyl-pyridin-3-yl)-4-((S)-pyrrolidin-3-yloxy)-5,6,7,8-tetrahydro-pyrido[4,3-d]pyrimidine (prepared using step 1, example 91 from intermediate 13) (44 mg, 0.11 mmol), 1-methyl-1H-pyrazole-4-carboxylic acid (15 mg, 0.12 mmol), benztriazol-1-ol (19 mg, 0.12 mmol) in CH$_2$Cl$_2$ (1.0 mL) was added EDC (34 mg, 0.18 mmol) and the resulting mixture was stirred at rt for 18 h. Partitioned between CH$_2$Cl$_2$ (10 mL) and sat. NaHCO$_3$ (aq) (2.0 mL) and the organic layer separated by filtering through a phase separation tube. Concentrated in vacuo and purified by flash chromatography through Biotage® amino silica gel eluting with cyclohexane/EtOAc, 100/0 to 0/100 to give {(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-(1-methyl-1H-pyrazol-4-yl)-methanone as a white lyophilized powder (44 mg, 75% yield). $^1$H NMR (400 MHz, CDCl$_3$-d, 298K) δ ppm 2.26-2.45 (m, 2H) 3.04-3.10 (m, 2H) 3.49-3.57 (m, 2H) 3.89-4.00 (m, 7H) 4.01 (s, 3H) 4.10-4.18 (m, 2H) 5.78-5.83 (m, 1H) 7.60-7.62 (m, 1H) 7.76-7.89 (m, 2H) 8.04-8.07 (m, 1H) 8.61-8.66 (m, 1H) MS: [M+H]$^+$=504.2, Rt$^{(3)}$=1.59 min. Example 55 was prepared using procedures analogous to those used in example 54 using appropriate starting materials.

| Example 55 | Structure | Rt(1) (min.) | MS: [M + H]+ |
|---|---|---|---|
| | 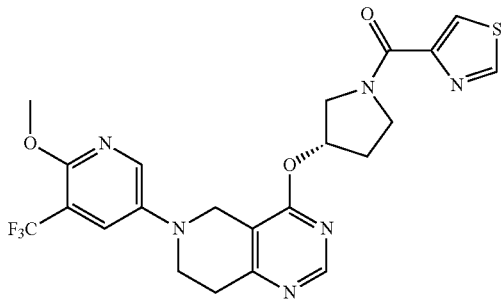 [SMILES: COc1ncc(N2CCc3ncnc(O[C@H]4CCN(C(=O)c5cscn5)C4)c3C2)cc1C(F)(F)F] | 1.77 | 507.2 |

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-thiazol-4-yl-methanone
Purification method: Flash chromatography on Biotage amino silica gel eluting with cyclohexane/EtOAc 100/0 to 0/100
Prepared using thiazole-4-carboxylic acid
$^1$H NMR (400 MHz, CDCl$_3$-d, 298K) δ ppm 2.29-2.40 (m, 2H) 3.05-3.12 (m, 2H) 3.49-3.56 (m, 2H) 3.80-4.45 (m, 9H) 5.80-5.86 (m, 1H) 7.60-7.62 (m, 1H) 8.04-8.18 (m, 1H) 8.21-8.25 (m, 1H) 8.64-8.68 (m, 1H) 8.79-8.84 (m, 1H)

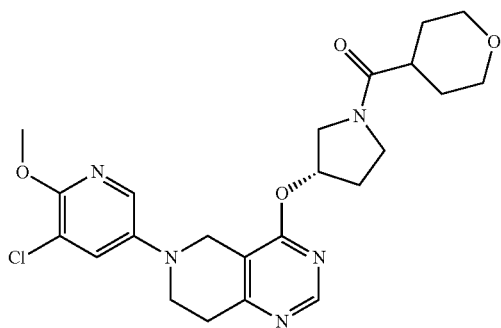 [SMILES: COc1ncc(N2CCc3ncnc(O[C@H]4CCN(C(=O)C5CCOCC5)C4)c3C2)cc1Cl]

Example 56

{(S)-3-[6-(5-Chloro-6-methoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone To a 6-(5-chloro-6-methoxy-pyridin-3-yl)-4-((S)-pyrrolidin-3-yloxy)-5,6,7,8-tetrahydro-pyrido[4,3-d]pyrimidine (97 mg, 0.196 mmol) in CH$_2$Cl$_2$ (5 mL) was added the acid chloride tetrahydro-2H-pyran-4-carbonyl chloride (36.7 mg, 0.235 mmol) and triethylamine (0.035 mL, 0.254 mmol) at temperature between 0-10° C. The reaction mixture was stirred at ~3° C. for 30 min. The reaction mixture was concentrated under vacuum. Purification by preparative reverse phase Gilson HPLC and subsequent neutralization of the combined fractions over PL-HCO$_3$ MP gave {(S)-3-[6-(5-chloro-6-methoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone (38 mg, 41% yield) as a white lyophilized powder. $^1$H NMR (400 MHz, CDCl$_3$-d, 298 K) δ ppm 1.56-1.68 (m, 2H) 1.86-2.04 (m, 2H) 2.20-2.40 (m, 2H) 2.50-2.72 (m, 1H) 3.05-3.13 (m, 2H) 3.38-4.16 (m, 16H) 5.70-5.78 (m, 1H) 7.42-7.45 (m, 1H) 7.78-7.81 (m, 1H) 8.61-8.66 (m, 1H). LCMS: [M+H]$^+$=474.2, Rt$^{(2)}$=1.52 min.

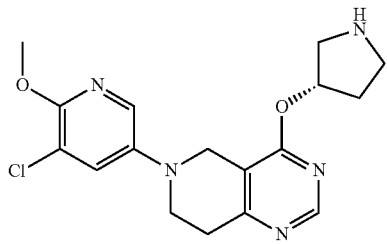 [SMILES: COc1ncc(N2CCc3ncnc(O[C@H]4CCNC4)c3C2)cc1Cl]

6-(5-Chloro-6-methoxy-pyridin-3-yl)-4-((S)-pyrrolidin-3-yloxy)-5,6,7,8-tetrahydro-pyrido[4,3-d]pyrimidine (S)-3-[6-(5-Chloro-6-methoxy-pyridin-3-yl)-5,6,7,8-tetrahydro-pyrido[4,3-d]pyrimidin-4-yloxy]-pyrrolidine-1-carboxylic acid tert-butyl ester (766.2 mg, 1.66 mmol) was dissolved in a TFA/CH$_2$Cl$_2$ (1/2) solution and stirred at rt for 1 h. The reaction mixture was concentrated under vacuum, the residue was diluted with CH$_2$Cl$_2$, the organic layer washed with NaOH 1N then brine, dried over Na$_2$SO$_4$, filtered and evaporated to give 6-(5-chloro-6-methoxy-pyridin-3-yl)-4-((S)-pyrrolidin-3-yloxy)-5,6,7,8-tetrahydro-pyrido[4,3-d]pyrimidine. LCMS: [M+H]$^+$=362.1, Rt$^{(3)}$=1.28 min.

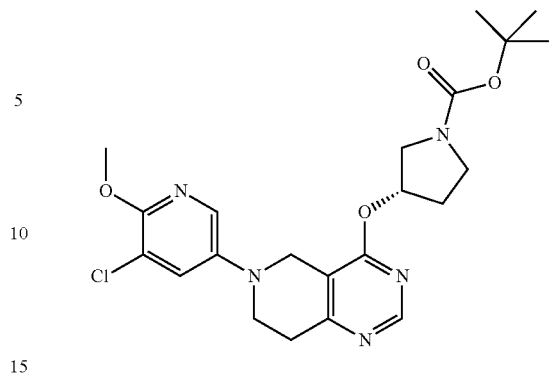

(S)-3-[6-(5-Chloro-6-methoxy-pyridin-3-yl)-5,6,7,8-tetrahydro-pyrido[4,3-d]pyrimidin-4-yloxy]-pyrrolidine-1-carboxylic acid tert-butyl ester X-Phos (0.073 g, 0.154 mmol), Pd$_2$(dba)$_3$ (0.100 g, 0.110 mmol), NaOtBu (0.395 g, 4.11 mmol) and 5-bromo-3-chloro-2-methoxy-pyridine (0.732 g, 3.29 mmol) were combined and flushed under a stream of argon for 10 min. To this mixture, a solution of (S)-3-(5,6,7,8-tetrahydro-pyrido[4,3-d]pyrimidin-4-yloxy)-pyrrolidine-1-carboxylic acid tert-butyl ester (Intermediate 7) (2.15 g, 6.72 mmol) in THF (6 mL) was added at rt and the reaction mixture was stirred at 90° C. for 3 h. The reaction was cooled down to rt, EtOAc was added, the mixture filtered through a celite pad and concentrated under vacuum. Purification by flash chromatography on silica gel (CH$_2$Cl$_2$/MeOH 99/1 to 95/5) gave (S)-3-[6-(5-chloro-6-methoxy-pyridin-3-yl)-5,6,7,8-tetrahydro-pyrido[4,3-d]pyrimidin-4-yloxy]-pyrrolidine-1-carboxylic acid tert-butyl ester as yellow foam (0.766 g, 60% yield). LCMS: [M+H]$^+$=462.1, Rt$^{(3)}$=1.84 min

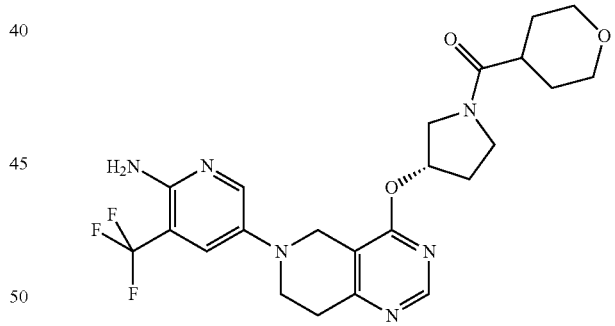

Example 57

{(S)-3-[6-(6-Amino-5-trifluoromethyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone To a solution of (S)-tert-butyl 3-(6-(6-(bis(tert-butoxycarbonyl)amino)-5-(trifluoromethyl)pyridin-3-yl)-5,6,7,8-tetrahydropyrido[4,3-d]pyrimidin-4-yloxy)pyrrolidine-1 (120 mg, 0.18 mmol) in CH$_2$Cl$_2$ (2.0 mL), was added TFA (2.0 mL) and the mixture stood at rt for 1 h. Concentrated in vacuo and eluted through an Isolute® SCX-2 cartridge, eluting with methanol, then with 2M ammonia in methanol. Basic fractions were concentrated in vacuo to give 5-[4-((S)-pyrrolidin- 3-yloxy)-7,8-dihydro-5H-pyrido[4,3-d]pyrimidin-6-yl]-3-(trifluoromethyl)pyridin-2-yl)amine (61 mg, 90% yield). 5-[4-((S)-pyrrolidin-3-yloxy)-7,8-dihydro-5H-pyrido[4,3-d]pyrimidin-6-yl]-3-(trifluoromethyl)pyridin-2-yl)amine (30 mg, 0.079 mmol) was dissolved in CH₂Cl₂ (2.0 mL) and was added simultaneously portionwise with sat.NaHCO₃(aq) (2.0 mL) to a vigorously stirring solution of tetrahydro-2H-pyran-4-carbonyl chloride (15 mg, 0.10 mmol) in CH₂Cl₂ (2.0 mL) at rt. The resulting biphasic mixture was stirred at rt for 1 h. Diluted with CH₂Cl₂ (10 mL) and the organic layer was separated by filtering through a phase separation tube and concentrated in vacuo. Purification by reverse phase Gilson HPLC (Method A) and subsequent neutralization of the combined fractions by elution through an Isolute® SCX-2 cartridge, eluting with methanol, then with 2M ammonia in methanol. Basic fractions were concentrated in vacuo to give {(S)-3-[6-(6-amino-5-trifluoromethyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone as a pale yellow powder (19 mg, 50% yield) ¹H NMR (400 MHz, CDCl₃, 298K) δ ppm 1.56-1.72 (m, 2H) 1.87-2.03 (m, 2H) 2.23-2.74 (m, 3H) 3.04-3.14 (m, 2H) 3.48-4.13 (m, 12H) 5.15-5.43 (m, 2H, Ar—NH2) 5.73-5.79 (m, 1H) 7.55-7.64 (m, 1H) 7.93-8.02 (m, 1H) 8.61-8.67 (m, 1H) LCMS: [M+H]+=397.1, Rt⁽³⁾=1.32 min.

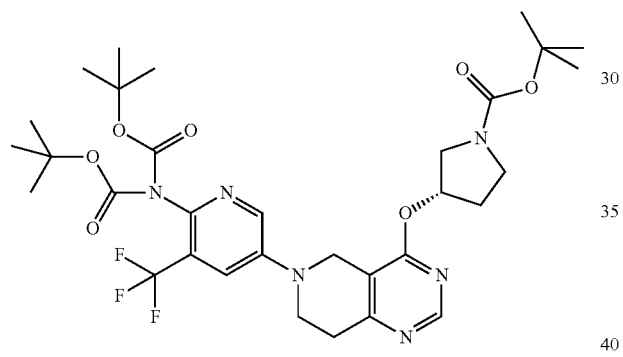

(S)-tert-butyl 3-(6-(6-(bis(tert-butoxycarbonyl)amino)-5-(trifluoromethyl)pyridin-3-yl)-5,6,7,8-tetrahydropyrido[4,3-d]pyrimidin-4-yloxy)pyrrolidine-1-carboxylate To a glass vial was added (S)-3-(5,6,7,8-Tetrahydro-pyrido[4,3-d]pyrimidin-4-yloxy)-pyrrolidine-1-carboxylic acid tert-butyl ester (Intermediate 7) (100 mg, 0.312 mmol), imidodicarbonic acid, 2-[5-bromo-3-(trifluoromethyl)-2-pyridinyl]-, 1,3-bis(1,1-dimethylethyl) ester (138 mg, 0.312 mmol), cesium carbonate (203 mg, 0.62 mmol), tris(dibenzylideneacetone)dipalladium(0) (29 mg, 0.03 mmol), X-Phos (51 mg, 0.11 mmol) and anhydrous dioxane (2 mL). The vial was flushed with a stream of argon for 15 sec and capped. The mixture was heated with stirring for 1 h at 110° C. and then stirred at room temperature for 18 h. Allowed to cool and partitioned between CH₂Cl₂ (10 mL) and water (2 mL) and filtered the biphasic mixture through a celite pad. The organic layer was separated by filtering through phase separation tube and concentrated in vacuo. Purification by reverse phase Gilson HPLC (Method A) to give (S)-tert-butyl 3-(6-(6-(bis(tert-butoxycarbonyl)amino)-5-(trifluoromethyl)pyridin-3-yl)-5,6,7,8-tetrahydropyrido[4,3-d]pyrimidin-4-yloxy)pyrrolidine-1-carboxylate trifluoroacetate (as a yellow gum (120 mg, 48% yield). LCMS: [M+H]+=681.5, Rt⁽⁴⁾=1.49 min.

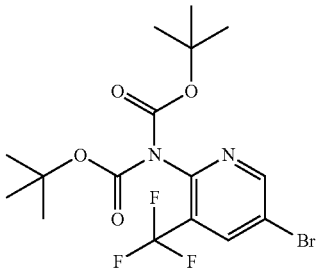 [SMILES: CC(C)(C)OC(=O)N(C(=O)OC(C)(C)C)c1ncc(Br)cc1C(F)(F)F]

Imidodicarbonic acid, 2-[5-bromo-3-(trifluoromethyl)-2-pyridinyl]-, 1,3-bis(1,1-dimethylethyl) ester To 5-bromo-3-(trifluoromethyl)pyridin-2-amine (1.72 g, 7.14 mmol), triethylamine (0.995 mL, 7.14 mmol) and 4-dimethylaminoyridine (20 mg, 0.164 mmol) in CH₂Cl₂ (50 mL) was added di-tert-butyl-dicarbonate (3.89 g, 17.84 mmol) and the resulting mixture stirred at room temperature for 18 h. Evaporated to dryness in vacuo and triturated in heptane (25 mL) for 72 h. The resulting precipitate was filtered and washed with heptane (10 mL) to give Imidodicarbonic acid, 2-[5-bromo-3-(trifluoromethyl)-2-pyridinyl]-, 1,3-bis(1,1-dimethylethyl) ester as a beige solid (2.23 g, 71% yield). ¹H NMR (400 Mhz, CDCl₃, 298K) 1.35 (s, 18H) 8.15 (d, 1H) 8.76 (d, 1H) LCMS: [M+H]+=441/443.1, Rt⁽⁴⁾=1.46 min.

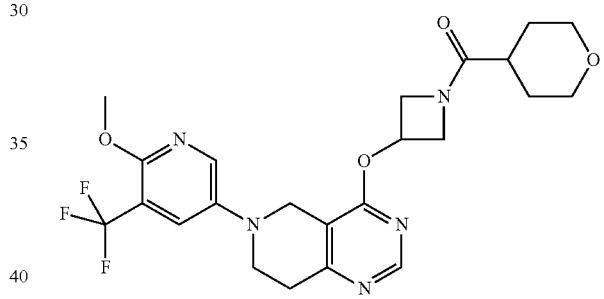

Example 58

{3-[6-(6-Methoxy-5-trifluoromethyl-pyridin-3-yl)-5,6,7,8-tetrahydro-pyrido[4,3-d]pyrimidin-4-yloxy]-azetidin-1-yl}-(tetrahydro-pyran-4-yl)-methanone 3-[6-(6-Methoxy-5-trifluoromethyl-pyridin-3-yl)-5,6,7,8-tetrahydro-pyrido[4,3-d]pyrimidin-4-yloxy]-azetidine-1-carboxylic acid tert-butyl ester (186 mg, 0.312 mmol) in CH₂Cl₂ (2.0 mL) was added TFA (1.0 mL) and the mixture stirred at room temperature for 1 h. Evaporated in vacuo to give 4-(azetidin-3-yloxy)-(6-(6-methoxy-5-trifluoromethyl-pyridin-3-yl)-5,6,7,8-tetrahydro-pyrido[4,3-d]pyrimidine ditrifluoroacetate as a brown gum (110 mg). To a vigorously stirring solution of tetrahydro-2H-pyran-4-carbonyl chloride (19 mg, 0.128 mmol) in CH₂Cl₂ was added simultaneously portionwise sat. NaHCO₃(aq) (2.0 mL) and a solution of 4-(azetidin-3-yloxy)-(6-(6-methoxy-5-trifluoromethyl-pyridin-3-yl)-5,6,7,8-tetrahydro-pyrido[4,3-d]pyrimidine ditrifluoroacetate (60 mg, 0.099 mmol) in CH₂Cl₂ (2.0 mL) at rt. The resulting biphasic mixture was stirred vigorously at rt for 1 h. Diluted with CH₂Cl₂ (10 mL), the organic layer separated, dried (MgSO₄), concentrated in vacuo and purified by reverse phase Gilson HPLC (Method A) and subsequent neutralization of the combined fractions by eluting through an Isolute® SCX-2 cartridge, eluting with methanol, then with 2M ammonia in methanol. Basic fractions were concentrated in vacuo to give {3-[6-(6-methoxy-5-trifluoromethyl-pyridin-3-yl)-5,6,7,8-tetrahydro-pyrido[4,3-d]pyrimidin-4-yloxy]-azetidin-1-yl}-(tetrahydro-pyran-4-yl)-methanone as a yellow solid (3.0 mg, 5% yield $2^{nd}$ step) $^1$H NMR (400 MHz, DMSO-d6, 298K) δ ppm 1.42-1.67 (m, 4H) 2.90-2.98 (m, 2H) 3.55-3.62 (m, 2H) 3.78-4.32 (m, 13H) 4.61-4.69 (m, 1H) 5.42-5.49 (m, 1H) 7.86-7.90 (m, 1H) 8.22-8.26 (m, 1H) 8.58-8.62 (s, 1H) LCMS: [M+H]+=494.6, $Rt^{(7)}$=0.98 min.

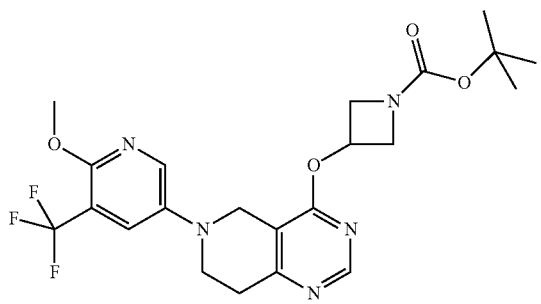 [SMILES: COc1ncc(N2CCc3ncnc(OC4CN(C(=O)OC(C)(C)C)C4)c3C2)cc1C(F)(F)F]

3-[6-(6-Methoxy-5-trifluoromethyl-pyridin-3-yl)-5,6,7,8-tetrahydro-pyrido[4,3-d]pyrimidin-4-yloxy]-azetidine-1-carboxylic acid tert-butyl ester To a glass vial was added 3-(5,6,7,8-tetrahydro-pyrido[4,3-d]pyrimidin-4-yloxy)-azetidine-1-carboxylic acid tert-butyl ester (110 mg, 0.359 mmol), 5-Bromo-2-methoxy-3-(trifluoromethyl)pyridine (92 mg, 0.359 mmol), cesium carbonate (234 mg, 0.718 mmol), tris(dibenzylideneacetone)dipalladium(0) (33 mg, 0.036 mmol), X-Phos (58 mg, 0.122 mmol) and anhydrous dioxane (2.0 mL). The vial was flushed with a stream of argon for 15 sec and capped. The mixture was heated with stirring for 1.5 h at 110° C. and then stirred at room temperature for 18 h. Diluted with CH₂Cl₂ (50 mL), filtered through a celite pad and concentrated in vacuo. Purified by reverse phase Gilson HPLC (Method A) to give the 3-[6-(6-methoxy-5-trifluoromethyl-pyridin-3-yl)-5,6,7,8-tetrahydro-pyrido[4,3-d]pyrimidin-4-yloxy]-azetidine-1-carboxylic acid tert-butyl ester trifluoroacetate as a brown gum (186 mg, 87% yield) LCMS: [M+H]+=482.3, $Rt^{(7)}$=1.56 min.

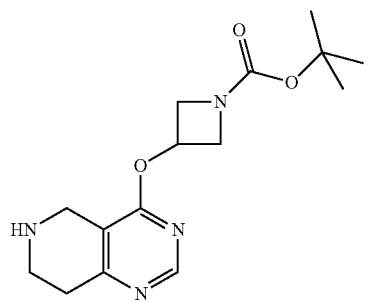 [SMILES: CC(C)(C)OC(=O)N1CC(Oc2ncnc3c2CNCC3)C1]

3-(5,6,7,8-Tetrahydro-pyrido[4,3-d]pyrimidin-4-yloxy)-azetidine-1-carboxylic acid tert-butyl ester To a solution of 3-(6-benzyl-5,6,7,8-tetrahydro-pyrido[4,3-d]pyrimidin-4-yloxy)-azetidine-1-carboxylic acid tert-butyl ester (425 mg, 1.07 mmol) in MeOH (20 mL) was added 20% palladium hydroxide on carbon (90 mg) then ammonium formate (473 mg, 7.51 mmol) and the mixture heated at reflux for 1 h. The reaction mixture was allowed to cool and filtered through a celite pad, washing with MeOH (20 mL) then CH₂Cl₂ (20 mL). The filtrate was evaporated in vacuo and purified by flash chromatography on silica gel with CH₂Cl₂/MeOH/0.88 NH₄OH, 100/0/0 to 90/10/1 to give 3-(5,6,7,8-tetrahydro-pyrido[4,3-d]pyrimidin-4-yloxy)-azetidine-1-carboxylic acid tert-butyl ester as a yellow gum (220 mg, 67% yield) LCMS: [M+H]+=307.3, $Rt^{(4)}$=0.81 min.

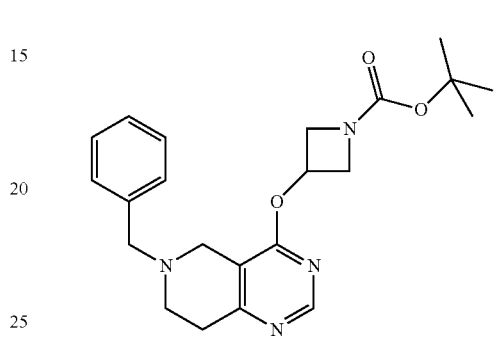

3-(6-Benzyl-5,6,7,8-tetrahydro-pyrido[4,3-d]pyrimidin-4-yloxy)-azetidine-1-carboxylic acid tert-butyl ester 3-Hydroxy-azetidine-1-carboxylic acid tert-butyl ester (217 mg, 1.25 mmol) was dissolved under argon in THF (10 mL) and NaH (58 mg, 1.44 mmol) was added. The resulting suspension was stirred at rt under argon for 15 min following by the addition of a solution of 6-benzyl-4-chloro-5,6,7,8-tetrahydro-pyrido[4,3d]pyrimidine (250 mg, 0.963 mmol). The reaction mixture was stirred at rt for 18 h, quenched with water (20 mL) and diluted with CH₂Cl₂. The organic layer was filtered through a phase separation tube and concentrated in vacuo. Purification by flash chromatography on silica gel with heptane/CH₂Cl₂, 50/50 to 0/100 then EtOAc to give 3-(6-benzyl-5,6,7,8-tetrahydro-pyrido[4,3-d]pyrimidin-4-yloxy)-azetidine-1-carboxylic acid tert-butyl ester as a yellow gum (425 mg, 111% yield) LCMS: [M+H]+=397.4, $Rt^{(4)}$=0.98 min.

Example 59 was prepared according the general procedure described in scheme 2.

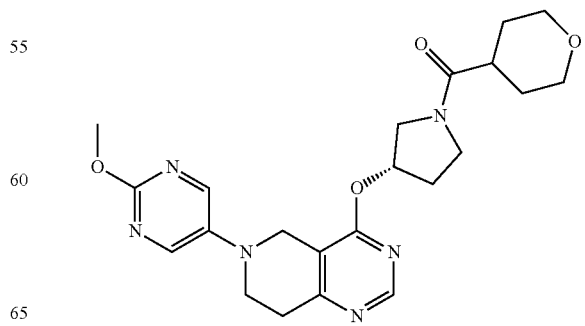

Example 59

{(S)-3-[6-(2-Methoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone

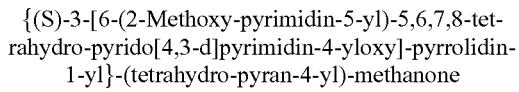

Step 4

A mixture of 5-bromo-2-methoxy-pyrimidine (0.218 mmol), X-Phos (28.4 mg, 0.060 mmol), Pd$_2$(dba)$_3$ (18.2 mg, 0.020 mmol) and Cs$_2$CO$_3$ (129 mg, 0.397 mmol) was flushed with argon before the addition of a solution of (tetrahydro-pyran-4-yl)-[(S)-3-(5,6,7,8-tetrahydro-pyrido[4,3-d]pyrimidin-4-yloxy)-pyrrolidin-1-yl]-methanone in dioxane (2 mL). The reaction mixture was heated at 120° C. for 1 h in a sealed vial, cooled down to rt and filtered over Hyflo, The recovered organic phase was washed with NaHCO$_3$ and brine, dried over Na$_2$SO$_4$, filtered and concentrated. Purification by preparative reverse phase Gilson HPLC and neutralization of the combined fractions by passing through a SCX-2 cartridge (The cartridge was washed with acetonitrile, CH$_2$Cl$_2$ and MeOH, then a solution of NH$_3$ in MeOH 3.5 N was used to released the expected product) gave {(S)-3-[6-(2-methoxy-pyrimidin-5-yl)-5,6,7,8-tetrahydro-pyrido[4,3-d]pyrimidin-4-yloxy]-pyrrolidin-1-yl}-(tetrahydro-pyran-4-yl]-methanone (18.7 mg, 21% yield) $^1$H NMR (400 MHz, CDCl$_3$-d, 298K) δ ppm 1.62-1.70 (m, 2H) 1.87-2.01 (m, 2H) 2.20-2.41 (m, 2H) 2.49-2.71 (m, 1H) 3.07-3.19 (m, 2H) 3.37-4.19 (m, 16H) 5.76 (m, 1H) 8.32 (s, 2H) 8.65-8.67 (m, 1H). LCMS: [M+H]+=441.2, Rt$^{(1)}$=1.12 min.

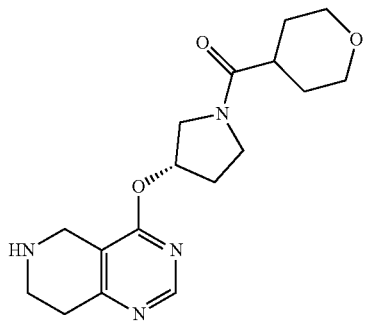 [SMILES: O=C(C1CCOCC1)N1CC[C@H](Oc2ncnc3c2CNCC3)C1]

(Tetrahydro-pyran-4-yl)-[(S)-3-(5,6,7,8-tetrahydro-pyrido[4,3-d]pyrimidin-4-yloxy)-pyrrolidin-1-yl]-methanone

Step 3

A solution of [(S)-3-(6-benzyl-5,6,7,8-tetrahydro-pyrido[4,3-d]pyrimidin-4-yloxy)-pyrrolidin-1-yl]-(tetrahydro-pyran-4-yl)-methanone (10.9 g, 25.8 mmol) was dissolved in methanol (300 mL) and Pd(OH)$_2$ on Carbon (2 g, 14.24 mmol) and ammonium formate (3.35 g, 51.6 mmol) were added. The reaction mixture was refluxed for 2 h. The reaction was cooled down to rt, the reaction mixture was filtered and evaporated under high vacuum for 2 h to yield (tetrahydro-pyran-4-yl)-[(S)-3-(5,6,7,8-tetrahydro-pyrido[4,3-d]pyrimidin-4-yloxy)-pyrrolidin-1-yl]-methanone (8.45 g, 95% yield) as a light yellow foam. $^1$H NMR (400 MHz, DMSO-d6, 298K) δ ppm 1.44-1.67 (m, 4H) 2.08-2.32 (m, 2H) 2.55-2.83 (m, 3H) 2.96 (t, 2H) 3.22-3.96 (m, 11H) 5.53-5.68 (m, 1H) 8.49-8.59 (m, 1H). LCMS: [M+H]+=333.5, Rt$^{(6)}$=1.24 min.

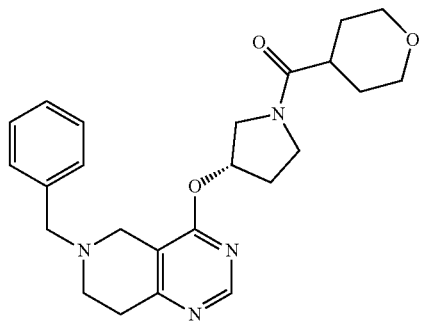 [SMILES: O=C(C1CCOCC1)N1CC[C@H](Oc2ncnc3c2CN(Cc2ccccc2)CC3)C1]

[(S)-3-(6-Benzyl-5,6,7,8-tetrahydro-pyrido[4,3-d]pyrimidin-4-yloxy)-pyrrolidin-1-yl]-(tetrahydro-pyran-4-yl)-methanone

Step 2

To a solution of 6-benzyl-4-((S)-pyrrolidin-3-yloxy)-5,6,7,8-tetrahydro-pyrido[4,3-d]pyrimidine (420 mg, 1.35 mmol) in 4 mL of CH$_2$Cl$_2$ was added tetrahydro-pyran-4-carbonyl chloride (0.210 mL, 1.637 mmol) and Et$_3$N (0.380 mL, 2.73 mmol). The reaction mixture was stirred at room temperature for 30 min then was quenched with H$_2$O, extracted with CH$_2$Cl$_2$, filtered and evaporated under vacuum. Purification by flash-chromatography on silica gel (CH$_2$Cl$_2$/MeOH 95/5) gave [(S)-3-(6-benzyl-5,6,7,8-tetrahydro-pyrido[4,3-d]pyrimidin-4-yloxy)-pyrrolidin-1-yl]-(tetrahydro-pyran-4-yl)-methanone (420 mg, 73% yield) as a yellow foam. $^1$H NMR (400 MHz, DMSO-d6, 298K) δ ppm 1.37-1.64 (m, 4H) 1.95-2.29 (m, 2H) 2.56-2.83 (m, 4H) 3.28-3.91 (m, 13H) 5.54-5.68 (m, 1H) 7.24-7.36 (m, 5H) 8.54-8.59 (m, 1H). LCMS: [M+H]+=423.6, Rt$^{(7)}$=0.68.

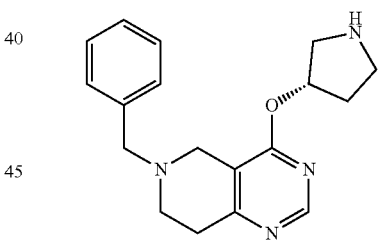

6-Benzyl-4-((S)-pyrrolidin-3-yloxy)-5,6,7,8-tetrahydro-pyrido[4,3-d]pyrimidine

Step 1

To a solution of (S)-3-(6-benzyl-5,6,7,8-tetrahydro-pyrido[4,3-d]pyrimidin-4-yloxy)-pyrrolidine-1-carboxylic acid tert-butyl ester (560 mg, 1.364 mmol) in 2 mL of CH$_2$Cl$_2$ was added TFA (1.576 mL, 20.46 mmol). The reaction mixture was stirred at rt for 1 h, concentrated and then eluted through an Isolute SCX-2 cartridge (10 g) to remove excess TFA with (i) MeOH (ii) NH$_3$/MeOH and the basic fraction evaporated in vacuum to give 6-benzyl-4-((S)-pyrrolidin-3-yloxy)-5,6,7,8-tetrahydro-pyrido[4,3-d]pyrimidine (420 mg, quantitative yield) as a yellow gum. LCMS: [M+H]+=311.2, Rt$^{(3)}$=0.11.

Examples 60-62 were prepared using procedures analogous to those used in Example 59 using appropriate starting materials.

| Example 60 | 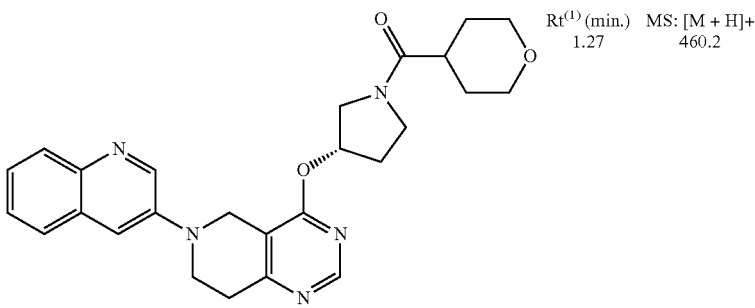 | Rt(1) (min.) 1.27 | MS: [M + H]+ 460.2 |

Name: [(S)-3-(6-Quinolin-3-yl-5,6,7,8-tetrahydro-pyrido[4,3-d]pyrimidin-4-yloxy)-pyrrolidin-1-yl]-(tetrahydro-pyran-4-yl)-methanone
Purification method: Reverse phase method A
Prepared using 3-bromo-quinoline
¹H NMR (400 MHz, CDCl₃-d, 298K) δ ppm 1.60-1.72 (m, 3H) 1.89-2.04 (m, 2H) 2.24-2.46 (m, 2H) 2.53-2.73 (m, 1H) 3.08-3.21 (m, 2H) 3.39-3.52 (m, 2H) 3.67-4.11 (m, 8H) 4.20-4.40 (m, 2H) 5.73-5.83 (m, 1H) 7.47-7.62 (m, 3H) 7.73-7.80 (m, 1H) 8.02-8.14 (m, 1H) 8.62-8.68 (m, 1H) 8.86-8.91 (m, 1H).

| Example 61 | 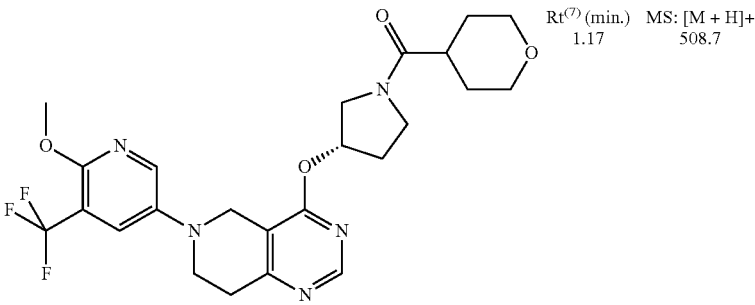 | Rt(7) (min.) 1.17 | MS: [M + H]+ 508.7 |

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone
Purification method: Reverse phase method A
Prepared using intermediate 1
¹H NMR (400 MHz, DMSO-d6, 298K) δ ppm 1.50-1.66 (m, 4H) 2.07-2.46 (m, 2H) 2.60-2.80 (m, 1H) 2.88-2.97 (m, 2H) 3.30-3.95 (m, 13H) 4.08-4.23 (m, 2H) 5.59-5.74 (m, 1H) 7.79-7.85 (m, 1H) 8.16-8.23 (m, 1H) 8.60-8.65 (m, 1H)

| Example 62 | 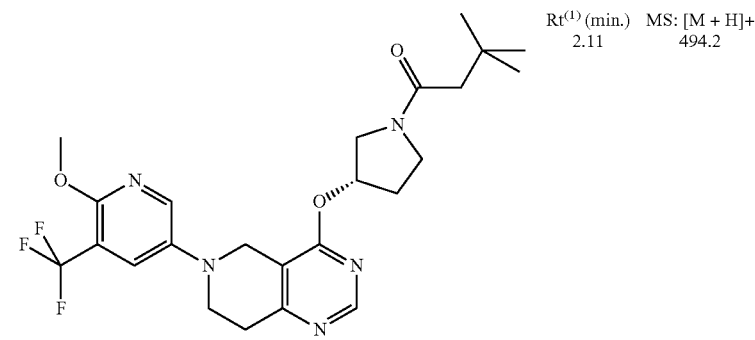 | Rt(1) (min.) 2.11 | MS: [M + H]+ 494.2 |

Name: 1-{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-3,3-dimethyl-butan-1-one
Purification method: Reverse phase method A
Prepared using step 2 of example 59 and 3,3-dimethyl-butyryl chloride followed by steps 3-4 of example 59 using intermediate 1
¹H NMR (400 MHz, CDCl₃, 298K) δ ppm 1.00-1.12 (m, 9H) 2.13-2.35 (m, 4H) 3.08-3.15 (m, 2H) 3.45-3.93 (m, 6H) 4.02 (s, 3H) 4.03-4.15 (m, 2H) 5.72-5.79 (m, 1H) 7.57-7.62 (m, 1H) 8.03-8.07 (m, 1H) 8.64-8.69 (m, 1H)

Example 63 was prepared according the general procedure described in scheme 2.

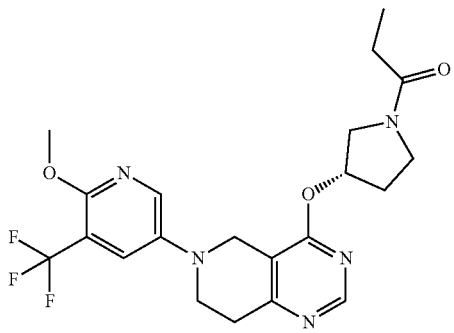 [SMILES: CCC(=O)N1CC[C@H](Oc2ncnc3c2CN(c2cnc(OC)c(C(F)(F)F)c2)CC3)C1]

Example 63

1-{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-propan-1-one Step 3

1-[(S)-3-(5,6,7,8-tetrahydro-pyrido[4,3-d]pyrimidin-4-yloxy)-pyrrolidin-1-yl]-propan-1-one (47.8 mg, 0.173 mmol), X-Phos (28 mg, 0.059 mmol) and $Pd_2(dba)_3 \cdot CHCl_3$ (17.90 mg, 0.017 mmol) were combined and flushed with argon during several min before addition of degassed dioxane. 5-Bromo-2-methoxy-3-trifluoromethyl-pyridine (intermediate 1) (54.5 mg, 0.213 mmol) and $Cs_2CO_3$ (113 mg, 0.346 mmol) were then added to the reaction mixture and the resulting mixture flushed with argon and heated at 150° C. for 30 min. in a sealed tube. The reaction mixture was cooled to rt, filtered over Hyflo and evaporated. Purification by preparative reverse phase Gilson HPLC and subsequent neutralization of the combined fractions over $PL-HCO_3$ MP gave 1-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-propan-1-one (26 mg, 33% yield) $^1$H NMR (400 MHz, DMSO-d6, 298K) δ ppm 0.94-1.00 (m, 3H) 2.05-2.17 (m, 4H) 2.95-3.0 (m, 2H) 3.45-3.97 (m, 9H) 4.07-4.11 (m, 2H) 5.58-5.72 (m, 1H) 7.81-7.86 (m, 1H) 8.18-8.23 (m, 1H) 8.62 (s, 1H). MS: [M+H]+=452.2, $Rt^{(1)}$=1.74 min.

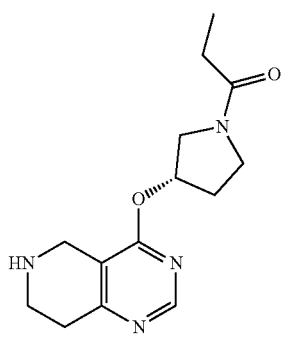

1-[(S)-3-(5,6,7,8-Tetrahydro-pyrido[4,3-d]pyrimidin-4-yloxy)-pyrrolidin-1-yl]-propan-1-one Step 2

$Pd(OH)_2$ (150 mg, 1.070 mmol) was put into a round flask and flushed under argon for 5 minutes. A solution of 1-[(S)-3-(6-benzyl-5,6,7,8-tetrahydro-pyrido[4,3-d]pyrimidin-4-yloxy)-pyrrolidin-1-yl]-propan-1-one (560 mg, 1.528 mmol) in 22 mL of MeOH was added followed by ammonium formate (482 mg, 7.64 mmol). The reaction mixture was stirred under reflux (70° C.) for 2 h. The mixture was filtered over a pad of celite and dried under high vacuum to give 1-[(S)-3-(5,6,7,8-tetrahydro-pyrido[4,3-d]pyrimidin-4-yloxy)-pyrrolidin-1-yl]-propan-1-one. No further purification (m=420 mg, quantitative yield). MS: [M+H]+=277.5 $Rt^{(6)}$=0.71 min.

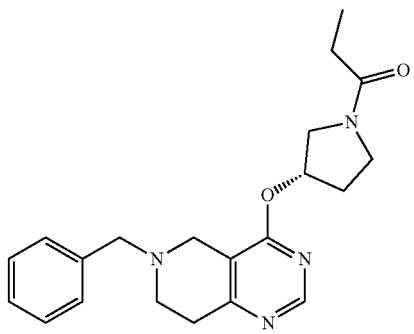 [SMILES: CCC(=O)N1CC[C@H](Oc2ncnc3c2CN(Cc2ccccc2)CC3)C1]

1-[(S)-3-(6-Benzyl-5,6,7,8-tetrahydro-pyrido[4,3-d]pyrimidin-4-yloxy)-pyrrolidin-1-yl]-propan-1-one Step 1

To a solution of 1-((S)-3-hydroxy-pyrrolidin-1-yl)-propan-1-one (intermediate 2) (358 mg, 2.503 mmol) in 5 mL of THF was added NaH (108 mg, 2.70 mmol) under Ar. The mixture was stirred at rt for 15 min, then 6-benzyl-4-chloro-5,6,7,8-tetrahydro-pyrido[4,3-d]pyrimidine (500 mg, 1.925 mmol) and 5 mL of THF were added and stirred at rt for 5 h. The reaction was quenched with $H_2O$ and extracted with ethylacetate, the org. layer was washed with brine, dried over $MgSO_4$, filtered and evaporated to dryness. The residue was purified by flash-chromatography using Isco Companion system (12 g of $SiO_2$) $CH_2Cl_2$/MeOH (95/5). The collected fractions were combined, evaporated and dried over high vacuum to give 1-[(S)-3-(6-benzyl-5,6,7,8-tetrahydro-pyrido[4,3-d]pyrimidin-4-yloxy)-pyrrolidin-1-yl]-propan-1-one. (m=560 mg, yield 78%) MS: [M+H]+=367.6, $Rt^{(7)}$=0.64 min.

Example 64 was prepared using procedures analogous to those used in Example 63 using appropriate starting materials.

| Example 64 | 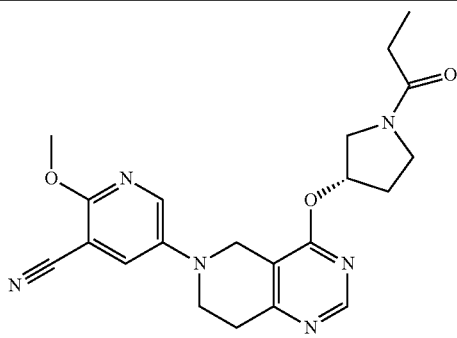 | Rt⁽¹⁾ (min.) 1.46 | MS: [M + H]+ 409.2 |
|---|---|---|---|

Name: 2-Methoxy-5-[4-((S)-1-propionyl-pyrrolidin-3-yloxy)-7,8-dihydro-5H-pyrido[4,3-d]pyrimidin-6-yl]-nicotinonitrile
Purification method: Reverse phase method A
Prepared using step 3 of example 59 and 5-bromo-2-methoxynicotinonitrile
$^1$H NMR (400 MHz, DMSO-d6, 298K) δ ppm 0.95-1.02 (m, 3H) 2.10-2.35 (m, 5H) 2.89-2.98 (m, 2H) 3.40-3.90 (m, 5H) 3.93 (s, 3H) 4.16 (s, 2H) 5.58-5.71 (m, 1H) 8.08-8.10 (m, 1H) 8.24-8.28 (m, 1H) 8.61 (m, 1H).

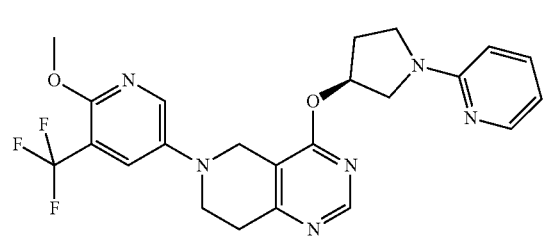 [SMILES: COc1ncc(N2CCc3ncnc(O[C@H]4CCN(c5ccccn5)C4)c3C2)cc1C(F)(F)F]

Example 65

6-(6-Methoxy-5-trifluoromethyl-pyridin-3-yl)-4-((S)-1-pyridin-2-yl-pyrrolidin-3-yloxy)-5,6,7,8-tetrahydro-pyrido[4,3-d]pyrimidine To a glass vial was added 6-(6-methoxy-5-trifluoromethyl-pyridin-3-yl)-4-((S)-pyrrolidin-3-yloxy)-5,6,7,8-tetrahydro-pyrido[4,3-d]pyrimidine dihydrochloride (prepared using step 1 of example 91 from intermediate 13) (75 mg, 0.16 mmol), 2-bromopyridine (1 mL, 10.25 mmol) and N,N-diisopropylethylamine (0.14 mL, 0.80 mmol). The vial was capped and the mixture heated in the microwave at 160° C. for 20 min. Purification by reverse phase Gilson HPLC (Method A) and subsequent neutralization of the combined fractions over PL-HCO₃ MP to give 6-(6-methoxy-5-trifluoromethyl-pyridin-3-yl)-4-((S)-1-pyridin-2-yl-pyrrolidin-3-yloxy)-5,6,7,8-tetrahydro-pyrido[4,3-d]pyrimidine as a light brown solid (19 mg, 25% yield) $^1$H NMR (400 MHz, DMSO-d6, 298K) δ ppm 2.24-2.44 (m, 2 H) 2.92 (t, 2 H) 3.47-3.69 (m, 5 H) 3.77-3.85 (m, 1H) 3.88-3.93 (m, 3 H) 4.12-17 (m, 2 H) 5.73-5.81 (m, 1 H) 6.40-6.52 (d, 1 H) 6.56-6.58 (m, 1 H) 7.43-7.54 (m, 1 H) 7.77-7.84 (m, 1 H) 8.02-8.09 (m, 1 H) 8.13-8.20 (m, 1 H) 8.61-8.66 (m, 1 H) LCMS: [M+H]+ =473.0, Rt⁽⁴⁾=0.85 min.

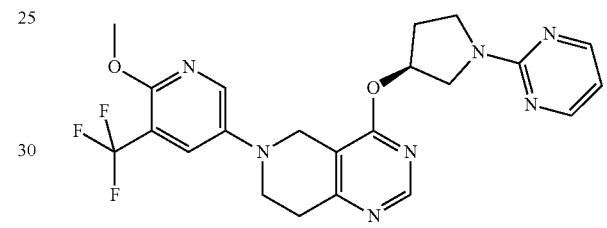

Example 66

6-(6-Methoxy-5-trifluoromethyl-pyridin-3-yl)-4-((S)-1-pyrimidin-2-yl-pyrrolidin-3-yloxy)-5,6,7,8-tetrahydro-pyrido[4,3-d]pyrimidine To a glass vial was added 6-(6-methoxy-5-trifluoromethyl-pyridin-3-yl)-4-((S)-pyrrolidin-3-yloxy)-5,6,7,8-tetrahydro-pyrido[4,3-d]pyrimidine dihydrochloride (prepared using step 1 of example 91 from intermediate 13) (75 mg, 0.16 mmol), 2-bromopyrimidine (55 mg, 0.342 mmol) and N,N-diisopropylethylamine (0.15 mL, 0.85 mmol). The vial was capped and the mixture heated in the microwave at 160° C. for 20 min. Purification by reverse phase Gilson HPLC (Method A) and subsequent neutralization of the combined fractions over PL-HCO₃ MP to give 6-(6-methoxy-5-trifluoromethyl-pyridin-3-yl)-4-((S)-1-pyrimidin-2-yl-pyrrolidin-3-yloxy)-5,6,7,8-tetrahydro-pyrido[4,3-d]pyrimidine as a brown solid (17 mg, 21% yield) $^1$H NMR (400 MHz, DMSO-d6, 298K) δ ppm 2.23-2.43 (m, 2 H) 2.85-2.99 (t, 2 H) 3.22-3.94 (m, 9 H) 4.08-4.27 (m, 2 H) 5.70-5.80 (m, 1 H) 6.56-6.66 (t, 1 H) 7.76-7.87 (m, 1 H) 8.12-8.27 (m, 1 H) 8.28-8.42 (m, 2 H) 8.59-8.68 (m, 1 H) LCMS: [M+H]+=474.2, Rt⁽¹⁾=1.91 min.

Example 67 was prepared according to the general procedure described in scheme 4

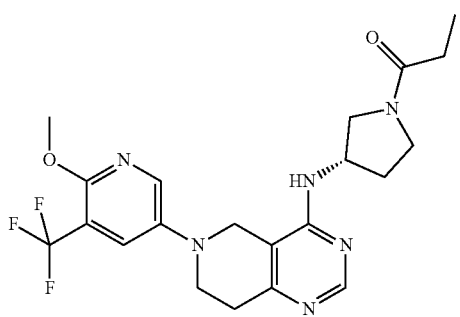 [SMILES: CCC(=O)N1CC[C@H](Nc2ncnc3c2CN(c2cnc(OC)c(C(F)(F)F)c2)CC3)C1]

Example 67

1-{(S)-3-[6-(6-Methoxy-5-trifluoromethyl-pyridin-3-yl)-5,6,7,8-tetrahydro-pyrido[4,3-d]pyrimidin-4-ylamino]-pyrrolidin-1-yl}-propan-1-one To a solution of (S)-3-[6-(6-methoxy-5-trifluoromethyl-pyridin-3-yl)-5,6,7,8-tetrahydro-pyrido[4,3-d]pyrimidin-4-ylamino]-pyrrolidine-1-carboxylic acid tert-butyl ester (intermediate 24) (13.4 g, 27.1 mmol) in $CH_2Cl_2$ (100 mL), was added TFA (41.8 mL) and the mixture stirred at rt for 1 h. Concentrated in vacuo and partitioned between 2M NaOH (aq) (300 mL) and $CH_2Cl_2$ (200 mL). The organic phase was separated and the aqueous phase extracted with $CH_2Cl_2$ (2×200 mL). The organic phases were combined, dried ($MgSO_4$) and evaporated in vacuo to give a brown foam. The foam was dissolved in $CH_2Cl_2$ (50 mL) and was added simultaneously portionwise with sat.$NaHCO_3$(aq) (50 mL) to a vigourously stirring solution of propionyl chloride (2.63 g, 28.5 mmol) in $CH_2Cl_2$ (50 mL) at rt. The resulting biphasic mixture was stirred at rt for 1 h. Further propionyl chloride (0.566 g, 6.12 mmol) was added and continued stirring vigorously for 20 min. The organic layer was separated and the aqueous layer extracted with $CH_2Cl_2$ (100 mL). The organic layers were combined, dried ($MgSO_4$) and concentrated in vacuo to give a brown gum. The gum was stirred in EtOAc (100 mL) and the resulting solid filtered (9.4 g). The mother liquors were concentrated in vacuo and purified by column chromatography through a Biotage® amino silica gel eluting with EtOAc/MeOH, 100/0 to 90/10 to give a yellow foam which was then stirred in EtOAc (20 mL) and the resulting solid filtered (870 mg). Both batches of solids were combined and stirred in refluxing EtOAc (50 mL) for 1 h. Filtered to give 1-{(S)-3-[6-(6-methoxy-5-trifluoromethyl-pyridin-3-yl)-5,6,7,8-tetrahydro-pyrido[4,3-d]pyrimidin-4-ylamino]-pyrrolidin-1-yl}-propan-1-one as a colourless solid (9.42 g, 76% yield). $^1$H NMR (400 MHz, DMSO-d6, 298K) δ ppm 0.95-1.05 (m, 3H) 1.87-2.32 (m, 4H) 2.77-2.86 (m, 2H) 3.25-3.88 (m, 6H) 3.93 (s, 3H) 3.98 (s, 2H) 4.55-4.80 (m, 1H) 6.70-6.80 (m, 1H, N—H) 7.86-7.92 (m, 1H) 8.27-8.33 (m, 1H) 8.33-8.37 (m, 1H) LCMS: [M+H]+=451.0, Rt$^{(6)}$=1.49 min.

Alternative Synthesis for Example 67

A solution of (S)-3-[6-(6-methoxy-5-trifluoromethyl-pyridin-3-yl)-5,6,7,8-tetrahydro-pyrido[4,3-d]pyrimidin-4-ylamino]-pyrrolidine-1-carboxylic acid tert-butyl ester (intermediate 24) (29.04 g, 58.73 mmol) in 2-Me-THF (100 mL) was dropwise added into aqueous HCl solution (150 mL, 31%) over 15 min. The reaction mixture was partitioned between water (300 mL) and isopropyl acetate (100 mL) and the upper organic phase was discarded. The aqueous phase was partitioned between 25% NaOH (aq) (200 g) and 2-Me-THF (200 mL), and the organic phase was collected and dried. Triethylamine (16.32 mL, 117.48 mmol) was added into the organic phase followed by dropwise addition of propionyl chloride (6.0 g, 64.6 mmol) at 0° C. The resulting mixture was stirred at 0° C. for 1 h. The reaction mixture was washed with water (110 mL) and the resulting organic phase was concentrated in vacuo to give a brown gum. The residue was recrystallized with isopropanol and methyl tert-butyl ether to give 1-{(S)-3-[6-(6-methoxy-5-trifluoromethyl-pyridin-3-yl)-5,6,7,8-tetrahydro-pyrido[4,3-d]pyrimidin-4-ylamino]-pyrrolidin-1-yl}-propan-1-one as a colourless solid (17.2 g, 65% yield).

Crystallization of Example 67 by Heating in Acetonitrile/Water 2.0 g of Example 67 (4.440 mol) were dissolved in 10 mL of acetonitrile and 0.5 mL of water at 75° C. The solution was allowed to cool down to rt within 30 min resulting in a suspension. The mixture was stirred for 16 h at rt. The crystals were collected by filtration. The filter cake was washed 2 times with 1 mL of acetonitrile and afterwards dried for 16 h at 24° C. and ca. 10 mbar vacuum. Elementary analysis of the material showed a waterless form.

List of most significant peaks from X-ray Powder Diffraction Pattern of Example 67 anhydrous form Method X1):

| 2-Theta in deg | Intensity in % |
| --- | --- |
| 7.9 | 31 |
| 9.6 | 88 |
| 11.5 | 29 |
| 13.4 | 8 |
| 15.2 | 7 |
| 15.9 | 100 |
| 16.8 | 57 |
| 17.6 | 9 |
| 18.7 | 20 |
| 20.0 | 8 |
| 20.6 | 40 |
| 22.0 | 32 |
| 22.4 | 53 |
| 22.7 | 26 |
| 23.4 | 17 |
| 23.9 | 23 |
| 24.5 | 41 |
| 25.1 | 20 |
| 25.8 | 13 |
| 26.7 | 31 |

Preparation of Phosphate Salt of Example 67

2.0 g of Example 67 (4.440 mol) were dissolved in 10 mL of acetonitrile and 0.5 mL of water at 75° C. 512 mg of ortho-phosphoric acid 85% (4.440 mol) were added at 70° C.

Crystallization occurs quickly at 70° C. The suspension was allowed to cool down to rt within 30 min. The suspension was diluted with 10 ml acetonitrile and stirred for 16 h at rt. The crystals were collected by filtration. The filter cake was washed 3 times with 1 mL of acetonitrile and afterwards dried for 16 h at 24° C. and ca. 10 mbar vacuum. Elementary analysis of the phosphate salt showed a 1:1 (waterless) form List of most significant peaks from X-ray Powder Diffraction Pattern of Example 67 phosphate salt (Method X1):

| 2-Theta in deg | Intensity in % |
| --- | --- |
| 5.2 | 51 |
| 9.8 | 56 |
| 10.3 | 19 |
| 11.6 | 100 |

| 2-Theta in deg | Intensity in % |
|---|---|
| 14.9 | 14 |
| 15.5 | 48 |
| 15.9 | 11 |
| 16.6 | 65 |
| 19.5 | 54 |
| 20.7 | 62 |
| 21.5 | 10 |
| 22.1 | 21 |
| 23.3 | 57 |
| 25.8 | 18 |
| 26.4 | 29 |
| 27.2 | 20 |
| 28.2 | 13 |

Preparation of Hydrochloride Salt of Example 67

2.0 g of Example 67 (4.440 mol) were dissolved in 20 mL of acetonitrile and 1.0 mL of water at 70° C. 459 mg of hydrochloric acid 37% (4.440 mol) were added at 70° C. Crystallization occurs quickly at 70° C. The suspension was allowed to cool down to rt within 30 min and stirred for 16 h at rt. The crystals were collected by filtration. The filter cake was washed 3 times with 1 mL of acetonitrile and afterwards dried for 16 h at 24° C. and ca. 10 mbar vacuum. Elementary analysis of the HCl salt showed a 1:1 (waterless) form List of most significant peaks from X-ray Powder Diffraction Pattern of Example 67 hydrochloride salt (Method X1):

| 2-Theta in deg | Intensity in % |
|---|---|
| 5.6 | 100 |
| 11.0 | 18 |
| 11.3 | 42 |
| 11.8 | 12 |
| 14.7 | 33 |
| 17.1 | 13 |
| 18.7 | 19 |
| 19.4 | 29 |
| 22.0 | 23 |
| 22.6 | 28 |
| 23.1 | 50 |
| 23.7 | 28 |
| 24.9 | 29 |
| 25.5 | 15 |

Preparation of Hippurate Salt of Example 67

0.4 g of Example 67 (0.888 mmol) were dissolved in 8 mL of acetonitrile and 0.2 mL of water at 70° C. 167 mg of hippuric acid (0.888 mmol) were added at 70° C. The solution was allowed to cool down to rt within 30 min. Crystallization occurs at 40° C. The suspension was stirred for 16 h at rt. The crystals were collected by filtration. The filter cake was washed 3 times with 1 mL of acetonitrile and afterwards dried for 16 h at 50° C. and ca. 10 mbar vacuum List of most significant peaks from X-ray Powder Diffraction Pattern of Example 67 hippurate salt (Method X1):

| 2-Theta in deg | Intensity in % |
|---|---|
| 5.2 | 76 |
| 7.5 | 100 |
| 10.3 | 60 |
| 10.9 | 63 |
| 11.8 | 9 |
| 13.1 | 16 |
| 16.1 | 44 |
| 16.7 | 26 |
| 17.7 | 49 |
| 18.4 | 38 |
| 21.2 | 49 |
| 23.2 | 74 |
| 24.2 | 67 |
| 26.2 | 28 |

Examples 68-69 were prepared using procedures analogous to those used in example 67 using appropriate starting materials.

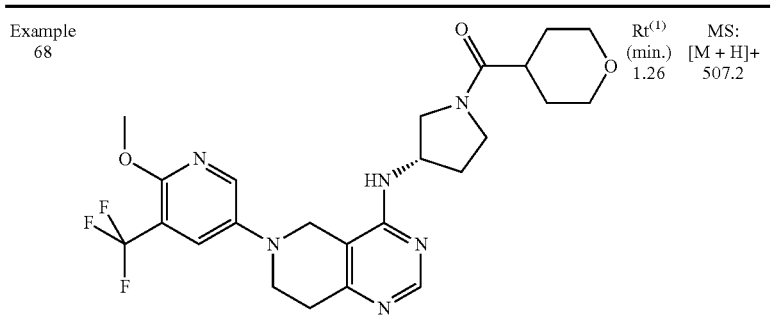

| Example 68 | | Rt(1) (min.) | MS: [M + H]+ |
|---|---|---|---|
| | | 1.26 | 507.2 |

Name: {(S)-3-[6-(6-Methoxy-5-trifluoromethyl-pyridin-3-yl)-5,6,7,8-tetrahydro-pyrido[4,3-d]pyrimidin-4-ylamino]-pyrrolidin-1-yl}-(tetrahydro-pyran-4-yl)-methanone
Purification method: Reverse phase HPLC Method A
Prepared using tetrahydro-pyran-4-carbonyl chloride
$^1$H NMR (400 MHz, DMSO-d6, 298K) δ ppm 1.48-1.67 (m, 4H) 1.88-2.35 (m, 2H) 2.59-2.87 (m, 3H) 3.26-4.03 (m, 15H) 4.56-4.83 (m, 1H) 6.82-6.92 (m, 1H, N—H) 7.86-7.90 (m, 1H) 8.26-8.32 (m, 1H) 8.37-8.42 (m, 1H)

| Example 69 | 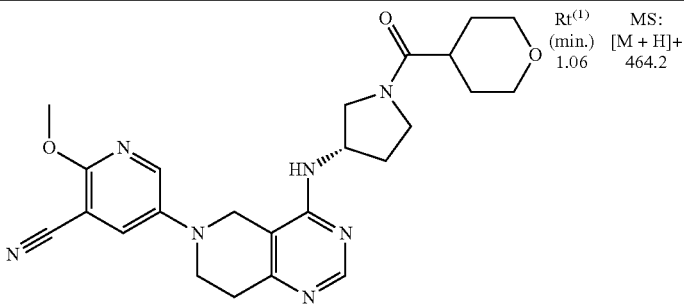 | Rt(1) (min.) 1.06 | MS: [M + H]+ 464.2 |
|---|---|---|---|

Name: 2-Methoxy-5-{4-[(S)-1-(tetrahydro-pyran-4-carbonyl)-pyrrolidin-3-ylamino]-7,8-dihydro-5H-pyrido[4,3-d]pyrimidin-6-yl}-nicotinonitrile
Purification method: Reverse phase HPLC Method A
Prepared using intermediate 25 and tetrahydro-pyran-4-carbonyl chloride
$^1$H NMR (400 MHz, MeOH-d4, 298K) δ ppm 1.59-1.86 (m, 4H) 2.07-2.47 (m, 2H) 2.75-2.98 (m, 3H) 3.44-4.13 (m, 15H) 4.64-5.24 (m, 1H, signal masked by water peak) 7.94-7.99 (m, 1H) 8.20-8.26 (m, 1H) 8.33-8.39 (m, 1H)

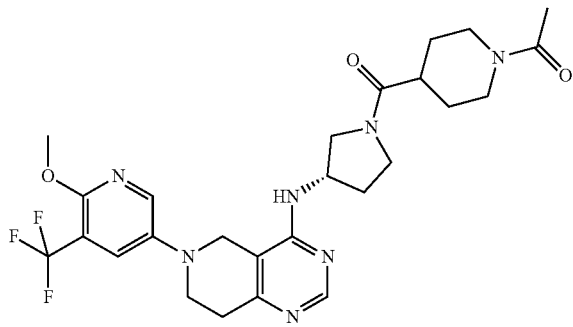 [SMILES: COc1ncc(N2CCc3ncnc(N[C@H]4CCN(C(=O)C5CCN(C(C)=O)CC5)C4)c3C2)cc1C(F)(F)F]

Example 70

1-(4-{(S)-3-[6-(6-methoxy-5-trifluoromethyl-pyridin-3-yl)-5,6,7,8-tetrahydro-pyrido[4,3-d]pyrimidin-4-ylamino]-pyrrolidine-1-carbonyl}-piperidin-1-yl)-ethanone (S)-3-[6-(6-Methoxy-5-trifluoromethyl-pyridin-3-yl)-5,6,7,8-tetrahydro-pyrido[4,3-d]pyrimidin-4-ylamino]-pyrrolidine-1-carboxylic acid tert-butyl ester (intermediate 24) (160 mg, 0.32 mmol) was dissolved in CH$_2$Cl$_2$ (2.0 mL) and TFA (1.0 mL) added. The resulting mixture was stirred at room temperature for 1 h then evaporated in vacuo to give [6-(6-methoxy-5-trifluoromethyl-pyridin-3-yl)-5,6,7,8-tetrahydro-pyrido[4,3-d]pyrimidin-4-yl]-(S)-pyrrolidin-3-yl-amine ditrifluoroacetate as a brown gum (160 mg), which was used without further purification. To [6-(6-methoxy-5-trifluoromethyl-pyridin-3-yl)-5,6,7,8-tetrahydro-pyrido[4,3-d]pyrimidin-4-yl]-(S)-pyrrolidin-3-yl-amine ditrifluoroacetate (40 mg, 0.06 mmol) was added 1-acetylpiperidine-4-carboxylic acid (12 mg, 0.07 mmol)), N,N-diisopropylethylamine (0.05 mL, 0.26 mmol), CH$_2$Cl$_2$ (3.0 mL) and then HBTU (29 mg, 0.08 mmol). The mixture was allowed to stir at room temperature for 18 h and then partitioned between CH$_2$Cl$_2$ (10 mL) and water (5 mL). The organic phase was filtered through a phase separation tube and evaporated in vacuo. Purification by reverse phase Gilson HPLC (Method A) and subsequent neutralization of the combined fractions by elution through an Isolute® SCX-2 cartridge, eluting with methanol, then with 2M ammonia in methanol. Basic fractions were concentrated in vacuo to give 1-(4-{(S)-3-[6-(6-methoxy-5-trifluoromethyl-pyridin-3-yl)-5,6,7,8-tetrahydro-pyrido[4,3-d]pyrimidin-4-ylamino]-pyrrolidine-1-carbonyl}-piperidin-1-yl)-ethanone as a pale yellow solid (19 mg, 50% yield for 2$^{nd}$ step) $^1$H NMR (400 MHz, DMSO-d6, 298K) δ ppm 1.20-1.70 (m, 4H) 1.79-2.35 (m, 5H) 2.53-2.85 (m, 4H) 3.04-3.14 (m, 1H) 3.35-4.79 (m, 14H) 6.80-6.87 (m, 1H, N—H) 7.87-7.91 (m, 1H) 8.26-8.31 (m, 1H) 8.35-8.41 (m, 1H) LCMS: [M+H]+=548.2, Rt$^{(1)}$=1.22 min.

Examples 71-80 were prepared using procedures analogous to those used in example 70 using appropriate starting materials

| Example 71 | 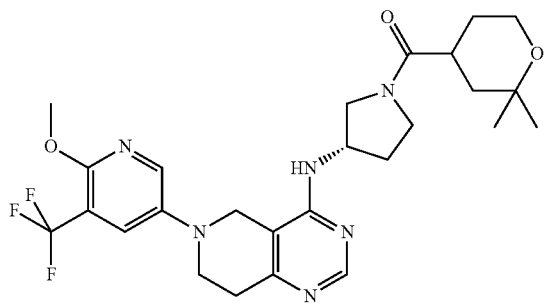 [SMILES: COc1ncc(N2CCc3ncnc(N[C@H]4CCN(C(=O)C5CCOC(C)(C)C5)C4)c3C2)cc1C(F)(F)F] | Rt(1) (min.) 1.40 | MS: [M + H]+ 535.3 |
|---|---|---|---|

Name: (2,2-Dimethyl-tetrahydro-pyran-4-yl)-{(S)-3-[6-(6-methoxy-5-trifluoromethyl-pyridin-3-yl)-5,6,7,8-tetrahydro-pyrido[4,3-d]pyrimidin-4-ylamino]-pyrrolidin-1-yl}-methanone Purification method: Reverse phase HPLC Method A
Prepared using 2,2-dimethyl-tetrahydro-pyran-4-carboxylic acid
$^1$H NMR (400 MHz, DMSO-d6, 298K) δ ppm 1.05-1.20 (m, 6H) 1.30-1.58 (m, 4H) 1.86-2.35 (m, 2H) 2.70-2.90 (m, 3H) 3.34-4.03 (m, 13H) 4.55-4.80 (m, 1H) 6.67-6.76 (m, 1H, N—H) 7.86-7.89 (m, 1H) 8.26-8.31 (m, 1H) 8.32-8.37 (m, 1H)

| | | Rt$^{(1)}$ (min.) | MS: [M + H]+ |
|---|---|---|---|
| Example 72 | 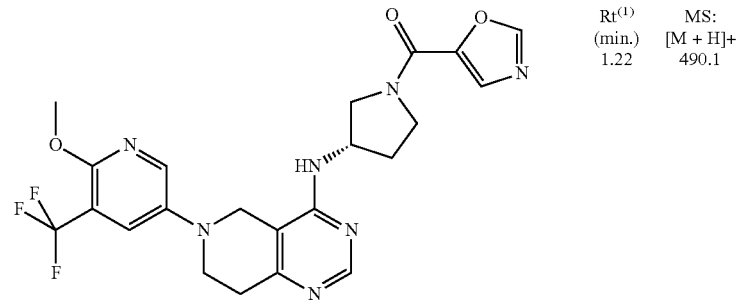 | 1.22 | 490.1 |

Name: {(S)-3-[6-(6-Methoxy-5-trifluoromethyl-pyridin-3-yl)-5,6,7,8-tetrahydro-pyrido[4,3-d]pyrimidin-4-ylamino]-pyrrolidin-1-yl}-oxazol-5-yl-methanone
Purification method: Reverse phase HPLC Method A
Prepared using oxazole-5-carboxylic acid
$^1$H NMR (400 MHz, DMSO-d6, 298K) δ ppm 1.89-2.39 (m, 2H) 2.78-2.86 (m, 2H) 3.50-4.20 (m, 11H) 4.65-4.84 (m, 1H) 6.75-6.83 (m, 1H, N—H) 7.75-7.83 (m, 1H) 7.86-7.92 (m, 1H) 8.26-8.32 (m, 1H) 8.35-8.38 (m, 1H) 8.55-8.60 (m, 1H)

| | | Rt$^{(1)}$ (min.) | MS: [M + H]+ |
|---|---|---|---|
| Example 73 | 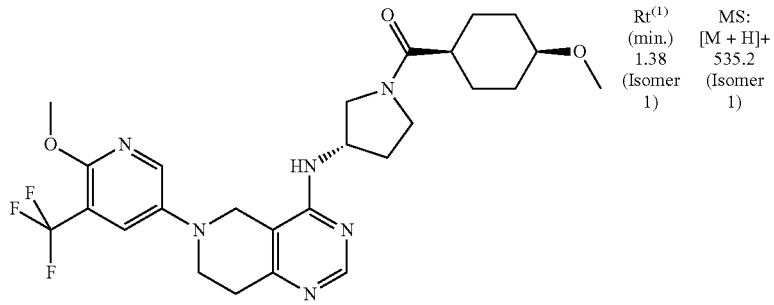 | 1.38 (Isomer 1) | 535.2 (Isomer 1) |
| Example 74 | 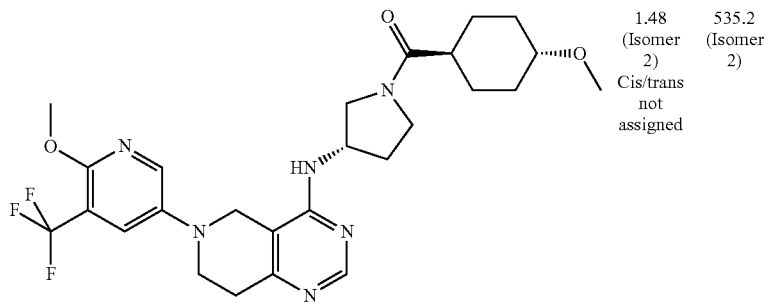 | 1.48 (Isomer 2) Cis/trans not assigned | 535.2 (Isomer 2) |

Name: ((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)((1R,4R)-4-methoxycyclohexyl)methanone
((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)((1R,4S)-4-methoxycyclohexyl)methanone
Purification method: Reverse phase HPLC Method A
Prepared using 4-methoxy-cyclohexanecarboxylic acid (mixture of cis/trans)
$^1$H NMR (Isomer 1 cis/trans not assigned) (400 MHz, DMSO-d6, 298K) δ ppm 1.04-1.47 (m, 4H) 1.64-2.45 (m, 7H) 2.77-2.86 (m, 2H) 3.00-3.77 (m, 10H) 3.87-4.03 (m, 5H) 4.53-4.80 (m, 1H) 6.67-6.78 (m, 1H, N—H) 7.85-7.91 (m, 1H) 8.26-8.32 (m, 1H) 8.33-8.38 (m, 1H)
$^1$H NMR (Isomer 2 cis/trans not assigned) (400 MHz, DMSO-d6, 298K) δ ppm 1.32-1.48 (m, 4H) 1.55-2.50 (m, 7H) 2.78-2.84 (m, 2H) 3.01-3.77 (m, 10H) 3.87-4.03 (m, 5H) 4.53-4.80 (m, 1H) 6.67-6.78 (m, 1H, N—H) 7.85-7.91 (m, 1H) 8.26-8.32 (m, 1H) 8.33-8.38 (m, 1H)

| Example 75 | 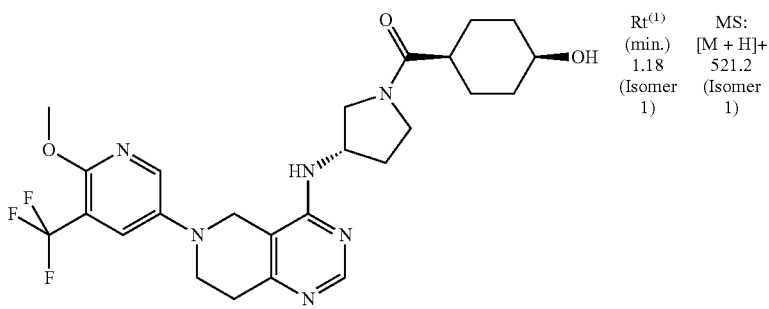 | Rt(1) (min.) 1.18 (Isomer 1) | MS: [M + H]+ 521.2 (Isomer 1) |
|---|---|---|---|
| Example 76 | 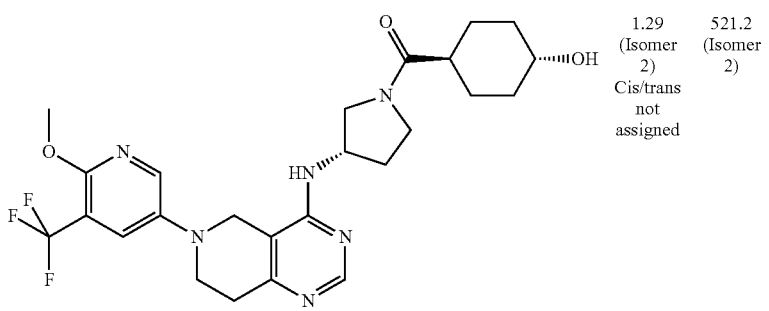 | 1.29 (Isomer 2) Cis/trans not assigned | 521.2 (Isomer 2) |

Name: ((1S,4R)-4-hydroxycyclohexyl)((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone
((1R,4S)-4-hydroxycyclohexyl)((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone
Purification method: Reverse phase HPLC Method A
Prepared using 4-hydroxy-cyclohexanecarboxylic acid (mixture of cis/trans)
$^1$H NMR (Isomer 1 cis/trans not assigned) (400 MHz, DMSO-d6, 298K) δ ppm 1.06-1.44 (m, 4H) 1.57-2.86 (m, 9H) 3.01-3.76 (m, 7H) 3.88-4.03 (m, 5H) 4.50-4.78 (m, 2H) 6.68-6.78 (m, 1H, N—H) 7.86-7.91 (m, 1H) 8.26-8.32 (m, 1H) 8.33-8.39 (m, 1H)
$^1$H NMR (Isomer 1 cis/trans not assigned) (400 MHz, DMSO-d6, 298K) δ ppm 1.28-1.52 (m, 4H) 1.59-2.85 (m, 9H) 3.03-3.83 (m, 8H) 3.88-4.03 (m, 5H) 4.55-4.79 (m, 1H) 6.68-6.77 (m, 1H, N—H) 7.85-7.91 (m, 1H) 8.26-8.32 (m, 1H) 8.33-8.39 (m, 1H)

| Example 77 | 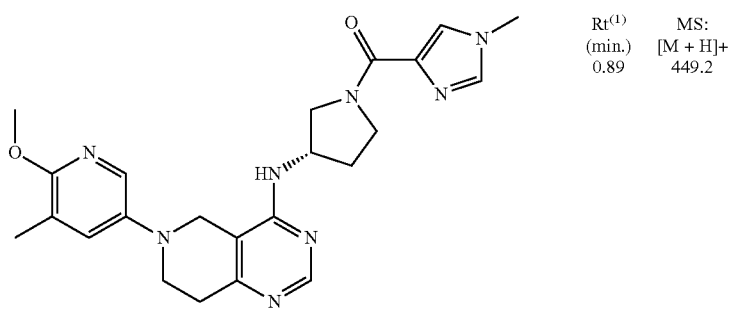 | Rt(1) (min.) 0.89 | MS: [M + H]+ 449.2 |
|---|---|---|---|

Name: -{(S)-3-[6-(6-Methoxy-5-methyl-pyridin-3-yl)-5,6,7,8-tetrahydro-pyrido[4,3-d]pyrimidin-4-ylamino]-pyrrolidin-1-yl}-(1-methyl-1H-imidazol-4-yl)-methanone
Purification method: Reverse phase HPLC Method A
Prepared using intermediate 20 and 1-methyl-1H-imidazole-4-carboxylic acid
$^1$H NMR (400 MHz, MeOH-d4, 298K) δ ppm 2.07-2.44 (m, 5H) 2.86-2.95 (m, 2H) 3.44-4.43 (m, 14H) 4.77-4.87 (m, 1H) 7.44-7.48 (m, 1H) 7.60-7.70 (m, 2H) 7.72-7.79 m, 1H) 8.32-8.41 (m, 1H)

Example 78

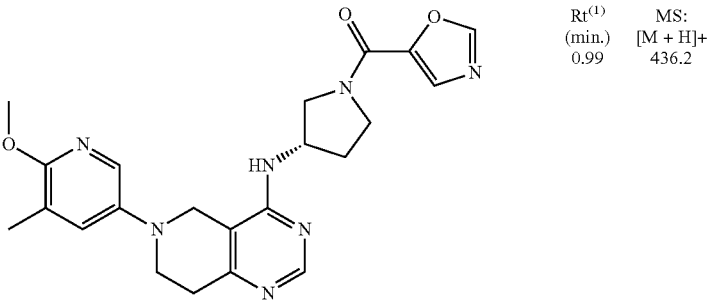

Rt(1) (min.) 0.99  
MS: [M + H]+ 436.2

Name: {(S)-3-[6-(6-Methoxy-5-methyl-pyridin-3-yl)-5,6,7,8-tetrahydro-pyrido[4,3-d]pyrimidin-4-ylamino]-pyrrolidin-1-yl}-oxazol-5-yl-methanone  
Purification method: Reverse phase HPLC Method A  
Prepared using intermediate 20 and oxazole-5-carboxylic acid  
1H NMR (400 MHz, DMSO-d6, 298K) δ ppm 1.95-2.35 (m, 5H) 2.74-2.83 (m, 2H) 3.35-4.20 (m, 11H) 4.62-4.83 (m, 1H) 6.73-6.81 (m, 1H) 7.44-7.49 (m, 1H) 7.75-7.85 (m, 2H) 8.33-8.38 (m, 1H) 8.54-8.59 (m, 1H)

Example 79

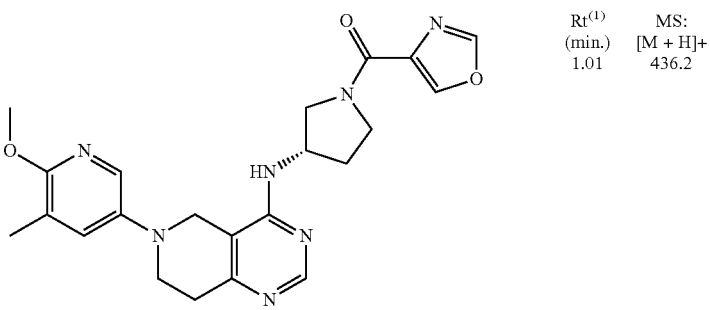

Rt(1) (min.) 1.01  
MS: [M + H]+ 436.2

Name: {(S)-3-[6-(6-Methoxy-5-methyl-pyridin-3-yl)-5,6,7,8-tetrahydro-pyrido[4,3-d]pyrimidin-4-ylamino]-pyrrolidin-1-yl}-oxazol-4-yl-methanone  
Purification method: Reverse phase HPLC Method A  
Prepared using intermediate 20 and oxazole-4-carboxylic acid  
1H NMR (400 MHz, DMSO-d6, 298K) δ ppm 1.93-2.35 (m, 5H) 2.75-2.82 (m, 2H) 3.38-4.27 (m, 11H) 4.61-4.78 (m, 1H) 6.74-6.80 (m, 1H) 7.45-7.49 (m, 1H) 7.78-7.84 (m, 1H) 8.32-8.37 (m, 1H) 8.47-8.53 (m, 1H) 8.61-8.66 (m, 1H)

Example 80

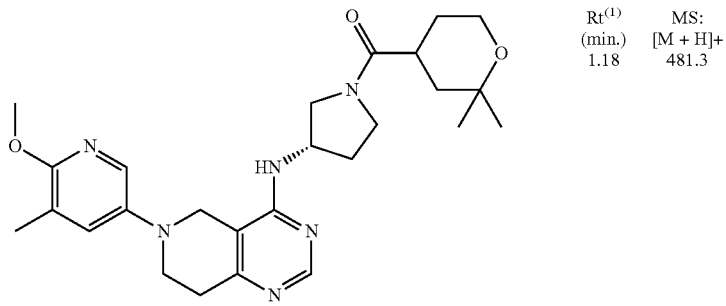

Rt(1) (min.) 1.18  
MS: [M + H]+ 481.3

Name: (2,2-Dimethyl-tetrahydro-pyran-4-yl)-{(S)-3-[6-(6-methoxy-5-methyl-pyridin-3-yl)-5,6,7,8-tetrahydro-pyrido[4,3-d]pyrimidin-4-ylamino]-pyrrolidin-1-yl}-methanone  
Purification method: Reverse phase HPLC Method A  
Prepared using intermediate 20 and 2,2-dimethyl-tetrahydro-pyran-4-carboxylic acid  
1H NMR (400 MHz, DMSO-d6, 298K) δ ppm 1.05-1.22 (m, 6H) 1.30-1.58 (m, 4H) 1.90-2.29 (m, 5H) 2.75-2.85 (m, 3H) 3.35-3.77 (m, 7H) 3.82 (s, 3H) 3.87-3.97 (m, 3H) 4.54-4.79 (m, 1H) 6.66-6.75 (m, 1H) 7.47 (d, 1H) 7.81 (d, 1H) 8.35 (d, 1H)

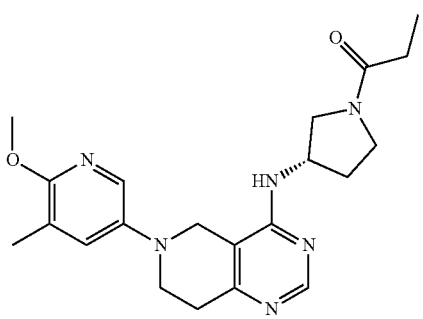 [SMILES: CCC(=O)N1CC[C@H](Nc2ncnc3c2CN(c2cnc(OC)c(C)c2)CC3)C1]

Example 81

1-{(S)-3-[6-(6-Methoxy-5-methyl-pyridin-3-yl)-5,6,7,8-tetrahydro-pyrido[4,3-d]pyrimidin-4-ylamino]-pyrrolidin-1-yl}-propan-1-one To a solution of (S)-3-[6-(6-methoxy-5-methyl-pyridin-3-yl)-5,6,7,8-tetrahydro-pyrido[4,3-d]pyrimidin-4-ylamino]-pyrrolidine-1-carboxylic acid tert-butyl ester trifluoroacetate (intermediate 20) (60 mg, 0.11 mmol) in $CH_2Cl_2$ (2.0 mL), was added TFA (2.0 mL) and the mixture stirred at rt for 1 h. Concentrated in vacuo to give [6-(6-methoxy-5-methylpyridin-3-yl)-5,6,7,8-tetrahydropyrido[4,3-d]pyrimidin-4-yl)]-(S)-pyrrolidin-3-yl)amine ditrifluoroacetate (60 mg). [6-(6-Methoxy-5-methyl-pyridin-3-yl)-5,6,7,8-tetrahydro-pyrido[4,3-d]pyrimidin-4-yl]-(S)-pyrrolidin-3-yl)amine ditrifluoroacetate (30 mg, 0.053 mmol) was dissolved in $CH_2Cl_2$ (2.0 mL) and was added simultaneously portionwise with sat.$NaHCO_3$(aq) (2.0 mL) to a vigourously stirring solution of propionyl chloride (7 mg, 0.07 mmol) in $CH_2Cl_2$ (2.0 mL) at rt. The resulting biphasic mixture was stirred at rt for 45 min. Diluted with $CH_2Cl_2$ (10 mL) and sat.$NaHCO_3$(aq) (2.0 mL). The organic layer was separated by filtering through phase separation tube and concentrated in vacuo. Purification by reverse phase Gilson HPLC (Method A) and subsequent neutralization of the combined fractions by elution through an Isolute® SCX-2 cartridge, eluting with methanol, then with 2M ammonia in methanol. Basic fractions were concentrated in vacuo gave 1-{(S)-3-[6-(6-methoxy-5-methyl-pyridin-3-yl)-5,6,7,8-tetrahydro-pyrido[4,3-d]pyrimidin-4-ylamino]-pyrrolidin-1-yl}-propan-1-one as a colourless powder (7 mg, 21% yield) $^1$H NMR (400 MHz, MeOH-d4, 298K) δ ppm 1.20-1.28 (m, 3H) 2.04-2.44 (m, 7H) 2.88-2.94 (m, 2H) 3.48-4.04 (m, 11H) 4.73-4.88 (m, 1H) 7.44-7.48 (m, 1H) 7.73-7.77 (m, 1H) 8.34-8.38 (m, 1H) LCMS: [M+H]+=397.1, Rt[(3)]=1.32 min.

Examples 82-83 were prepared using procedures analogous to those used in Example 81 using appropriate starting materials.

| Example 82 | 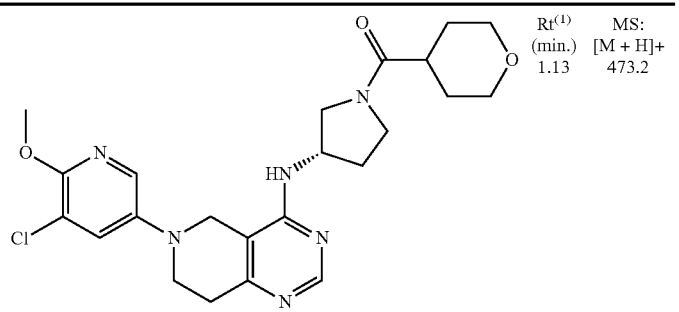 | Rt[(1)] (min.) 1.13 | MS: [M + H]+ 473.2 |
|---|---|---|---|

Name: {(S)-3-[6-(5-Chloro-6-methoxy-pyridin-3-yl)-5,6,7,8-tetrahydro-pyrido[4,3-d]pyrimidin-4-ylamino]-pyrrolidin-1-yl}-(tetrahydro-pyran-4-yl)-methanone
Purification method: Reverse phase HPLC Method A
Prepared using intermediate 21 and tetrahydro-pyran-4-carbonyl chloride
$^1$H NMR (400 MHz, MeOH-d4, 298K) δ ppm 1.58-1.87 (m, 4H) 2.04-2.45 (m, 2H) 2.73-2.96 (m, 3H) 3.39-4.14 (m, 15H) 4.71-4.90 (m, 1H) 7.67-7.74 (m, 1H) 7.88-7.93 (m, 1H) 8.34-8.39 (m, 1H)

| Example 83 | 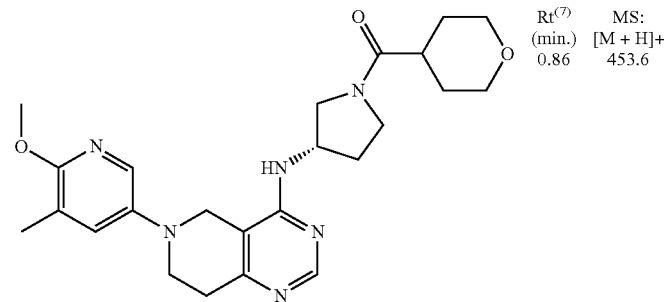 | Rt[(7)] (min.) 0.86 | MS: [M + H]+ 453.6 |
|---|---|---|---|

Name: {(S)-3-[6-(6-Methoxy-5-methyl-pyridin-3-yl)-5,6,7,8-tetrahydro-pyrido[4,3-d]pyrimidin-4-ylamino]-pyrrolidin-1-yl}-(tetrahydro-pyran-4-yl)-methanone
Purification method: Reverse phase HPLC Method A then Method C
Prepared using intermediate 20 and tetrahydro-pyran-4-carbonyl chloride
$^1$H NMR (400 MHz, MeOD-d6, 298K) δ ppm 1.57-1.88 (m, 4H) 2.04-2.45 (m, 5H) 2.73-2.96 (m, 3H) 3.37-4.12 (m, 15H) 4.73-4.88 (m, 1H) 7.45-7.48 (m, 1H) 7.73-7.77 (m, 1H) 8.36-8.39 (m, 1H)

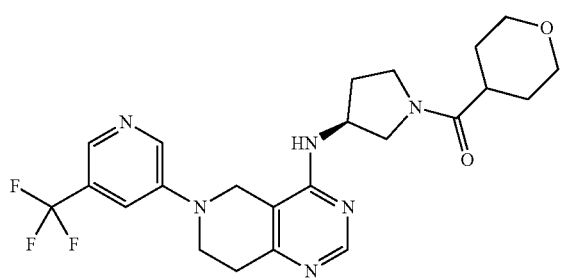 [SMILES: O=C(C1CCOCC1)N1CC[C@H](Nc2ncnc3c2CN(c2cncc(C(F)(F)F)c2)CC3)C1]

Example 84

(Tetrahydro-pyran-4-yl)-{(S)-3-{6-(5-(trifluoromethyl)pyridin-3-yl)-5,6,7,8-tetrahydropyrido[4,3-d]pyrimidin-4-ylamino)pyrrolidin-1-yl}-methanone To 6-(5-(trifluoromethyl-pyridin-3-yl)-5,6,7,8-tetrahydropyrido[4,3-d]pyrimidin-4-ol (intermediate 19) (59 mg) in acetonitrile (1.0 ml) was added BOP (114 mg, 0.258 mmol) and DBU (0.060 ml, 0.398 mmol). The resulting solution was stood at RT for 1 min then added [(S)-3-Amino-pyrrolidin-1-yl-(tetrahydro-pyran-4-yl)-methanone (intermediate 5) (79 mg, 0.398 mmol) in acetonitrile (1.0 ml) and heated the mixture at 85° C. for 25 h. The reaction mixture was evaporated in vacuo and purified by reverse phase Gilson HPLC and subsequent neutralization of the combined fractions by eluting through an Isolute® SCX-2 cartridge, eluting with methanol, then with 2M ammonia in methanol. Basic fractions were concentrated in vacuo gave crude title compound which was further purified by flash chromatography on silica gel with EtOAc/MeOH 100/0 to 80/20 to give (Tetrahydro-pyran-4-yl)-{(S)-3-{6-(5-(trifluoromethyl)pyridin-3-yl)-5,6,7,8-tetrahydropyrido[4,3-d]pyrimidin-4-ylamino)pyrrolidin-1-yl}-methanone (19 mg, 6% yield) as a colourless solid. $^1$H NMR (400 MHz, DMSO-d6, 298K) δ ppm 1.47-1.69 (m, 4H) 1.83-2.37 (m, 2H) 2.58-2.89 (m, 3H) 3.23-4.20 (m, 12H) 4.56-4.82 (m, 1H) 6.75-6.89 (m, 1H, N—H) 7.68-7.79 (m, 1H) 8.28-8.42 (m, 2H) 8.74-8.83 (m, 1H). LCMS: [M+H]+=477.6, Rt$^{(7)}$=0.84 min.

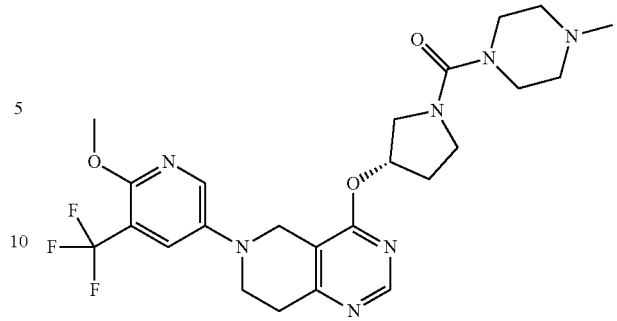

Example 85

{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-(4-methyl-piperazin-1-yl)-methanone To a solution of 6-(6-methoxy-5-trifluoromethyl-pyridin-3-yl)-4-((S)-pyrrolidin-3-yloxy)-5,6,7,8-tetrahydro-pyrido[4,3-d]pyrimidine (prepared using step 1, example 91 from intermediate 13) (23.0 mg, 0.058 mmol) and triethylamine (0.016 mL, 0.116 mmol) in $CH_2Cl_2$ (2 mL) was added 4-methylpiperazine-1-carbonyl chloride hydrochloride (11.6 mg, 0.058 mmol) and the mixture stirred at rt for 18 h. Diluted with $CH_2Cl_2$ (10 mL) and washed with sat. $NaHCO_3$(aq) (2 mL). The organic layer was filtered through a phase separation tube and evaporated in vacuo. Purification was performed by reverse phase Gilson HPLC (Method A) and subsequent neutralization of the combined fractions by elution through an Isolute® SCX-2 cartridge, eluting with methanol, then with 2M ammonia in methanol. Basic fractions were concentrated in vacuo to give {(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-(4-methyl-piperazin-1-yl)-methanone (25 mg, 58% yield) as a yellow powder. $^1$H NMR (400 MHz, CDCl$_3$, 298K) δ ppm 2.17-2.27 (m, 2H) 2.55 (s, 3H) 2.65-2.78 (m, 4H) 3.07 (t, 2H) 3.45-3.73 (m, 9H) 3.86-3.95 (m, 1H) 4.02 (s, 3H) 4.13 (s, 2H) 5.66-5.73 (m, 1H) 7.62 (d, 1H) 8.06 (d, 1H) 8.64 (s, 1H) LCMS: [M+H]+=522.3, Rt$^{(1)}$=1.21 min.

Example 86 was prepared using procedures analogous to those used in Example 85 using appropriate starting materials.

| Example 86 | | Rt$^{(1)}$ (min.) | MS: [M + H]+ |
|---|---|---|---|
| | 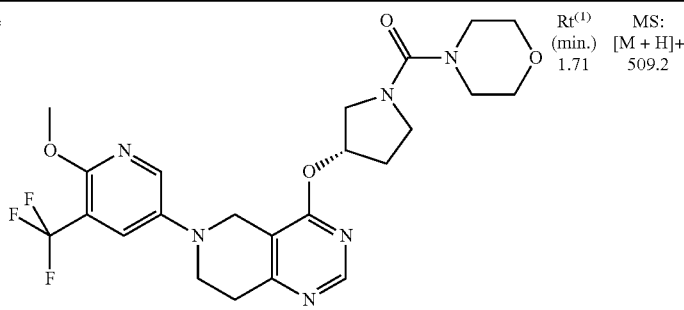 | 1.71 | 509.2 |

Name: -{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-morpholin-4-yl-methanone
Purification method: Reverse phase HPLC Method A
Prepared using morpholine 4-carbonyl chloride
$^1$H NMR (400 MHz, MeOH-d4, 298K) δ ppm 2.21-2.31 (m, 2H) 3.03 (t, 2H) 3.23-3.42 (m, 4H) 3.48-3.81 (m, 9H) 3.82-3.88 (m, 1H) 3.99 (s, 3H) 4.17 (s, 2H) 5.72-5.77 (m, 1H) 7.79 (d, 1H) 8.13 (d, 1H) 8.59 (s, 1H)

Example 87

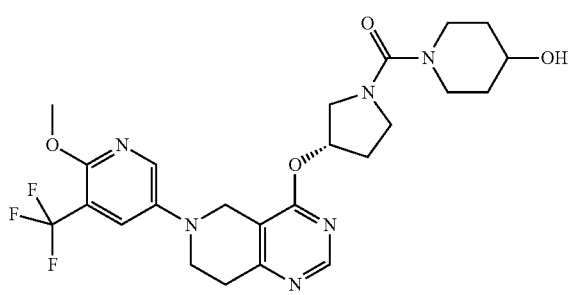 [SMILES: COc1ncc(N2CCc3ncnc(O[C@H]4CCN(C(=O)N5CCC(O)CC5)C4)c3C2)cc1C(F)(F)F]

(4-Hydroxy-piperidin-1-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone To $CH_2Cl_2$ (5 mL) in a round bottomed flask was added phosgene (20% solution in toluene, 0.20 mL, 0.379 mmol) and the resulting solution cooled to 5° C. under argon. A solution of 6-(6-methoxy-5-trifluoromethyl-pyridin-3-yl)-4-((S)-pyrrolidin-3-yloxy)-5,6,7,8-tetrahydro-pyrido[4,3-d]pyrimidine (prepared using step 1, example 91 from intermediate 13) (50.0 mg, 0.126 mmol) and triethylamine (0.053 mL, 0.380 mmol) in $CH_2Cl_2$ (1.0 mL) was added and the mixture allowed to warm to room temperature with stirring under argon over 1 h. Evaporated to dryness by bubbling a stream of argon into the mixture to give a brown gum. Dissolved in $CH_2Cl_2$ (3 mL) to give (S)-3-[6-(6-methoxy-5-trifluoromethyl-pyridin-3-yl)-5,6,7,8-tetrahydro-pyrido[4,3-d]pyrimidin-4-yloxy]-pyrrolidine-1-carbonyl chloride as a solution in $CH_2Cl_2$. LCMS: 458.4 [M+1]$^+$, Rt$^{(7)}$=1.38 min. This solution was used without further purification. 1.5 mL of this solution was added to a solution of piperidin-4-ol (6.4 mg, 0.063 mmol) and triethylamine (0.053 mL, 0.380 mmol) in $CH_2Cl_2$ and the mixture stirred at room temperature under argon for 1 h. N,N-dimethylformamide (0.5 mL) was added and stirring continued for 2 h. Diluted with $CH_2Cl_2$ (2 mL) and washed with sat. $NaHCO_3$(aq) (2 mL). The organic layer was filtered through a phase separation tube and evaporated in vacuo. Purification by reverse phase Gilson HPLC (Method A) and subsequent neutralization of the combined fractions by elution through an Isolute® SCX-2 cartridge, eluting with methanol, then with 2M ammonia in methanol. Basic fractions were concentrated in vacuo to give (4-hydroxy-piperidin-1-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone as a pale yellow powder (22 mg, 64% yield). $^1$H NMR (400 MHz, MeOH-d4, 298K) δ ppm 1.35-1.57 (m, 2H) 1.80-1.94 (m, 2H) 2.20-2.31 (m, 2H) 2.94-3.09 (m, 4H) 3.45-3.87 (m, 10H) 3.98 (s, 3H) 4.17 (s, 2H) 5.70-5.76 (m, 1H) 7.78 (d, 1H) 8.13 (d, 1H) 8.58 (s, 1H) LCMS: [M+H]+=523.2, Rt$^{(1)}$=1.58 min.

Example 88 was prepared using procedures analogous to those used in Example 87 using appropriate starting materials.

| Example 88 | | Rt$^{(1)}$ (min.) | MS: [M + H]+ |
|---|---|---|---|
| 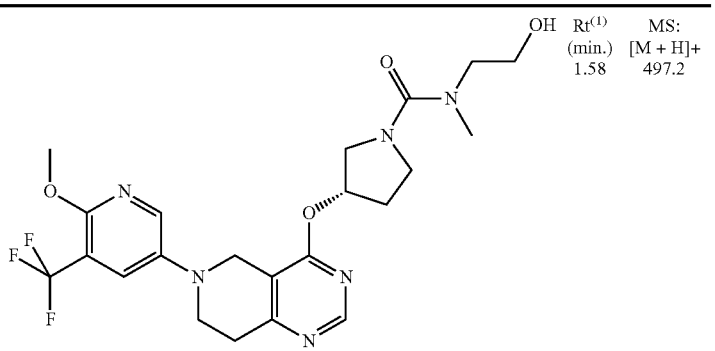 | | 1.58 | 497.2 |
| Name: (S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carboxylic acid (2-hydroxy-ethyl)-methyl-amide<br>Purification method: Reverse phase HPLC Method A<br>Prepared using 2-methylamino-ethanol<br>$^1$H NMR (400 MHz, MeOH-d4, 298K) δ ppm 2.20-2.32 (m, 2H) 2.97 (s, 3H) 2.98-3.06 (t, 2H) 3.27-3.38 (m, 1H) 3.40-3.80 (m, 8H) 3.82-3.89 (m, 1H) 3.98 (s, 3H) 4.18 (s, 2H) 5.71-5.76 (m, 1H) 7.78 (d, 1H) 8.14 (d, 1H) 8.58 (s, 1H) | | | |

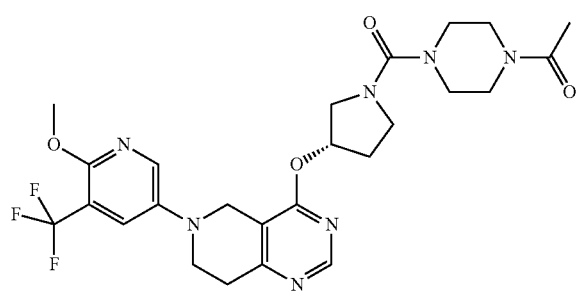 [SMILES: COc1ncc(N2CCc3ncnc(O[C@H]4CCN(C(=O)N5CCN(C(C)=O)CC5)C4)c3C2)cc1C(F)(F)F]

Example 89

1-(4-{(S)-3-[6-(6-methoxy-5-trifluoromethyl-pyridin-3-yl)-5,6,7,8-tetrahydro-pyrido[4,3-d]pyrimidin-4-yloxy]-pyrrolidine-1-carbonyl}-piperazin-1-yl)-ethanone To a solution of 6-(6-methoxy-5-trifluoromethyl-pyridin-3-yl)-4-((S)-pyrrolidin-3-yloxy)-5,6,7,8-tetrahydro-pyrido[4,3-d]pyrimidine (prepared using step 1, example 91 from intermediate 13) (25 mg, 0.063 mmol) and triethylamine (0.013 mL, 0.095 mmol) in $CH_2Cl_2$ (2 mL) was added 3-(4-acetyl-piperazine-1-carbonyl)-1-methyl-3H-imidazol-3-ium iodide (Intermediate 6) (15 mg, 0.063 mmol) and the mixture stirred at room temperature under argon for 18 h. Partitioned between $CH_2Cl_2$ (10 mL) and sat. $NaHCO_3$(aq) (2 mL) and the organic layer was filtered through a phase separation tube and evaporated in vacuo. Purification by reverse phase Gilson HPLC (Method A) and subsequent neutralization of the combined fractions by elution through an Isolute SCX-2 cartridge, eluting with methanol, then with 2M ammonia in methanol. Basic fractions were concentrated in vacuo to give 1-(4-{(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-piperazin-1-yl)-ethanone as a pale yellow powder (9 mg, 25% yield). $^1$H NMR (400 MHz, MeOH-d4, 298K) δ ppm 2.14 (s, 3H) 2.24-2.33 (m, 2H) 3.04 (t, 2H) 3.25-3.91 (m, 13H) 3.99 (s, 3H) 4.18 (s, 2H) 5.74-5.78 (m, 1H) 7.79 (d, 1H) 8.14 (d, 1H) 8.60 (s, 1H) LCMS: [M+H]+=550.2, $Rt^{(1)}$=1.58 min.

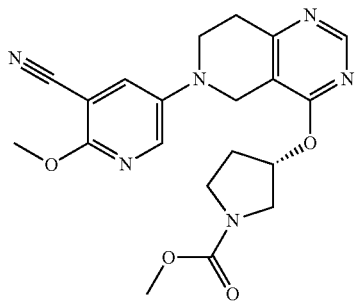 [SMILES: COC(=O)N1CC[C@H](Oc2ncnc3c2CN(c2cnc(OC)c(C#N)c2)CC3)C1]

Example 90

(S)-3-[6-(5-cyano-6-methoxy-pyridin-3-yl)-5,6,7,8-tetrahydro-pyrido[4,3-d]pyrimidin-4-yloxy]-pyrrolidine-1-carboxylic acid methyl ester To a solution of 2-methoxy-5-[4-((S)-pyrrolidin-3-yloxy)-7,8-dihydro-5H-pyrido[4,3-d]pyrimidin-6-yl]-nicotinonitrile (prepared using intermediate 11 and method 1b, process step 2, example 1) (25.0 mg, 0.071 mmol) and triethylamine (0.04 mL, 0.29 mmol) in $CH_2Cl_2$ (2 mL) was added methyl carbonochloridate (0.006 mL, 0.078 mmol) and the mixture stirred at room temperature for 18 h. Diluted with $CH_2Cl_2$ (2 mL) and washed with sat. $NaHCO_3$(aq) (1 mL). The organic layer was filtered through a phase separation tube and evaporated in vacuo. Purification was performed by reverse phase Gilson HPLC (Method A) and subsequent neutralization of the combined fractions by elution through an Isolute® SCX-2 cartridge, eluting with methanol, then with 2M ammonia in methanol. Basic fractions were concentrated in vacuo gave (S)-3-[6-(5-cyano-6-methoxy-pyridin-3-yl)-5,6,7,8-tetrahydro-pyrido[4,3-d]pyrimidin-4-yloxy]-pyrrolidine-1-carboxylic acid methyl ester (10 mg, 35% yield) as a yellow powder. $^1$H NMR (400 MHz, DMSO-d6, 298K) δ ppm 2.09-2.31 (m, 2H) 2.91 (t, 2H) 3.45-3.75 (m, 9H) 3.93 (s, 3H) 4.17 (s, 2H) 5.58-5.65 (m, 1H) 8.09 (d, 1H) 8.27 (d, 1H) 8.61 (s, 1H) LCMS: [M+H]+=411.1, $Rt^{(1)}$=1.58 min.

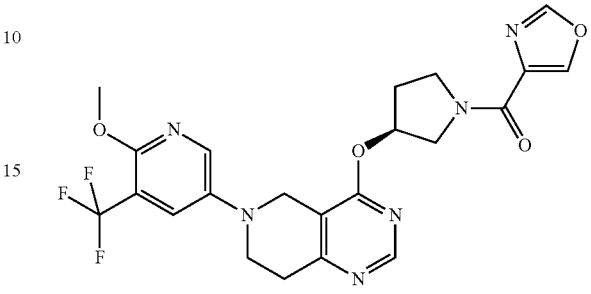

Example 91

{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-oxazol-4-yl-methanone Step 2

To the oxazole-4-carboxylic acid (27 mg, 0.24 mmol)) and HBTU (89 mg, 0.24 mmol) in DMF (1 mL) was added N,N-diisopropylethylamine (0.08 mL, 0.45 mmol). The mixture was stirred for 20 min and then 6-(6-methoxy-5-trifluoromethyl-pyridin-3-yl)-4-((S)-pyrrolidin-3-yloxy)-5,6,7,8-tetrahydro-pyrido[4,3-d]pyrimidine dihydrochloride (100 mg, 0.214 mmol) and additional N,N-diisopropylethylamine (0.08 mL, 0.45 mmol) were added. The mixture was allowed to stir at room temperature for 30 min. Purified by reverse phase Gilson HPLC (Method A) and subsequent neutralization of the combined fractions over $PL-HCO_3$ MP to give {(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-oxazol-4-yl-methanone as a yellow solid (38 mg, 36% yield) $^1$H NMR (400 MHz, DMSO-d6, 298K) δ ppm 2.11-2.39 (m, 2 H) 2.80-3.01 (m, 2 H) 3.22-4.29 (m, 11 H) 5.59-5.80 (m, 1 H) 7.72-7.94 (m, 1 H) 8.10-8.29 (m, 1 H) 8.41-8.55 (m, 1 H) 8.57-8.77 (m, 2 H) LCMS: [M+H]+=491.1, $Rt^{(1)}$=1.69 min.

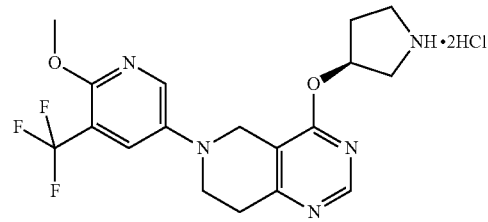 [SMILES: COc1ncc(N2CCc3ncnc(O[C@H]4CCNC4)c3C2)cc1C(F)(F)F]

6-(6-Methoxy-5-trifluoromethyl-pyridin-3-yl)-4-((S)-pyrrolidin-3-yloxy)-5,6,7,8-tetrahydro-pyrido[4,3-d]pyrimidine dihydrochloride Step 1

(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carboxylic acid tert-butyl ester (1.0 g, 1.69 mmol) in CH$_2$Cl$_2$ (5 mL) was added 2M anhydrous HCl in diethyl ether (25.3 mL, 50.5 mmol) and the mixture stirred at rt for 3 h. The resulting precipitate was filtered and washed with diethyl ether to give 6-(6-methoxy-5-trifluoromethyl-pyridin-3-yl)-4-((S)-pyrrolidin-3-yloxy)-5,6,7,8-tetrahydro-pyrido[4,3-d]pyrimidine dihydrochloride as a yellow solid (1.01 g, 128% yield). [M+H]+=396.0, Rt$^{(4)}$=0.71 min. The free base can be generated by partitioning the dihydrochloride salt between dichloromethane and 1N sodium hydroxide solution(aq), separating the organic phase and evaporating in vacuo. [M+H]+=396.0, Rt$^{(4)}$=0.71 min.

Example 92 was prepared using procedures analogous to those used in Example 91 using appropriate starting materials.

Example 92 — Rt$^{(1)}$ (min.) 1.58 — MS: [M + H]+ 549.2

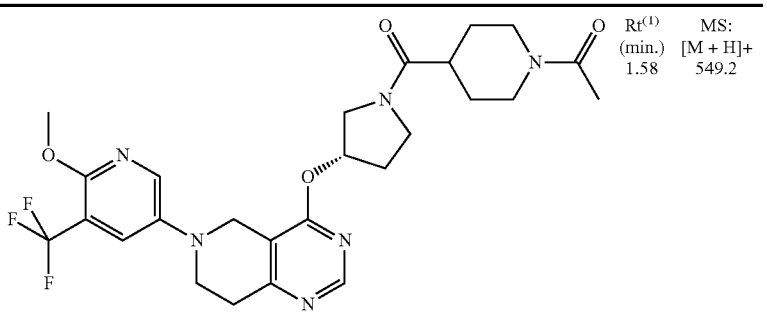

Name: 1-(4-{(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-piperidin-1-yl)-ethanone
Purification method: Reverse phase method A
Prepared using 1-acetyl-piperidine-4-carboxylic acid
$^1$H NMR (400 MHz, DMSO-d6, 298K) δ ppm 1.21-1.77 (m, 4H) 1.92 -2.02 (m, 3H) 2.08-2.36 (m, 2H) 2.42-2.80 (m, 2H) 2.88-2.98 (m, 2H) 3.00-3.18 (m, 1H) 3.39-4.24 (m, 13H) 5.60-5.74 (m, 1H) 7.80-7.87 (m, 1H) 8.15-8.22 (m, 1H) 8.59-8.65 (m, 1H)

Example 93 — Rt$^{(1)}$ (min.) 1.37 — MS: [M + H]+ 504.1

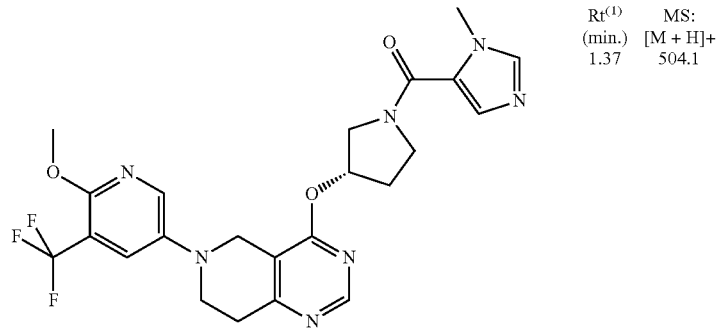

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone
Purification method: Reverse phase method A
Prepared using 3-methyl-3H-imidazole-4-carboxylic acid
$^1$H NMR (400 MHz, DMSO-d6, 298K) δ pm 2.14-2.38 (m, 2H) 2.78-3.08 (m, 2H) 3.44-4.04 (m, 12H) 4.08-4.27 (m, 2H) 5.66-5.73 (m, 1H) 7.32-7.57 (m, 1H) 7.70-7.97 (m, 2H) 8.13-8.28 (m, 1H) 8.56-8.69 (m, 1H)

Example 94 — Rt$^{(1)}$ (min.) 0.95 — MS: [M + H]+ 490.9

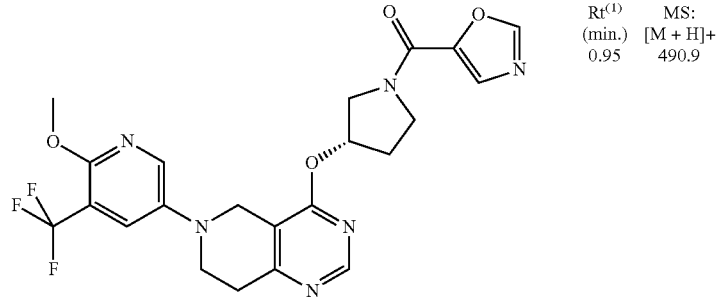

Name: {(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-oxazol-5-yl-methanone
Purification method: Reverse phase method A
Prepared using oxazole-5-carboxylic acid
$^1$H NMR (400 MHz, DMSO-d6, 298K) δ ppm 2.28-2.43 (m, 2H) 2.86-3.00 (m, 2H) 3.39-4.27 (m, 11H) 5.60-5.85 (m, 1H) 7.72-7.91 (m, 2H) 8.15-8.30 (m, 1H) 8.53-8.68 (m, 2H)

Example 95 was prepared using procedures analogous to those used in Example 1, method 1a using appropriate starting materials according to scheme 8.

| Example | Structure | Rt[(3)] (min.) | MS: [M + H]+ |
|---|---|---|---|
| 95 | 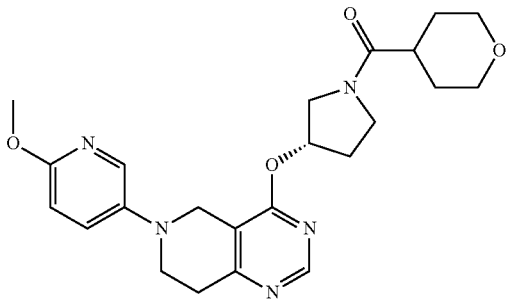 [SMILES: COc1ccc(N2CCc3ncnc(O[C@H]4CCN(C(=O)C5CCOCC5)C4)c3C2)cn1] | 1.39( | 440.1 |

Name: {(S)-3-[6-(6-Methoxy-pyridin-3-yl)-5,6,7,8-tetrahydro-pyrido[4,3-d]pyrimidin-4-yloxy)pyrrolidin-1-yl}-(tetrahydro-pyran-4-yl)-methanone
Purification method: Flash-chromatography on silica gel with $CH_2Cl_2$/MeOH
Prepared using 1-benzyl-1-methyl-4-oxo-piperidinium iodide (Ref: Tortolani, R.; Org. Lett., Vol. 1, No 8, 1999) and 2-methoxypyridine
$^1$H NMR (400 MHz, DMSO-d6, 298K) δ ppm 1.48-1.65 (m, 4H) 2.05-2.30 (m, 2H) 2.59-2.78 (m, 1H) 2.85-2.93 (m, 2H) 3.25-4.11 (m, 15H) 5.59-5.73 (m, 1H) 6.73-6.79 (m, 1H) 7.53-7.59 (m, 1H) 7.86-7.89 (m, 1H) 8.58-8.64 (m, 1H).

The pharmaceutical composition or combination of the present invention can be in unit dosage of about 1-2000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

BIOLOGICAL EVALUATION

The activity of a compound according to the present invention can be assessed by the following in vitro & in vivo methods.
Biological Assays
1 Determination of Enzymatic PI3K Alpha and PI3K Delta Isoform Inhibition
1.1 Test of Lipid Kinase Activity
The efficacy of the compounds of examples 1-117 as PI3 kinase inhibitors can be demonstrated as follows:
The kinase reaction is performed in a final volume of 50 μl per well of a half area COSTAR, 96 well plate. The final concentrations of ATP and phosphatidyl inositol in the assay are 5 μM and 6 μg/mL, respectively. The reaction is started by the addition of PI3 kinase, e.g. PI3 kinase δ.

p110δ. The components of the assay are added per well as follows:
10 μl test compound in 5% DMSO per well in columns 2-1.
Total activity is determined by addition 10 μl of 5% vol/vol DMSO in the first 4 wells of column 1 and the last 4 wells of column 12.
The background is determined by addition of 10 μM control compound to the last 4 wells of column 1 and the first 4 wells of column 12.
2 mL 'Assay mix' are prepared per plate:
  1.912 mL of HEPES assay buffer
  8.33 μl of 3 mM stock of ATP giving a final concentration of 5 μM per well
  1 μl of [$^{33}$P]ATP on the activity date giving 0.05 μCi per well
  30 μl of 1 mg/mL PI stock giving a final concentration of 6 μg/mL per well
  5 μl of 1 M stock $MgCl_2$ giving a final concentration of 1 mM per well
20 μl of the assay mix are added per well.
2 mL 'Enzyme mix' are prepared per plate (x* μl PI3 kinase p110β in 2 mL of kinase buffer). The 'Enzyme mix' is kept on ice during addition to the assay plates.
20 μl 'Enzyme mix' are added/well to start the reaction.
The plate is then incubated at room temperature for 90 minutes.
The reaction is terminated by the addition of 50 μl WGA-SPAbead (wheat germ agglutinin-coated Scintillation Proximity Assay beads) suspension per well.
The assay plate is sealed using TopSeal-S (heat seal for polystyrene microplates, PerkinElmer LAS [Deutschland] GmbH, Rodgau, Germany) and incubated at room temperature for at least 60 minutes.
The assay plate is then centrifuged at 1500 rpm for 2 minutes using the Jouan bench top centrifuge (Jouan Inc., Nantes, France).
The assay plate is counted using a Packard TopCount, each well being counted for 20 seconds.
The volume of enzyme is dependent on the enzymatic activity of the batch in use.

In a more preferred assay, the kinase reaction is performed in a final volume of 10 μl per well of a low volume non-binding CORNING, 384 well black plate (Cat. No. #3676). The final concentrations of ATP and phosphatidyl inositol (PI) in the assay are 1 μM and 10 μg/mL, respectively. The reaction is started by the addition of ATP.

The components of the assay are added per well as follows: 50 nl test compounds in 90% DMSO per well, in columns 1-20, 8 concentrations (1/3 and 1/3.33 serial dilution step) in single.

Low control: 50 nl of 90% DMSO in half the wells of columns 23-24 (0.45% in final).
High control: 50 nl of reference compound (e.g. compound of Example 7 in WO 2006/122806) in the other half of columns 23-24 (2.5 μM in final).
Standard: 50 nl of reference compound as just mentioned diluted as the test compounds in columns 21-22.
20 mL 'buffer' are prepared per assay:
  200 μl of 1M TRIS HCl pH7.5 (10 mM in final)
  60 μl of 1M MgCl$_2$ (3 mM in final)
  500 μl of 2M NaCl (50 mM in final)
  100 μl of 10% CHAPS (0.05% in final)
  200 μl of 100 mM DTT (1 mM in final)
  18.94 mL of nanopure water
10 mL 'PI' are prepared per assay:
  200 μl of 1 mg/mL 1-alpha-Phosphatidylinositol (Liver Bovine, Avanti Polar Lipids Cat. No. 840042C MW=909.12) prepared in 3% OctylGlucoside (10 μg/mL in final)
  9.8 mL of 'buffer'
10 mL 'ATP' are prepared per assay:
  6.7 μl of 3 mM stock of ATP giving a final concentration of 1 μM per well 10 mL of 'buffer'
2.5 mL of each PI3K construct are prepared per assay in 'PI' with the following final concentration:
  10 nM PI3K alfa EMV B1075
  25 nM beta EMV BV949
  10 nM delta EMV BV1060
  150 nM gamma EMV BV950
5 μl of 'PI/PI3K' are added per well.
5 μl 'ATP' are added per well to start the reaction.
The plates are then incubated at room temperature for 60 minutes (alfa, beta, delta) or 120 minutes (gamma).
The reaction is terminated by the addition of 10 μl Kinase-Glo (Promega Cat. No. #6714).
The assay plates are read after 10 minutes in Synergy 2 reader (BioTek, Vermont USA) with an integration time of 100 milliseconds and sensitivity set to 191.
Output: The High control is around 60'000 counts and the Low control is 30'000 or lower
This luminescence assay gives a useful Z' ratio between 0.4 and 0.7

The Z' value is a universal measurement of the robustness of an assay. A Z' between 0.5 and 1.0 is considered an excellent assay.

For this assay, the PI3K constructs mentioned are prepared as follows:

1.2 Generation of Gene Constructs

Two different constructs, BV 1052 and BV 1075, are used to generate the PI3 Kinase α proteins for compound screening.

PI3Kα BV-1052 p85(iSH2)-Gly Linker-p110a(D20Oaa)-C-Term His Tag

PCR products for the inter SH2 domain (iSH2) of the p85 subunit and for the p110-a subunit (with a deletion of the first 20 amino acids) are generated and fused by overlapping PCR. The iSH2 PCR product is generated from first strand cDNA using initially primers

```
gwG130-p01
                                        (SEQ ID NO: 1)
(5'-CGAGAATATGATAGATTATATGAAGAAT-3')
and gwG130-p02
                                        (SEQ ID NO: 2)
(5'-TGGTTT-AATGCTGTTCATACGTTTGTCAAT-3').
```

Subsequently in a secondary PCR reaction, Gateway (Invitrogen AG, Basel, Switzerland) recombination AttB1 sites and linker sequences are added at the 5' end and 3' end of the p85 iSH2 fragment respectively, using primers

```
gwG130-p03
                                        (SEQ ID NO: 3)
(5'-GGGACAAGTTTGTACAAAAAAGCAGGCTACGAAGGAGATATACATA

T-GCGAGAATATGATAGATTATATGAAGAAT-3')
and gwG152-p04
                                        (SEQ ID NO: 4)
(5'-TACCATAATTCCACCACCACCACCGGAAATTCCCCCTGGTTT-

AATGCTGTTCATACGTTTGTCAAT-3').
```

The p110-a fragment is also generated from first strand cDNA, initially using primers

```
                                        (SEQ ID NO: 5)
gwG152-p01 (5'-CTAGTGGAATGTTTACTACCAAATGG-3')
and (SEQ ID NO: 6)
gwG152-p02 (5'-GTTCAATG-CATGCTGTTTAATTGTGT-3').
```

In a subsequent PCR reaction, linker sequence and a Histidine tag are added at the 5' end and 3' end of the p110-a fragment respectively, using primers

```
gw152-p03
                                        (SEQ ID NO: 7)
(5'-GGGGGAATTTCCGGTGGTGGTGGTGGAATTATGGTAC-

TAGTGGAATGTTTACTACC-AAATGGA-3')
and gwG152-p06
                                        (SEQ ID NO: 8)
(5'-AGCTCCGTGATGGTGATGGTGATGTGCTCCGTTCAATG-

CATGCTGTTTAATTGTGT-3').
```

The p85-iSH2/p110-a fusion protein is assembled in a third PCR reaction by the overlapping linkers at the 3' end of the iSH2 fragment and the 5' end of the p110-a fragment, using the above mentioned gwG130-p03 primer and a primer containing an overlapping Histidine tag and the AttB2 recombination sequences

```
                                        (SEQ ID NO: 9)
(5'-GGGACCACTTTGTACAAGAAAGCTGGGTTTAAGCTCCGTGATGGTG

ATGGTGAT-GTGCTCC-3').
```

This final product is recombined in a (Invitrogen) OR reaction into the donor vector pDONR201 to generate the ORF318 entry clone. This clone is verified by sequencing and used in a Gateway LR reaction to transfer the insert into the Gateway adapted pBlueBac4.5 (Invitrogen) vector for generation of the baculovirus expression vector LR410.

PI3Kα BV-1075 p85(iSH2)-12 XGly Linker-p110a (D20Oaa)-C-Term His Tag

The construct for Baculovirus BV-1075 is generated by a three-part ligation comprised of a p85 fragment and a p110-a fragment cloned into vector pBlueBac4.5. The p85 fragment is derived from plasmid p1661-2 digested with Nhe/Spe. The p110-a fragment derived from LR410 (see above) as a SpeI/HindIII fragment. The cloning vector pBlueBac4.5 (Invitrogen) is digested with Nhe/HindIII. This results in the construct PED 153.8

The p85 component (iSH2) is generated by PCR using ORF 318 (described above) as a template and one forward primer

```
KAC1028
                                      (SEQ ID NO: 10)
(5'-GCTAGCATGCGAGAATATGATAGATTATATGAAGAATATACC)

and two reverse primers,

KAC1029
                                      (SEQ ID NO: 11)
(5'-GCCTCCACCACCTCCGCCTGGTTTAATGCTGTTCATACGTTTGTC)
and KAC1039
                                      (SEQ ID NO: 12)
(5'-TACTAGTCCGCCTCCACCACCTCCGCCTCCACCACCTCCGCC).
```

The two reverse primers overlap and incorporate the 12× Gly linker and the N-terminal sequence of the p110a gene to the SpeI site. The 12× Gly linker replaces the linker in the BV1052 construct. The PCR fragment is cloned into pCR2.1 TOPO (Invitrogen). Of the resulting clones, p1661-2 is determined to be correct. This plasmid is digested with Nhe and SpeI and the resulting fragment is gel-isolated and purified for sub-cloning. The p110-a cloning fragment is generated by enzymatic digest of clone LR410 (see above) with Spe I and HindIII. The SpeI site is in the coding region of the p110a gene. The resulting fragment is gel-isolated and purified for sub-cloning.

The cloning vector, pBlueBac4.5 (Invitrogen) is prepared by enzymatic digestion with Nhe and HindIII. The cut vector is purified with Qiagen (Quiagen N.V, Venlo, Netherlands) column and then dephosphorylated with Calf Intestine alkaline phosphatase (CIP) (New England BioLabs, Ipswich, Mass.). After completion of the CIP reaction the cut vector is again column purified to generate the final vector. A 3 part ligation is performed using Roche Rapid ligase and the vendor specifications.

PI3Kβ BV-949 p85(iSH2)-Gly Linker-p110b (Full-Length)-C-Term His Tag

PCR products for the inter SH2 domain (iSH2) of the p85 subunit and for the full-length p110-b subunit are generated and fused by overlapping PCR.

The iSH2 PCR product is generated from first strand cDNA initially using primers

```
      gwG130-p01
                                      (SEQ ID NO: 1)
      (5'-CGAGAATATGATAGATTATATGAAGAAT-3')
      and
```

```
      gwG130-p02
                                      (SEQ ID NO: 2)
      (5'-TGGTTT-AATGCTGTTCATACGTTTGTCAAT-3').
```

Subsequently, in a secondary PCR reaction Gateway (Invitrogen) recombination AttB1 sites and linker sequences are added at the 5' end and 3' end of the p85 iSH2 fragment respectively, using primers

```
      gwG130-p03
                                      (SEQ ID NO: 3)
      (5'-GGGACAAGTTTGTACAAAAAAGCAGGCTACGAAGGAGATA-

TACATATGCGAGAATATGATAGATTATATGAAGAAT-3')
      and gwG130-p05
                                      (SEQ ID NO: 13)
      (5'-ACTGAAGCATCCTCCTCCTCCTCCTCCTGGTTTAAT-

GCTGTTCATACGTTTGTC-3').
```

The p110-b fragment is also generated from first strand cDNA initially using primers

```
      gwG130-p04
                                      (SEQ ID NO: 4)
      (5'-ATTAAACCAGGAGGAGGAGGAGGAGGATGCTTCAGTTTCATAATGC

C-TCCTGCT-3')
``` which contains linker sequences and the 5' end of p110-b and

```
      gwG130-p06
                                      (SEQ ID NO: 14)
      (5'-AGCTCCGTGATGGTGATGGTGATGTGCTCCAGATCTGTAGTCTTT-

CCGAACTGTGTG-3')
``` which contains sequences of the 3' end of p110-b fused to a Histidine tag.

The p85-iSH2/p110-b fusion protein is assembled by an overlapping PCR reaction of the linkers at the 3' end of the iSH2 fragment and the 5' end of the p110-b fragment, using the above mentioned gwG130-p03 primer and a primer containing an overlapping Histidine tag and the AttB2 recombination sequences

```
                                      (SEQ ID NO: 15)
      (5'-GGGACCACTTTGTACAAGAAAGCTGGGTTT-

AAGCTCCGTGATGGTGATGGTGATGTGCTCC-3').
```

This final product is recombined in a Gateway (Invitrogen) OR reaction into the donor vector pDONR201 to generate the ORF253 entry clone. This clone is verified by sequencing and used in a Gateway LR reaction to transfer the insert into the Gateway adapted pBlueBac4.5 (Invitrogen) vector for generation of the baculovirus expression vector LR280.

PI3Kδ BV-1060 p85(iSH2)-Gly Linker-p110d (Full-Length)-C-Term His Tag

PCR products for the inter SH2 domain (iSH2) of the p85 subunit and for the full-length p110-d subunit are generated and fused by overlapping PCR.

The iSH2 PCR product is generated from first strand cDNA using initially primers

```
gwG130-p01
                                            (SEQ ID NO: 1)
(5'-CGAGAATATGATAGATTATATGAAGAAT-3')
and gwG130-p02
                                            (SEQ ID NO: 2)
(5'-TGGTTT-AATGCTGTTCATACGTTTGTCAAT-3').
```

Subsequently, in a secondary PCR reaction Gateway (Invitrogen) recombination AttB1 sites and linker sequences are added at the 5' end and 3' end of the p85 iSH2 fragment respectively, using primers

```
gwG130-p03
                                            (SEQ ID NO: 3)
(5'-GGGACAAGTTTGTACAAAAAAGCAGGCTACGAAGGAGATATACAT-

ATGCGAGAATATGATAGATTATATGAAGAAT-3')
and gwG154-p04
                                            (SEQ ID NO: 16)
(5'-TCCTCCTCCTCCTCCTCCTGGTTTAATGCTGTTCATACGTTTGT

C-3').
```

The p110-a fragment is also generated from first strand cDNA using initially primers

```
                                            (SEQ ID NO: 17)
gwG154-p01 (5'-ATGCCCCCTGGGGTGGACTGCCCCAT-3')
and (SEQ ID NO: 18)
gwG154-p02 (5'-CTACTG-CCTGTTGTCTTTGGACACGT-3').
```

In a subsequent PCR reaction linker sequences and a Histidine tag is added at the 5' end and 3' end of the p110-d fragment respectively, using primers

```
gw154-p03
                                            (SEQ ID NO: 19)
(5'-ATTAAACCAGGAGGAGGAGGAGGAGGACCCCCTGGGGTGGAC-

TGCCCCATGGA-3')
and gwG154-p06
                                            (SEQ ID NO: 20)
(5'-AGCTCCGTGATGGTGAT-GGTGATGTGCT-CCCTGCCTGTTGTCTT

TGGACACGTTGT-3').
```

The p85-iSH2/p110-d fusion protein is assembled in a third PCR reaction by the overlapping linkers at the 3' end of the iSH2 fragment and the 5' end of the p110-d fragment, using the above mentioned gwG130-p03 primer and a primer containing an overlapping Histidine tag and the Gateway (Invitrogen) AttB2 recombination sequences

```
                                            (SEQ ID NO: 21)
(5'-GGGACCACTTTGTA-CAAGAAAGCTGGGTTT-

AAGCTCCGTGATGGTGATGGTGATGTGCTCC-3').
```

This final product is recombined in a Gateway (Invitrogen) OR reaction into the donor vector pDONR201 to generate the ORF319 entry clone. This clone is verified by sequencing and used in a Gateway LR reaction to transfer the insert into the Gateway adapted pBlueBac4.5 (Invitrogen) vector for generation of the baculovirus expression vector LR415.

PI3Kγ BV-950 p110q(D144aa)-C-Term His Tag

This construct is obtained from Roger Williams lab, MRC Laboratory of Molecular Biology, Cambridge, UK (November, 2003). Description of the construct in: Pacold M. E. et al. (2000) Cell 103, 931-943.

1.3 Protein Expression and Purification

Methods to generate recombinant baculovirus and protein for PI3K isoforms: The pBlue-Bac4.5 (for a, b, and d isoforms) or pVL1393 (for g) plasmids containing the different PI3 kinase genes are co-transfected with BaculoGold WT genomic DNA (BD Biosciences, Franklin Lakes, N.J., USA) using methods recommended by the vendor. Subsequently, the recombinant baculovirus obtained from the transfection is plaque-purified on Sf9 insect cells to yield several isolates expressing recombinant protein. Positive clones are selected by anti-HIS or anti-isoform antibody western. For PI3K alpha and delta isoforms, a secondary plaque-purification is performed on the first clonal virus stocks of PI3K. Amplification of all baculovirus isolates is performed at low multiplicity of infection (moi) to generate high-titer, low passage stock for protein production. The baculoviruses are designated BV1052 (α) and BV1075 (α), BV949 (β), BV1060 (δ) and BV950 (γ).

Protein production involves infection (passage 3 or lower) of suspended Tn5 (*Trichoplusia ni*) or TiniPro (Expression Systems, LLC, Woodland, Calif., USA) cells in protein-free media at moi of 2-10 for 39-48 hours in 2 l glass Erlenmyer flasks (110 rpm) or wave-bioreactors (22-25 rpm). Initially, 10 l working volume wave-bioreactors are seeded at a density of 3e5 cells/mL at half capacity (5 L). The reactor is rocked at 15 rpm during the cell growth phase for 72 hours, supplemented with 5% oxygen mixed with air (0.2 l per minute). Immediately prior to infection, the wave-reactor cultures are analyzed for density, viability and diluted to approximately 1.5e6 cell/mL. 100-500 mL of high titer, low passage virus is added following 2-4 hours of additional culture. Oxygen is increased to 35% for the 39-48 hour infection period and rocking platform rpm increased to 25. During infection, cells are monitored by Vicell viability analyzer (Beckman Coulter, Inc, Fullerton, Calif., USA) bioprocess for viability, diameter and density. Nova Bioanalyzer (NOVA Biomedical Corp., Waltham, Mass., USA) readings of various parameters and metabolites (pH, $O_2$ saturation, glucose, etc.) are taken every 12-18 hours until harvest. The wave-bioreactor cells are collected within 40 hours post infection. Cells are collected by centrifugation (4 degrees C. at 1500 rpm), and subsequently maintained on ice during pooling of pellets for lysis and purification. Pellet pools are made with small amounts of cold, un-supplemented Grace's media (w/o protease inhibitors).

PI3K alpha Purification Protocol For HTS (BV1052)

PI3K alpha is purified in three chromatographic steps: immobilized metal affinity chromato-graphy on a Ni Sepharose resin (GE Healthcare, belonging to General Electric Company, Fairfield, Conn., USA), gel filtration utilizing a Superdex 200 26/60 column (GE Healthcare), and finally a cation exchange step on a SP-XL column (GE Healthcare). All buffers are chilled to 4° C. and lysis is performed chilled on ice. Column fractionation is performed rapidly at room temperature.

Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing target protein are pooled and applied to a prepared GFC column. Fractions from the GFC column are analyzed by Coomassie stained SDS-PAGE gels, and fractions containing target protein are pooled. The pool from the GFC column is diluted into a low salt buffer and applied to a prepared SP-XL column. The column is washed with low salt buffer until a stable A280 baseline absorbance is achieved, and eluted using a 20 column volume gradient from 0 mM NaCl to 500 mM NaCl. Again, fractions from the SP-XL column are analyzed by Coomassie stained SDS-PAGE gels, and fractions containing the target protein are pooled. The final pool is dialyzed into a storage buffer containing 50% glycerol and stored at −20° C. The final pool is assayed for activity in a phosphoinositol kinase assay.

PI3K Beta Purification Protocol For HTS (BV949)

PI3K beta is purified in two chromatographic steps: immobilized metal affinity chromatography (IMAC) on a Ni Sepharose resin (GE Healthcare) and gel filtration (GFC) utilizing a Superdex 200 26/60 column (GE Healthcare). All buffers are chilled to 4° C. and lysis is performed chilled on ice. Column fractionation is performed rapidly at room temperature.

Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing target protein are pooled and applied to a prepared GFC column. Fractions from the GFC column are analyzed by Coomassie stained SDS-PAGE gels, and fractions containing target protein are pooled. The final pool is dialyzed into a storage buffer containing 50% glycerol and stored at −20° C. The final pool is assayed for activity in the phosphoinositol kinase assay.

PI3K Gamma Purification Protocol For HTS (BV950)

PI3K gamma is purified in two chromatographic steps: immobilized metal affinity chromatography (IMAC) on a Ni Sepharose resin (GE Healthcare) and gel filtration (GFC) utilizing a Superdex 200 26/60 column (GE Healthcare). All buffers are chilled to 4° C. and lysis is performed chilled on ice. Column fractionation is performed rapidly at room temperature. Typically frozen insect cells are lysed in a hypertonic lysis buffer and applied to a prepared IMAC column. The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing target protein are pooled and applied to a prepared GFC column. Fractions from the GFC column are analyzed by Coomassie stained SDS-PAGE gels, and fractions containing target protein are pooled. The final pool is dialyzed into a storage buffer containing 50% glycerol and stored at −20° C. The final pool is assayed for activity in the phosphoinostitol kinase assay.

PI3K Delta Purification Protocol For HTS (BV1060)

PI3K delta is purified in three chromatographic steps: immobilized metal affinity chromatography on a Ni Sepharose resin (GE Healthcare), gel filtration utilizing a Superdex 200 26/60 column (GE Healthcare), and finally a anion exchange step on a Q-HP column (GE Healthcare). All buffers are chilled to 4° C. and lysis is performed chilled on ice. Column fractionation is performed rapidly at room temperature. Typically frozen insect cells are lysed in a hypertonic lysis buffer and applied to a prepared IMAC column.

The resin is washed with 3-5 column volumes of lysis buffer, followed by 3-5 column volumes wash buffer containing 45 mM imidazole, and the target protein is then eluted with a buffer containing 250 mM imidazole. Fractions are analyzed by Coomassie stained SDS-PAGE gels, and fractions containing the target protein are pooled and applied to a prepared GFC column. Fractions from the GFC column are analyzed by Coomassie stained SDS-PAGE gels, and fractions containing the target protein are pooled. The pool from the GFC column is diluted into a low salt buffer and applied to a prepared Q-HP column. The column is washed with low salt buffer until a stable A280 baseline absorbance is achieved, and eluted using a 20 column volume gradient from 0 mM NaCl to 500 mM NaCl. Again, fractions from the Q-HP column are analyzed by Coomassie stained SDS-PAGE gels, and fractions containing the target protein are pooled. The final pool is dialyzed into a storage buffer containing 50% glycerol and stored at −20° C. The final pool is assayed for activity in the phosphoinostitol kinase assay.

$IC_{50}$ is determined by a four parameter curve fitting routine that comes along with "excel fit". A four parameter logistic equation is used to calculate $IC_{50}$ values (IDBS XLfit) of the percentage inhibition of each compound at 8 concentrations (usually 10, 3.0, 1.0, 0.3, 0.1, 0.030, 0.010 and 0.003 µM). Alternatively, $IC_{50}$ values are calculated using idbsXLfit model 204, which is a 4 parameter logistic model.

Yet alternatively, for an ATP depletion assay, compounds of the formula I to be tested are dissolved in DMSO and directly distributed into a white 384-well plate at 0.5 µl per well. To start the reaction, 10 µl of 10 nM PI3 kinase and 5 µg/mL 1-alpha-phosphatidylinositol (P1) are added into each well followed by 10 µl of 2 µM ATP. The reaction is performed until approx 50% of the ATP is depleted, and then stopped by the addition of 20 µl of Kinase-Glo solution (Promega Corp., Madison, Wis., USA). The stopped reaction is incubated for 5 minutes and the remaining ATP is then detected via luminescence. $IC_{50}$ values are then determined.

Some of the compounds of examples 1-49 and 51-95 show a certain level of selectivity against the different paralogs PI3K α, β, γ and δ.

Suitably, the compounds of examples 1-49 and 51-95 show a certain level of selectivity for the isoform PI3Kδ, e.g. as indicated in in vitro and in vivo tests against the different paralogs PI3K α and β.

The range of activity, expressed as $IC_{50}$, in these assays, is preferably between 1 nM and 5000 nM, more preferably between 1 nM and about 1000 nM.

2. Cellular Assays 2.1 Phosphoinositide-3 Kinase (PI3K)-Mediated Akt 1/2 (S473) Phosphorylation in Rat-1 Cells Rat-1 cells stably overexpressing a myristoylated form of the catalytic subunit of human phosphoinositide-3 kinase (PI3K) alpha, beta or delta were plated in 384-well plates at a density of 7500 (PI3K alpha), 6200 (PI3K beta), or 4000 (PI3K delta) cells in 30 ul complete growth medium (Dulbecco's modified Eagle's medium (DMEM high glucose) supplemented with 10% (v/v) fetal bovine serum, 1% (v/v) MEM non essential amino acids, 10 mM HEPES, 2 mM L-glutamine, 10 µg/mL puromycin and 1% (v/v) Penicillin/Streptomycin) and were incubated at 37% C/5% $CO_2$/95% humidity for 24 h. Compounds were diluted in 384-well compound plates to obtain 8-point serial dilutions for 40 test compounds in 90% DMSO, as well as 4 reference compounds plus 16 high controls and 16 low (inhibited) controls. Predilution plates were prepared by dispensing pipetting 250 nl of compound solutions into 384-well polypropylen plates using a Hummingwell nanoliter dispenser. Compounds were prediluted by the addition of 49.75 ul complete growth medium. 10 ul of prediluted compound solution were transferred to the cell plate using a 384-well pipettor, resulting in a final DMSO concentration of 0.11%. Cells were incubated for 1 h at 37% C/5% $CO_2$/95% humidity. The supernatant was removed, the cells were lysed in 20 ul of lysis buffer for AlphaScreen® SureFire® detection.

For detection of p-AKT (Ser473), the SureFire® p-Akt 1/2 (Ser473) Assay Kit (PerkinElmer, U.S.A) was used. 5 ul of cell lysate was transferred to 384-well low volume Proxiplates for detection using a 384-well pipettor. Addition of AlphaScreen® SureFire® reagents was done according to the manufacturer's protocol. First, 5 ul of reaction buffer plus activation buffer mix containing AlphaScreen® acceptor beads was added, the plate was sealed, and incubated on a plate shaker for 2 hours at room temperature. Second, 2 ul of dilution buffer containing AlphaScreen® donor beads was added, and the plate was incubated on plate shaker as above for a further 2 hours. The plate was read on an AlphaScreen® compatible plate reader, using standard AlphaScreen® settings.

2.2 Determination of Murine B Cell Activation

PI3Kδ has been recognized to modulate B cell function when cells are stimulated through the B cell receptor (BCR) (Okkenhaug et al. Science 297:1031 (2002). For assessing the inhibitory property of compounds on B cell activation, the upregulation of activation markers CD86 and CD69 on murine B cells derived from mouse spleen antibody is measured after stimulation with anti-IgM. CD69 is a well known activation marker for B and T cells (Sancho et al. Trends Immunol. 26:136 (2005). CD86 (also known as B7-2) is primarily expressed on antigen-presenting cells, including B cells. Resting B cells express CD86 at low levels, but upregulate it following stimulation of e.g. the BCR or IL-4 receptor. CD86 on a B cell interacts with CD28 on T cells. This interaction is required for optimal T cell activation and for the generation of an optimal IgG1 response (Carreno et al. Annu Rev Immunol. 20:29 (2002)).

Spleens from Balb/c mice were collected, splenocytes were isolated and washed twice with RPMI containing 10% foetal bovine serum (FBS), 10 mM HEPES, 100 Units/mL penicilline/streptomycine. RPMI supplemented in this way is subsequently referred to as medium. The cells were adjusted to $2.5 \times 10^6$ cells/mL in medium and 200 μl cell suspension ($5 \times 10^6$ cells) were added to the appropriate wells of 96 well plates.

Then the cells were stimulated by adding 50 μl anti-IgM mAb in medium (final concentration: 30 μg/mL). After incubation for 24 hours at 37° C., the cells were stained with the following antibody cocktails: anti-mouse CD86-FITC, anti-mouse CD69-PerCP-Cy5.5, anti-mouse CD19-PerCP for the assessment of B cells, and anti-mouse CD3-FITC, anti-mouse CD69-PE for the assessment of T cells (2 μl of each antibody/well). After one hour at room temperature (RT) in the dark the cells were transferred to 96 Deepwell plates. The cells were washed once with 1 mL PBS containing 2% FBS and after re-suspension in 200 μl the samples were analyzed on a FACS Calibur flow cytometer. Lymphocytes were gated in the FSC/SSC dot plot according to size and granularity and further analyzed for expression of CD19, CD3 and activation markers (CD86, CD69). Data were calculated from dot blots as percentage of cells positively stained for activation markers within the CD19+ or CD3+ population using BD CellQest Software.

For assessing the inhibitory property of compounds, compounds were first dissolved and diluted in DMSO followed by a 1:50 dilution in medium. Splenocytes from Balb/c mice were isolated, re-suspended and transferred to 96 well plates as described above (200 μl/well). The diluted compounds or solvent were added to the plates (25 μl) and incubated at 37° C. for 1 hour. Then the cultures were stimulated with 25 μl anti-IgM mAb/well (final concentration 30 pg/mL) for 24 hours at 37° C. and stained with anti-mouse CD86-FITC and anti-mouse CD19-PerCP (2 μl of each antibody/well). CD86 expression on CD19 positive B cells was quantified by flow cytometry as described above.

3 Determination of Antibody Production to Sheep Red Blood Cells (SRBC).

In brief, OFA rats were injected i.v. with sheep erythrocytes on d0 and treated orally on four consecutive days (d0 to d3) with the compounds under investigation. Spleen cell suspensions were prepared on d4 and lymphocytes were plated onto soft agar in presence of indicator cells (SRBC) and complement. Lysis of the indicator cells due to secretion of SRBC-specific antibody (predominantly of the IgM subclass) and presence of complement yielded plaques. The number of plaques per plate were counted and expressed as number of plaques per spleen.

Immunization: Groups of five female OFA rats were immunized on day 0 with $2 \times 10^8$/ml SRBC (obtained from Laboratory Animal Services LAS, Novartis Pharma AG) in a volume of 0.5 ml per rat by i.v. injection.

Compound treatment: Animals were treated with compound suspended in 0.5% CMC, 0.5% Tween80 in for 4 consecutive days (days 0, 1, 2 and 3) starting on the day of immunization. Compound was administered orally twice daily with 12 hours intervals between doses in an application volume of 5 ml/kg body weight.

Preparation of Spleen Cell Suspensions:

On day 4, animals were euthanized with $CO_2$ Spleens were removed, weighed, and deposited in plastic tubes containing 10 ml of cold (4° C.) Hank's balanced salt solution (HBSS; Gibco, pH 7.3, containing 1 mg Phenolred/100 ml) for each rat spleen. Spleens were homogenized with a glass potter, left on ice for 5 minutes and 1 ml supernatant was transferred into a new tube. Cells were washed once in 4 ml HBSS then supernatants were discarded and pellets re-suspended in 1 ml of HBSS. Lymphocyte numbers per spleen were determined by automated cell counter and spleen cell suspensions were adjusted to a cell concentration of $30 \times 10^6$/ml.

Plaque Forming Assay:

Soft agar petri dishes were prepared with 0.7% agarose (SERVA) in HBSS.

In addition, one ml of 0.7% agarose was prepared in plastic tubes and kept at 48° C. in a water bath. Some 50 μl of a $30 \times 10^6$/ml spleen cell suspension and 50 μl of SRBC at $40 \times 10^8$/ml were added, mixed rapidly (Vortex) and poured onto the prepared agarose dishes. Petri dishes were slightly tilted to achieve even distribution of cell mixture on agarose layer. The dishes were left at room temperature for 15 minutes and were then incubated at 37° C. for 60 minutes. Then, 1.4 ml guinea pig complement (Harlan; 10%) was added and the incubation continued for another 60 minutes at 37° C. SRBC-specific antibodies released by the plated-out B cells bound to the antigen (SRBC) in their vicinity. These antigen-antibody complexes activated complement and led to the lysis of the SRBC leaving a bright spot (plaque) within the red erythrocyte layer. Plaques were counted with a microscope.

The following formula for determination of inhibition of plaque formation was used:

% Inhibition=C*100/V−100 with: V=mean number of plaques/spleen for vehicle group; C=mean number of plaques/spleen for compound treated group

REFERENCES

N. K. Jerne & A. A. Nordin (1963) Plaque formation in agar by single antibody-producing cells. Science 140:405.
N. K. Jerne, A. A. Nordin & C. Henry (1963) The agar plaque technique for recognizing antibody-producing cells. In: "Cell Bound Antibodies", B. Amos & H. Koprowski, Eds., Wistar Inst. Press, Philadelphia pp. 109-125.

Biological Data

Enzymatic Assay

| Example | PI3K alpha (uM) | PI3K delta (uM) |
|---|---|---|
| 1 | 2.0378 | 0.015 |
| 2 | 3.391 | 0.009 |
| 3 | 2.386 | 0.015 |
| 4 | 1.764 | 0.033 |
| 5 | 0.749 | 0.020 |
| 6 | 0.987 | 0.044 |
| 7 | 1.973 | 0.013 |
| 8 | 2.494 | 0.027 |
| 9 | 2.906 | 0.009 |
| 10 | 0.668 | 0.009 |
| 11 | 1.199 | 0.011 |
| 12 | 0.952 | 0.012 |
| 13 | 1.802 | 0.013 |
| 14 | 1.832 | 0.013 |
| 15 | 1.631 | 0.014 |
| 16 | 1.684 | 0.016 |
| 17 | 7.678 | 0.017 |
| 18 | 0.871 | 0.033 |
| 19 | 3.056 | 0.033 |
| 20 | 1.839 | 0.048 |
| 21 | 0.320 | 0.008 |
| 22 | 0.580 | 0.008 |
| 23 | 0.129 | 0.010 |
| 24 | 0.374 | 0.009 |
| 25 | 0.820 | 0.026 |
| 26 | 0.368 | 0.021 |
| 27 | 3.410 | 0.040 |
| 28 | 1.214 | 0.004 |
| 29 | 2.585 | 0.011 |
| 30 | 2.831 | 0.040 |
| 31 | 3.024 | 0.021 |
| 32 | 2.036 | 0.023 |
| 33 | 1.967 | 0.018 |
| 34 | 1.648 | 0.014 |
| 35 | 4.232 | 0.049 |
| 36 | 4.103 | 0.025 |
| 37 | 7.021 | 0.031 |
| 38 | 3.306 | 0.016 |
| 39 | 0.434 | 0.009 |
| 40 | 0.260 | 0.006 |
| 41 | 0.515 | 0.014 |
| 42 | 0.863 | 0.013 |
| 43 | 0.728 | 0.016 |
| 44 | 1.189 | 0.016 |
| 45 | 0.860 | 0.018 |
| 46 | 0.803 | 0.027 |
| 47 | 0.656 | 0.025 |
| 48 | 0.518 | 0.029 |
| 49 | 0.388 | 0.034 |
| 51 | 0.912 | 0.044 |
| 52 | 1.024 | 0.046 |
| 53 | 0.504 | 0.006 |
| 54 | 0.384 | 0.005 |
| 55 | 0.661 | 0.005 |
| 56 | 0.860 | 0.013 |
| 57 | 0.590 | 0.025 |
| 58 | 3.060 | 0.030 |
| 59 | 9.100 | 0.028 |
| 60 | 3.333 | 0.045 |
| 61 | 0.589 | 0.012 |
| 62 | 0.489 | 0.023 |
| 63 | 0.791 | 0.051 |
| 64 | 2.331 | 0.032 |
| 65 | 0.738 | 0.023 |
| 66 | 1.280 | 0.014 |
| 67 | 0.262 | 0.023 |
| 68 | 0.043 | 0.007 |
| 69 | 0.056 | 0.003 |
| 70 | 0.121 | 0.006 |
| 71 | 0.057 | 0.003 |
| 72 | 0.093 | 0.004 |
| 73 | 0.054 | 0.004 |
| 74 | 0.113 | 0.004 |
| 75 | 0.118 | 0.004 |
| 76 | 0.106 | 0.007 |
| 77 | 1.290 | 0.044 |
| 78 | 0.384 | 0.012 |
| 79 | 0.781 | 0.017 |
| 80 | 0.430 | 0.016 |
| 81 | 0.651 | 0.02 |
| 82 | 0.066 | 0.003 |
| 83 | 0.432 | 0.017 |
| 84 | 0.058 | 0.009 |
| 85 | 0.569 | 0.021 |
| 86 | 1.330 | 0.020 |
| 87 | 0.452 | 0.012 |
| 88 | 1.336 | 0.034 |
| 89 | 1.189 | 0.029 |
| 90 | 1.991 | 0.038 |
| 91 | 0.924 | 0.011 |
| 92 | 2.545 | 0.009 |
| 93 | 0.872 | 0.024 |
| 94 | 1.714 | 0.021 |
| 95 | 0.757 | 0.053 |

Cellular Assays

| Example | Cell PI3Kδ/ IC50 [umol l − 1] | mCD86/IC50 CD86 [nmol l − 1] |
|---|---|---|
| 1 | 0.153 | 94.9 |
| 5 | 0.455 | 125 |
| 20 | 0.2538 | 120 |
| 28 | 0.268 | 71.6 |
| 65 | 0.191 | 570 |
| 67 | 0.047 | 48.3 |
| 68 | 0.053 | 14.9 |
| 71 | 0.035 | 24.7 |
| 81 | 0.246 | 86.5 |
| 82 | 0.116 | 46.2 |

SRBC Assay

| | Plaques/spleen |
|---|---|
| Example 1 10 mg/kg bid | 12608 ± 4986 |
| Vehicle (0.5% CMC 0.5% Tween80) | 168363 ± 49142 |

What is claimed is:

1. A tetrahydro-pyrido-pyrimidine compound of the formula (I) and/or tautomers and/or N-oxides and/or pharmaceutically acceptable salts thereof,

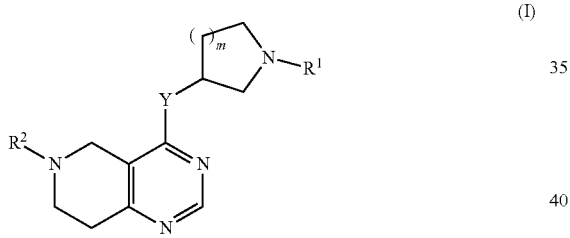

(I)

wherein
Y is selected from O or $NR^3$;
$R^1$ is selected from phenyl, pyridyl, pyrimidinyl, pyrazinyl, pyridazinyl, 1,2,3-triazinyl, 1,2,4-triazinyl, 1,3,5-triazinyl,
or
—C(O)—$R^4$
wherein
$R^4$ is selected from $C_1$-$C_8$-alkyl, halo-$C_1$-$C_8$-alkyl, hydroxy-$C_1$-$C_8$-alkyl, $C_1$-$C_8$-alkoxy-$C_1$-$C_8$-alkyl, $C_1$-$C_8$-alkyl-sulfonyl-$C_1$-$C_8$-alkyl, heterocyclyl, heterocyclyl-oxy, heterocyclyl-$C_1$-$C_8$-alkyl, $C_3$-$C_{12}$-cycloalkyl, $C_3$-$C_{12}$-cycloalkyl-$C_1$-$C_8$-alkyl, heteroaryl, heteroaryl-oxy, heteroaryl-$C_1$-$C_8$-alkyl, hydroxy, $C_1$-$C_8$-alkoxy, amino, N—$C_1$-$C_8$-alkyl-amino or N,N-di-$C_1$-$C_8$-alkyl-amino,
wherein '$C_1$-$C_8$-alkyl' in N—$C_1$-$C_8$-alkyl-amino and N,N-di-$C_1$-$C_8$-alkyl-amino may be unsubstituted or substituted by halogen, hydroxy or $C_1$-$C_4$-alkoxy;
wherein '$C_3$-$C_{12}$-cycloalky' in $C_3$-$C_{12}$-cycloalkyl and $C_3$-$C_{12}$-cycloalkyl-$C_1$-$C_8$-alkyl may be unsubstituted or substituted by 1-5 substituents independently selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl;
wherein 'heterocyclyl' is selected from oxiranyl, aziridinyl, oxetanyl, thiethanyl, azetidinyl, pyrrolidinyl, tetrahydrofuranyl, tetrahydrothiophenyl, 2,3-dihydrofuranyl, 2,5-dihydrofuranyl, 2,3-dihydrothiophenyl, 1-pyrrolinyl, 2-pyrrolinyl, 3-pyrrolinyl, tetrahydropyranyl, piperidinyl, tetrahydrothiopyranyl, morpholinyl, thiomorpholinyl, piperazinyl, azepanyl, thiepanyl or oxepanyl; each of which is unsubstituted or substituted by 1-5 substituents independently selected from oxo, halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl;
wherein 'heterocyclyl' can be attached at a heteroatom or a carbon atom and where the N and/or S heteroatoms can also optionally be oxidized to various oxidation states;
wherein 'heteroaryl' is selected from furanyl, thiophenyl, pyrrolyl, imidazolyl, pyrazolyl, thiazolyl, isothiazolyl, oxazolyl, isoxazolyl, 1,2,5-oxadiazolyl, 1,2,4-oxadiazolyl, 1,2,3-oxadiazolyl,1,3,4-oxadiazolyl, 1,2,5-thiadiazolyl, 1,2,4-thiadiazolyl, 1,2,3-thiadiazolyl,1,3,4-thiadiazolyl, 1,2,3-triazolyl, 1,2,4-triazolyl, 1,2,5-triazolyl, pyridyl, pyrimidinyl, pyrazinyl, pyridazinyl, 1,2,3-triazinyl, 1,2,4-triazinyl or 1,3,5-triazinyl; each of which is unsubstituted or substituted by 1-5 substituents independently selected from halogen, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo- $C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl;

wherein 'heteroaryl' can be attached at a heteroatom or a carbon atom and where the N and/or S heteroatoms can also optionally be oxidized to various oxidation states;

$R^2$ is selected from phenyl, naphthyl, pyridyl, pyrimidinyl, pyrazinyl, pyridazinyl, quinolinyl or isoquinolinyl, each of which is unsubstituted or substituted by 1-5 substituents independently selected from halogen, cyano, nitro, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl;

$R^3$ is selected from H, $C_1$-$C_4$-alkyl or halo-$C_1$-$C_4$-alkyl; and m is selected from 0 or 1.

2. A compound according to claim 1, of the formula (Id')

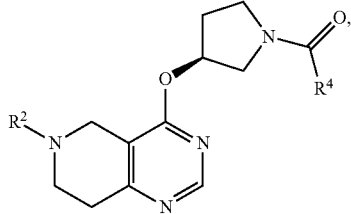

(Id')

and/or tautomers and/or N-oxides and/or pharmaceutically acceptable salts thereof.

3. A compound according to claim 1, of the formula (Ie')

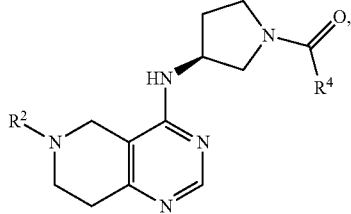

(Ie')

and/or tautomers and/or N-oxides and/or pharmaceutically acceptable salts thereof.

4. A compound according to claim 1, wherein $R^2$ is selected from naphthyl, pyridyl or pyrimidinyl; each of which is unsubstituted or substituted by 1-3 substituents independently selected from halogen, cyano, nitro, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl.

5. A compound according to claim 1, wherein $R^1$ is —C(O)—$R^4$, wherein $R^4$ is selected from heterocyclyl, $C_4$-$C_8$-cycloalkyl or heteroaryl;

wherein '$C_3$-$C_{12}$-cycloalkyl' may be unsubstituted or substituted by 1-3 substituents independently selected from fluoro, $C_1$-$C_4$-alkyl, hydroxyl, $C_1$-$C_4$-alkoxy;

wherein 'heterocyclyl' is selected from pyrrolidinyl, tetrahydropyranyl, piperidinyl, tetrahydrothiopyranyl, morpholinyl or piperazinyl; each of which is unsubstituted or substituted by 1-3 substituents independently selected from oxo, halogen, $C_1$-$C_4$-alkyl, hydroxyl, $C_1$-$C_4$-alkyl-carbonyl;

wherein 'heterocyclyl' can be attached at a heteroatom or a carbon atom and where the N and/or S heteroatoms can also optionally be oxidized to various oxidation states;

wherein 'heteroaryl' is selected from furanyl, imidazolyl, pyrazolyl, thiazolyl, oxazolyl, isoxazolyl, 1,3,4-oxadiazolyl, pyridyl, pyrazinyl; each of which is unsubstituted or substituted by 1-3 substituents independently selected from $C_1$-$C_4$-alkyl, hydroxyl;

wherein 'heteroaryl' can be attached at a heteroatom or a carbon atom and where the N and/or S heteroatoms can also optionally be oxidized to various oxidation states.

6. A compound according to claim 1, wherein $R^1$ is —C(O)—$R^4$, and $R^4$ is selected from $C_1$-$C_8$-alkyl, $C_1$-$C_8$-alkoxy-$C_1$-$C_8$-alkyl, $C_1$-$C_8$-alkoxy or N,N-di-$C_1$-$C_8$-alkyl-amino, wherein '$C_1$-$C_8$-alkyl' in N,N-di-$C_1$-$C_8$-alkyl-amino may be unsubstituted or substituted by halogen, hydroxy or $C_1C_4$alkoxy.

7. A compound according to claim 1, which is selected from the group consisting of {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone;

{3-[6-(6-Methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone;

{(S)-3-[6-(2,4-Dimethoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone;

{3-[6-(2,4-Dimethoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone;

2-Methoxy-5-{4-[(S)-1-(tetrahydro-pyran-4-carbonyl)-pyrrolidin-3-yloxy]-7,8-dihydro-5H-pyrido[4,3-d]pyrimidin-6-yl}-nicotinonitrile;

2-Methoxy-5-{4-[1-(tetrahydro-pyran-4-carbonyl)-pyrrolidin-3-yloxy]-7,8-dihydro-5H-pyrido[4,3-d]pyrimidin-6-yl}-nicotinonitrile;

1-{(S)-3-[6-(5,6-Dimethoxy-pyridin-3-yl)-5,6,7,8-tetrahydro-pyrido[4,3-d]pyrimidin-4-yloxy]-pyrrolidin-1-yl}-propan-1-one;

1-{3-[6-(5,6-Dimethoxy-pyridin-3-yl)-5,6,7,8-tetrahydro-pyrido[4,3-d]pyrimidin-4-yloxy]-pyrrolidin-1-yl}-propan-1-one;

{(S)-3-[6-(5,6-Dimethoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone;

{3-[6-(5,6-Dimethoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone;

2-Amino-5-{4-[(S)-1-(tetrahydro-pyran-4-carbonyl)-pyrrolidin-3-yloxy]-7,8-dihydro-5H-pyrido[4,3-d]pyrimidin-6-yl}-nicotinonitrile;

2-Amino-5-{4-[1-(tetrahydro-pyran-4-carbonyl)-pyrrolidin-3-yloxy]-7,8-dihydro-5H-pyrido[4,3-d]pyrimidin-6-yl}-nicotinonitrile;

(S)-(3-(6-(5-Fluoro-6-methoxypyridin-3-yl)-5,6,7,8-tetrahydropyrido[4,3-d]pyrimidin-4-yloxy)pyrrolidin-1-yl)tetrahydro-2H-pyran-4-yl)methanone;

(3-(6-(5-Fluoro-6-methoxypyridin-3-yl)-5,6,7,8-tetrahydropyrido[4,3-d]pyrimidin-4-yloxy)pyrrolidin-1-yl)tetrahydro-2H-pyran-4-yl)methanone;
(S)-2-Methoxy-5-(4-(1-(2-methoxyacetyl)pyrrolidin-3-yloxy)-7,8-dihydropyrido[4,3-d]pyrimidin-6(5H)-yl)nicotinonitrile;
2-Methoxy-5-(4-(1-(2-methoxyacetyl)pyrrolidin-3-yloxy)-7,8-dihydropyrido[4,3-d]pyrimidin-6(5H)-yl)nicotinonitrile;
(S)-5-(4-(1-(Cyclopentanecarbonyl)pyrrolidin-3-yloxy)-7,8-dihydropyrido[4,3-d]pyrimidin-6(5H)-yl)-2-methoxynicotinonitrile;
5-(4-(1-(Cyclopentanecarbonyl)pyrrolidin-3-yloxy)-7,8-dihydropyrido[4,3-d]pyrimidin-6(5H)-yl)-2-methoxynicotinonitrile;
(2,4-Dimethyl-oxazol-5-yl)-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
(2,4-Dimethyl-oxazol-5-yl)-{3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
Furan-3-yl-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
Furan-3-yl-{3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
Furan-3-yl-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
Furan-3-yl-{3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone;
{3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone;
{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(2-methyl-oxazol-4-yl)-methanone;
{3-[6-(6-Methoxy-5-methyl-pyridin-3-yl)-5,6,7,8-tetrahydro-pyrido[4,3-d]pyrimidin-4-yloxy]-pyrrolidin-1-yl}-(2-methyl-oxazol-4-yl)-methanone;
(3-Methoxy-cyclobutyl)-{(S)-3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
(3-Methoxy-cyclobutyl)-{3-[6-(6-methoxy-5-methyl-pyridin-3-yl)-5,6,7,8-tetrahydro-pyrido[4,3-d]pyrimidin-4-yloxy]-pyrrolidin-1-yl}-methanone;
({(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-oxazol-4-yl-methanone;
({3-[6-(6-Methoxy-5-methyl-pyridin-3-yl)-5,6,7,8-tetrahydro-pyrido[4,3-d]pyrimidin-4-yloxy]-pyrrolidin-1-yl}-oxazol-4-yl-methanone;
1-(4-{(S)-3-[6-(6-Methoxy-5-methyl-pyridin-3-yl)-5,6,7,8-tetrahydro-pyrido[4,3-d]pyrimidin-4-yloxy]-pyrrolidine-1-carbonyl}-piperidin-1-yl)-ethanone;
1-(4-{3-[6-(6-Methoxy-5-methyl-pyridin-3-yl)-5,6,7,8-tetrahydro-pyrido[4,3-d]pyrimidin-4-yloxy]-pyrrolidine-1-carbonyl}-piperidin-1-yl)-ethanone;
{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(4-methyl-oxazol-5-yl)-methanone;
{3-[6-(6-Methoxy-5-methyl-pyridin-3-yl)-5,6,7,8-tetrahydro-pyrido[4,3-d]pyrimidin-4-yloxy]-pyrrolidin-1-yl}-(4-methyl-oxazol-5-yl)-methanone;
5-{(S)-3-[6-(6-Methoxy-5-methyl-pyridin-3-yl)-5,6,7,8-tetrahydro-pyrido[4,3-d]pyrimidin-4-yloxy]-pyrrolidine-1-carbonyl}-1H-pyridin-2-one;
5-{3-[6-(6-Methoxy-5-methyl-pyridin-3-yl)-5,6,7,8-tetrahydro-pyrido[4,3-d]pyrimidin-4-yloxy]-pyrrolidine-1-carbonyl}-1H-pyridin-2-one;
{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(1-methyl-1H-imidazol-4-yl)-methanone;
{3-[6-(6-Methoxy-5-methyl-pyridin-3-yl)-5,6,7,8-tetrahydro-pyrido[4,3-d]pyrimidin-4-yloxy]-pyrrolidin-1-yl}-(1-methyl-1H-imidazol-4-yl)-methanone;
{(S)-3-[6-(5,6-Dimethoxy-pyridin-3-yl)-5,6,7,8-tetrahydro-pyrido[4,3-d]pyrimidin-4-yloxy]-pyrrolidin-1-yl}-oxazol-4-yl-methanone;
{3-[6-(5,6-Dimethoxy-pyridin-3-yl)-5,6,7,8-tetrahydro-pyrido[4,3-d]pyrimidin-4-yloxy]-pyrrolidin-1-yl}-oxazol-4-yl-methanone;
{(S)-3-[6-(5,6-Dimethoxy-pyridin-3-yl)-5,6,7,8-tetrahydro-pyrido[4,3-d]pyrimidin-4-yloxy]-pyrrolidin-1-yl}-oxazol-5-yl-methanone;
{3-[6-(5,6-Dimethoxy-pyridin-3-yl)-5,6,7,8-tetrahydro-pyrido[4,3-d]pyrimidin-4-yloxy]-pyrrolidin-1-yl}-oxazol-5-yl-methanone;
{(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2-methyl-oxazol-4-yl)-methanone;
{3-[6-(5,6-Dimethoxy-pyridin-3-yl)-5,6,7,8-tetrahydro-pyrido[4,3-d]pyrimidin-4-yloxy]-pyrrolidin-1-yl}-(2-methyl-oxazol-4-yl)-methanone;
{(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2,2-dimethyl-tetrahydro-pyran-4-yl)-methanone;
{3-[6-(5,6-Dimethoxy-pyridin-3-yl)-5,6,7,8-tetrahydro-pyrido[4,3-d]pyrimidin-4-yloxy]-pyrrolidin-1-yl}-(2,2-dimethyl-tetrahydro-pyran-4-yl)-methanone;
{(S)-3-[6-(5,6-Dimethoxy-pyridin-3-yl)-5,6,7,8-tetrahydro-pyrido[4,3-d]pyrimidin-4-yloxy]-pyrrolidin-1-yl}-(2,4-dimethyl-oxazol-5-yl)-methanone;
{3-[6-(5,6-Dimethoxy-pyridin-3-yl)-5,6,7,8-tetrahydro-pyrido[4,3-d]pyrimidin-4-yloxy]-pyrrolidin-1-yl}-(2,4-dimethyl-oxazol-5-yl)-methanone;
(4,4-Difluoro-cyclohexyl)-{(S)-3-[6-(5,6-dimethoxy-pyridin-3-yl)-5,6,7,8-tetrahydro-pyrido[4,3-d]pyrimidin-4-yloxy]-pyrrolidin-1-yl}-methanone;
(4,4-Difluoro-cyclohexyl)-{3-[6-(5,6-dimethoxy-pyridin-3-yl)-5,6,7,8-tetrahydro-pyrido[4,3-d]pyrimidin-4-yloxy]-pyrrolidin-1-yl}-methanone;
2-Methoxy-5-{4-[(S)-1-(2-tetrahydro-pyran-4-yl-acetyl)-pyrrolidin-3-yloxy]-7,8-dihydro-5H-pyrido[4,3-d]pyrimidin-6-yl}-nicotinonitrile;
2-Methoxy-5-{4-[1-(2-tetrahydro-pyran-4-yl-acetyl)-pyrrolidin-3-yloxy]-7,8-dihydro-5H-pyrido[4,3-d]pyrimidin-6-yl}-nicotinonitrile;
5-{4-[(S)-1-(2,4-Dimethyl-oxazole-5-carbonyl)-pyrrolidin-3-yloxy]-7,8-dihydro-5H-pyrido[4,3-d]pyrimidin-6-yl}-2-methoxy-nicotinonitrile;
5-{4-[1-(2,4-Dimethyl-oxazole-5-carbonyl)-pyrrolidin-3-yloxy]-7,8-dihydro-5H-pyrido[4,3-d]pyrimidin-6-yl}-2-methoxy-nicotinonitrile;
5-{4-[(S)-1-(2,2-Dimethyl-tetrahydro-pyran-4-carbonyl)-pyrrolidin-3-yloxy]-7,8-dihydro-5H-pyrido[4,3-d]pyrimidin-6-yl}-2-methoxy-nicotinonitrile;

5-{4-[1-(2,2-Dimethyl-tetrahydro-pyran-4-carbonyl)-pyrrolidin-3-yloxy]-7,8-dihydro-5H-pyrido[4,3-d]pyrimidin-6-yl}-2-methoxy-nicotinonitrile;
{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-oxazol-4-yl)-methanone;
{3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-oxazol-4-yl)-methanone;
{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-isoxazol-4-yl)-methanone;
{3-[6-(6-Methoxy-5-methyl-pyridin-3-yl)-5,6,7,8-tetrahydro-pyrido[4,3-d]pyrimidin-4-yloxy]-pyrrolidin-1-yl}-(5-methyl-isoxazol-4-yl)-methanone;
{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-yl)-methanone;
{3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-yl)-methanone;
{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-yl)-methanone;
{3-[6-(6-Methoxy-5-methyl-pyridin-3-yl)-5,6,7,8-tetrahydro-pyrido[4,3-d]pyrimidin-4-yloxy]-pyrrolidin-1-yl}-(3-methyl-isoxazol-4-yl)-methanone;
Isoxazol-3-yl-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
Isoxazol-3-yl-{3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
Isoxazol-5-yl-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
Isoxazol-5-yl-{3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
2-Methoxy-5-{4-[(S)-1-(thiazole-4-carbonyl)-pyrrolidin-3-yloxy]-7,8-dihydro-5H-pyrido[4,3-d]pyrimidin-6-yl}-nicotinonitrile;
2-Methoxy-5-{4-[1-(thiazole-4-carbonyl)-pyrrolidin-3-yloxy]-7,8-dihydro-5H-pyrido[4,3-d]pyrimidin-6-yl}-nicotinonitrile;
2-Methoxy-5-{4-[(S)-1-(1-methyl-1H-pyrazole-4-carbonyl)-pyrrolidin-3-yloxy]-7,8-dihydro-5H-pyrido[4,3-d]pyrimidin-6-yl}-nicotinonitrile;
2-Methoxy-5-{4-[1-(1-methyl-1H-pyrazole-4-carbonyl)-pyrrolidin-3-yloxy]-7,8-dihydro-5H-pyrido[4,3-d]pyrimidin-6-yl}-nicotinonitrile;
2-Methoxy-5-{4-[(S)-1-(1-methyl-1H-pyrazole-3-carbonyl)-pyrrolidin-3-yloxy]-7,8-dihydro-5H-pyrido[4,3-d]pyrimidin-6-yl}-nicotinonitrile;
2-Methoxy-5-{4-[1-(1-methyl-1H-pyrazole-3-carbonyl)-pyrrolidin-3-yloxy]-7,8-dihydro-5H-pyrido[4,3-d]pyrimidin-6-yl}-nicotinonitrile;
(2,2-Dimethyl-tetrahydro-pyran-4yl)-{(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
(2,2-Dimethyl-tetrahydro-pyran-4yl)-{3-[6-(6-Methoxy-5-methyl-pyridin-3-yl)-5,6,7,8-tetrahydro-pyrido[4,3-d]pyrimidin-4-yloxy]-pyrrolidin-1-yl}-methanone;
(1,1-Dioxo-hexahydro-1lambda*6*-thiopyran-4-yl)-{(S)-3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone;
(1,1-Dioxo-hexahydro-1lambda*6*-thiopyran-4-yl)-{3-[6-(6-methoxy-5-trifluoromethyl-pyridin-3-yl)-5,6,7,8-tetrahydro-pyrido[4,3-d]pyrimidin-4-yloxy]-pyrrolidin-1-yl}-methanone;
(S)-(2,4-Dimethyloxazol-5-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(2,4-Dimethyloxazol-5-yl)(3-(6-(6-methoxy-5-(trifluoromethyhpyridin-3-yl)-5,6,7,8-tetrahydropyrido[4,3-d]pyrimidin-4-yloxy)pyrrolidin-1-yl)methanone;
(S)-(3-(6-(6-Methoxy-5-(trifluoromethyhpyridin-3-yl)-5,6,7,8-tetrahydropyrido[4,3-d]pyrimidin-4-yloxy)pyrrolidin-1-yl)(thiazol-5-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(thiazol-5-yl)methanone;
(S)-(3-(6-(6-Methoxy-5-(trifluoromethyhpyridin-3-yl)-5,6,7,8-tetrahydropyrido[4,3-d]pyrimidin-4-yloxy)pyrrolidin-1-yl)(1-methyl-1H-pyrazol-5-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1-methyl-1H-pyrazol-5-yl)methanone;
4-((S)-3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)pyrrolidin-2-one;
4-(3-(6-(6-Methoxy-5-(trifluoromethyhpyridin-3-yl)-5,6,7,8-tetrahydropyrido[4,3-d]pyrimidin-4-yloxy)pyrrolidine-1-carbonyl)pyrrolid in-2-one;
(S)-(3-(6-(6-Methoxy-5-(trifluoromethyhpyridin-3-yl)-5,6,7,8-tetrahydropyrido[4,3-d]pyrimidin-4-yloxy)pyrrolidin-1-yl)(pyridin-3-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyridin-3-yl)methanone;
(S)-(1H-Imidazol-4-yl)(3-(6-(6-methoxy-5-(trifluoromethyhpyridin-3-yl)-5,6,7,8-tetrahydropyrido[4,3-d]pyrimidin-4-yloxy)pyrrolidin-1-yl)methanone;
(1H-Imidazol-4-yl)(3-(6-(6-methoxy-5-(trifluoromethyhpyridin-3-yl)-5,6,7,8-tetrahydropyrido[4,3-d]pyrimidin-4-yloxy)pyrrolidin-1-yl)methanone;
5-((S)-3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)pyrrolidin-2-one;
5-(3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)pyrrolid in-2-one;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyridin-4-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(pyridin-4-yl)methanone;
(S)-(1,3-Dimethyl-1H-pyrazol-4-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(1,3-Dimethyl-1H-pyrazol-4-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;
(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1H-pyrazol-4-yl)methanone;
(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(1H-pyrazol-4-yl)methanone;

(S)-(3-(6-(6-methoxy-5-(trifluoromethyl)pyridin-3-yl)-5, 6,7,8-tetrahydropyrido[4,3-d]pyrimidin-4-yloxy)pyrrolidin-1-yl)(5-methyl-1,3,4-oxadiazol-2-yl)methanone;

(3-(6-(6-methoxy-5-(trifluoromethyl)pyridin-3-yl)-5,6,7, 8-tetrahydropyrido[4,3-d]pyrimidin-4-yloxy)pyrrolidin-1-yl)(5-methyl-1,3,4-oxadiazol-2-yl)methanone;

(S)-(3-(6-(6-Methoxy-5-(trifluoromethyl)pyridin-3-yl)-5, 6,7,8-tetrahydropyrido[4,3-d]pyrimidin-4-yloxy)pyrrolidin-1-yl)(pyrazin-2-yl)methanone;

(3-(6-(6-Methoxy-5-(trifluoromethyl)pyridin-3-yl)-5,6,7, 8-tetrahydropyrido[4,3-d]pyrimidin-4-yloxy)pyrrolidin-1-yl)(pyrazin-2-yl)methanone;

(S)-(3-(6-(6-Methoxy-5-(trifluoromethyl)pyridin-3-yl)-5, 6,7,8-tetrahydropyrido[4,3-d]pyrimidin-4-yloxy)pyrrolidin-1-yl)(1-methyl-1H-imidazol-4-yl)methanone;

(3-(6-(6-Methoxy-5-(trifluoromethyl)pyridin-3-yl)-5,6,7, 8-tetrahydropyrido[4,3-d]pyrimidin-4-yloxy)pyrrolidin-1-yl)(1-methyl-1H-imidazol-4-yl)methanone;

{(S)-3-[6-(6-Methoxy-5-trifluoromethyl-pyridin-3-yl)-5, 6,7,8-tetrahydro-pyrido[4,3-d]pyrimidin-4-yloxy]-pyrrolidin-1-yl}-(1-methyl-1H-pyrazol-4-yl)-methanone;

{3-[6-(6-Methoxy-5-trifluoromethyl-pyridin-3-yl)-5,6,7, 8-tetrahydro-pyrido[4,3-d]pyrimidin-4-yloxy]-pyrrolidin-1-yl}-(1-methyl-1H-pyrazol-4-yl)-methanone;

{(S)-3-[6-(6-Methoxy-5-trifluoromethyl-pyridin-3-yl)-5, 6,7,8-tetrahydro-pyrido[4,3-d]pyrimidin-4-yloxy]-pyrrolidin-1-yl}-thiazol-4-yl-methanone;

{3-[6-(6-Methoxy-5-trifluoromethyl-pyridin-3-yl)-5,6,7, 8-tetrahydro-pyrido[4,3-d]pyrimidin-4-yloxy]-pyrrolidin-1-yl}-thiazol-4-yl-methanone;

{(S)-3-[6-(5-Chloro-6-methoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone;

{3-[6-(5-Chloro-6-methoxy-pyridin-3-yl)-5,6,7,8-tetrahydro-pyrido[4,3-d]pyrimidin-4-yloxy]-pyrrolidin-1-yl}-(tetrahydro-pyran-4-yl)-methanone;

(S)-(3-(6-(6-Amino-5-(trifluoromethyl)pyridin-3-yl)-5,6, 7,8-tetrahydropyrido[4,3-d]pyrimidin-4-yloxy)pyrrolidin-1-yl)(tetrahydro-2H-pyran-4-yl)methanone;

(3-(6-(6-Amino-5-(trifluoromethyl)pyridin-3-yl)-5,6,7,8-tetrahydropyrido[4,3-d]pyrimidin-4-yloxy)pyrrolidin-1-yl)-tetrahydro-2H-pyran-4-yl)methanone;

(3-(6-(6-Methoxy-5-(trifluoromethyl)pyridin-3-yl)-5,6,7, 8-tetrahydropyrido[4,3-d]pyrimidin-4-yloxy)azetidin-1-yl)(tetrahydro-2H-pyran-4-yl)methanone;

{(S)-3-[6-(2-Methoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone;

{3-[6-(2-Methoxy-pyrimidin-5-yl)-5,6,7,8-tetrahydro-pyrido[4,3-d]pyrimidin-4-yloxy]-pyrrolidin-1-yl}-(tetrahydro-pyran-4-yl)-methanone;

[(S)-3-(6-Quinolin-3-yl-5,6,7,8-tetrahydro-pyrido[4,3-d] pyrimidin-4-yloxy)-pyrrolidin-1-yl]-(tetrahydro-pyran-4-yl)-methanone;

[3-(6-Quinolin-3-yl-5,6,7,8-tetrahydro-pyrido[4,3-d]pyrimidin-4-yloxy)-pyrrolidin-1-yl]-(tetrahydro-pyran-4-yl)-methanone;

(S)-(3-(6-(6-Methoxy-5-(trifluoromethyl)pyridin-3-yl)-5, 6,7,8-tetrahydropyrido[4,3-d]pyrimidin-4-yloxy)pyrrolidin-1-yl)(tetrahydro-2H-pyran-4-yl)methanone;

(3-(6-(6-Methoxy-5-(trifluoromethyl)pyridin-3-yl)-5,6,7, 8-tetrahydropyrido[4,3-d]pyrimidin-4-yloxy)pyrrolidin-1-yl)(tetrahydro-2H-pyran-4-yl)methanone;

(S)-1-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)-3,3-dimethylbutan-1-one;

1-(3-(6-(6-Methoxy-5-(trifluoromethyl)pyridin-3-yl)-5,6, 7,8-tetrahydropyrido[4,3-d]pyrimidin-4-yloxy)pyrrolidin-1-yl)-3,3-dimethylbutan-1-one;

1-{(S)-3-[6-(6-Methoxy-5-trifluoromethyl-pyrid in-3-yl)-5,6,7,8-tetrahyd ro-pyrido[4,3-d]pyrimidin-4-yloxy]-pyrrolidin-1-yl}-propan-1-one;

1-{3-[6-(6-Methoxy-5-trifluoromethyl-pyridin-3-yl)-5,6, 7,8-tetrahydro-pyrido[4,3-d]pyrimidin-4-yloxy]pyrrolidin-1-yl}-propan-1-one;

2-Methoxy-5-[4-((S)-1-propionyl-pyrrolidin-3-yloxy)-7, 8-dihydro-5H-pyrido[4,3-d]pyrimidin-6-yl]-nicotinonitrile;

2-Methoxy-5-[4-(1-propionyl-pyrrolidin-3-yloxy)-7,8-dihydro-5H-pyrido[4,3-d]pyrimidin-6-yl]-nicotinonitrile;

(S)-6-(6-Methoxy-5-(trifluoromethyl)pyridin-3-yl)-4-(1-(pyridin-2-yl)pyrrolidin-3-yloxy)-5,6,7,8-tetrahydropyrido[4,3-d]pyrimidine;

6-(6-Methoxy-5-(trifluoromethyl)pyridin-3-yl)-4-(1-(pyridin-2-yl)pyrrolidin-3-yloxy)-5,6,7,8-tetrahydropyrido[4,3-d]pyrimidine;

(S)-6-(6-Methoxy-5-(trifluoromethyl)pyridin-3-yl)-4-(1-(pyrimidin-2-yl)pyrrolidin-3-yloxy)-5,6,7,8-tetrahydropyrido[4,3-d]pyrimidine;

6-(6-Methoxy-5-(trifluoromethyl)pyridin-3-yl)-4-(1-(pyrimidin-2-yl)pyrrolidin-3-yloxy)-5,6,7,8-tetrahydropyrido[4,3-d]pyrimidine;

(S)-1-(3-(6-(6-Methoxy-5-(trifluoromethyl)pyridin-3-yl)-5,6,7,8-tetrahydropyrido[4,3-d]pyrimidin-4-ylamino) pyrrolidin-1-yl)propan-1-one;

1-(3-(6-(6-Methoxy-5-(trifluoromethyl)pyridin-3-yl)-5,6, 7,8-tetrahydropyrido[4,3-d]pyrimidin-4-ylamino)pyrrolidin-1-yl)propan-1-one;

(S)-(3-(6-(6-Methoxy-5-(trifluoromethyl)pyridin-3-yl)-5, 6,7,8-tetrahydropyrido[4,3-d]pyrimidin-4-ylamino) pyrrolidin-1-yl)(tetrahydro-2H-pyran-4-yl)methanone;

(3-(6-(6-Methoxy-5-(trifluoromethyl)pyridin-3-yl)-5,6,7, 8-tetrahydropyrido[4,3-d]pyrimidin-4-ylamino)pyrrolidin-1-yl)(tetrahydro-2H-pyran-4-yl)methanone;

(S)-2-Methoxy-5-(4-(1-(tetrahydro-2H-pyran-4-carbonyl)pyrrolidin-3-ylamino)-7,8-dihydropyrido[4,3-d] pyrimidin-6(5H)-yl)nicotinonitrile;

2-Methoxy-5-(4-(1-(tetrahydro-2H-pyran-4-carbonyl) pyrrolidin-3-ylamino)-7,8-dihydropyrido[4,3-d]pyrimidin-6(5H)-yl)nicotinonitrile;

(S)-1-(4-(3-(6-(6-Methoxy-5-(trifluoromethyl)pyridin-3-yl)-5,6,7,8-tetrahydropyrido[4,3-d]pyrimidin-4-ylamino)pyrrolidine-1-carbonyl)piperidin-1-yl)ethanone;

1-(4-(3-(6-(6-Methoxy-5-(trifluoromethyl)pyridin-3-yl)-5,6,7,8-tetrahydropyrido[4,3-d]pyrimidin-4-ylamino) pyrrolidine-1-carbonyl)piperidin-1-yl)ethanone;

(2,2-Dimethyltetrahydro-2H-pyran-4-yl((S)-3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

(2,2-Dimethyltetrahydro-2H-pyran-4-yl)(3-(6-(6-methoxy-5-(trifluoromethyl)pyridin-3-yl)-5,6,7,8-tetrahydropyrido[4,3-d]pyrimidin-4-ylamino)pyrrolidin-1-yl) methanone;

(S)-(3-(6-(6-Methoxy-5-(trifluoromethyl)pyridin-3-yl)-5, 6,7,8-tetrahydropyrido[4,3-d]pyrimidin-4-ylamino) pyrrolidin-1-yl)(oxazol-5-yl)methanone;

(3-(6-(6-Methoxy-5-(trifluoromethyl)pyridin-3-yl)-5,6,7, 8-tetrahydropyrido[4,3-d]pyrimidin-4-ylamino)pyrrolidin-1-yl)(oxazol-5-yl)methanone;

((S)-3-(6-(6-Methoxy-5-(trifluoromethyl)pyridin-3-yl)-5,6,7,8-tetrahydropyrido[4,3-d]pyrimidin-4-ylamino)pyrrolidin-1-yl)((1s,4R)-4-methoxycyclohexyl)methanone;

(3-(6-(6-Methoxy-5-(trifluoromethyl)pyridin-3-yl)-5,6,7,8-tetrahydropyrido[4,3-d]pyrimidin-4-ylamino)pyrrolidin-1-yl)((1s,4R)-4-methoxycyclohexyl)methanone;

((S)-3-(6-(6-Methoxy-5-(trifluoromethyl)pyridin-3-yl)-5,6,7,8-tetrahydropyrido[4,3-d]pyrimidin-4-ylamino)pyrrolidin-1-yl)((1r,4S)-4-methoxycyclohexyl)methanone;

(3-(6-(6-Methoxy-5-(trifluoromethyl)pyridin-3-yl)-5,6,7,8-tetrahydropyrido[4,3-d]pyrimidin-4-ylamino)pyrrolidin-1-yl)((1r,4S)-4-methoxycyclohexyl)methanone;

((1s,4R)-4-Hydroxycyclohexyl)((S)-3-(6-(6-methoxy-5-(trifluoromethyl)pyriclin-3-yl)-5,6,7,8-tetrahydropyrido[4,3-d]pyrimid in-4-ylamino)pyrrolidin-1-yl)methanone;

((1s,4R)-4-Hydroxycyclohexyl)(3-(6-(6-methoxy-5-(trifluoromethyl)pyridin-3-yl)-5,6,7,8-tetrahydropyrido[4,3-d]pyrimidin-4-ylamino)pyrrolidin-1-yl)methanone;

((1r,4S)-4-Hydroxycyclohexyl)((S)-3-(6-(6-methoxy-5-(trifluoromethyl)pyridin-3-yl)-5,6,7,8-tetrahydropyrido[4,3-d]pyrimid in-4-ylamino)pyrrolidin-1-yl)methanone;

((1r,4S)-4-Hydroxycyclohexyl)(3-(6-(6-methoxy-5-(trifluoromethyhpyridin-3-yl)-5,6,7,8-tetrahydropyrido[4,3-d]pyrimidin-4-ylamino)pyrrolidin-1-yl)methanone;

(S)-(3-(6-(6-Methoxy-5-methylpyridin-3-yl)-5,6,7,8-tetrahydropyrido[4,3-d]pyrimidin-4-ylamino)pyrrolidin-1-yl)(1-methyl-1H-imidazol-4-yl)methanone;

(3-(6-(6-Methoxy-5-methylpyridin-3-yl)-5,6,7,8-tetrahydropyrido[4,3-d]pyrimidin-4-ylamino)pyrrolidin-1-yl)(1-methyl-1H-imidazol-4-yl)methanone;

(S)-(3-(6-(6-Methoxy-5-methylpyridin-3-yl)-5,6,7,8-tetrahydropyrido[4,3-d]pyrimidin-4-ylamino)pyrrolidin-1-yl)(oxazol-5-yl)methanone;

(3-(6-(6-Methoxy-5-methylpyridin-3-yl)-5,6,7,8-tetrahydropyrido[4,3-d]pyrimidin-4-ylamino)pyrrolidin-1-yl)(oxazol-5-yl)methanone;

(S)-(3-(6-(6-Methoxy-5-methylpyridin-3-yl)-5,6,7,8-tetrahydropyrido[4,3-d]pyrimidin-4-ylamino)pyrrolidin-1-yl)(oxazol-4-yl)methanone;

(3-(6-(6-Methoxy-5-methylpyridin-3-yl)-5,6,7,8-tetrahydropyrido[4,3-d]pyrimidin-4-ylamino)pyrrolidin-1-yl)(oxazol-4-yl)methanone;

(2,2-Dimethyltetrahydro-2H-pyran-4-yl)((S)-3-(6-(6-methoxy-5-methylpyridin-3-yl)-5,6,7,8-tetrahydropyrido[4,3-d]pyrimid in-4-ylamino)pyrrolidin-1-yl)methanone;

(2,2-Dimethyltetrahydro-2H-pyran-4-yl)(3-(6-(6-methoxy-5-methylpyridin-3-yl)-5,6,7,8-tetrahydropyrido[4,3-d]pyrimid in-4-ylamino)pyrrolidin-1-yl)methanone;

(S)-1-(3-(6-(6-Methoxy-5-methylpyridin-3-yl)-5,6,7,8-tetrahydropyrido[4,3-d]pyrimidin-4-ylamino)pyrrolidin-1-yl)propan-1-one;

1-(3-(6-(6-Methoxy-5-methylpyridin-3-yl)-5,6,7,8-tetrahydropyrido[4,3-d]pyrimidin-4-ylamino)pyrrolidin-1-yl)propan-1-one;

(S)-3-(6-(5-Chloro-6-methoxypyridin-3-yl)-5,6,7,8-tetrahydropyrido[4,3-d]pyrimidin-4-ylamino)pyrrolidin-1-yl)(tetrahydro-2H-pyran-4-yl)methanone;

(3-(6-(5-Chloro-6-methoxypyridin-3-yl)-5,6,7,8-tetrahydropyrido[4,3-d]pyrimidin-4-ylamino)pyrrolidin-1-yl)(tetrahydro-2H-pyran-4-yl)methanone;

(S)-(3-(6-(6-Methoxy-5-methylpyridin-3-yl)-5,6,7,8-tetrahydropyrido[4,3-d]pyrimidin-4-ylamino)pyrrolidin-1-yl)(tetrahydro-2H-pyran-4-yl)methanone;

(3-(6-(6-Methoxy-5-methylpyridin-3-yl)-5,6,7,8-tetrahydropyrido[4,3-d]pyrimidin-4-ylamino)pyrrolidin-1-yl)(tetrahydro-2H-pyran-4-yl)methanone;

(Tetrahydro-pyran-4-yl)-{(S)-3-{6-(5-(trifluoromethyl)pyridin-3-yl)-5,6,7,8-tetrahydropyrido[4,3-d]pyrimidin-4-ylamino)pyrrolidin-1-yl}-methanone;

(Tetrahydro-pyran-4-yl)-{3-{6-(5-(trifluoromethyl)pyridin-3-yl)-5,6,7,8-tetrahydropyrido[4,3-d]pyrimidin-4-ylamino)pyrrolidin-1-yl}-methanone;

(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(4-methylpiperazin-1-yl)methanone;

(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(4-methylpiperazin-1-yl)methanone;

(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(morpholino)methanone;

(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(morpholino)methanone;

(S)-(4-Hydroxypiperidin-1-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;

4-Hydroxypiperidin-1-yl)(3-(6-(6-methoxy-5-(trifluoromethyl)pyridin-3-yl)-5,6,7,8-tetrahydropyrido[4,3-d]pyrimidin-4-yloxy)pyrrolidin-1-yl)methanone;

(S)—N-(2-Hydroxyethyl)-3-(6-(6-methoxy-5-(trifluoromethyl)pyridin-3-yl)-5,6,7,8-tetrahydropyrido[4,3-d]pyrimidin-4-yloxy)-N-methylpyrrolidine-1-carboxamide;

N-(2-Hydroxyethyl)-3-(6-(6-methoxy-5-(trifluoromethyl)pyridin-3-yl)-5,6,7,8-tetrahydropyrido[4,3-d]pyrimidin-4-yloxy)-N-methylpyrrolidine-1-carboxamide;

(S)-1-(4-(3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)piperazin-1-yl)ethanone;

1-(4-(3-(6-(6-Methoxy-5-(trifluoromethyl)pyridin-3-yl)-5,6,7,8-tetrahydropyrido[4,3-d]pyrimidin-4-yloxy)pyrrolidine-1-carbonyl)piperazin-1-yl)ethanone;

(S)-2-Methoxy-5-(4-(1-(morpholine-4-carbonyl)pyrrolidin-3-yloxy)-7,8-dihydropyrido[4,3-d]pyrimidin-6(5H)-yl)nicotinonitrile;

2-Methoxy-5-(4-(1-(morpholine-4-carbonyl)pyrrolidin-3-yloxy)-7,8-dihydropyrido[4,3-d]pyrimidin-6(5H)-yl)nicotinonitrile;

(S)-(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(oxazol-4-yl)methanone;

(3-(6-(6-Methoxy-5-(trifluoromethyl)pyridin-3-yl)-5,6,7,8-tetrahydropyrido[4,3-d]pyrimidin-4-yloxy)pyrrolidin-1-yl)(oxazol-4-yl)methanone;

1-(4-{(S)-3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-piperidin-1-yl)-ethanone;

1-(4-{3-[6-(6-Methoxy-5-trifluoromethyl-pyridin-3-yl)-5,6,7,8-tetrahydro-pyrido[4,3-d]pyrimidin-4-yloxy]-pyrrolidine-1-carbonyl}-piperidin-1-yl)-ethanone;

{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone;

{3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-(3-methyl-3H-imidazol-4-yl)-methanone;

{(S)-3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-oxazol-5-yl-methanone;

{3-[6-(6-Methoxy-5-trifluoromethyl-pyridin-3-yl)-5,6,7,8-tetrahydro-pyrido[4,3-d]pyrimidin-4-yloxy]-pyrrolidin-1-yl}-oxazol-5-yl-methanone;

{(S)-3-[6-(6-Methoxy-pyridin-3-yl)-5,6,7,8-tetrahydro-pyrido[4,3-d]pyrimidin-4-yloxy)pyrrolidin-1-yl}-(tetrahydro-pyran-4-yl)-methanone; and {3-[6-(6-Methoxy-pyridin-3-yl)-5,6,7,8-tetrahydropyrido[4,3-d]pyrimidin-4-yloxy)pyrrolidin-1-yl}-(tetrahydro-pyran-4-yl)-methanone.

8. A compound according to claim 2, wherein
$R^2$ is selected from naphthyl, pyridyl or pyrimidinyl; each of which is unsubstituted or substituted by 1-3 substituents independently selected from halogen, cyano, nitro, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl.

9. A compound according to claim 2, wherein
$R^4$ is selected from heterocyclyl, $C_4$-$C_8$-cycloalkyl or heteroaryl;
wherein '$C_3$-$C_{12}$-cycloalkyl' may be unsubstituted or substituted by 1-3 substituents independently selected from fluoro, $C_1$-$C_4$-alkyl, hydroxyl, $C_1$-$C_4$-alkoxy;
wherein 'heterocyclyl' is selected from pyrrolidinyl, tetrahydropyranyl, piperidinyl, tetrahydrothiopyranyl, morpholinyl or piperazinyl; each of which is unsubstituted or substituted by 1-3 substituents independently selected from oxo, halogen, $C_1$-$C_4$-alkyl, hydroxyl, $C_1$-$C_4$-alkyl-carbonyl;
wherein 'heterocyclyl' can be attached at a heteroatom or a carbon atom and where the N and/or S heteroatoms can also optionally be oxidized to various oxidation states;
wherein 'heteroaryl' is selected from
furanyl, imidazolyl, pyrazolyl, thiazolyl, oxazolyl, isoxazolyl, 1,3,4-oxadiazolyl, pyridyl, pyrazinyl; each of which is unsubstituted or substituted by 1-3 substituents independently selected from $C_1$-$C_4$-alkyl, hydroxyl;
wherein 'heteroaryl' can be attached at a heteroatom or a carbon atom and where the N and/or S heteroatoms can also optionally be oxidized to various oxidation states.

10. A compound according to any claim 2, wherein
$R^4$ is selected from $C_1$-$C_8$-alkyl, $C_1$-$C_8$-alkoxy-$C_1$-$C_8$-alkyl, $C_1$-$C_8$-alkoxy or N,N-di-$C_1$-$C_8$-alkyl-amino,
wherein '$C_1$-$C_8$-alkyl' in N,N-di-$C_1$-$C_8$-alkyl-amino may be unsubstituted or substituted by halogen, hydroxy or $C_1$-$C_4$-alkoxy.

11. A compound according to claim 3, wherein
$R^2$ is selected from naphthyl, pyridyl or pyrimidinyl; each of which is unsubstituted or substituted by 1-3 substituents independently selected from halogen, cyano, nitro, $C_1$-$C_8$-alkyl, halo-$C_1$-$C_8$-alkyl, hydroxy-$C_1$-$C_8$-alkyl, hydroxyl, $C_1$-$C_8$-alkoxy, $C_1$-$C_8$-alkoxy-$C_1$-$C_8$-alkyl, amino, N—$C_1$-$C_8$-alkyl-amino, N,N-di-$C_1$-$C_8$-alkyl-amino, $C_1$-$C_8$-alkyl-carbonyl, halo-$C_1$-$C_8$-alkyl-carbonyl, hydroxy-$C_1$-$C_8$-alkyl-carbonyl or $C_1$-$C_8$-alkoxy-$C_1$-$C_8$-alkyl-carbonyl.

12. A compound according to claim 3, wherein
$R^4$ is selected from heterocyclyl, $C_4$-$C_8$-cycloalkyl or heteroaryl;
wherein '$C_3$-$C_{12}$-cycloalkyl' may be unsubstituted or substituted by 1-3 substituents independently selected from fluoro, $C_1$-$C_4$-alkyl, hydroxyl, $C_1$-$C_4$-alkoxy;
wherein 'heterocyclyl' is selected from pyrrolidinyl, tetrahydropyranyl, piperidinyl, tetrahydrothiopyranyl, morpholinyl or piperazinyl; each of which is unsubstituted or substituted by 1-3 substituents independently selected from oxo, halogen, $C_1$-$C_4$-alkyl, hydroxyl, $C_1$-$C_4$-alkyl-carbonyl;
wherein 'heterocyclyl' can be attached at a heteroatom or a carbon atom and where the N and/or S heteroatoms can also optionally be oxidized to various oxidation states;
wherein 'heteroaryl' is selected from
furanyl, imidazolyl, pyrazolyl, thiazolyl, oxazolyl, isoxazolyl, 1,3,4-oxadiazolyl, pyridyl, pyrazinyl; each of which is unsubstituted or substituted by 1-3 substituents independently selected from $C_1$-$C_4$-alkyl, hydroxyl;
wherein 'heteroaryl' can be attached at a heteroatom or a carbon atom and where the N and/or S heteroatoms can also optionally be oxidized to various oxidation states.

13. A compound according to any claim 3, wherein
$R^4$ is selected from $C_1$-$C_8$-alkyl, $C_1$-$C_8$-alkoxy-$C_1$-$C_8$-alkyl, $C_1$-$C_8$-alkoxy or N,N-di-$C_1$-$C_8$-alkyl-amino,
wherein '$C_1$-$C_8$-alkyl' in N,N-di-$C_1$-$C_8$-alkyl-amino may be unsubstituted or substituted by halogen, hydroxy or $C_1$$C_4$alkoxy.

14. A compound of the claim 1 in form of a salt selected from
a) citrate, fumarate or napadisylate; or
b) phosphate, hydrochloride or hippurate.

15. A combination comprising a therapeutically effective amount of a compound of claim 1, and one or more therapeutically active agents.

16. A pharmaceutical composition comprising a therapeutically effective amount of a compound of claim 1, and one or more pharmaceutically acceptable carriers.

17. {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(tetrahydro-pyran-4-yl)-methanone or a pharmaceutically acceptable salt thereof.

18. {(S)-3-[6-(6-Methoxy-5-methyl-pyridin-3-yl)-5,6,7,8-tetrahydro-pyrido[4,3-d]pyrimidin-4-yloxy]-pyrrolidin-1-yl}-(1-methyl-1H-imidazol-4-yl)-methanone or a pharmaceutically acceptable salt thereof.

19. 1-{(S)-3-[6-(6-Methoxy-5-trifluoromethyl-pyridin-3-yl)-5,6,7,8-tetrahydro-pyrido[4,3-d]pyrimidin-4-ylamino]-pyrrolidin-1-yl}-propan-1-one or a pharmaceutically acceptable salt thereof.

20. {(S)-3-[6-(6-Methoxy-5-trifluoromethyl-pyridin-3-yl)-5,6,7,8-tetrahydro-pyrido[4,3-d]pyrimidin-4-ylamino]-pyrrolidin-1-yl}-(tetrahydro-pyran-4-yl)-methanone or a pharmaceutically acceptable salt thereof.

21. 1-{(S)-3-[6-(6-Methoxy-5-methyl-pyridin-3-yl)-5,6,7,8-tetrahydro-pyrido[4,3-d]pyrimidin-4-ylamino]-pyrrolidin-1-yl}-propan-1-one or a pharmaceutically acceptable salt thereof.

* * * * *

SEQUENCE LISTING

<160> NUMBER OF SEQ ID NOS: 21

<210> SEQ ID NO 1
<211> LENGTH: 28
<212> TYPE: DNA
<213> ORGANISM: Artificial
<220> FEATURE:
<223> OTHER INFORMATION: Primer

<400> SEQUENCE: 1
cgagaatatg atagattata tgaagaat                                          28

<210> SEQ ID NO 2
<211> LENGTH: 30
<212> TYPE: DNA
<213> ORGANISM: Artificial
<220> FEATURE:
<223> OTHER INFORMATION: Primer

<400> SEQUENCE: 2
tggtttaatg ctgttcatac gtttgtcaat                                        30

<210> SEQ ID NO 3
<211> LENGTH: 76
<212> TYPE: DNA
<213> ORGANISM: Artificial
<220> FEATURE:
<223> OTHER INFORMATION: Primer

<400> SEQUENCE: 3
gggacaagtt tgtacaaaaa agcaggctac gaaggagata tacatatgcg agaatatgat      60
agattatatg aagaat                                                      76

<210> SEQ ID NO 4
<211> LENGTH: 66
<212> TYPE: DNA
<213> ORGANISM: Artificial
<220> FEATURE:
<223> OTHER INFORMATION: Primer

<400> SEQUENCE: 4
taccataatt ccaccaccac caccggaaat tcccccctggt ttaatgctgt tcatacgttt     60
gtcaat                                                                 66

<210> SEQ ID NO 5
<211> LENGTH: 26
<212> TYPE: DNA
<213> ORGANISM: Artificial
<220> FEATURE:
<223> OTHER INFORMATION: Primer

<400> SEQUENCE: 5
ctagtggaat gtttactacc aaatgg                                           26

<210> SEQ ID NO 6
<211> LENGTH: 26
<212> TYPE: DNA
<213> ORGANISM: Artificial
<220> FEATURE:
<223> OTHER INFORMATION: Primer

<400> SEQUENCE: 6
gttcaatgca tgctgtttaa ttgtgt                                           26

```
<210> SEQ ID NO 7
<211> LENGTH: 63
<212> TYPE: DNA
<213> ORGANISM: Artificial
<220> FEATURE:
<223> OTHER INFORMATION: Primer

<400> SEQUENCE: 7
gggggaattt ccggtggtgg tggtggaatt atggtactag tggaatgttt actaccaaat    60
gga                                                                 63

<210> SEQ ID NO 8
<211> LENGTH: 56
<212> TYPE: DNA
<213> ORGANISM: Artificial
<220> FEATURE:
<223> OTHER INFORMATION: Primer

<400> SEQUENCE: 8
agctccgtga tggtgatggt gatgtgctcc gttcaatgca tgctgtttaa ttgtgt        56

<210> SEQ ID NO 9
<211> LENGTH: 61
<212> TYPE: DNA
<213> ORGANISM: Artificial
<220> FEATURE:
<223> OTHER INFORMATION: Primer

<400> SEQUENCE: 9
gggaccactt tgtacaagaa agctgggttt aagctccgtg atggtgatgg tgatgtgctc    60
c                                                                   61

<210> SEQ ID NO 10
<211> LENGTH: 42
<212> TYPE: DNA
<213> ORGANISM: Artificial
<220> FEATURE:
<223> OTHER INFORMATION: Primer

<400> SEQUENCE: 10
gctagcatgc gagaatatga tagattatat gaagaatata cc                      42

<210> SEQ ID NO 11
<211> LENGTH: 45
<212> TYPE: DNA
<213> ORGANISM: Artificial
<220> FEATURE:
<223> OTHER INFORMATION: Primer

<400> SEQUENCE: 11
gcctccacca cctccgcctg gtttaatgct gttcatacgt ttgtc                   45

<210> SEQ ID NO 12
<211> LENGTH: 42
<212> TYPE: DNA
<213> ORGANISM: Artificial
<220> FEATURE:
<223> OTHER INFORMATION: Primer

<400> SEQUENCE: 12
tactagtccg cctccaccac ctccgcctcc accacctccg cc                      42

<210> SEQ ID NO 13
<211> LENGTH: 54
<212> TYPE: DNA
```

-continued

```
<213> ORGANISM: Artificial
<220> FEATURE:
<223> OTHER INFORMATION: Primer

<400> SEQUENCE: 13
actgaagcat cctcctcctc ctcctcctgg tttaatgctg ttcatacgtt tgtc          54

<210> SEQ ID NO 14
<211> LENGTH: 57
<212> TYPE: DNA
<213> ORGANISM: Artificial
<220> FEATURE:
<223> OTHER INFORMATION: Primer

<400> SEQUENCE: 14
agctccgtga tggtgatggt gatgtgctcc agatctgtag tctttccgaa ctgtgtg       57

<210> SEQ ID NO 15
<211> LENGTH: 61
<212> TYPE: DNA
<213> ORGANISM: Artificial
<220> FEATURE:
<223> OTHER INFORMATION: Primer

<400> SEQUENCE: 15
gggaccactt tgtacaagaa agctgggttt aagctccgtg atggtgatgg tgatgtgctc    60
c                                                                    61

<210> SEQ ID NO 16
<211> LENGTH: 45
<212> TYPE: DNA
<213> ORGANISM: Artificial
<220> FEATURE:
<223> OTHER INFORMATION: Primer

<400> SEQUENCE: 16
tcctcctcct cctcctcctg gtttaatgct gttcatacgt ttgtc                    45

<210> SEQ ID NO 17
<211> LENGTH: 26
<212> TYPE: DNA
<213> ORGANISM: Artificial
<220> FEATURE:
<223> OTHER INFORMATION: Primer

<400> SEQUENCE: 17 atgcccctg gggtggactg ccccat                                          26

<210> SEQ ID NO 18
<211> LENGTH: 26
<212> TYPE: DNA
<213> ORGANISM: Artificial
<220> FEATURE:
<223> OTHER INFORMATION: Primer

<400> SEQUENCE: 18
ctactgcctg ttgtctttgg acacgt                                         26

<210> SEQ ID NO 19
<211> LENGTH: 53
<212> TYPE: DNA
<213> ORGANISM: Artificial
<220> FEATURE:
<223> OTHER INFORMATION: Primer

<400> SEQUENCE: 19
```

```
attaaaccag gaggaggagg aggaggaccc cctggggtgg actgccccat gga        53
```

<210> SEQ ID NO 20
<211> LENGTH: 56
<212> TYPE: DNA
<213> ORGANISM: Artificial
<220> FEATURE:
<223> OTHER INFORMATION: Primer

<400> SEQUENCE: 20

```
agctccgtga tggtgatggt gatgtgctcc ctgcctgttg tctttggaca cgttgt     56
```

<210> SEQ ID NO 21
<211> LENGTH: 61
<212> TYPE: DNA
<213> ORGANISM: Artificial
<220> FEATURE:
<223> OTHER INFORMATION: Primer

<400> SEQUENCE: 21

```
gggaccactt tgtacaagaa agctgggttt aagctccgtg atggtgatgg tgatgtgctc  60
c                                                                 61
```